(12) United States Patent
Gallop et al.

(10) Patent No.: US 11,026,963 B2
(45) Date of Patent: Jun. 8, 2021

(54) SENOLYTIC COMPOSITIONS AND USES THEREOF

(71) Applicant: Rubedo Life Sciences, Inc., Sunnyvale, CA (US)

(72) Inventors: Mark A. Gallop, San Francisco, CA (US); Julian Klein, Los Altos, CA (US); Marco Quarta, Sunnyvale, CA (US)

(73) Assignee: Rubedo Life Sciences, Inc., Sunnyvale, CA (US)

( * ) Notice: Subject to any disclaimer, the term of this patent is extended or adjusted under 35 U.S.C. 154(b) by 0 days.

(21) Appl. No.: 16/508,477

(22) Filed: Jul. 11, 2019

(65) Prior Publication Data

US 2020/0016185 A1 Jan. 16, 2020

Related U.S. Application Data

(60) Provisional application No. 62/696,486, filed on Jul. 11, 2018.

(51) Int. Cl.
*A61K 31/7072* (2006.01)
*C07H 5/04* (2006.01)
*A61P 35/04* (2006.01)

(52) U.S. Cl.
CPC .......... *A61K 31/7072* (2013.01); *A61P 35/04* (2018.01); *C07H 5/04* (2013.01)

(58) Field of Classification Search
None
See application file for complete search history.

(56) References Cited

U.S. PATENT DOCUMENTS

| | | | |
|---|---|---|---|
| 5,369,108 A | 11/1994 | Breslow et al. | |
| 5,932,616 A | 8/1999 | Breslow et al. | |
| 6,087,367 A | 7/2000 | Breslow et al. | |
| 6,511,990 B1 | 1/2003 | Breslow et al. | |
| 6,664,443 B1 | 12/2003 | Hutton et al. | |
| 9,829,481 B2 | 11/2017 | Cotton et al. | |
| 2010/0267655 A1* | 10/2010 | Thorson | A61P 35/00 514/42 |
| 2011/0053991 A1* | 3/2011 | Gore | A61K 31/506 514/357 |
| 2012/0005765 A1 | 1/2012 | Kumar et al. | |
| 2012/0071468 A1 | 3/2012 | John et al. | |
| 2015/0168374 A1 | 6/2015 | Cotton et al. | |
| 2016/0339019 A1 | 11/2016 | Laberge et al. | |

FOREIGN PATENT DOCUMENTS

| | | |
|---|---|---|
| CN | 1534046 A | 10/2004 |
| JP | 6328098 B2 | 5/2018 |
| WO | 2012/177927 A1 | 12/2012 |
| WO | 2013/090645 A1 | 6/2013 |
| WO | 2014/205244 A1 | 12/2014 |
| WO | 2017184995 A1 | 10/2017 |
| WO | 2018146506 A1 | 8/2018 |

OTHER PUBLICATIONS

Thomas, M., Rivault, F., Tranoy-Opalinski, I., Roche, J., Gesson, J. P., & Papot, S. (2007). Synthesis and biological evaluation of the suberoylanilide hydroxamic acid (SAHA) β-glucuronide... Bioorganic & medicinal chemistry letters, 17(4), 983-986. (Year: 2007).*
Coppe et al., PLoS. Biol., vol. 6, (2008), pp. 2853-2868.
Sis et al., Kidney Int., vol. 7, (2007), pp. 218-226.
Katzman et al., J. Orthop. Sports Phys. Ther., vol. 40, (2010), pp. 352-360.
De Boer et al., Science, vol. 296, (2002), pp. 1276-1279.
Itahana et al., Methods Mol. Biol., vol. 371, (2007), pp. 21-31.
Yu et al., Immunol. Methods, vol. 350, (2009), pp. 29-35.
Centers for Disease Control and Prevention, National Diabetes Fact Sheet: National Estimates and General Information on Diabetes and Pre-Diabetes in the United States, (2011).
International Search Report in corresponding International Patent Application PCT/US2019/041283, dated Nov. 21, 2019, 14 pgs.
Punchem, Substance Record for SID 26657149, Available Date: Aug. 20, 2007 [retrieved on Sep. 5, 2019.] Retrieved from the Internet: <URL: https://pubchem.ncbi.nlm.nih.gov/substance/26657149> entire document.
Investigation of quercetin and hyperoside as senolytics in adult human endothelial cells, reasearch article (Jan. 9, 2018), 14 pages.
Childs et al., Nat. Rev. Drug Discov., vol. 16, (2017), pp. 718-735.
Demaria et al., Cancer Discovery, vol. 7, (2017), pp. 165-176.
Schafer et al., Nat. Commun., vol. 8, (2017) doi:10.1038/ncomms14532.
Zhu et al., Aging, vol. 9, (2017), pp. 955-965.
Yosef et al., Nature Commun., (2016), doi:10.1038).
Zhu et al., Aging Cell, vol. 14, (2015), pp. 654-658.

(Continued)

*Primary Examiner* — Dale R Miller
(74) *Attorney, Agent, or Firm* — Young Basile Hanlon & MacFarlane, P.C.

(57) ABSTRACT

Provided herein are senolytic agents for selectively killing senescent cells that are associated with numerous pathologies and diseases, including age-related pathologies and diseases. As disclosed herein, senescent cell-associated diseases and disorders may be treated or prevented by administering at least one senolytic agent or pharmaceutical compositions thereof. The senescent cell-associated diseases or disorders treated or prevented by the methods described herein include, but are not limited to, cardiovascular diseases or disorders, cardiovascular diseases and disorders associated with arteriosclerosis, such as atherosclerosis, idiopathic pulmonary fibrosis (IPF), chronic obstructive pulmonary disease (COPD), osteoarthritis, inflammatory diseases or disorders, autoimmune diseases or disorders, pulmonary diseases or disorders, neurological diseases or disorders, dermatological diseases or disorders, chemotherapeutic side effects, radiotherapy side effects, metastasis and metabolic diseases.

16 Claims, 7 Drawing Sheets

(56) References Cited

OTHER PUBLICATIONS

Whittaker et al., Pharmacol. Ther., vol. 173, (2017), pp. 83-105.
Laberge et al., Nat. Cell. Biol., vol. 17, (2015), pp. 1049-1061.
Fuhrmann-Stroissnigg et al., Nat. Commun., vol. 8, (2017) doi:10.1038/s41467-017-00314-z).
Samaraweera et al., Sci. Rep., vol. 7, (2017), pp. 1900.
Leverson et al., Sci. Trans!. Med., (2015) 7:279ra40.doi:10.1126/scitranslmed.aaa4642).
Mottamal et al., Molecules, vol. 20, (2015) pp. 3898-3941.
Roche et al., Eur. J. Med. Chem., vol. 121, (2016), pp. 451-483.
K. Guillory, Polymorphism in Pharmaceutical Solids, Chapter 5, Marcel Dekker, Inc., (1999), pp. 202-205.
H. Brittain, Polymorphism in Pharmaceutical Solids, Chapter 6, Marcel Dekker, Inc., (1999), pp. 205-208.
L. Galluzzi et al., Cell Senescene: Methods and Protocols, Methods in Molecular Biology, vol. 965, (2013).
Li et al., Proteomics, vol. 13, (2013), pp. 2585-2596.
Cao et al., Am. J. Respir. Cell Mol. Biol., vol. 25, (2001), pp. 562-568.
Rada-Iglesias et al., Genome Res., vol. 17, (2007), pp. 708-719.
Frys et al., Br. J. Haematol, vol. 169, (2015), pp. 506-519.
Hou et al., Mater. Cjem. Front., vol. 1, (2017), pp. 660-667.
Shie et al., Carbohydrate Res. vol. 341, (2006), pp. 443-456.
Brough et al., J. Med. Chem., vol. 51, (2008), pp. 196-218.
Jain et al., Current Genomics, vol. 18, (2017), pp. 75-92.
Cinelli et al., J. Med. Chem., vol. 55, (2012), pp. 10844-10862.
Lv et al., J. Med. Chem., vol. 59, (2016), pp. 4890-4899.
Sooryakumar et al., Mol. Cancer Ther., vol. 10, (2011), pp. 1490-1499.
Tietze et al., Agnew. Chem. Int. Ed., vol. 45, (2006), pp. 6574-6577.
Tietze et al., J. Med. Chem., vol. 52, (2009), pp. 537-543.
Antonow et al., Chem Rev., vol. 111, (2011), pp. 2815-2864.
Mantaj et al., Agnew Chem Int. Ed., vol. 56, (2017), pp. 462-488.
Kamal et al., Chem. Med. Chem., vol. 3, (2008), pp. 794-802.
Baker et al., Nature, vol. 479, (2011), pp. 232-236.
Pennesi et al., Mol. Aspects Med., vol. 33, (2012), pp. 487-509.
Zeiss et al., Vet. Pathol., vol. 47, (2010), pp. 396-413.
Peng et al., PLoS One, vol. 8, Issue 4, (2013).
Mouratis et al., Curr. Opin. Pulm. Med., vol. 17, (2011), pp. 355-361.
Campisi, Annu. Rev. Physiol., vol. 75, (2013), pp. 685-705.
Naylor et al., Clin. Pharmacol. Ther., vol. 93, (2013), pp. 105-116.
Fried et al., J. Gerontol. A Biol. Sci. Med. Sci., vol. 56, Issue 3, (2001), pp. 1-15.
Park et al., J. Clin. Invest., vol. 113, (2004), pp. 175-179.
Sousa-Victor, Nature, vol. 506, (2014), pp. 316-321.
Shapiro et al., Am. J. Respir. Cell Mol. Biol., vol. 32, (2005), pp. 367-372.
Minagawa et al., Am. J. Physiol. Lung Cell. Mol. Physiol., vol. 300, (2011), pp. L391-L401.
Alder et al., Proc. Natl. Acad. Sci. USA, vol. 105, (2008), pp. 13051-13056.
Fischer et al., Am. J. Physiol. Lung Cell. Mol. Physiol., vol. 304, Issue 6, (2013), pp. L394-L400.
Cohen et al., J. Neural Transm. Suppl., vol. 19, (1983), pp. 89-103.
Klunk et al., Ann. Neurol., vol. 55, (2004), pp. 306-319.
Appel et al., Proc. Natl. Acad. Sci. USA, vol. 88, (1991), pp. 647-651.
Krag et al., Invest. Ophthalmol. Vis. Sci., vol. 38, (1997), pp. 357-363.
Gonzalez-Gualda et al., Galacto-conjugation of Navitoclas as an efficient strategy to increase senolytic specificity and reduce platelet toxicity; Aging Cell. 2020;00;e13142.; wileyonlinelibrary.com/journal/acel; Mar. 3, 2020; 19 pages.

* cited by examiner

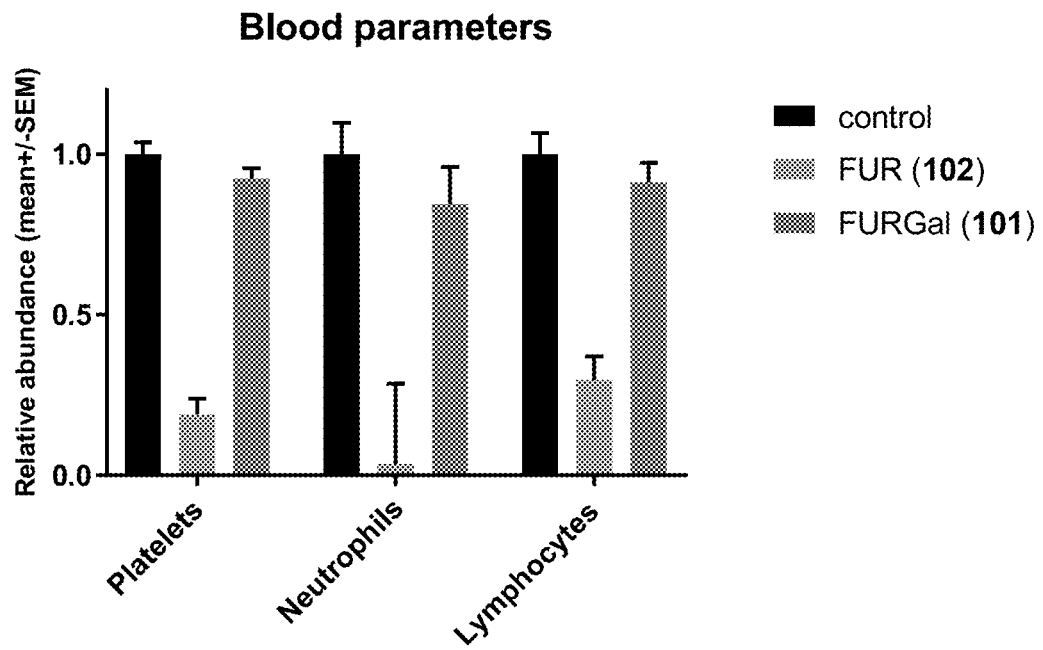
FIG. 2A
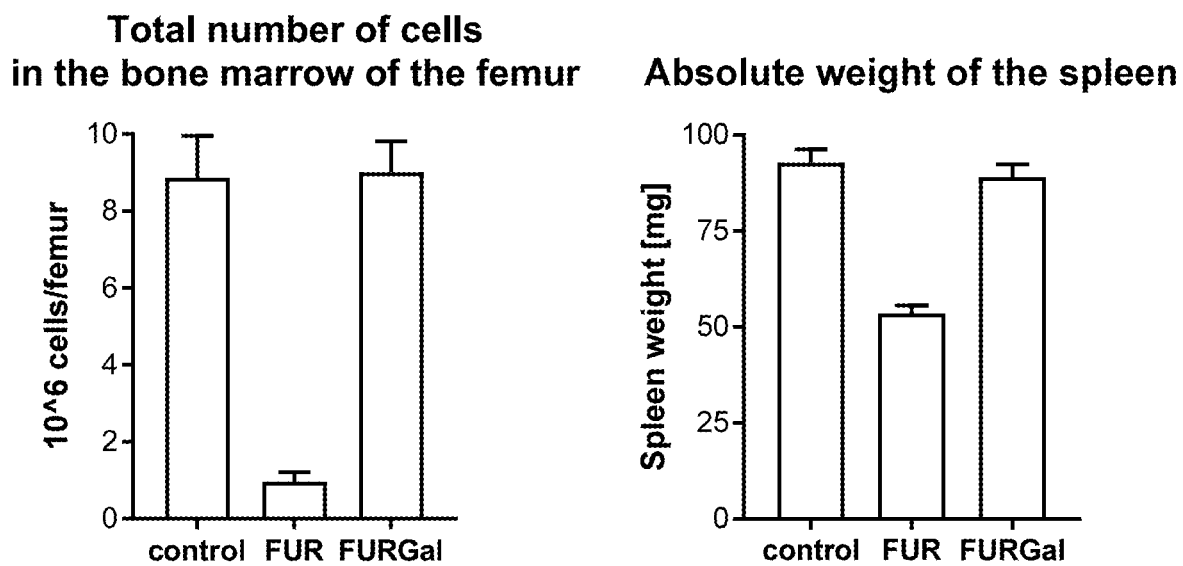
FIG. 2B
FIG. 2C

Senescence associated ß-galactosidase (SAßGal) activity in liver (left lateral lobe)

Senescence associated ß-galactosidase activity in lung (left lobe)

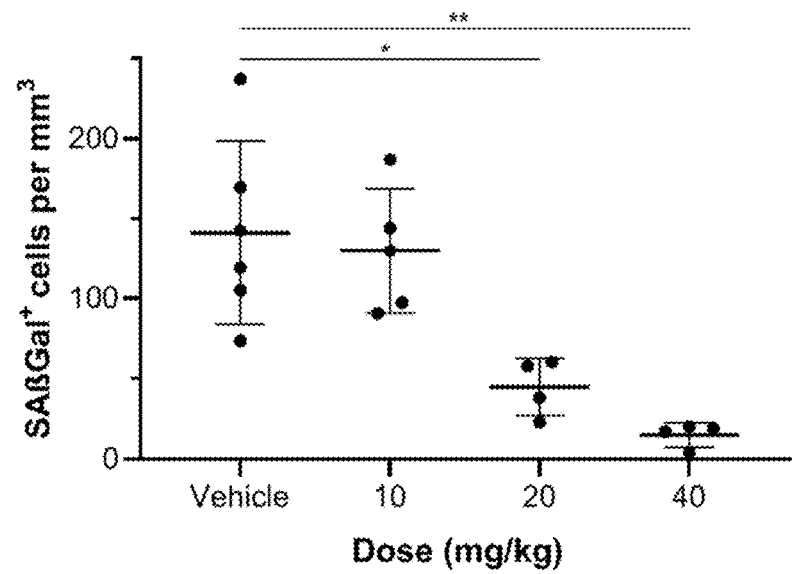
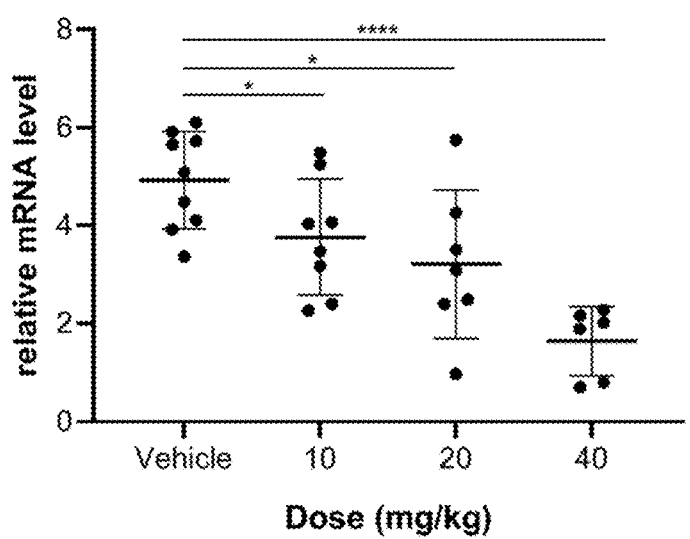

SENOLYTIC COMPOSITIONS AND USES THEREOF

CROSS-REFERENCE TO RELATED APPLICATION(S)

This application claims priority to and the benefit of U.S. Provisional Application Patent Ser. No. 62/696,486, filed Jul. 11, 2018, the disclosure of which is incorporated by reference herein in its entirety for all purposes.

TECHNICAL FIELD

Provided herein are senolytic agents for selectively killing senescent cells that are associated with numerous pathologies and diseases, including age-related pathologies and diseases. As disclosed herein, senescent cell-associated diseases and disorders may be treated or prevented by administering at least one senolytic agent or pharmaceutical compositions thereof. The senescent cell-associated diseases or disorders treated or prevented by the methods described herein include, but are not limited to, cardiovascular diseases or disorders, cardiovascular diseases and disorders associated with arteriosclerosis, such as atherosclerosis, idiopathic pulmonary fibrosis (IPF), chronic obstructive pulmonary disease (COPD), osteoarthritis, inflammatory diseases or disorders, autoimmune diseases or disorders, pulmonary diseases or disorders, neurological diseases or disorders, dermatological diseases or disorders, chemotherapeutic side effects, radiotherapy side effects, metastasis and metabolic diseases.

BACKGROUND

Aging is a risk factor for most chronic diseases, disabilities and poor health. Senescent cells, which are cells in replicative arrest, accumulate in aging individuals and may contribute partially or significantly to cell and tissue deterioration that underlies aging and age related diseases (see e.g., Childs et al., Nat. Rev. Drug Discov. 16 (2017) 718-735). Cells may also become senescent after exposure to an environmental, chemical, biological insult or as a result of disease (see e.g., Demaria et al., Cancer Discovery 7 (2017) 165-176; and Schafer et al., Nat. Commun. 8 (2017) doi: 10.1038/ncomms14532).

Senolytic agents with a diverse range of pharmacological mechanisms are known in the art. The senolytic agent may be a specific inhibitor of one or more Bcl-2 anti-apoptotic protein family members where the inhibitor inhibits at least Bcl-xL (e.g., a Bcl-2/Bcl-xL/Bcl-w inhibitor; a selective Bcl-xL inhibitor; a Bcl-xL/Bcl-w inhibitor, (e.g., Navitoclax, ABT-737, A1331852, A1155463); (see e.g., Childs et al., supra; Zhu et al., Aging 9 (2017) 955-965; Yosef et al., Nature Commun. (2016) doi:10.1038); an Akt kinase specific inhibitor (e.g., MK-2206); a receptor tyrosine kinase inhibitor (e.g., dasatinib, see e.g., Zhu et al., Aging Cell 14 (2015) 654-658); a CDK4/6 inhibitor (e.g., palbociclib, (see e.g., Whittaker et al., Pharmacol. Ther. 173 (2017) 83-105)); an mTOR inhibitor (e.g., rapamycin, (see e.g., Laberge et al., Nat. Cell Biol. 17 (2015) 1049-1061)); an MDM2 inhibitor (e.g., Nutlin-3; and RG-7112, see e.g., U.S. Pat. Appl. 2016/0339019)); an Hsp90 inhibitor (e.g., 17-DMAG; and ganetespib, see e.g., Fuhrmann-Stroissnigg et al., Nat. Commun. 8 (2017) doi: 10.1038/s41467-017-00314-z)); a flavone (e.g., quercetin; and fisetin, (see e.g., Zhu et al., Aging Cell 14 (2015) 654-658; Zhu et al., Aging 9 (2017) 955-965)); or a histone deacetylase inhibitor (e.g., panobinostat, (see e.g., Samaraweera et al., Sci. Rep. 7 (2017) 1900. doi: 10.1038/s41598-017-01964-1)).

A significant challenge has been the identification of senolytic agents which selectively kill senescent cells while sparing non-senescent cells. Moreover, many known senolytic agents were initially developed as cytotoxic anti-cancer agents and subsequently repurposed for 'selective' removal of senescent cell populations. Because proliferating cells are frequently more sensitive to the cytotoxic or cytostatic effect of anti-tumor agents, dose-limiting toxicity in hematopoietic cells is a frequently observed side-effect which limits the clinical utility of anti-senescence therapy (e.g., neutropenia is a well-characterized toxicity associated with the use of anti-apoptotic Bcl-2 family protein inhibitors, see Leverson et al., Sci. Transl. Med. (2015) 7:279ra40. doi: 10.1126/scitranslmed.aaa4642). Pulsatile administration of such senolytic drugs has been proposed as a mechanism to minimize exposure of non-senescent cells to these molecules and potentially limit off-target effects. Accordingly, what is needed is are senolytic agents with improved selectivity for killing senescent cells which have minimal toxicity towards non-senescent cells.

SUMMARY

Disclosed herein are non-toxic prodrugs of senolytic agents which are activated by hydrolase enzymes that preferentially accumulate inside senescent cells which satisfies these and other needs. In one aspect, the hydrolase enzymes are glycosidases and the senescence-associated elevated intracellular glycosidase activities are exploited to convert a non-toxic prodrug derivative (I) of a pro-apoptotic agent into a toxic, apoptosis-promoting parent compound (II), leading to specific killing of the senescent cell.

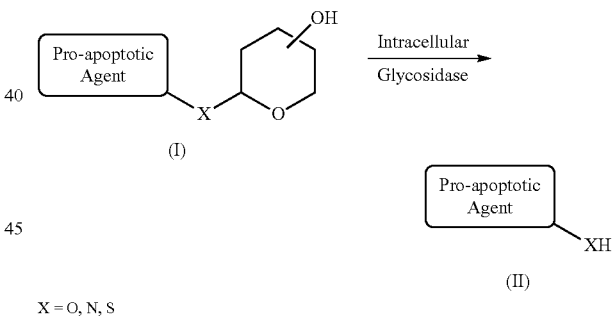

X = O, N, S

In some embodiments, compound (II) is capable of promoting apoptosis in non-proliferating cells.

In another aspect, non-toxic prodrugs of toxic senolytic agents, which when cleaved to the active senolytic agent inside a senescent cell, specifically lead to senescent cell death are provided. In some embodiments, prodrugs of histone deacetylase inhibitors are provided. In other embodiments, prodrugs of Hsp90 inhibitors are provided. In still other embodiments, prodrugs of topoisomerase 1 inhibitors are provided. In still other embodiments, prodrugs of DNA alkylating agents are provided. In still other embodiments, prodrugs of Akt1 inhibitors are provided. In still other embodiments, prodrugs of proteasome inhibitors are provided. Also provided are derivatives, including salts, solvates, hydrates, metabolites of the prodrugs described herein. Further provided are compositions, which include the prodrugs provided herein and a vehicle.

In another aspect, methods of treating, preventing, or ameliorating symptoms of medical disorders such as, for example, cardiovascular diseases or disorders, cardiovascular diseases and disorders associated with arteriosclerosis, such as atherosclerosis, idiopathic pulmonary fibrosis (IPF), chronic obstructive pulmonary disease (COPD), osteoarthritis, inflammatory disease or disorders, autoimmune diseases or disorders, pulmonary diseases or disorders, neurological diseases or disorders, dermatological diseases or disorders, chemotherapeutic side effects, radiotherapy side effects, metastasis and metabolic diseases in a subject are also provided herein. In practicing the methods, therapeutically effective amounts of the senolytic agents or pharmaceutical compositions thereof are administered to a subject.

In still another aspect, a method of treating an age-related disease or condition is provided. The method comprises administering therapeutically effective amounts of the senolytic agents or pharmaceutical compositions thereof are administered to a subject.

In still another aspect, a method for delaying at least one feature of aging in a subject is provided. The method comprises administering therapeutically effective amounts of the senolytic agents or pharmaceutical compositions thereof are administered to a subject.

In still another aspect, a method of killing therapy-induced senescent cells is provided. The method comprises administering a The method comprises administering therapeutically effective amounts of the senolytic agents or pharmaceutical compositions thereof are administered to a subject that has received DNA damaging therapy.

BRIEF DESCRIPTION OF THE DRAWINGS

FIG. 2A illustrates quantitation of blood cell counts, from w.t. C57BL/6 mice dosed by single intraperitoneal injection with FUR (102) (100 mg/kg) or FURGal (101) (160 mg/kg) 6 days after treatment (N=3 mice/group).

FIG. 2B illustrates quantitation of number of bone marrow cells in femur from w.t. C57BL/6 mice dosed by single intraperitoneal injection with FUR (102) (100 mg/kg) or FURGal (101) (160 mg/kg) 6 days after treatment (N=3 mice/group).

FIG. 2C illustrates quantitation of total spleen weight from w.t. C57BL/6 mice dosed by single intraperitoneal injection with FUR (102) (100 mg/kg) or FURGal (101) (160 mg/kg) 6 days after treatment (N=3 mice/group).

FIG. 5C illustrates quantification of SA-β-Gal in lung sections after i.v. dosing of compound (119) at 10 mg/kg, 20 mg/kg or 40 mg/kg along with a control.

FIG. 5D illustrates quantification of Cdkn2a expression in lung of C57BL/6 mice injected with doxorubicin (15 mg/kg) followed by vehicle or compound (119) at 10 mg/kg, 20 mg/kg or 40 mg/kg.

DETAILED DESCRIPTION

Definitions

Figures 1A, 1B:
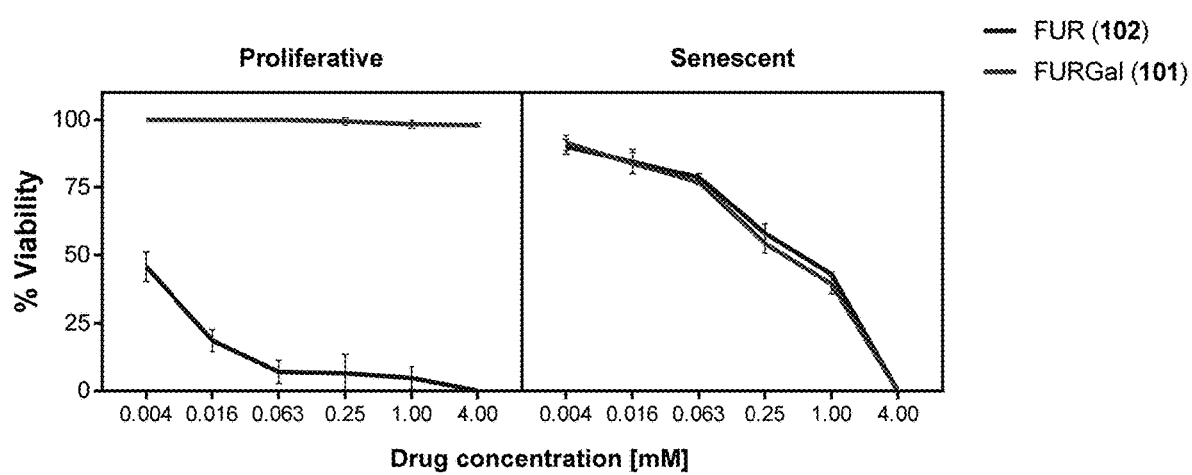
FIG. 1A illustrates the viability of proliferative mouse embryonic fibroblasts (MEFs) treated with κ-fluorouridine (FUR) (102) or 5-fluorouridine-5'-O-β-D-galactopyranoside (FURGal) (101) at various drug concentrations.
FIG. 1B illustrates the viability of senescent mouse embryonic fibroblasts (MEFs) treated with 5-fluorouridine (FUR) (102) or 5-fluorouridine-5'-O-β-D-galactopyranoside (FURGal) (101) at various drug concentrations.

"A feature of aging" as used herein, includes, but is not limited to, systemic decline of the immune system, muscle atrophy and decreased muscle strength, decreased skin elasticity, delayed wound healing, retinal atrophy, reduced lens transparency, reduced hearing, osteoporosis, sarcopenia, hair graying, skin wrinkling, poor vision, frailty, and cognitive impairment.

"Acyl" means an H—CO—, alkyl CO alkenyl-CO— or cycloalkyl-CO— group, in which the alkyl, alkenyl or cycloalkyl group is as described herein.

"Acylamino" is an acyl-NH— group wherein acyl is as defined herein.

"Age-related disease or condition" as used herein includes, but is not limited to, a degenerative disease or a function-decreasing disorder such as Alzheimer's disease, Parkinson's disease, cataracts, macular degeneration, glaucoma, frailty, muscle weakness, cognitive impairment, atherosclerosis, acute coronary syndrome, myocardial infarction, stroke, hypertension, idiopathic pulmonary fibrosis (IPF), chronic obstructive pulmonary disease (COPD), osteoarthritis, type 2 diabetes, obesity, fat dysfunction, coronary artery disease, cerebrovascular disease, periodontal disease, cancer treatment-related disability such as atrophy and fibrosis in various tissues, brain and heart injury, and therapy-related myelodysplastic syndromes, and diseases associated with accelerated aging and/or defects in DNA damage repair and telomere maintenance such as progeroid syndromes (i.e. Hutchinson-Gilford progeria syndrome, Werner syndrome, Bloom syndrome, Rothmund-Thomson Syndrome, Cockayne syndrome, xeroderma pigmentosum, trichothiodystrophy, combined xeroderma pigmentosum-Cockayne syndrome, restrictive dermopathy), ataxia telangiectasia, Fanconi anemia, Friedreich's ataxia, dyskeratosis congenital, aplastic anemia, and others.

"Alkenyl" means an aliphatic hydrocarbon group containing a carbon-carbon double bond and which may be straight or branched having 2 to 20 carbon atoms in the chain. In some embodiments, alkenyl groups have 2 to 12 carbon atoms in the chain. In other embodiments, alkenyl groups have about 2 to 6 carbon atoms in the chain. In still other embodiments, alkenyl groups have 2 to 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include, but are not limited to, ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include, but are not limited to, vinylene and propylene.

"Alkoxy" means an alkyl-O— group in which the alkyl group is as described herein. Exemplary alkoxy groups include, but are not limited to, methoxy, ethoxy, n-propoxy, i-propoxy, n-butoxy and heptoxy.

"Alkoxycarbonyl" means an alkyl-O—CO— group in which the alkyl group is as described herein. Exemplary include, but are not limited to, alkoxycarbonyl groups include methoxy and ethoxycarbonyl.

"Alkyl" means, unless otherwise specified, an aliphatic hydrocarbon group which may be straight or branched having 1 to 20 carbon atoms in the chain. In some embodiments, alkyl groups have from 1 to 6 carbon atoms. "Lower alkyl" as a group or part of a lower alkoxy, lower alkylthio, lower alkylsulfinyl or lower alkylsulfonyl group means unless otherwise specified, an aliphatic hydrocarbon group which may be straight or branched having 1 to 4 carbon atoms in the chain. Exemplary alkyl groups include, but are not limited to, methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched alkyl group, in which the alkyl group is as described herein. Exemplary alkylene radicals include, but are not limited to, methylene, ethylene and trimethylene.

"Alkylenedioxy" means an —O-alkylene-O— group in which alkylene is as defined above. Exemplary alkylenedioxy groups include, but are not limited to, methylenedioxy and ethylenedioxy.

"Alkylsulfinyl" means an alkyl-SO— group in which the alkyl group is as previously described. Exemplary alkylsulfinyl groups include, but are not limited to those in which the alkyl group is $C_{1-4}$ alkyl.

"Alkylsulfonyl" means an alkyl-$SO_2$— group in which the alkyl group is as previously described. In some embodiments, alkylsulfonyl groups are those in which the alkyl group is $C_{1-4}$ alkyl.

"Alkylthio" means an alkyl-S— group in which the alkyl group is as previously described. Exemplary alkylthio groups include, but are not limited to, methylthio, ethylthio, isopropylthio and heptylthio.

"Alkynyl" means an aliphatic hydrocarbon group containing a carbon-carbon triple bond and which may be straight or branched having about 2 to about 20 carbon atoms in the chain. In some embodiments, alkynyl groups have 2 to 12 carbon atoms in the chain. In other embodiments, alkynyl groups have 2 to 6 carbon atoms in the chain. In still other embodiments, alkynyl groups have 2 to 4 carbon atoms in the chain. Exemplary alkynyl groups include, but are not limited to, ethynyl, propynyl, n-butynyl, i-butynyl, 3-methylbut-2-ynyl, and n-pentynyl.

"Alkynylene" means an aliphatic bivalent radical derived from a straight or branched alkynyl group, in which the alkynyl group is as described herein Exemplary alkynylene radicals include, but are not limited to, ethynylene and propynylene.

"Amino acid side chains" means the substituent found on the carbon between the amino and carboxy groups in α-amino acids. For examples of "corresponding protected derivatives" of amino acid side chains, see T. W. Greene and P. G. M. Wuts in "Protective Groups in Organic Chemistry" John Wiley and Sons, 1991.

"Aroyl" means an aryl-CO— group in which the aryl group is as described herein Exemplary aroyl groups include benzoyl and 1- and 2-naphthoyl.

"Aryl" as a group or part of a group denotes. (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring.

"Arylalkyl" means an aryl-alkyl-group in which the aryl and alkyl moieties are as previously described. Exemplary arylalkyl groups include, but are not limited to, benzyl, 2-phenethyl and naphthlenemethyl.

"Aryldiyl" means an optionally substituted bivalent radical derived from an aryl group Exemplary aryldiyl groups include, but are not limited to, optionally substituted phenylene, naphthylene and indanylene. Suitable substituents include one or more "aryl group substituents" as defined above, particularly halogen, methyl or methoxy.

"Aryloxy" means an aryl-O— group in which the aryl group is as previously described. Exemplary aryloxy groups include, but are not limited to, optionally substituted phenoxy and naphthoxy.

"Aryloxycarbonyl" means an aryl-O—C(=O)— group in which the aryl group is as previously described. Exemplary aryloxycarbonyl groups include, but are not limited to, phenoxycarbonyl and naphthoxycarbonyl.

"Arylsulfinyl" means an aryl-SO— group in which the aryl group is as previously described.

"Arylsulfonyl" means an aryl-$SO_2$— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulfur, or nitrogen. Examples of azaheteroaryl groups include pyridyl, pyrimidinyl, quinolinyl, isoquinolinyl, quinazolinyl, imidazolyl, and benzimidazolyl.

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e. geometric isomers), enantiomers or diastereomers. Accordingly, the chemical structures depicted herein encompass the stereoisomerically pure form depicted in the structure (e.g., geometrically pure, enantiomerically pure or diastereomerically pure). The chemical structures depicted herein also encompass the enantiomeric and stereoisomeric derivatives of the compound depicted, unless clearly identified otherwise. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"Cyclic amine" means a 3 to 8 membered monocyclic cycloalkyl ring system where one of the ring carbon atoms is replaced by nitrogen and which may also contain a further heteroatom selected from O, S, SO$_2$, or NY (where Y is hydrogen, alkyl, aryl, arylalkyl, acyl, acyloxyalkyl, cycloalkyl, heteroaryl, heterocycloalkyl or sulfonyl. Exemplary cyclic amines include, but are not limited to, pyrrolidinyl, piperidinyl, morpholinyl, piperazinyl, indolinyl, pyrindolinyl, tetrahydroquinolinyl.

"Cycloalkenyl" means a non-aromatic monocyclic or multicyclic ring system containing at least one carbon-carbon double bond and having 3 to 10 carbon atoms. Exemplary monocyclic cycloalkenyl rings include, but are not limited to, cyclopentenyl, cyclohexenyl or cycloheptenyl.

"Cycloalkyl" means a saturated monocyclic or bicyclic ring system of 3 to 10 carbon atoms optionally substituted by oxo. Exemplary monocyclic cycloalkyl rings include, but are not limited to, cyclopropyl, cyclobutyl, cyclopentyl, cyclohexyl and cycloheptyl.

"Cycloalkylene" means a bivalent radical derived from a cycloalkyl group. Exemplary cycloalkenylene radicals include, but are not limited to, cyclopentylene and cyclohexylene.

"DNA-damaging therapy" as used herein, includes, but is not limited to γ-irradiation, alkylating agents such as nitrogen mustards (e.g., chlorambucil, cyclophosphamide, ifosfamide, melphalan), nitrosoureas (streptozocin, carmustine, lomustine), alkyl sulfonates (e.g., busulfan), triazines (dacarbazine, temozolomide) and ethylenimines (e.g., thiotepa, altretamine), platinum drugs such as, for example, cisplatin, carboplatin, oxalaplatin, antimetabolites such as, for example, 5-fluorouracil, 6-mercaptopurine, capecitabine, cladribine, clofarabine, cytarabine, floxuridine, fludarabine, gemcitabine, hydroxyurea, methotrexate, pemetrexed, pentostatin, thioguanine, anthracyclines such as, for example, daunorubicin, doxorubicin, epirubicin, idarubicin, anti-tumor antibiotics such as actinomycin-D, bleomycin, mitomycin-C, mitoxantrone, topoisomerase inhibitors such as topoisomerase I inhibitors (e.g., topotecan, irinotecan) and topoisomerase II inhibitors (e.g., etoposide, teniposide, mitoxantrone), mitotic inhibitors such as taxanes (e.g, paclitaxel, docetaxel), epothilones (e.g., ixabepilone), vinca alkaloids (e.g., vinblastine, vincristine, vinorelbine) and estramustine.

"Halo" or "halogen" means fluoro, chloro, bromo, or iodo.

"Heteroaroyl" means a heteroaryl-C(=O)— group in which the heteroaryl group is as described herein. An exemplary group is pyridylcarbonyl.

"Heteroaryl" as a group or part of a group denotes: (i) an aromatic monocyclic or multicyclic organic moiety of about 5 to about 10 ring members in which one or more of the ring members is/are element(s) other than carbon, for example nitrogen, oxygen or sulphur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above), (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups).

"Heteroaryldiyl" means a bivalent radical derived from a heteroaryl group.

"Heteroaryloxy" means an heteroaryl-O— group in which the heteroaryl group is as previously described. An exemplary heteroaryloxy group is optionally substituted pyridyloxy.

"Heterocycle" denotes an optionally substituted saturated, partially saturated or fully unsaturated monocyclic organic moiety of 5 or 6 ring members in which one or more of the ring members is/are element(s) other than carbon, for example nitrogen, oxygen or sulfur. Exemplary 5 or 6 membered heterocycles include furyl, imidazolyl, isoxazolyl, isothiazolyl, oxadiazolyl, oxazolyl, oxazinyl, piperidinyl, pyrazinyl, pyridazinyl, pyrazolyl, pyridyl, pyrimidinyl, pyrrolyl, pyrrolidinyl, pyrrolinyl, 1,3,4-thiadiazolyl, thiazolyl, thienyl and triazolyl groups.

"Heterocycloalkyl" means: (i) a cycloalkyl group of about 3 to 7 ring members which contains one or more heteroatoms selected from O, S or N and optionally substituted by oxo, (ii) an partially saturated multicyclic heterocarbocyclic moiety in which an aryl (or heteroaryl ring), and a heterocycloalkyl group are fused together to form a cyclic structure (examples of such groups include chromanyl, dihydrobenzofuranyl, indolinyl and pyrindolinyl groups).

"Histone deacetylase inhibitors" or "HDAC inhibitors," as used herein are compounds that are capable of inhibiting the deacetylation of histones in vivo, in vitro or both (e.g., see Mottamal et al., Molecules 20 (2015) 3898-3941; Roche and Bertrand, Eur. J. Med. Chem. 121 (2016) 451-483). As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202205 in *Polymorphism in Pharmaceutical Solids*, (Brittain, H. ed.), Marcel Dekker, Inc., New York, N.Y., 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (http://www.holodiag.com).

"Hydroxamic acid derivative histone deacetylase inhibitor," as used herein, refers to the class of histone deacetylase inhibitors that are hydroxamic acid derivatives.

"A residue of a hydroxamic acid derivative histone deacetylase inhibitor" as used herein, refers to the entire portion of the hydroxamic acid derivative histone deacetylase inhibitor excluding the hydroxamic acid moiety.

"Pharmaceutical composition" as used herein, refers to at least one compound and a pharmaceutically acceptable vehicle, with which the compound is administered to a patient.

"Pharmaceutically acceptable salt" as used herein, refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" as used herein, refers to a diluent, adjuvant, excipient or carrier with which a compound sis administered.

"Patient" includes humans. The terms "human" and "patient" are used interchangeably herein.

"Preventing" or "prevention," as used herein, refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" as used herein, refers to a derivative of a drug molecule that requires a transformation within the body to release the active drug. Prodrugs are frequently, although not necessarily, pharmacologically inactive until converted to the parent drug.

"Promoiety" as used herein, refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" as used herein, refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("Cbz"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("Fmoc"), nitro-veratryloxycarbonyl ("Nvoc") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Senescence" or "senescent cells" as used herein, refers to a state wherein cells have acquired one or more markers for senescence in response to some cellular stress. Such markers may typically include permanent withdrawal from the cell cycle, the expression of a bioactive secretome of inflammatory factors, altered methylation, senescence-associated heterochromatin foci (SAHF), expression markers for oxidative stress, expression of markers for DNA damage, protein and lipid modifications, morphological features of senescence, altered lysosome/vacuoles and expression of senescence-associated β-galactosidase (see Lorenzo Galluzzi et al. (eds.), Cell Senescence: Methods and Protocols, Methods in Molecular Biology, vol. 965, DOI 10.1007/978-1-62703-239-1_4, C Springer Science+Business Media, LLC 2013).

"Senolytic agent" as used herein refers to an agent that "selectively" (preferentially or to a greater degree) destroys, kills, removes, or facilitates selective destruction of senescent cells. In other words, the senolytic agent destroys or kills a senescent cell in a biologically, clinically, and/or statistically significant manner compared with its capability to destroy or kill a non-senescent cell. A senolytic agent is used in an amount and for a time sufficient that selectively kills established senescent cells but is insufficient to kill a non-senescent cell in a clinically significant or biologically significant manner. In certain embodiments, the senolytic agents described herein alter at least one signaling pathway in a manner that induces (i.e., initiates, stimulates, triggers, activates, promotes) and results in death of the senescent cell.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202205 in *Polymorphism in Pharmaceutical Solids*, (Brittain, H. ed.), Marcel Dekker, Inc., New York, N.Y., 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (http://www.holodiag.com).

"Substituted" as used herein, when used to modify a specified group or radical, means that one or more hydrogen atoms of the specified group or radical are each, independently of one another, replaced with the same or different substituent(s).

Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$,
trihalomethyl, —$CF_3$, —CN, —OCN, —SCN, —NO, —$NO_2$, —N—$OR^b$, —N—$NR^cR^c$, —$NR^bS(O)_2R^b$, =$N_2$, —$N_3$, —$S(O)_2R^b$, —$S(O)_2NR^bR^b$, —$S(O)_2O^-$, —$S(O)_2OR^b$, —$OS(O)_2R^b$, —$OS(O)_2O^-$, —$OS(O)_2OR^b$, —$OS(O)_2NR^cNR^c$, \—$P(O)(O^-)_2$, —$P(O)(OR^b)(O^-)$, —$P(O)(OR^b)(OR^b)$, —$C(O)R^b$, —$C(O)NR^b$—$OR^b$—$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S) R^b$, —$OC(O)O^-$, —$OC(O)OR^b$, —$OC(O)NR^cR^c$, —$OC(NCN)NR^cR^c$, —$OC(S)OR^b$, —$NR^bC(O)R^b$, —$NR^bC(S)R^b$, —$NR^bC(O)O^-$, —$NR^bC(O)OR^b$, —$NR^bC(NCN)OR^b$, —$NR^bS(O)_2NR^cR^c$, —$NR^bC(S)OR^b$, —$NR^bC(O)NR^cR^c$, —$NR^bC(S)NR^cR^c$, —$NR^bC(S)NR^bC(O)R^a$, —$NR^bS(O)_2OR^b$, —$NR^bS(O)_2R^b$, —$NR^bC(NCN)NR^cR^c$, —$NR^bC(NR^b)R^b$ and —$NR^bC(NR^b)NR^cR^c$,
where $R^a$ is independently alkyl, heteroalkyl, aryl, arylalkyl, heteroaryl and heteroarylalkyl; each $R^b$ is independently hydrogen, $R^a$, substituted alkyl, substituted heteroalkyl, substituted aryl, substituted arylalkyl, substituted heteroaryl and substituted heteroarylalkyl; and each $R^c$ is independently $R^b$ or alternatively, the two $R^c$s are taken together with the nitrogen atom to which they are bonded form a 4-, 5-, 6- or 7-membered cycloheteroalkyl, substituted cycloheteroalkyl or a cycloheteroalkyl fused with an aryl group which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$,
trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$OC(O)NR^cR^c$, —$OS(O)_2NR^cNR^c$, —$NR^bC(O)R^b$, —$NR^bC(S)R^b$, —$NR^bC(O)O^-$, —$NR^bC(O)OR^b$, —$NR^bS(O)_2OR^a$, —$NR^bS(O)_2R^a$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined. Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$,
trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined. Substituent groups from the above lists useful for substituting other specified groups or atoms will be apparent to those of skill in the art. In some embodiments, the substituents used to substitute a specified group can be further substituted, typically with one or more of the same or different groups selected from the various groups specified above.

"Treating" or "treatment" of any disease or disorder as used herein, refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter), or both. In still other embodiments, "treating" or "treatment" refers to delaying the onset of the disease or disorder.

"Therapeutically effective amount" as used herein, refers to the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to particular embodiments of compounds and methods. The disclosed embodiments are not intended to be limiting of the claims.

To the contrary, is the claims are intended to cover all alternatives, modifications and equivalents

DETAILED DESCRIPTION

Senolytic Agents

Hydroxamic acid derivative HDAC inhibitors that have been approved for the clinical treatment of hematologic cancers (such as T-cell lymphomas, leukemias and multiple myeloma) include vorinostat (suberoylanilide hydroxamic acid or SAHA (1)), belinostat (2) and panobinostat (3). A number of other hydroxamic acid derivative HDAC inhibitors (e.g., compounds (4)-(13)) have been under clinical investigation for treatment of both hematologic and solid tumors, either as single agents or in combination therapies with other oncolytic compounds. In addition to variously inhibiting enzymes within HDAC Classes I, II and IV, hydroxamic acid derivatives have been designed to concurrently inhibit other therapeutic targets, e.g., CUDC-101 (12) (which potently inhibits the EGFR and HER-2 kinases) and CUDC-907 (13) (which additionally inhibits various PBK isoforms). Many other hydroxamic acid derivative HDAC inhibitors have been disclosed, including the natural product trichostatin A (14) isolated from *Streptomyces* and numerous synthetically derived compounds, exemplars of which include compounds (15)-(21) as well as others disclosed in Roche and Bertrand, supra; or any of the hydroxamic acids disclosed in U.S. Pat. Nos. 5,369,108, 5,932,616, 6,087,367 and 6,511,990.

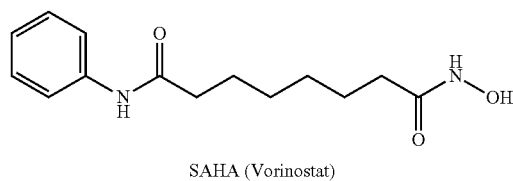

SAHA (Vorinostat) (1)

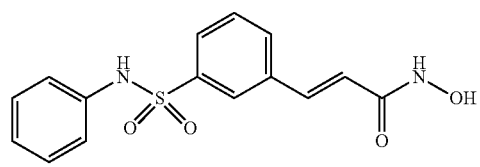

Belinostat (Beleodaq) (2)

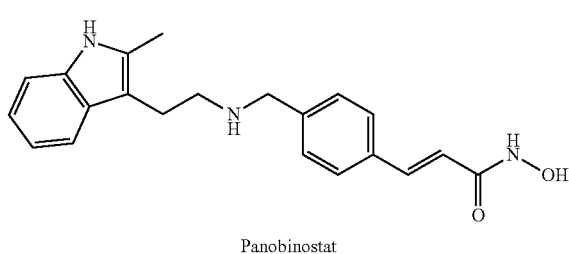

Panobinostat (3)

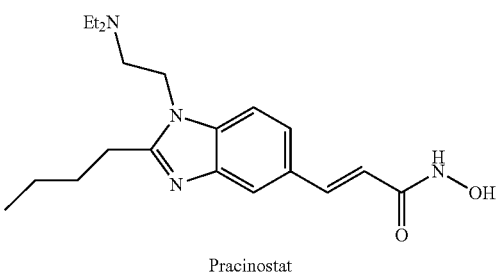

Pracinostat (4)

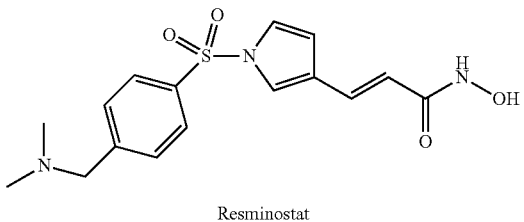

Resminostat (5)

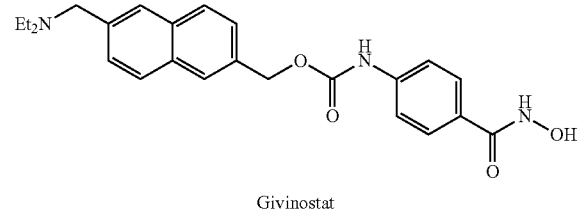

Givinostat (6)

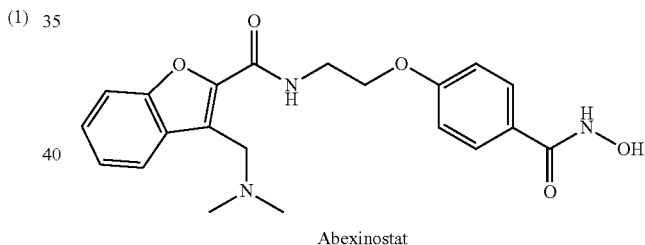

Abexinostat (7)

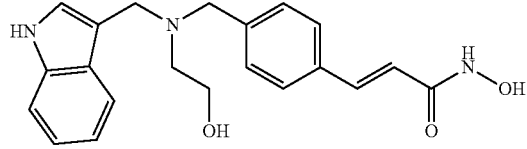

Dacinostat (LAQ824) (8)

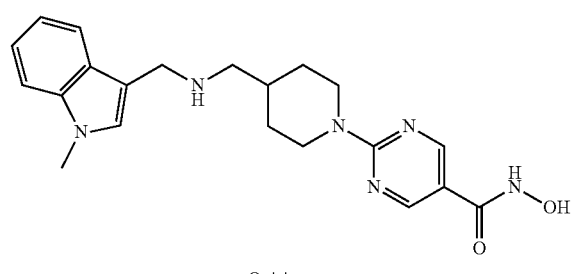

Quisinostat (9)

(10) Ricolinostat

(11) AR-42

(12) CUDC-101

(13) CUDC-907

(14) Trichostatin A (TSA)

(15) Pyroxamide

(16) APHA (17)

(18)

(19)

(20)

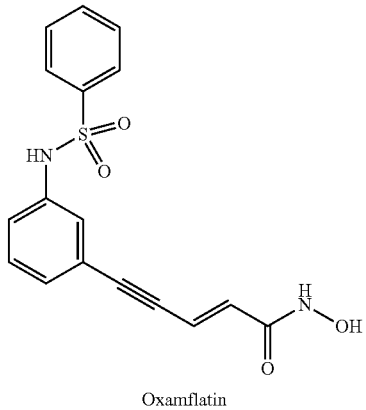

Oxamflatin

Senolytic activity has previously been reported for the pan-HDAC inhibitor panobinostat (3) (Samaraweera et al., supra) and senescence has been shown to be associated with decreased global histone acetylation (Li et al., Proteomics 13 (2013) 2585-2596). Several reports have documented HDAC inhibitor-mediated reduction of Bcl-xL expression (e.g., see Cao et al., Am. J. Respir. Cell Mol. Biol. 25 (2001) 562-568; Rada-Iglesias et al., Genome Res. 17 (2007) 708-719; and Frys et al., Br. J. Haematol. 169 (2015) 506-519). Without wishing to be bound by any theory, it is possible that one pharmacologic basis for the senolytic activity of HDAC inhibitors is mediated through a reduction in anti-apoptotic Bcl-xL protein levels.

In some embodiments, compounds effective as senolytic agents are compounds of formula (IV) or (V):

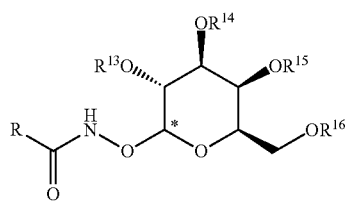

(IV)

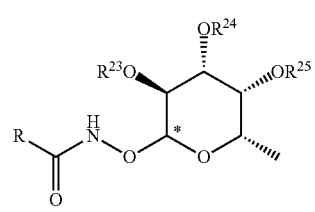

(V)

wherein: R is a residue of a hydroxamic acid derivative histone deacetylase inhibitor; each $R^{13}$, $R^{14}$, $R^{15}$, $R^{16}$, $R^{23}$, $R^{24}$ and $R^{25}$ are independently hydrogen, —C(O)—$R^1$, a moiety of formula (VI) or a moiety of formula (VII):

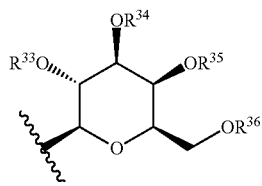

(VI)

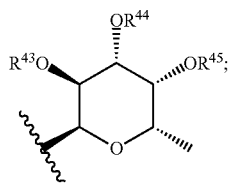

(VII)

each $R^{33}$, $R^{34}$, $R^{35}$, $R^{36}$, $R^{43}$, $R^{44}$ and $R^{45}$ are independently hydrogen or —C(O)—$R^2$; each $R^1$ is independently $C_{1-4}$ alkyl or phenyl, with the proviso that if one of $R^{13}$, $R^{14}$, $R^{15}$ or $R^{16}$ is a moiety of formula (VI) or formula (VII) then the remainder of $R^{13}$, $R^{14}$, $R^{15}$ and $R^{16}$ are hydrogen or C(O)—$R^1$; and each $R^2$ is independently hydrogen, $C_{1-4}$ alkyl or phenyl, with the proviso that if one of $R^{23}$, $R^{24}$ or $R^{25}$ is a moiety of formula (VI) or formula (VII) then the remainder of $R^{23}$, $R^{24}$ or $R^{25}$ is hydrogen or —C(O)—$R^1$; provided that when each of $R^{13}$, $R^{14}$, $R^{15}$ and $R^{16}$ is hydrogen, R is not 7-heptanoyl phenylamide.

In some embodiments of compounds of formulae (IV) or (V), the anomeric carbon of the pyranose ring (labelled *) is of the S configuration and the compounds are respectively β-D-galactoside and α-L-fucoside conjugates of hydroxamic acid derivative histone deacetylase inhibitors.

In some embodiments of compounds of formulae (IV) or (V), R is a residue of a hydroxamic acid derivative histone deacetylase inhibitor wherein the histone deacetylase inhibitor is selected from the group consisting of panobinostat, quisinostat, vorinostat, dacinostat, givinostat, CUDC-907, CUDC-101, abexinostat, belinostat, pracinostat, resminostat, ricolinostat, pyroxamide, APHA, trichostatin A, oxamflatin and AR-42.

In some embodiments of compounds of formula (IV), each of $R^{13}$, $R^{14}$, $R^{15}$ and $R^{16}$ are hydrogen. In some embodiments of compounds of formula (V), each of $R^{23}$, $R^{24}$ and $R^{25}$ are hydrogen.

In other embodiments of compounds of formula (IV), each of $R^{13}$, $R^{14}$, $R^{15}$ and $R^{16}$ are independently —C(O)—$R^1$, wherein $R^1$ is $C_{1-4}$ alkyl or phenyl. In other embodiments of compounds of formula (V), each of $R^{23}$, $R^{24}$ and $R^{25}$ are independently —C(O)—$R^1$, wherein $R^1$ is $C_{1-4}$ alkyl or phenyl.

In yet other embodiments of compounds of formula (IV), each of $R^{13}$, $R^{14}$, $R^{15}$ and $R^{16}$ are independently —C(O)—$R^1$, wherein $R^1$ is methyl. In yet other embodiments of compounds of formula (V), each of $R^{23}$, $R^{24}$ and $R^{25}$ are —C(O)—$R^1$, wherein $R^1$ is methyl.

In yet other embodiments of compounds of formula (IV), each of $R^{13}$, $R^{14}$, $R^{15}$ and $R^{16}$ are independently —C(O)—$R^1$, wherein $R^1$ is ethyl. In yet other embodiments of compounds of formula (V), each of $R^{23}$, $R^{24}$ and $R^{25}$ are —C(O)—$R^1$, wherein $R^1$ is ethyl.

In further embodiments, compounds of formula (IV) are compounds having any of the structures:

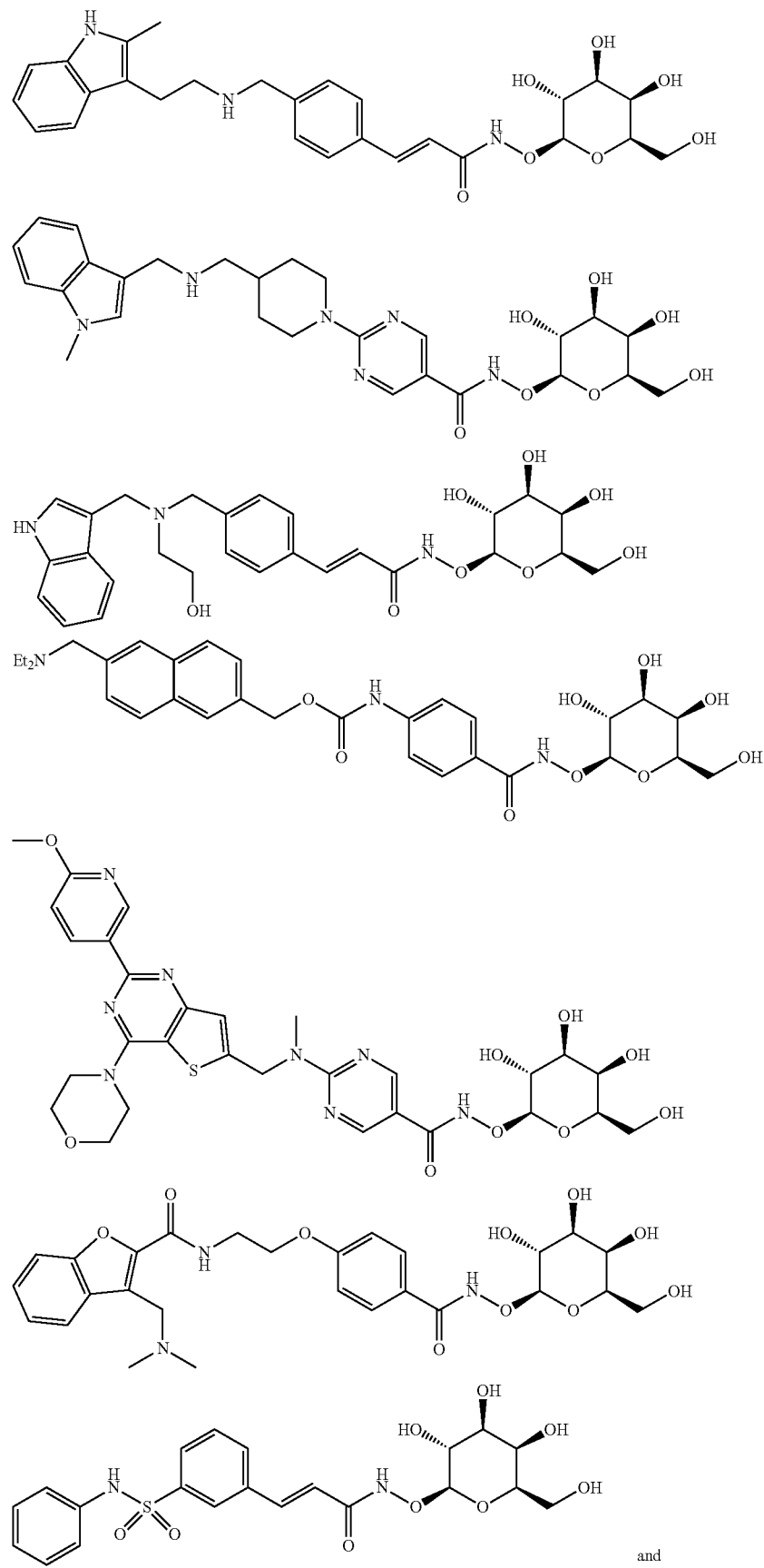

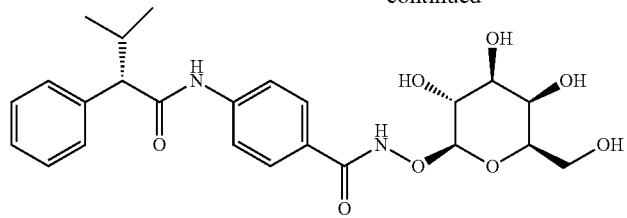
In further embodiments, compounds of formula (V) are compounds having any of the structures:
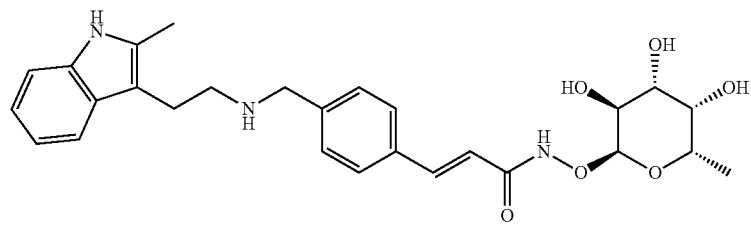
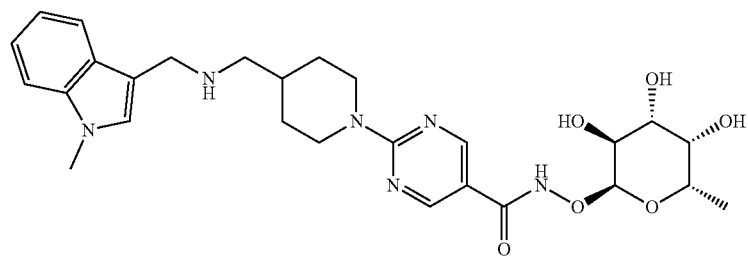
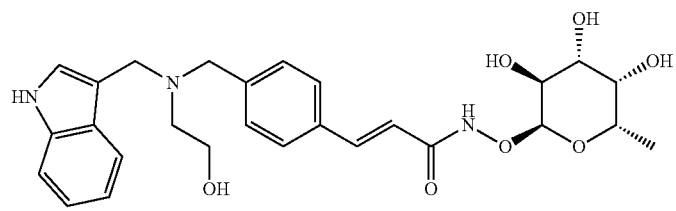
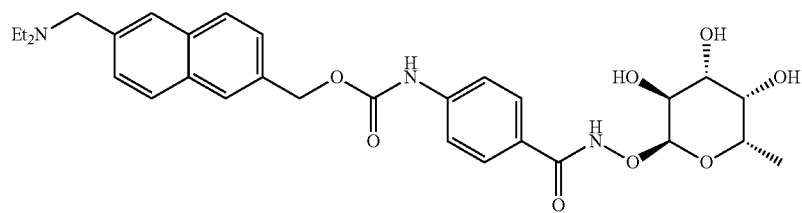
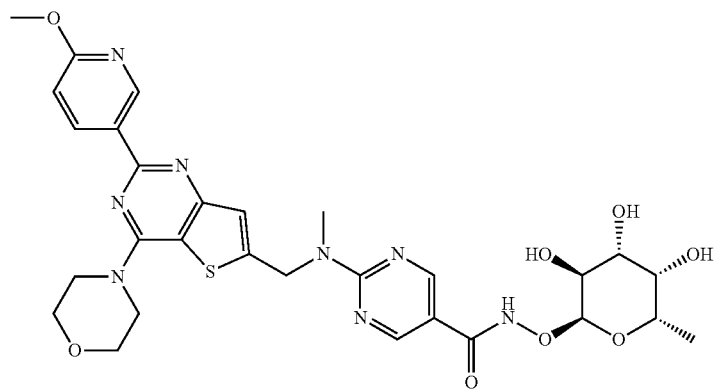

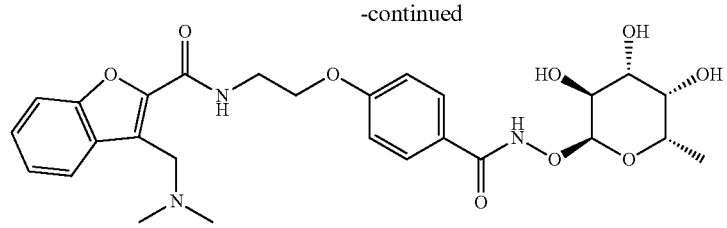
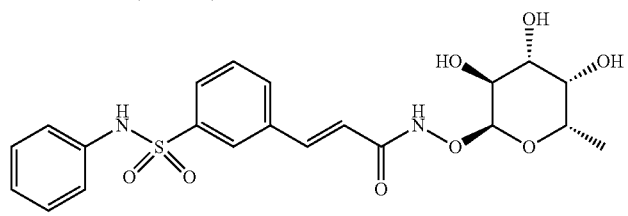
and
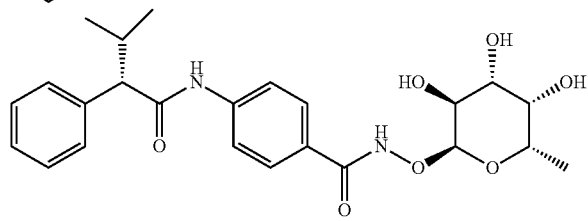
In yet further embodiments, compounds of formula (IV) are compounds having any of the structures:
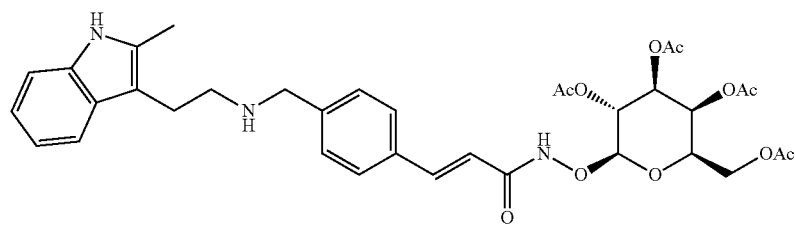
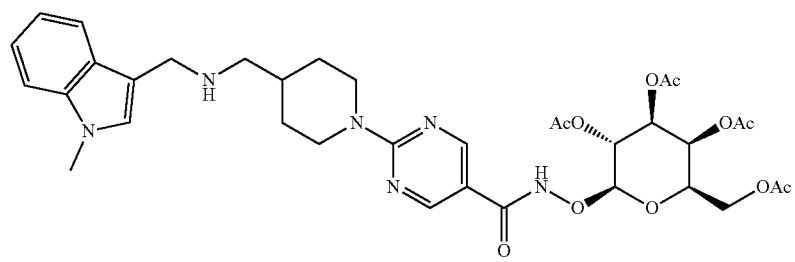
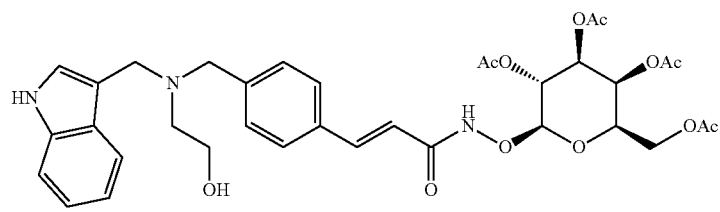
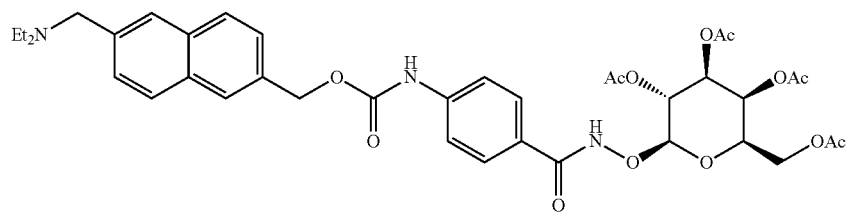

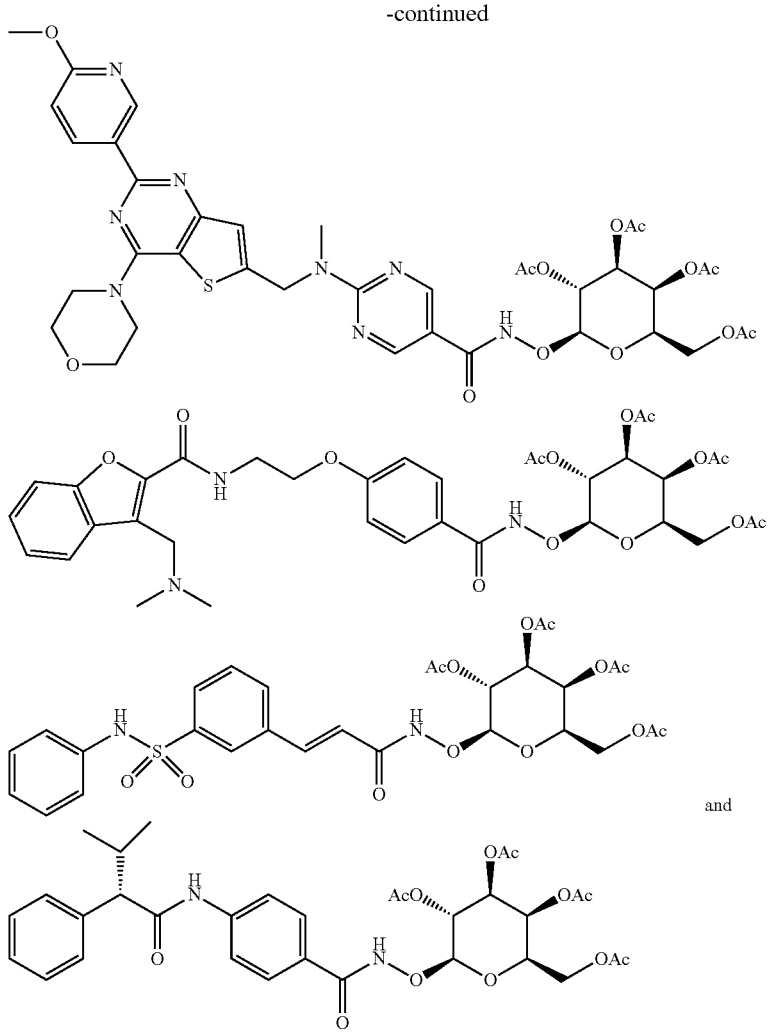
In yet further embodiments, compounds of formula (V) are compounds having any of the structures:
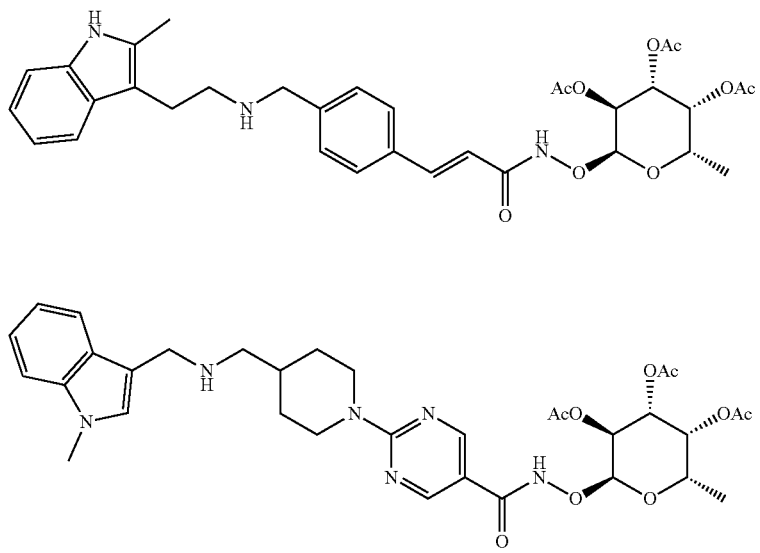

-continued
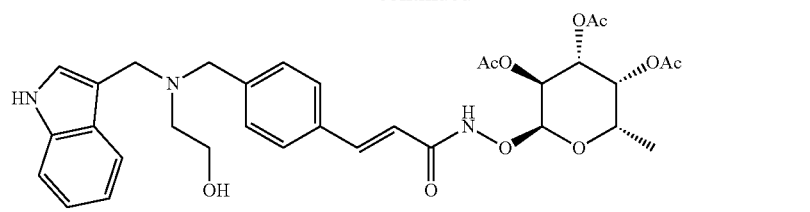
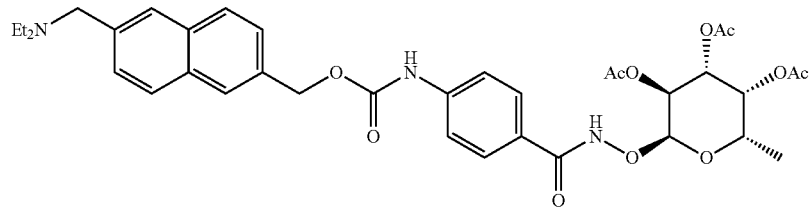
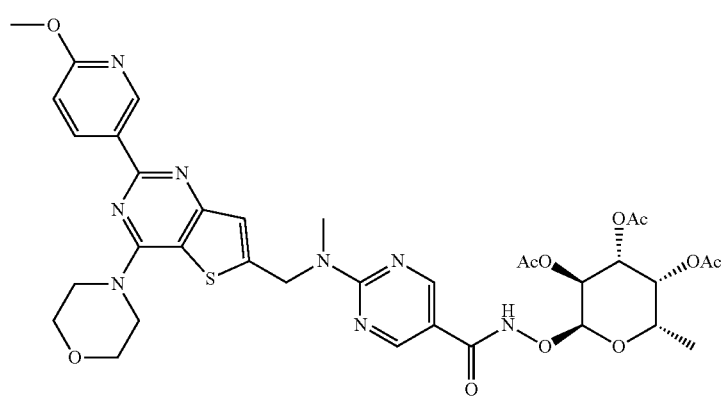
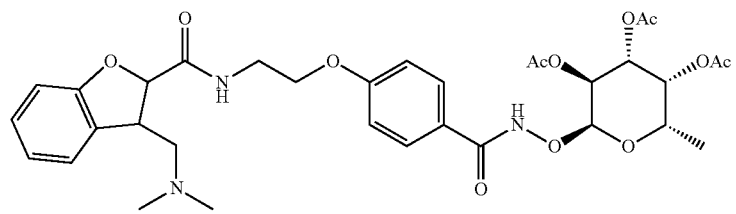
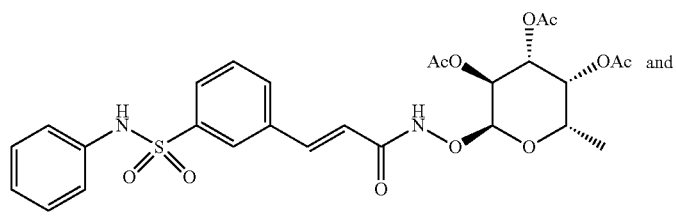
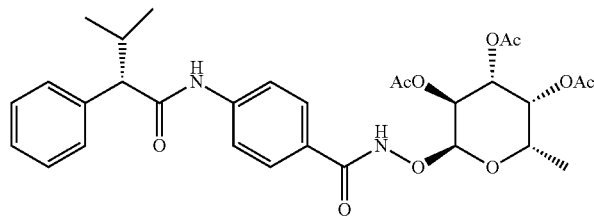

In still further embodiments, compounds of formula (IV) are compounds having any of the structures:
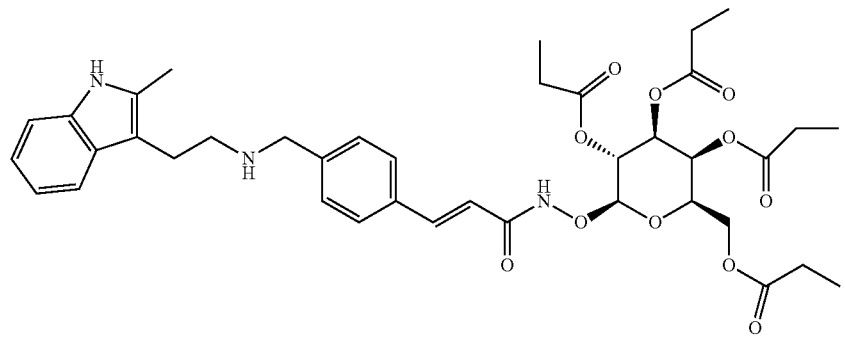
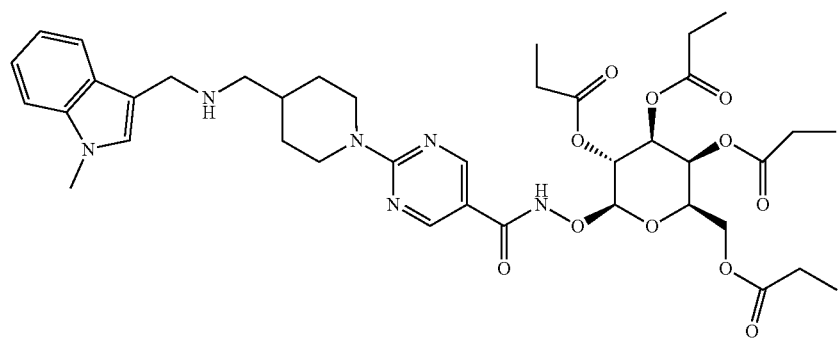
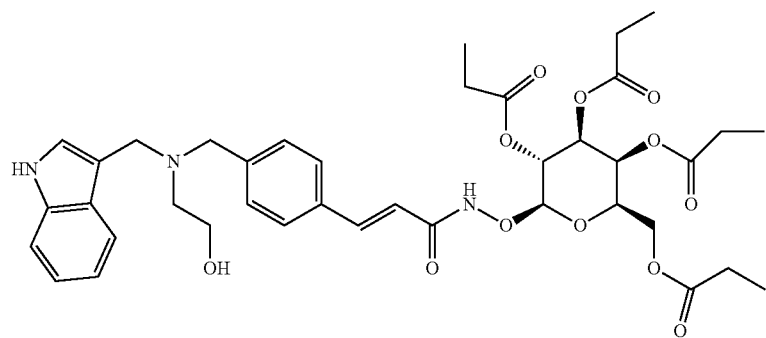
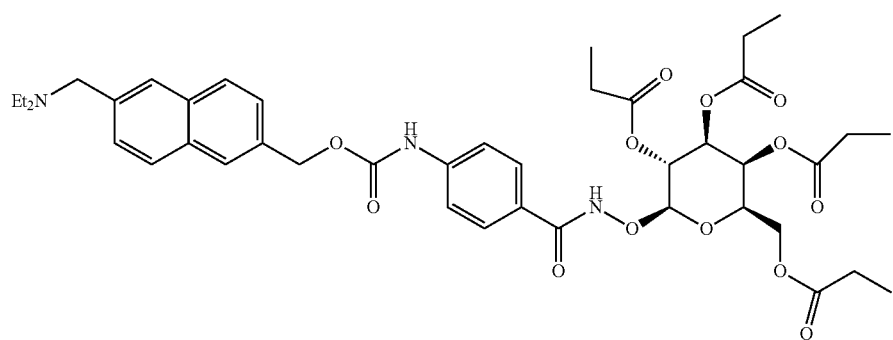

-continued
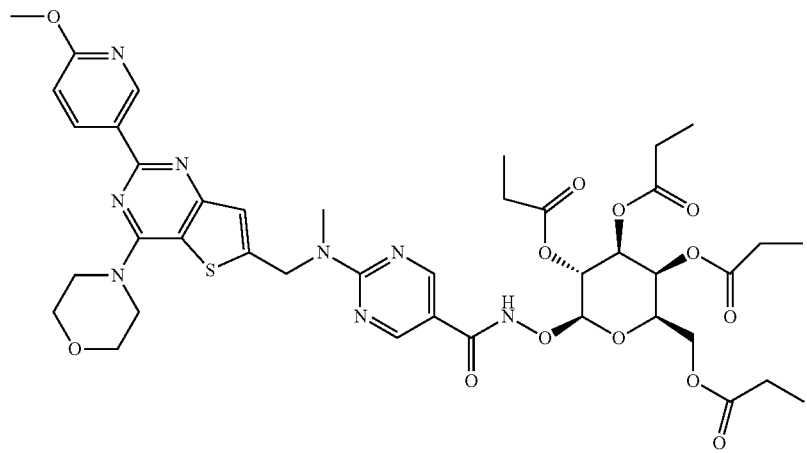
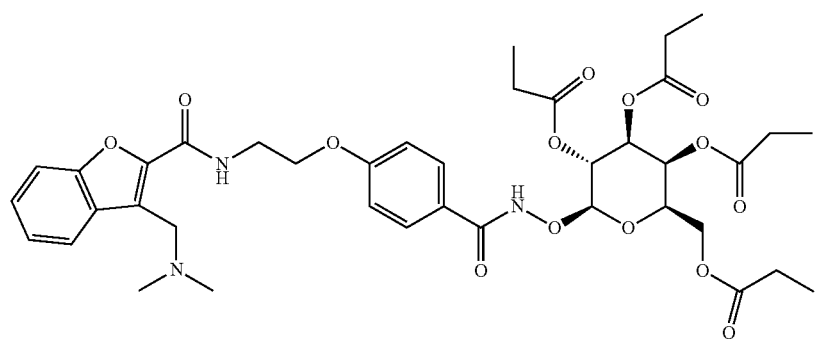
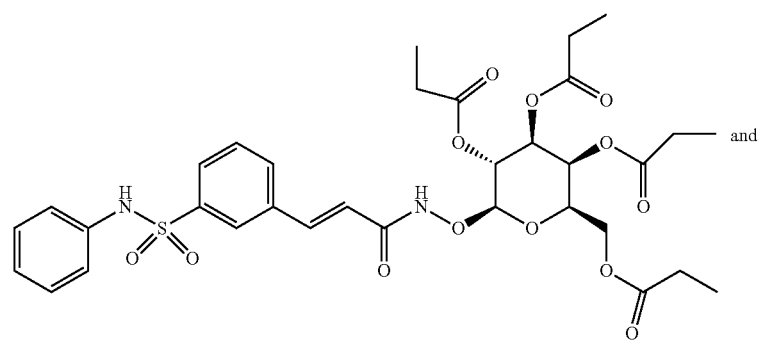
and
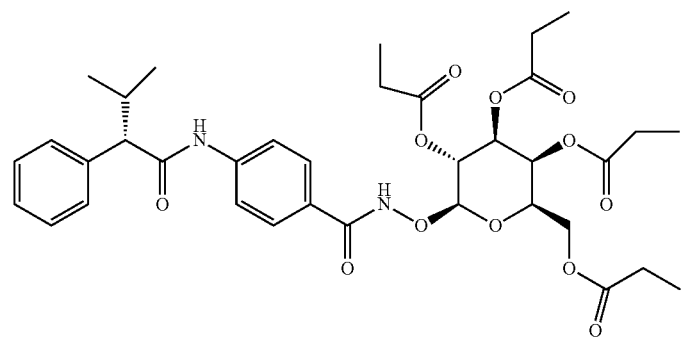

In still further embodiments, compounds of formula (V) are compounds having any of the structures:
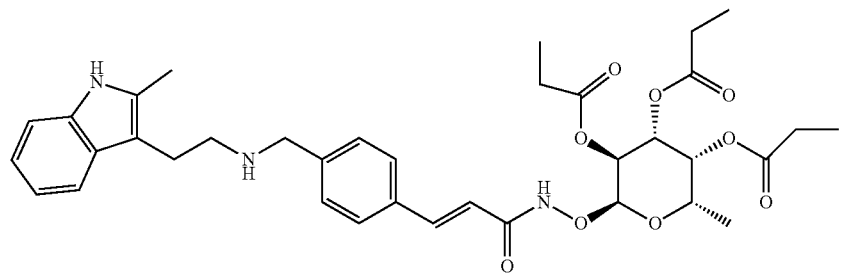
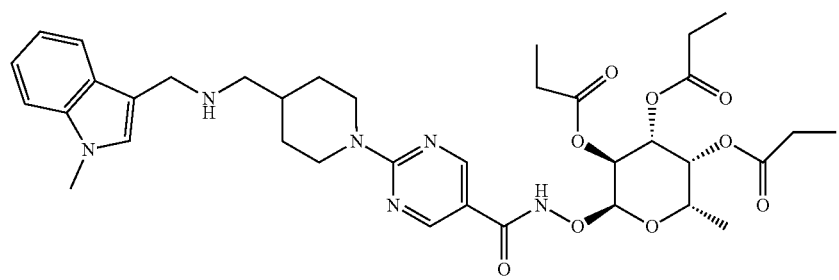
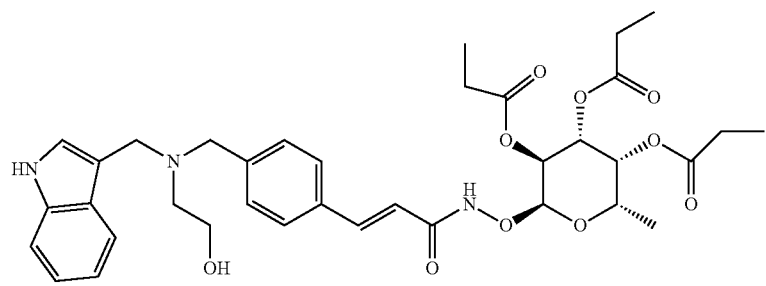
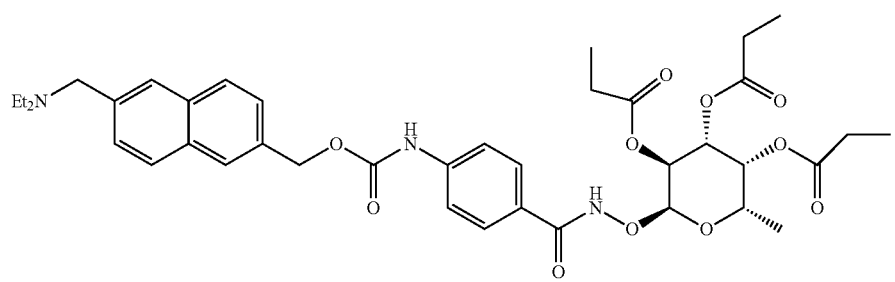
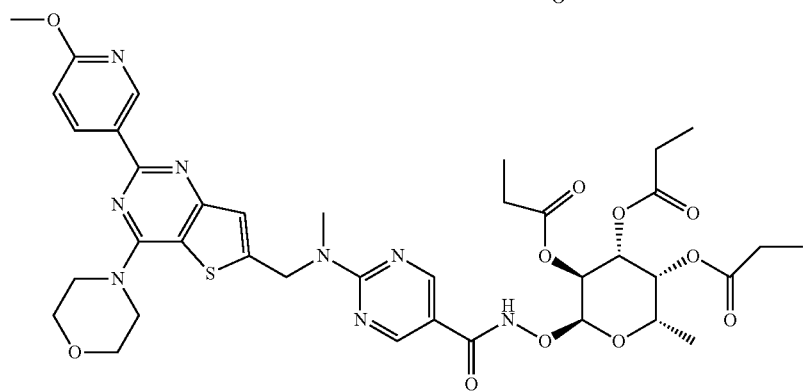

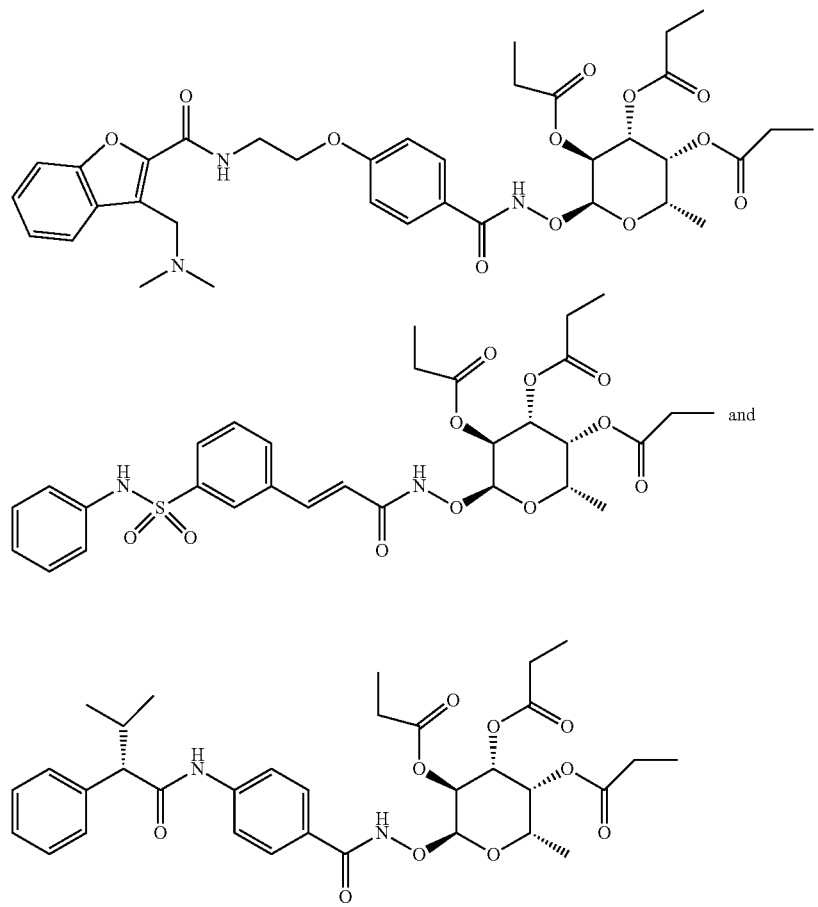

Compounds of formula (IV) or (V) may be synthesized by coupling the carboxylic acid precursor $RCO_2H$ (VIII) of the hydroxamic acid HDAC inhibitor with sugar oxime compounds (IX) and (X) respectively, in the presence of an acyl coupling reagent such as a carbodiimide (e.g., EDC), or alternatively after prior activation as the acyl chloride or a mixed anhydride acylating agent as shown below.

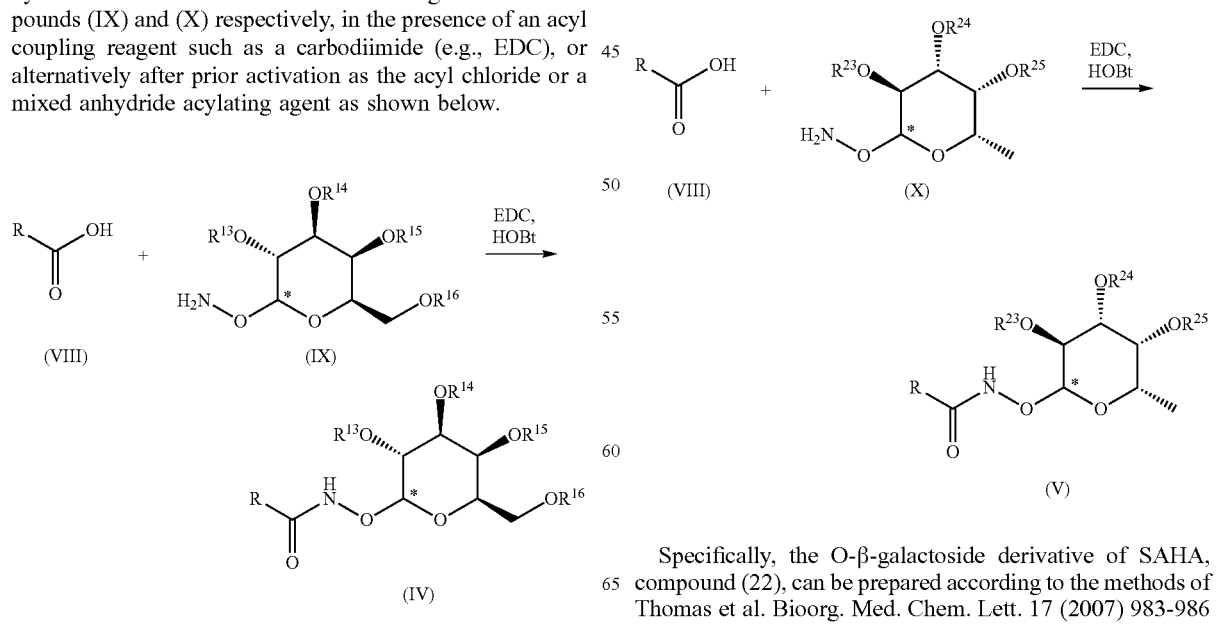

Specifically, the O-β-galactoside derivative of SAHA, compound (22), can be prepared according to the methods of Thomas et al. Bioorg. Med. Chem. Lett. 17 (2007) 983-986 from the known bromogalactoside (23):

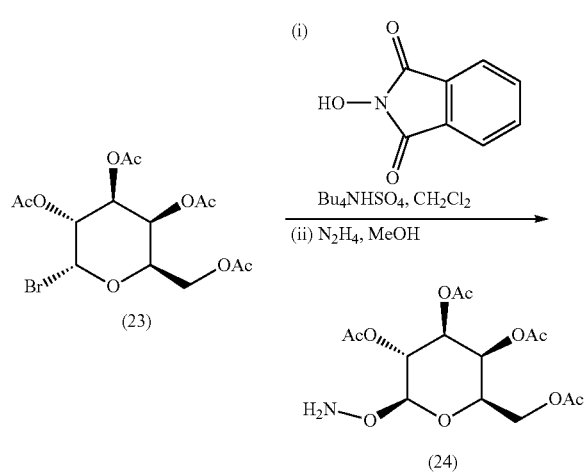

Incubation of compound (22) with β-galactosidase showed quantitative conversion to (1). It is well known that the HDAC inhibitory activity of hydroxamic acid derivative compounds is critically dependent on the zinc-chelating activity of the free hydroxamic acid moiety (e.g., see Roche and Bertrand, supra). Thus, masking the hydroxamic acid functionality as a glycoside derivative in compounds of formula (IV) or (V) ensures that these prodrugs are inactive as HDAC inhibitors, but will become activated upon hydrolysis within the lysosomes of senescent cells.

Similarly, the O-β-galactoside derivative of panobinostat, compound (26), can be elaborated by reductive amination of 4-formyl cinnamic acid (27) with 2-(2-methyl-1H-indol-3-yl)ethylamine (28) (as described in International Application No. WO02/22577) and the basic nitrogen of the resulting amino acid protected, e.g., as a fluorenylmethyloxycarbamate (Fmoc) derivative (29). Coupling with compound (24) as before followed by sequential deprotection affords panobinostat prodrug (26).

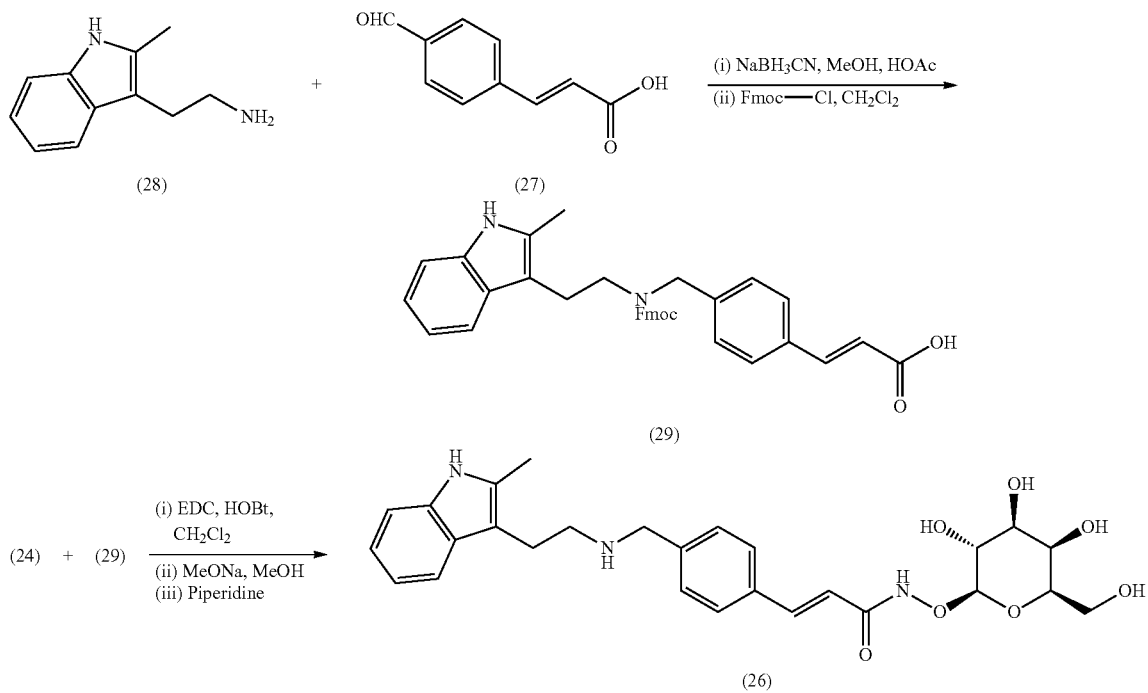

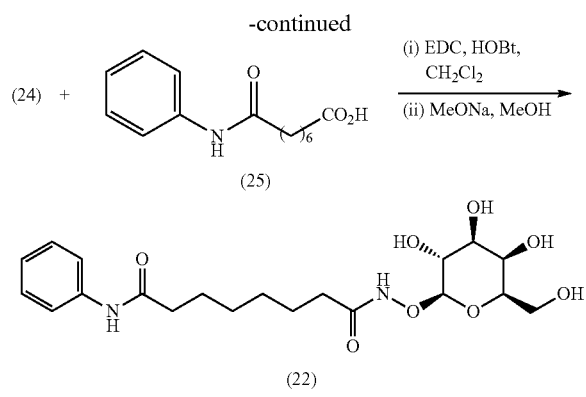

In an alternative route to compound (26), compound (24) is first coupled with (27) (e.g., using EDC, HOBt) and the resulting aldehyde is treated in a reductive amination reaction with tryptamine derivative (28), with sodium methoxide-mediated removal of the acetyl protecting groups affording prodrug (26).

Specific α-L-fucoside conjugates of hydroxamic acid derivative histone deacetylase inhibitors may be prepared in an analogous manner starting with appropriately protected and activated fucose derivatives, prepared as described in Hou et al., Mater. Chem. Front. 1 (2017) 660-667 or United States Application No. 2015/0168374. For example, 1-fluoro-2,3,4-tri-O-acetyl-fucose (30) is treated with N-hydroxyphthalimide to give a mixture of the α and β-L-fucosyl oxime derivatives, with the desired α anomer (31) being the less polar product. Deprotection with hydrazine then affords the α-L-fucosyl oxime (32), which may be further elaborated to the α-L-fucoside prodrugs of SAHA and panobinostat, compounds (33) and (35) respectively:

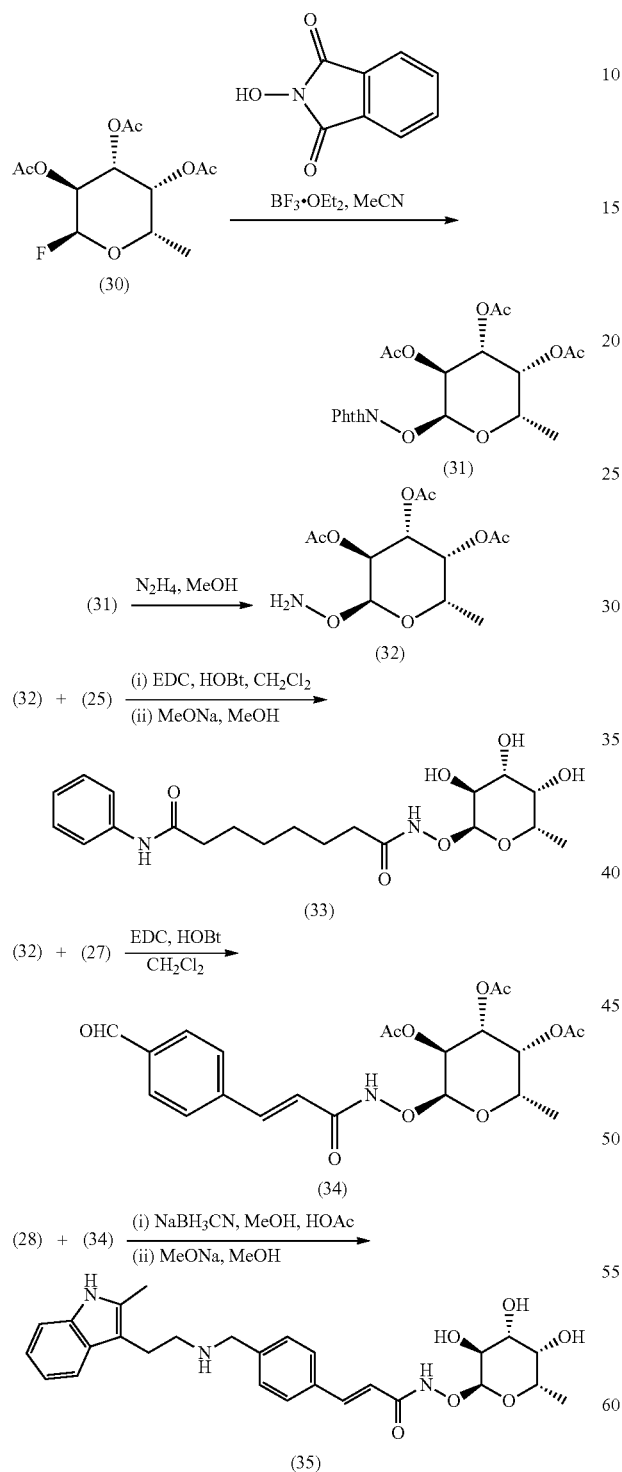

Hsp90 inhibitors are exemplified by resorcinol compounds AT13387 (onalespib, (36), NYP-AUY922 (luminespib, (37)), ganetespib (38), VER-50589 (39), VER-49009 (40), CCT018159 (41) and KW-2478 (42), 2-(4-aminocyclohexanol)-benzamide derivatives exemplified by SNX-2112 (43) and (SNX-7081) (44). In some embodiments, O-galactoside or O-fucoside conjugates of Hsp90 inhibitors are senolytic compounds. In other embodiments, O-β-D-galactoside or O-α-L-fucoside conjugates of Hsp90 inhibitors are senolytic compounds.

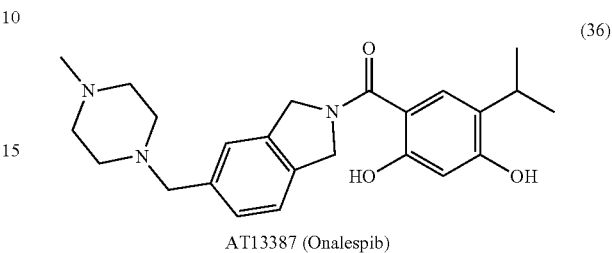

AT13387 (Onalespib)

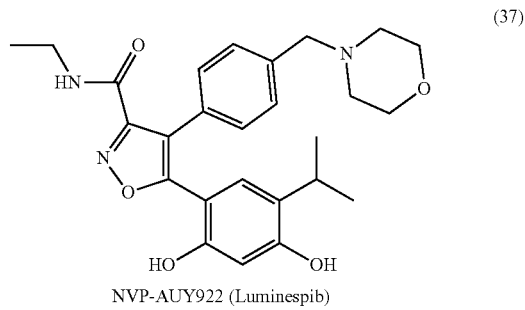

NVP-AUY922 (Luminespib)

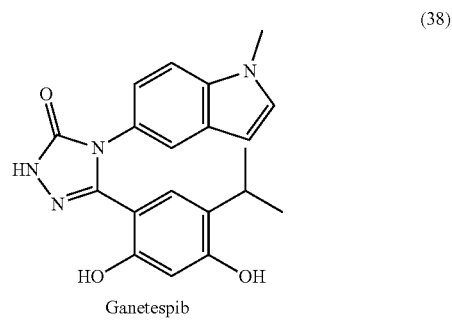

Ganetespib

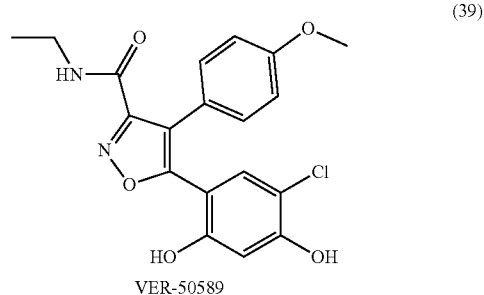

VER-50589

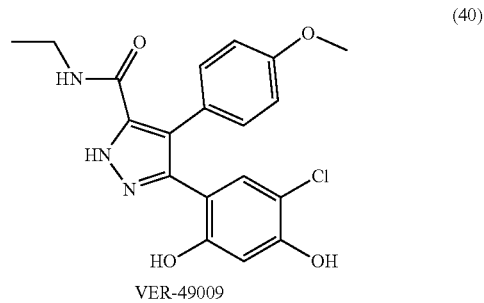

VER-49009

-continued

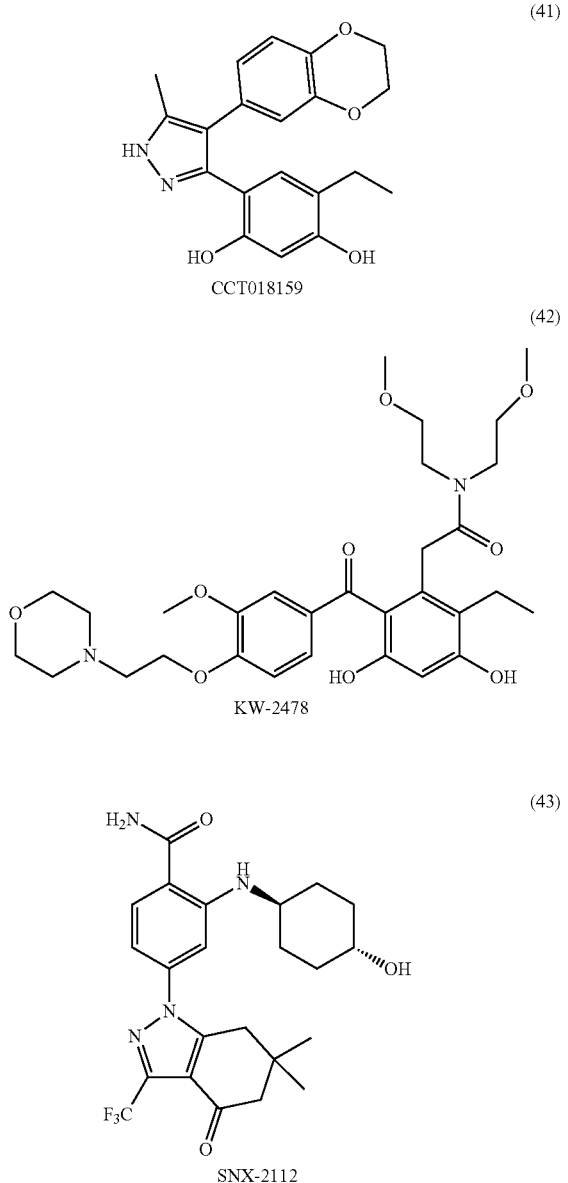

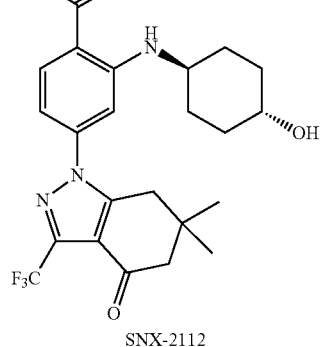

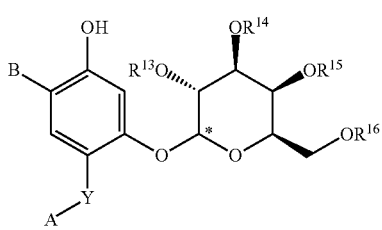

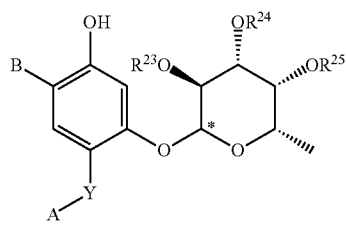

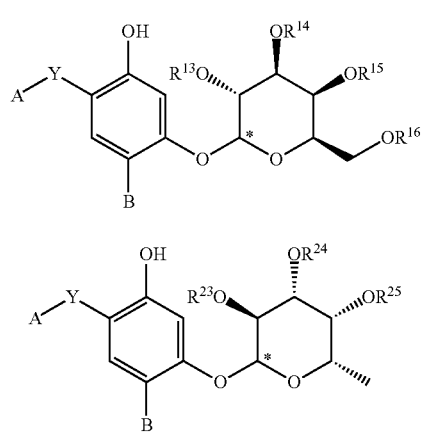

wherein Y is carbonyl or is absent; A is a substituted or benzofused 5-membered heteroaryl or heterocyclic group containing at least one nitrogen atom; B is selected from the group consisting of ethyl, isopropyl or chloro; each $R^{13}$, $R^{14}$, $R^{15}$, $R^{16}$, $R^{23}$, $R^{24}$ and $R^{25}$ are independently hydrogen, C(O)—$R^1$, a moiety of formula (VI) or a moiety of formula (VII);

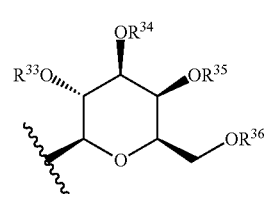

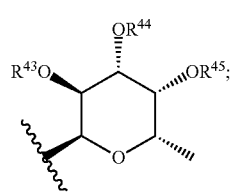

In some embodiments, compounds of formula (XI), (XII), (XIII) or (XIV) are senolytic agents:

each $R^{33}$, $R^{34}$, $R^{35}$, $R^{36}$, $R^{43}$, $R^{44}$ and $R^{45}$ are independently hydrogen or —C(O)—$R^2$; each $R^1$ is independently $C_{1-4}$ alkyl or phenyl, with the proviso that if one of $R^{13}$, $R^{14}$, $R^{15}$ or $R^{16}$ is a moiety of formula (VI) or formula (VII) then the remainder of $R^{13}$, $R^{14}$, $R^{15}$ and $R^{16}$ are hydrogen or C(O)—$R^1$; and each $R^2$ is independently $C_{1-4}$ alkyl or phenyl, with the proviso that if one of $R^{23}$, $R^{24}$ or $R^{25}$ is a moiety of formula (VI) or formula (VII) then the remainder of $R^{23}$, $R^{24}$ or $R^{25}$ is hydrogen or —C(O)—$R^1$.

In some embodiments of compounds of formulae (XI), (XII), (XIII) or (XIV), the anomeric carbon of the pyranose ring (labelled *) is of the S configuration and the compounds are respectively β-D-galactoside and α-L-fucoside conjugates of resorcinol Hsp90 inhibitors.

In some embodiments of compounds of formulae (XI), (XII), (XIII) or (XIV), the moiety A-Y—$C_6H_2(OH)_2$—B is an Hsp90 inhibitor selected from the group consisting of luminespib (NVP-AUY922), ganetespib, VER-50589, AT13387 and KW-2478.

In some embodiments of compounds of formula (XI), each of $R^{13}$, $R^{14}$, $R^{15}$ and $R^{16}$ are hydrogen. In some embodiments of compounds of formula (XII), each of $R^{23}$, $R^{24}$ and $R^{25}$ are hydrogen. In some embodiments of compounds of formula (XIII), each of $R^{13}$, $R^{14}$, $R^{15}$ and $R^{16}$ are hydrogen. In some embodiments of compounds of formula (XIV), each of $R^{23}$, $R^{24}$ and $R^{25}$ are hydrogen.

In some embodiments of compounds of formula (XI), each of $R^{13}$, $R^{14}$, $R^{15}$ and $R^{16}$ are independently —C(O)—$R^1$, wherein $R^1$ is $C_{1-4}$ alkyl or phenyl. In some embodiments of compounds of formula (XII), each of $R^{23}$, $R^{24}$ and $R^{25}$ are independently —C(O)—$R^1$, wherein $R^1$ is $C_{1-4}$ alkyl or phenyl. In some embodiments of compounds of formula (XIII), each of $R^{13}$, $R^{14}$, $R^{15}$ and $R^{16}$ are independently —C(O)—$R^1$, wherein $R^1$ is $C_{1-4}$ alkyl or phenyl. In some embodiments of compounds of formula (XIV), each of $R^{23}$, $R^{24}$ and $R^{25}$ are independently —C(O)—$R^1$, wherein $R^1$ is $C_{1-4}$ alkyl or phenyl.

In some embodiments of compounds of formula (XI), each of $R^{13}$, $R^{14}$, $R^{15}$ and $R^{16}$ are —C(O)—$R^1$, where $R^1$ is methyl. In some embodiments of compounds of formula (XII), each of $R^{23}$, $R^{24}$ and $R^{25}$ are —C(O)—$R^1$, where $R^1$ is methyl. In some embodiments of compounds of formula (XIII), each of $R^{13}$, $R^{14}$, $R^{15}$ and $R^{16}$ are —C(O)—$R^1$, where $R^1$ is methyl. In some embodiments of compounds of formula (XIV), each of $R^{23}$, $R^{24}$ and $R^{25}$ are —C(O)—$R^1$, wherein $R^1$ is methyl.

In some embodiments of compounds of formula (XI), each of $R^{13}$, $R^{14}$, $R^{15}$ and $R^{16}$ are —C(O)—$R^1$, where $R^1$ is ethyl. In some embodiments of compounds of formula (XII), each of $R^{23}$, $R^{24}$ and $R^{25}$ are —C(O)—$R^1$, where $R^1$ is ethyl. In some embodiments of compounds of formula (XIII), each of $R^{13}$, $R^{14}$, $R^{15}$ and $R^{16}$ are —C(O)—$R^1$, where $R^1$ is ethyl. In some embodiments of compounds of formula (XIV), each of $R^{23}$, $R^{24}$ and $R^{25}$ are —C(O)—$R^1$, wherein $R^1$ is ethyl.

In further embodiments, a compound of formula (XI) is a compound having any of the structures:

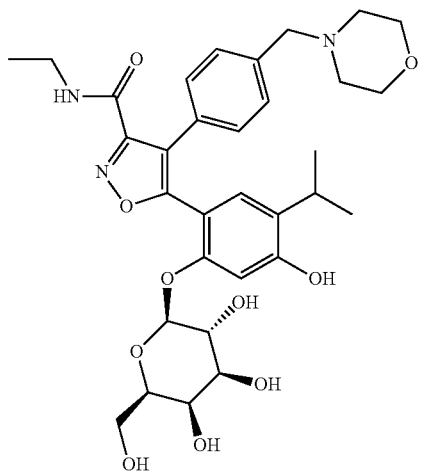

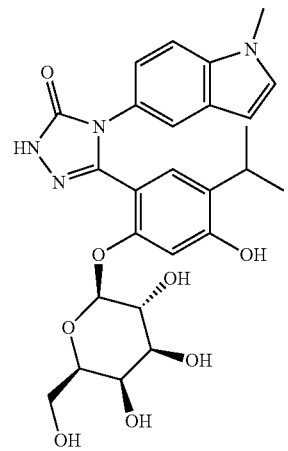

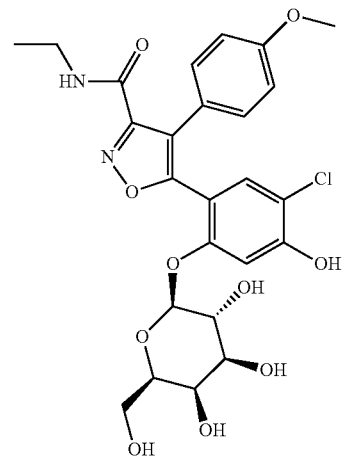

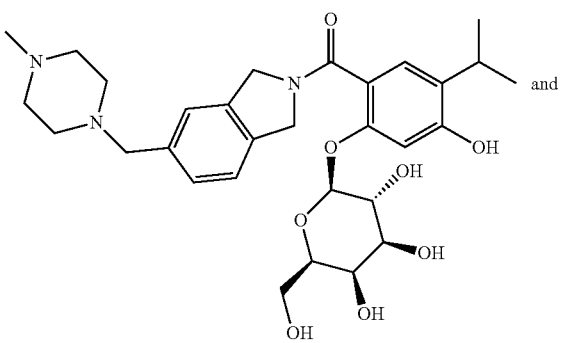

and

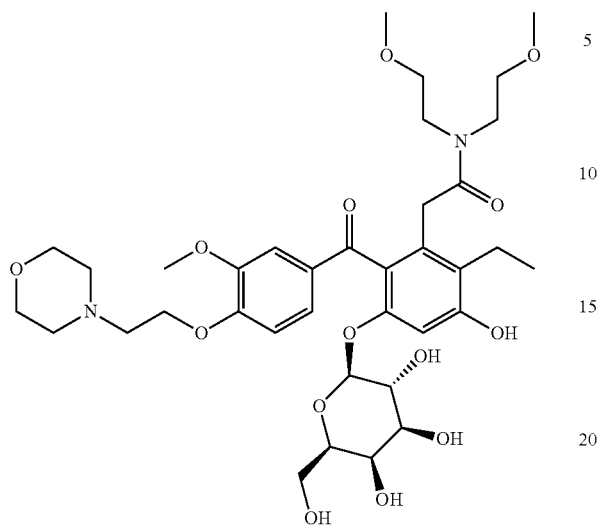
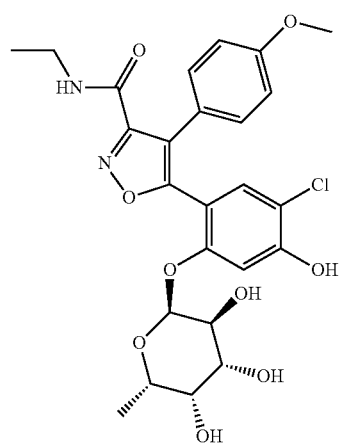
In further embodiments, a compound of formula (XII) is a compound having any of the structures:
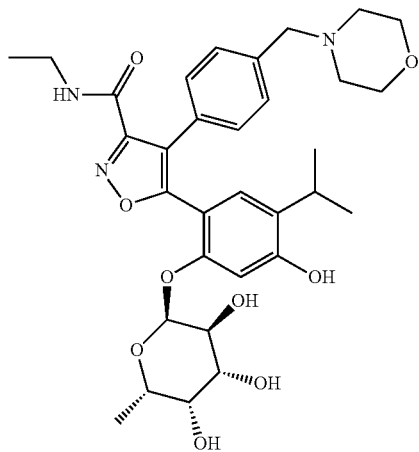
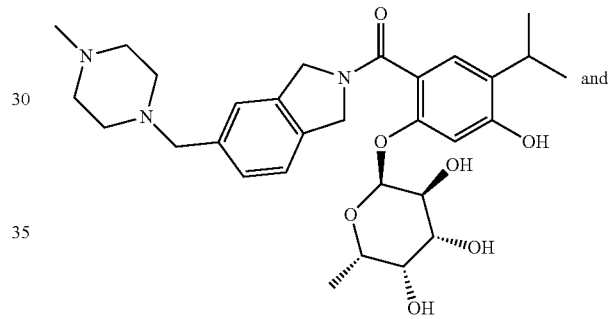
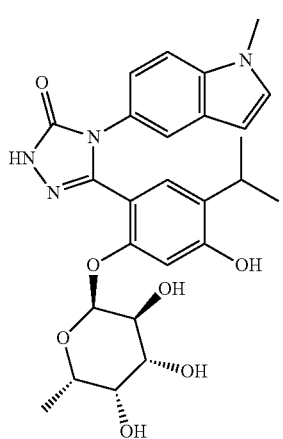
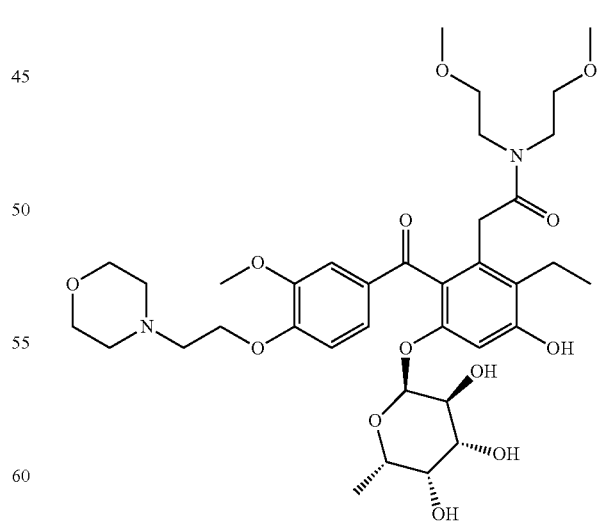
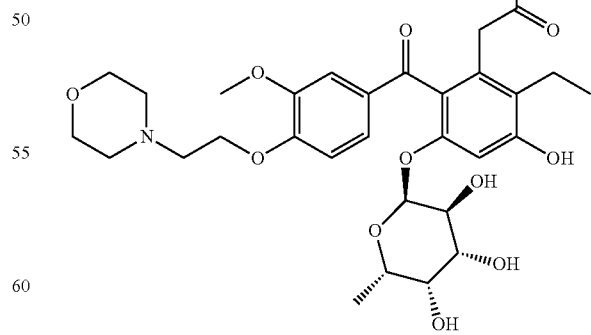
In further embodiments, a compound of formula (XIII) is a compound having any of the structures:

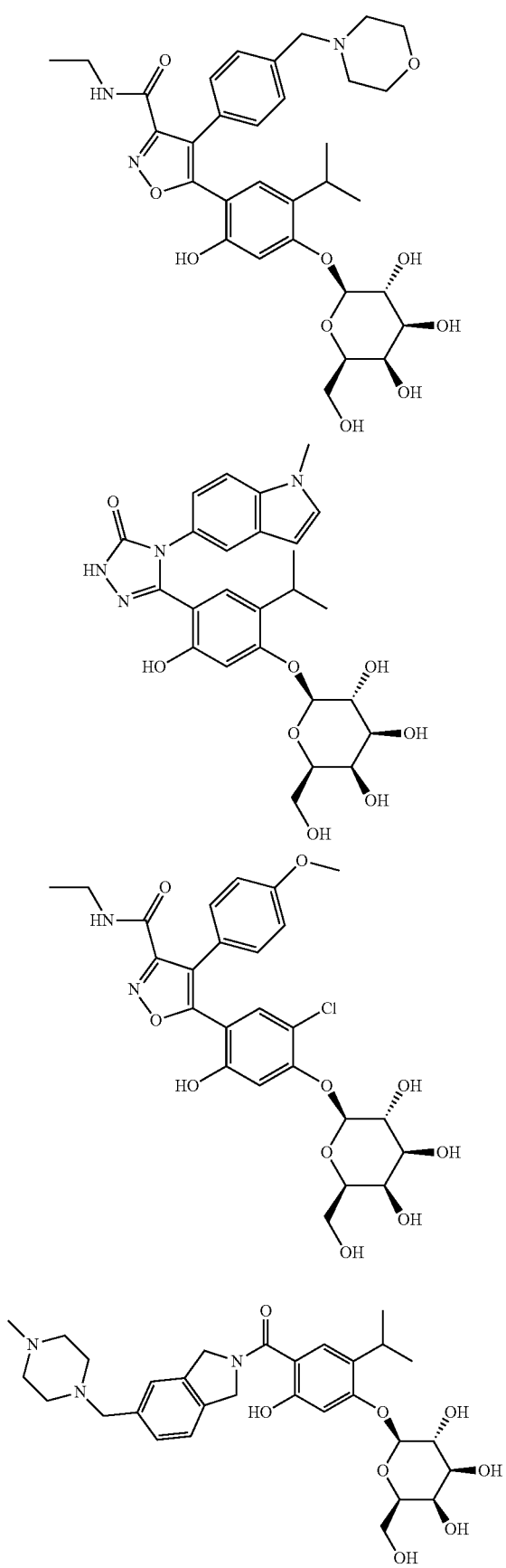
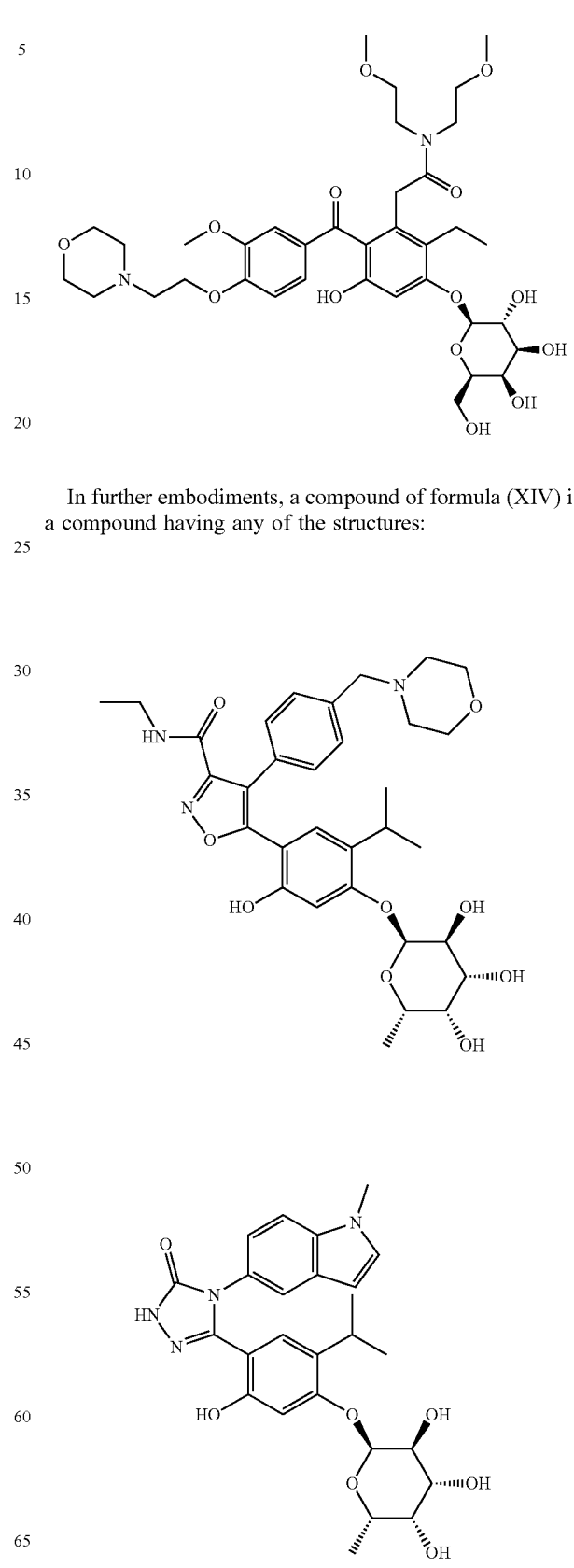
In further embodiments, a compound of formula (XIV) is a compound having any of the structures:

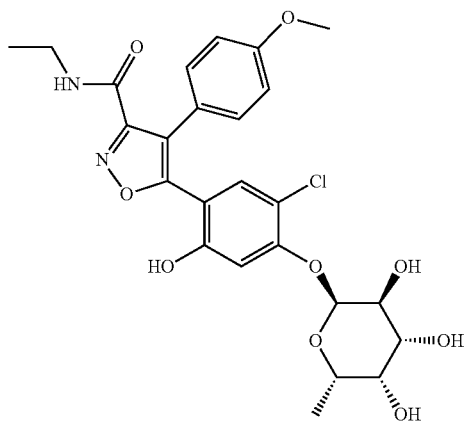

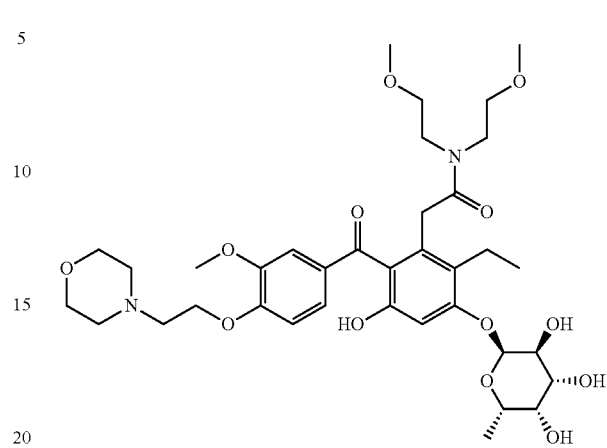

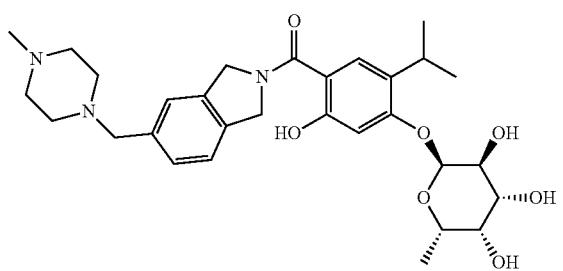

Compounds of formula (XI) and (XIII) can be prepared by reaction of a compound of formula (XV) with a protected D-galactosyl donor moiety under classical $BF_3$-mediated glycosylation or Koenigs-Knorr coupling conditions, with the resulting regioisomers being separated by chromatographic means. Alternatively, the phenolic hydroxyls of resorcinol compound (XV) may first be selectively protected to allow for regioselective glycosylation.

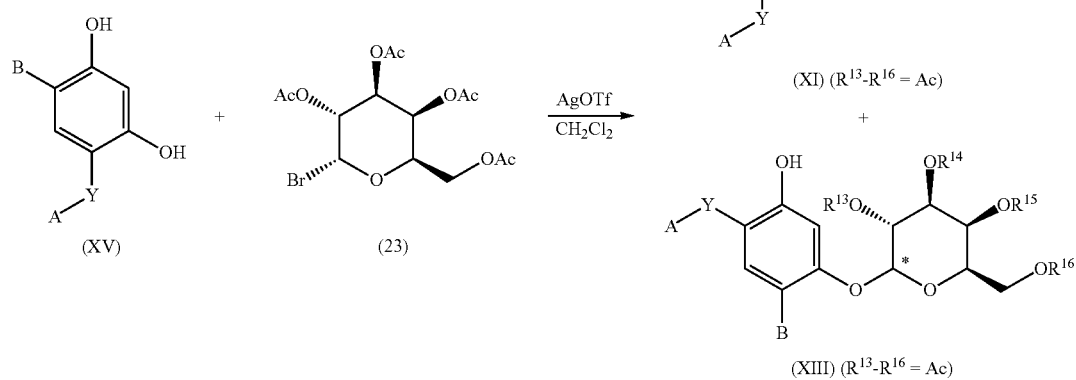

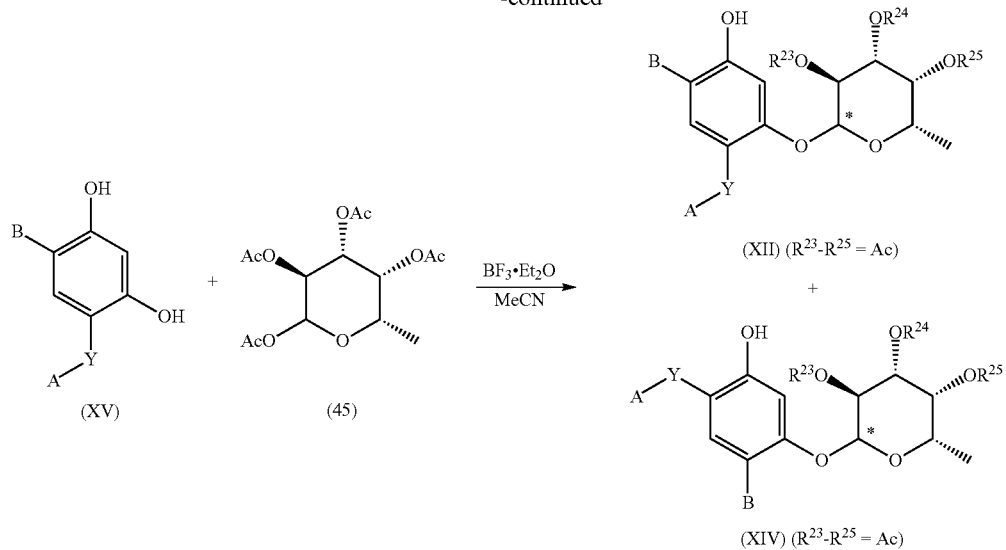
Specifically, the O-β-galactoside conjugates of AT13387 (36) (prepared as described in U.S. Pat. No. 8,779,132), i.e. compounds (46) and (47), may be prepared by reaction of (36) with (23) following the method of Shie et al., Carbohydrate Res. 341 (2006) 443-456.
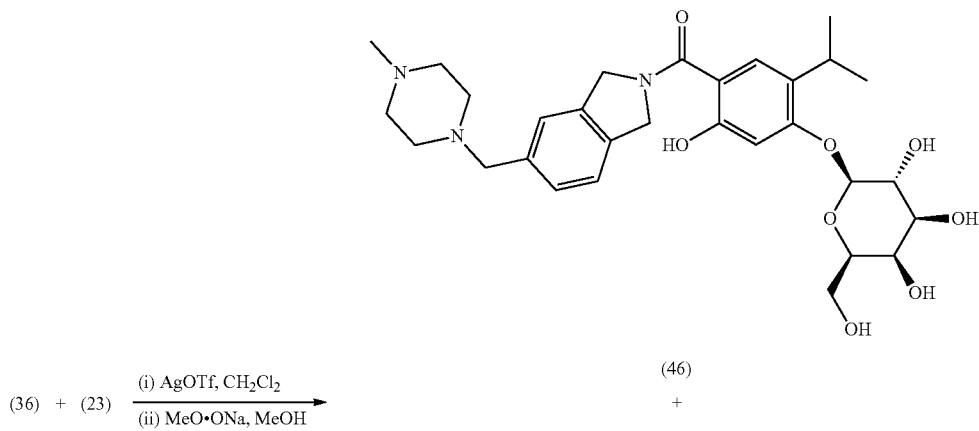
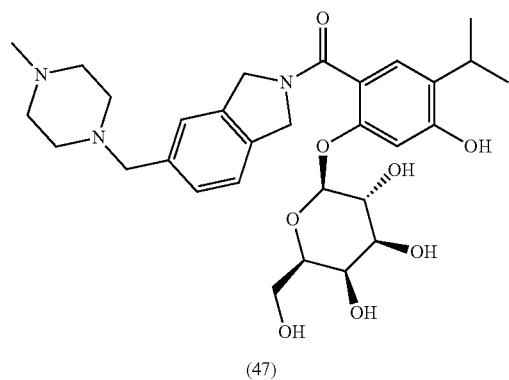

Similarly, the O-β-galactoside conjugates of NVP-AUY922 (37) (prepared as described in Brough et al., J. Med. Chem. 51 (2008) 196-218), i.e. compounds (48) and (49), may be prepared by reaction of (37) with (23):
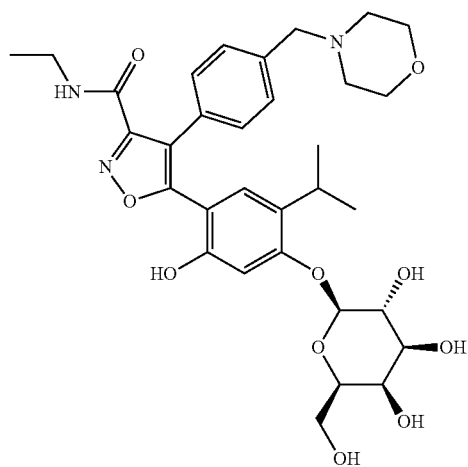
(48)
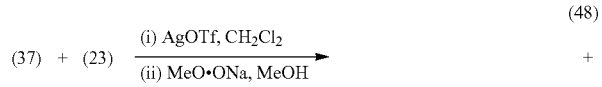
+
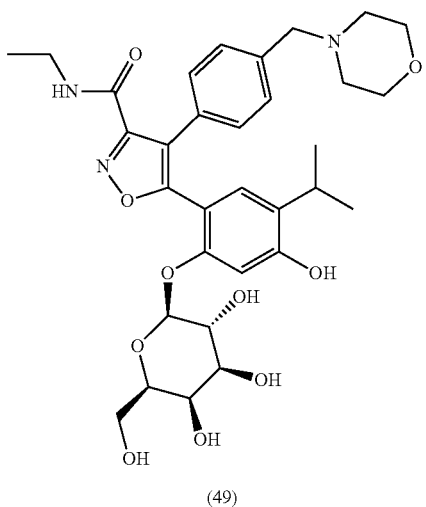
(49)

Compounds (50)-(53), specific α-L-fucoside conjugates of Hsp90 inhibitors (36) and (37), may be prepared in an analogous manner starting from the protected fucose derivatives (45):
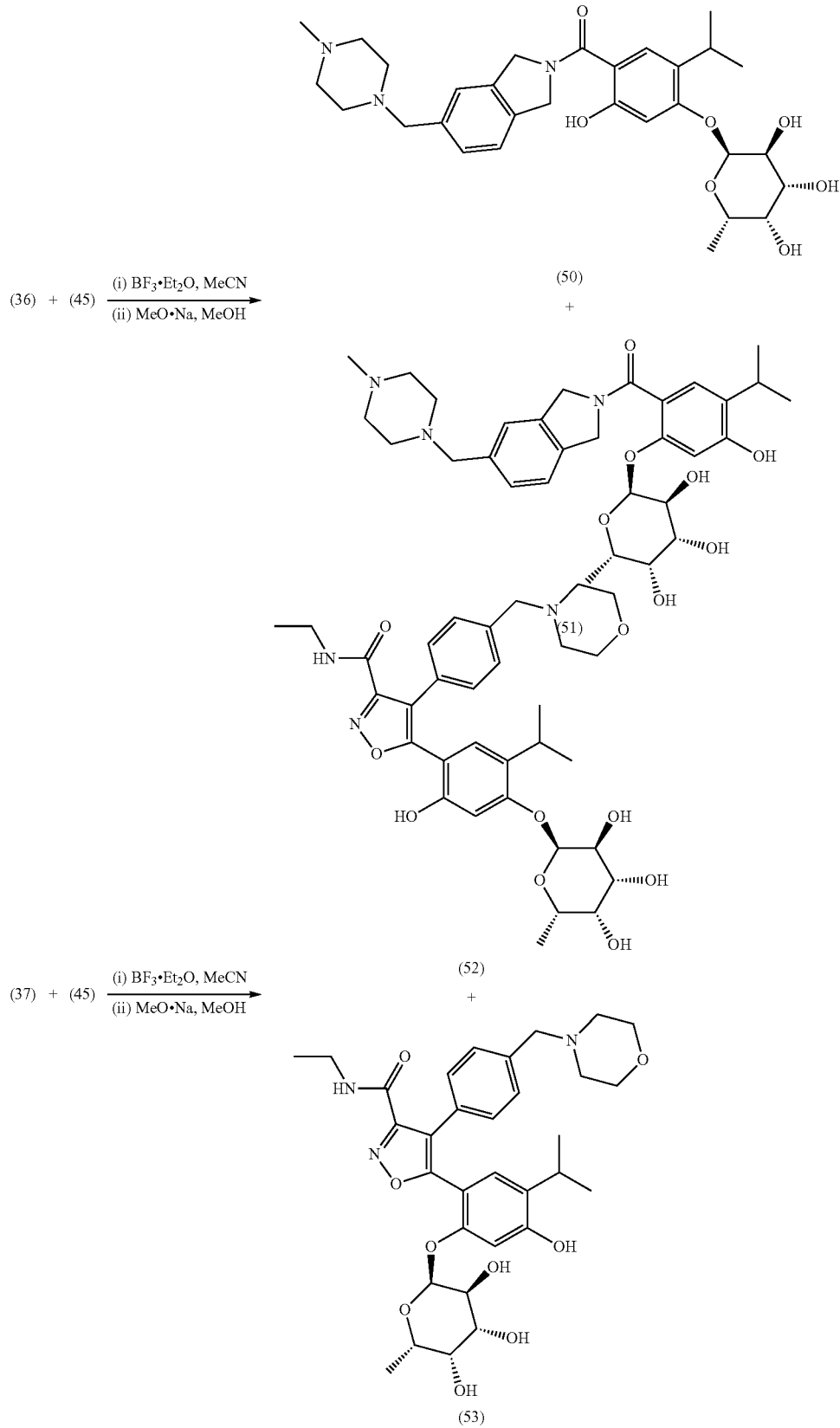

O-β-Galactoside conjugates of KW-2478 (42) (i.e. compounds (54) and (55)), SNX-2112 (43), (i.e. compound (56)) and SNX-7081 (44) (i.e. compound (57)) and the O-α-fucoside conjugates of KW-2478 (42) (i.e. compounds (58) and (59)), SNX-2112 (43), (i.e. compound (60)) and SNX-7081 (44) (i.e. compound (61)) may be prepared in an analogous fashion.
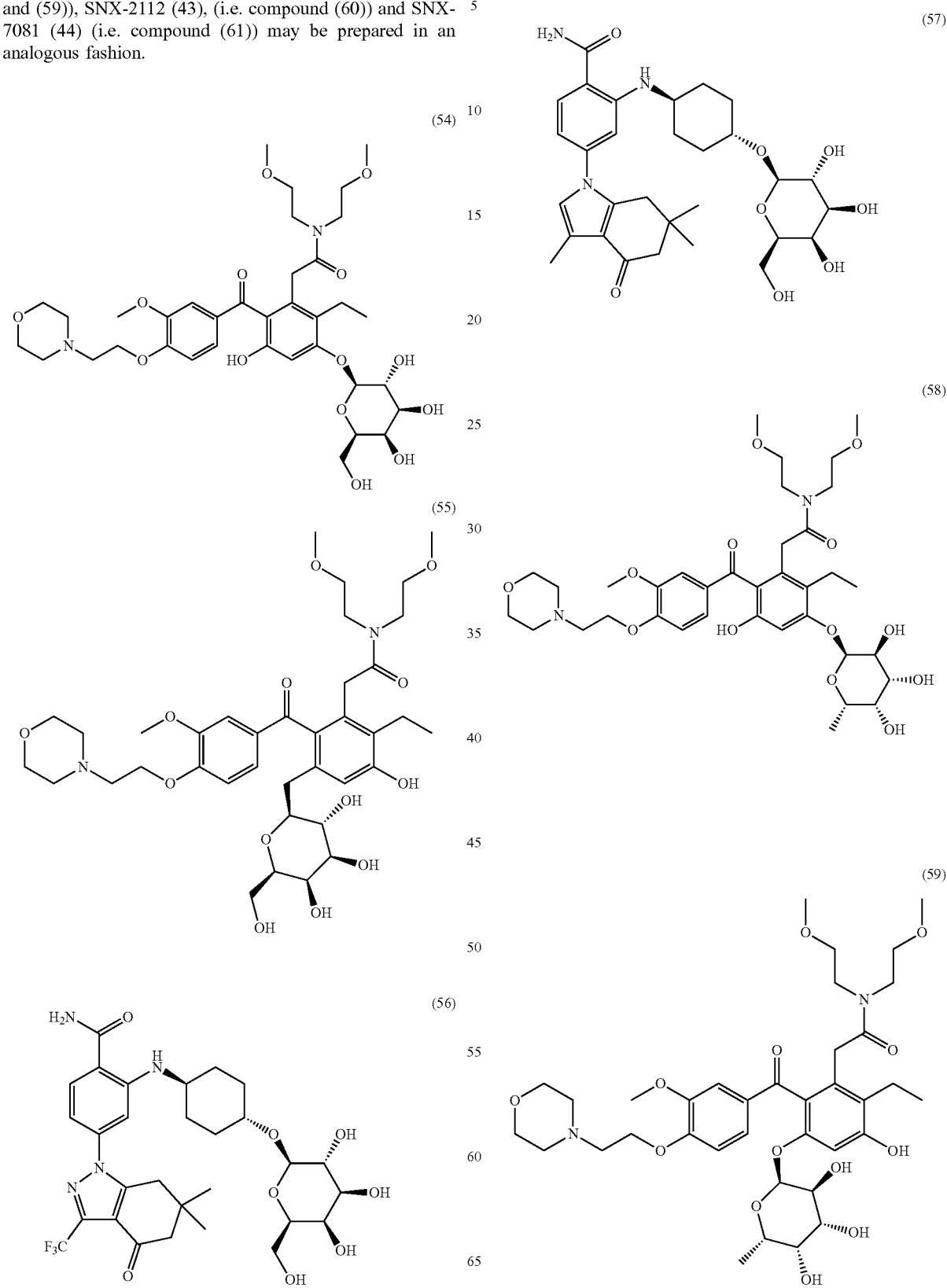

-continued (60)

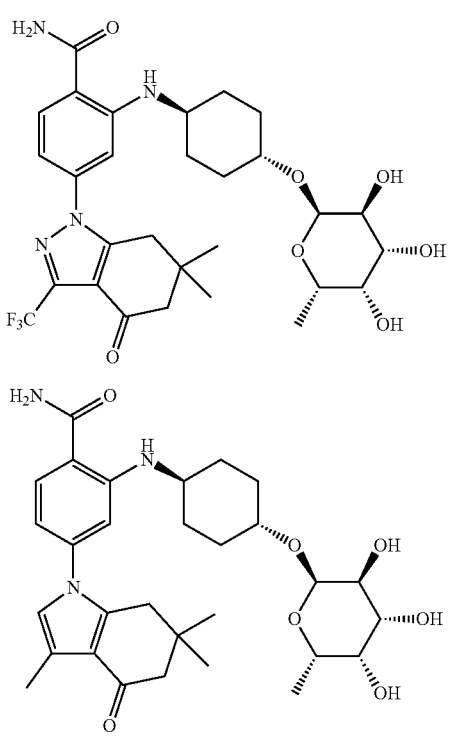

(61)

Yet other embodiments are directed to O-D-galactosyl and O-L-fucosyl conjugates of topoisomerase I (TOP1) inhibitory compounds as senolytic compounds. Camptothecin (62), a cytotoxic pentacyclic quinoline alkaloid natural product, is the archetypal TOP1 inhibitor and numerous synthetic analogs (including SN-38 (63) and topotecan (64)) have been studied clinically or preclinically as anti-cancer agents (see, e.g., Jain et al., Current Genomics 1.8 (2017) 75-92; and Liu et al., Med. Res. Rev. 35 (2015) 753-789). Other important structural classes of TOP1 inhibitors include the indenol soquinolines (exemplified by compounds (65)-(70), (see e.g., Cinelli et al., J. Med. Chem. 55 (2012) 10844-10862; and Lv et al., J. Med. Chem. 59 (2016) 4890-4899)) and the dibenzonaphthyridones (exemplified by compounds (71)-(73), (see, e.g., Sooryakumar et al., Mol. Cancer Ther. 10 (2011) 1490-1499)).

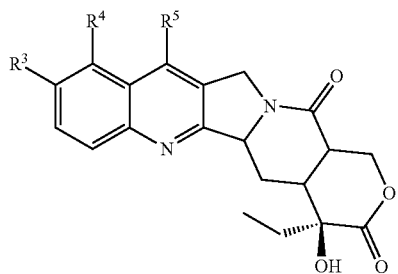

$R^3 = R^4 = R^5 = H$; Camptothecin (62)
$R^3 = OH, R^4 = H, R^5 = Et$; SN-38 (63)
$R^3 = OH, R^4 = CH_2NMe_2, R^5 = H$; Topotecan (64)

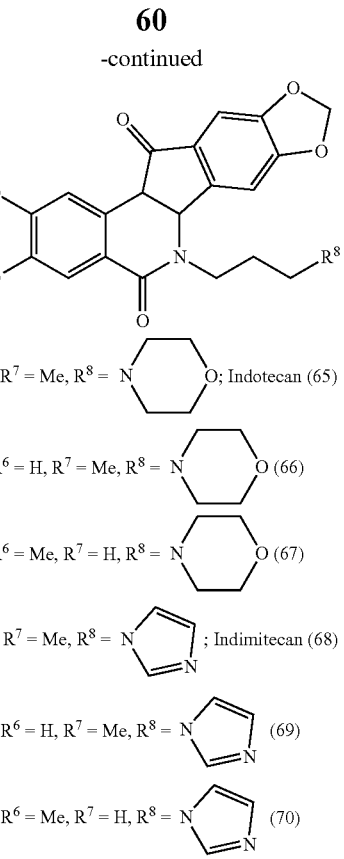

$R^6 = R^7 = Me, R^8 =$ 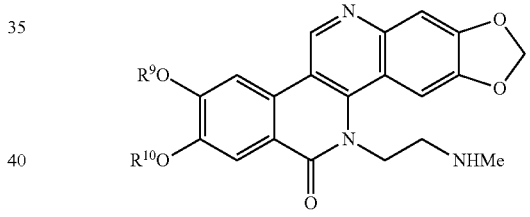 O; Indotecan (65)

$R^6 = H, R^7 = Me, R^8 = $ N O (66)

$R^6 = Me, R^7 = H, R^8 = $ N O (67)

$R^6 = R^7 = Me, R^8 = $ N ; Indimitecan (68)

$R^6 = H, R^7 = Me, R^8 = $ N (69)

$R^6 = Me, R^7 = H, R^8 = $ N (70)

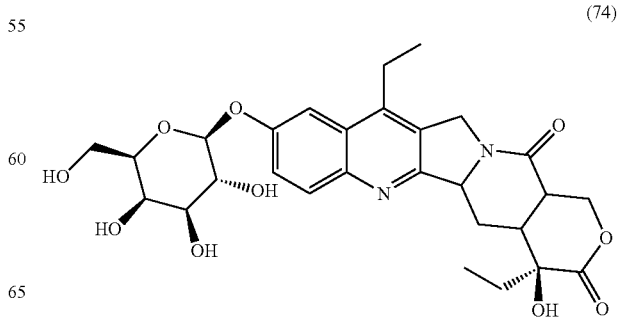

$R^9 = R^{10} = Me$; Genz-644282 (71)
$R^9 = H, R^{10} = Me$ (72)
$R^9 = Me, R^{10} = H$ (73)

The O-β-D-galactoside conjugate of SN-38 (74) (Chinese Patent No. CN 1534046, 2004) and the O-β-L-fucoside conjugate of SN-38 (75) (Japanese Patent No. JP 6328098, 1988) have been previously disclosed as anti-tumor agents.

(74)

(75)
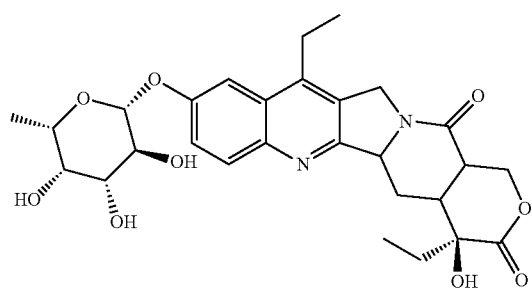
In some embodiments, compounds of formula (XVI), (XVII), (XVIII), (XIX), (XX), (XXI), (XXII), (XXIII), (XXIV) or (XXV) are senolytic agents:
(XVI)
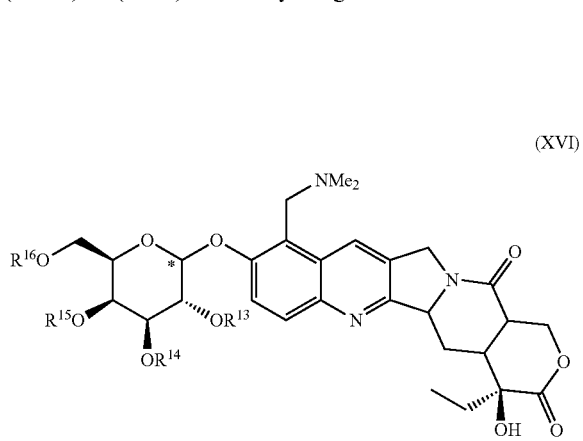
(XVII)
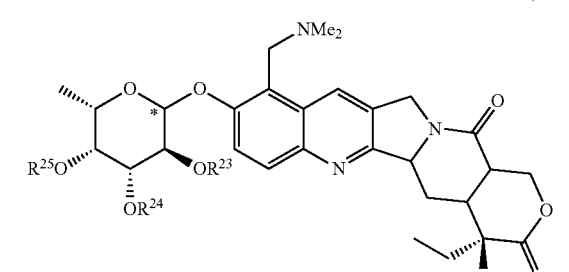
(XVIII)
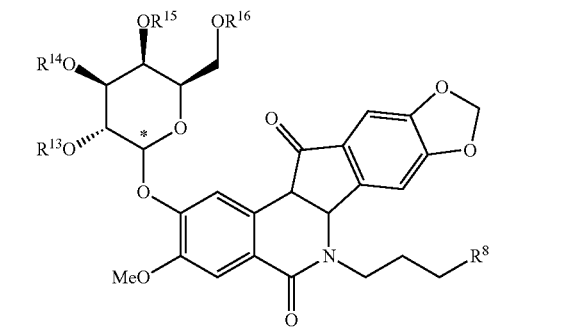
(XIX)
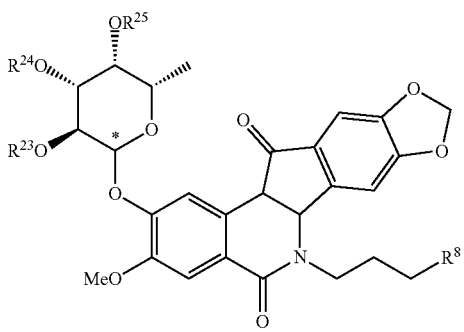
(XX)
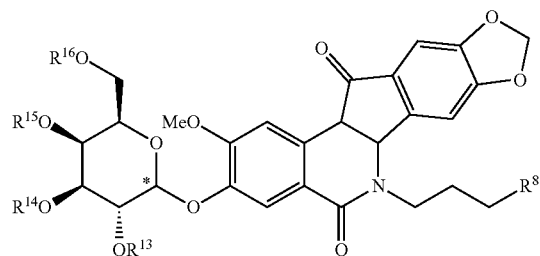
(XXI)
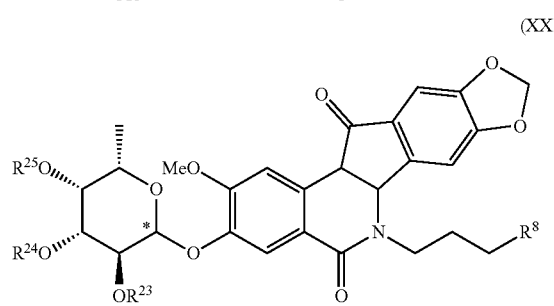
(XXII)
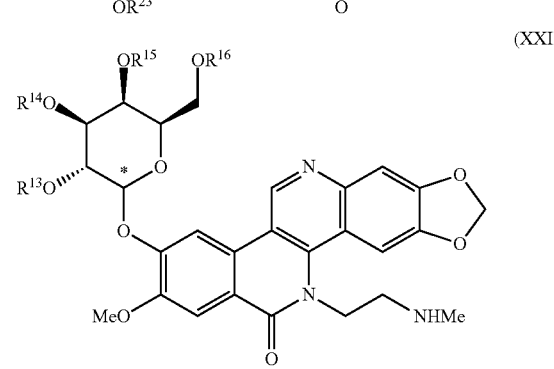
(XXIII)
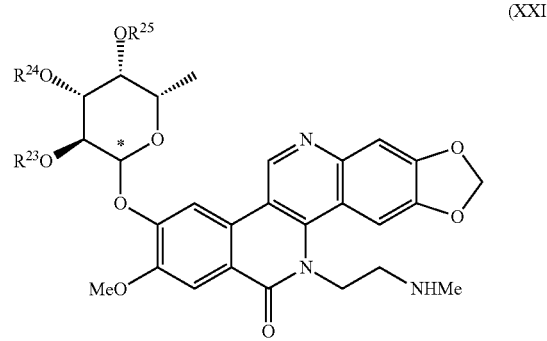

-continued

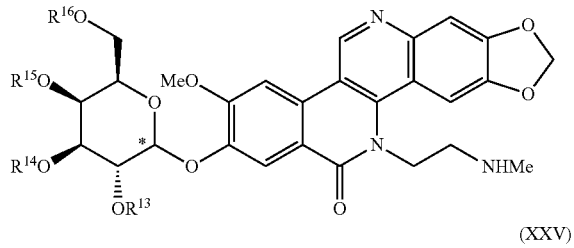

(XXIV)

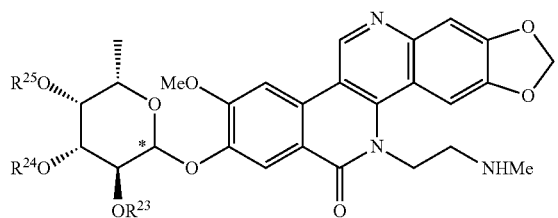

(XXV)

wherein $R^8$ is a heteroaryl or heterocyclic group containing at least one nitrogen atom; each $R^{13}$, $R^{14}$, $R^{15}$, $R^{16}$, $R^{23}$, $R^{24}$ and $R^{25}$ are independently hydrogen, —C(O)—$R^1$, a moiety of formula (VI) or a moiety of formula (VII):

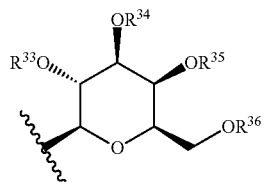

(VI)

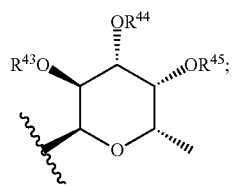

(VII)

each $R^{33}$, $R^{34}$, $R^{35}$, $R^{36}$, $R^{43}$, $R^{44}$ and $R^{45}$ are independently hydrogen or —C(O)—$R^2$; each $R^1$ is independently $C_{1-4}$ alkyl or phenyl, with the proviso that if one of $R^{13}$, $R^{14}$, $R^{15}$ or $R^{16}$ is a moiety of formula (VI) or formula (VII) then the remainder of $R^{13}$, $R^{14}$, $R^{15}$ and $R^{16}$ are hydrogen or C(O)—$R^1$; and each $R^2$ is independently $C_{1-4}$ alkyl or phenyl, with the proviso that if one of $R^{23}$, $R^{24}$ or $R^{25}$ is a moiety of formula (VI) or formula (VII) then the remainder of $R^{23}$, $R^{24}$ or $R^{25}$ is hydrogen or —C(O)—$R^1$.

In some embodiments, of compounds of formulae (XVI), (XVII), (XVIII), (XIX), (XX), (XXI), (XXII), (XXIII), (XXIV) or (XXV), the anomeric carbon of the pyranose ring (labelled *) is of the S configuration and the compounds are respectively β-D-galactoside and α-L-fucoside conjugates of TOP1 inhibitors. In other embodiments, of compound of formulae (XVIII), (XIX), (XX) or (XXI), $R^8$ is 4-morpholinyl or 1-imidazolyl.

In some embodiments of compounds of formula (XVI), each of $R^{13}$, $R^{14}$, $R^{15}$ and $R^{16}$ are hydrogen. In some embodiments of compounds of formula (XVII), each of $R^{23}$, $R^{24}$ and $R^{25}$ are hydrogen. In some embodiments of compounds of formula (XVIII), each of $R^{13}$, $R^{14}$, $R^{15}$ and $R^{16}$ are hydrogen. In some embodiments of compounds of formula (XIX), each of $R^{23}$, $R^{24}$ and $R^{25}$ are hydrogen. In some embodiments of compounds of formula (XX), each of $R^{13}$, $R^{14}$, $R^{15}$ and $R^{16}$ are hydrogen. In some embodiments of compounds of formula (XXI), each of $R^{23}$, $R^{24}$ and $R^{25}$ are hydrogen. In some embodiments of compounds of formula (XXII), each of $R^{13}$, $R^{14}$, $R^{15}$ and $R^{16}$ are hydrogen. In some embodiments of compounds of formula (XXIII), each of $R^{23}$, $R^{24}$ and $R^{25}$ are hydrogen. In some embodiments of compounds of formula (XXIV), each of $R^{13}$, $R^{14}$, $R^{15}$ and $R^{16}$ are hydrogen. In some embodiments of compounds of formula (XXV), each of $R^{23}$, $R^{24}$ and $R^{25}$ are hydrogen.

In some embodiments of compounds of formula (XVI), each of $R^{13}$, $R^{14}$, $R^{15}$ and $R^{16}$ are independently —C(O)—$R^1$, wherein $R^1$ is $C_{1-4}$ alkyl or phenyl. In some embodiments of compounds of formula (XVII), each of $R^{23}$, $R^{24}$ and $R^{25}$ are independently —C(O)—$R^1$, wherein $R^1$ is $C_{1-4}$ alkyl or phenyl. In some embodiments of compounds of formula (XVIII), each of $R^{13}$, $R^{14}$, $R^{15}$ and $R^{16}$ are independently —C(O)—$R^1$, wherein $R^1$ is $C_{1-4}$ alkyl or phenyl. In some embodiments of compounds of formula (XIX), each of $R^{23}$, $R^{24}$ and $R^{25}$ are independently —C(O)—$R^1$, wherein $R^1$ is $C_{1-4}$ alkyl or phenyl. In some embodiments of compounds of formula (XX), each of $R^{13}$, $R^{14}$, $R^{15}$ and $R^{16}$ are independently —C(O)—$R^1$, wherein $R^1$ is $C_{1-4}$ alkyl or phenyl. In some embodiments of compounds of formula (XXI), each of $R^{23}$, $R^{24}$ and $R^{25}$ are independently —C(O)—$R^1$, wherein $R^1$ is $C_{1-4}$ alkyl or phenyl. In some embodiments of compounds of formula (XXII), each of $R^{13}$, $R^{14}$, $R^{15}$ and $R^{16}$ are independently —C(O)—$R^1$, wherein $R^1$ is $C_{1-4}$ alkyl or phenyl. In some embodiments of compounds of formula (XXIII), each of $R^{23}$, $R^{24}$ and $R^{25}$ are independently —C(O)—$R^1$, wherein $R^1$ is $C_{1-4}$ alkyl or phenyl. In some embodiments of compounds of formula (XXIV), each of $R^{13}$, $R^{14}$, $R^{15}$ and $R^{16}$ are independently —C(O)—$R^1$, wherein $R^1$ is $C_{1-4}$ alkyl or phenyl. In some embodiments of compounds of formula (XXV), each of $R^{23}$, $R^{24}$ and $R^{25}$ are independently —C(O)—$R^1$, wherein $R^1$ is $C_{1-4}$ alkyl or phenyl.

In some embodiments of compounds of formula (XVI), each of $R^{13}$, $R^{14}$, $R^{15}$ and $R^{16}$ are —C(O)—$R^1$, where $R^1$ is methyl. In some embodiments of compounds of formula (XVII), each of $R^{23}$, $R^{24}$ and $R^{25}$ are —C(O)—$R^1$, where $R^1$ is methyl. In some embodiments of compounds of formula (XVIII), each of $R^{13}$, $R^{14}$, $R^{15}$ and $R^{16}$ are —C(O)—$R^1$, where $R^1$ is methyl. In some embodiments of compounds of formula (XIX), each of $R^{23}$, $R^{24}$ and $R^{25}$ are —C(O)—$R^1$, wherein $R^1$ is methyl. In some embodiments of compounds of formula (XX), each of $R^{13}$, $R^{14}$, $R^{15}$ and $R^{16}$ are —C(O)—$R^1$, where $R^1$ is methyl. In some embodiments of compounds of formula (XXI), each of $R^{23}$, $R^{24}$ and $R^{25}$ are —C(O)—$R^1$, where $R^1$ is methyl. In some embodiments of compounds of formula (XXII), each of $R^{13}$, $R^{14}$, $R^{15}$ and $R^{16}$ are —C(O)—$R^1$, where $R^1$ is methyl. In some embodiments of compounds of formula (XIII), each of $R^{23}$, $R^{24}$ and $R^{25}$ are —C(O)—$R^1$, wherein $R^1$ is methyl. In some embodiments of compounds of formula (XXIV), each of $R^{13}$, $R^{14}$, $R^{15}$ and $R^{16}$ are —C(O)—$R^1$, where $R^1$ is methyl. In some embodiments of compounds of formula (XXV), each of $R^{23}$, $R^{24}$ and $R^{25}$ are —C(O)—$R^1$, wherein $R^1$ is methyl.

In some embodiments of compounds of formula (XVI), each of $R^{13}$, $R^{14}$, $R^{15}$ and $R^{16}$ are —C(O)—$R^1$, where $R^1$ is ethyl. In some embodiments of compounds of formula (XVII), each of $R^{23}$, $R^{24}$ and $R^{25}$ are —C(O)—$R^1$, where $R^1$ is ethyl. In some embodiments of compounds of formula (XVIII), each of $R^{13}$, $R^{14}$, $R^{15}$ and $R^{16}$ are —C(O)—$R^1$, where $R^1$ is ethyl. In some embodiments of compounds of formula (XIX), each of $R^{23}$, $R^{24}$ and $R^{25}$ are —C(O)—$R^1$, wherein $R^1$ is ethyl. In some embodiments of compounds of formula (XX), each of $R^{13}$, $R^{14}$, $R^{15}$ and $R^{16}$ are —C(O)—$R^1$, where $R^1$ is ethyl. In some embodiments of compounds of formula (XXI), each of $R^{23}$, $R^{24}$ and $R^{25}$ are —C(O)—$R^1$, where $R^1$ is ethyl. In some embodiments of compounds of formula (XXII), each of $R^{13}$, $R^{14}$, $R^{15}$ and $R^{16}$ are —C(O)—$R^1$, where $R^1$ is ethyl. In some embodiments of compounds of formula (XXIII), each of $R^{23}$, $R^{24}$ and $R^{25}$ are —C(O)—$R^1$, wherein $R^1$ is ethyl. In some embodiments of compounds of formula (XXIV), each of $R^{13}$, $R^{14}$, $R^{15}$ and $R^{16}$ are —C(O)—$R^1$, where $R^1$ is ethyl. In some embodiments of compounds of formula (XXV), each of $R^{23}$, $R^{24}$ and $R^{25}$ are —C(O)—$R^1$, wherein $R^1$ is ethyl.

In still other embodiments, O-D-galactosyl and O-L-fucosyl conjugates of DNA alkylating agents based on the cytotoxic duocarmycin family antibiotics are senolytic agents. Duocarmycin SA (76) isolated from *Streptomyces* DO-113 contains a highly reactive spirocyclopropylcyclohexadienone moiety and has been used as the inspiration for design of monosaccharide and disaccharide derivatives such as galactosyl compound (77) (e.g., see Tietze et al., Angew. Chem. Int. Ed. 45 (2006) 6574-6577; Tietze et al., J. Med. Chem. 52 (2009) 537-543). Compound (77) is greater than 4000-fold less cytotoxic than its hydrolyzed seco product (78), which undergoes a so-called Winstein cyclization in situ to afford the DNA-reactive spirocyclopropylcyclohexadienone (79).

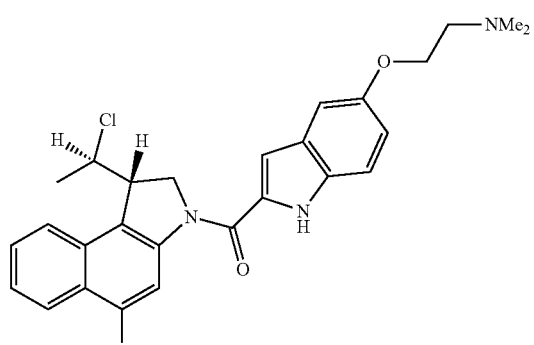

In some embodiments, compounds of formula (XXVI) or (XXVII) are senolytic agents:

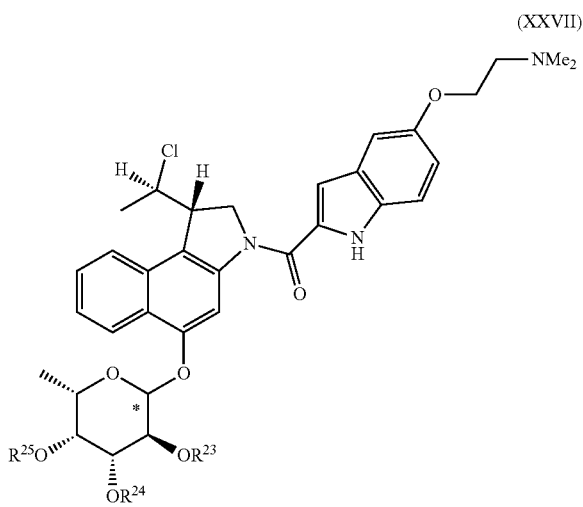

(XXVII)

wherein each of $R^{13}$, $R^{14}$, $R^{15}$, $R^{16}$, $R^{23}$, $R^{24}$ and $R^{25}$ is independently hydrogen, C(O)—$R^1$, a moiety of formula (VI) or a moiety of formula (VII):

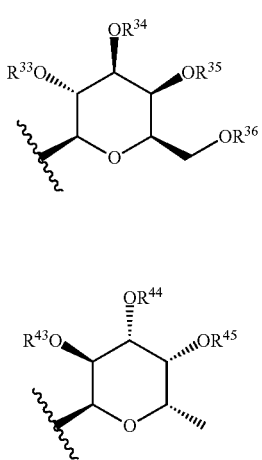

(VI)

(VII)

each $R^{33}$, $R^{34}$, $R^{35}$, $R^{36}$, $R^{43}$, $R^{44}$ and $R^{45}$ are independently hydrogen or —C(O)—$R^2$; each $R^1$ is independently $C_{1-4}$ alkyl or phenyl, with the proviso that if one of $R^{13}$, $R^{14}$, $R^{15}$ or $R^{16}$ is a moiety of formula (VI) or formula (VII) then the remainder of $R^{13}$, $R^{14}$, $R^{15}$ and $R^{16}$ are hydrogen or C(O)—$R^4$; and each $R^2$ is independently $C_{1-4}$ alkyl or phenyl, with the proviso that if one of $R^{23}$, $R^{24}$ or $R^{25}$ is a moiety of formula (VI) or formula (VII) then the remainder of $R^{23}$, $R^{24}$ or $R^{25}$ is hydrogen or —C(O)—$R^1$; provided that in a compound of formula (XXVI) each of $R^{13}$, $R^{14}$, $R^{15}$, $R^{16}$ are not simultaneously hydrogen or acetyl.

In some embodiments, of compounds of formulae (XXVI) or (XXVII), the anomeric carbon of the pyranose ring (labelled *) is of the S configuration and the compounds are respectively β-D-galactoside and α-L-fucoside conjugates of duocarmycin analogs.

In some embodiments of compounds of formula (XXVI), each of $R^{13}$, $R^{14}$, $R^{15}$ and $R^{16}$ are hydrogen. In some embodiments of compounds of formula (XXVII), each of $R^{23}$, $R^{24}$ and $R^{25}$ are hydrogen.

In some embodiments of compounds of formula (XXVI), each of $R^{13}$, $R^{14}$, $R^{15}$ and $R^{16}$ are independently —C(O)—$R^1$, wherein $R^1$ is $C_{1-4}$ alkyl or phenyl. In some embodiments of compounds of formula (XXVII), each of $R^{23}$, $R^{24}$ and $R^{25}$ are independently —C(O)—$R^1$, wherein $R^1$ is $C_{1-4}$ alkyl or phenyl.

In some embodiments of compounds of formula (XXVI), each of $R^{13}$, $R^{14}$, $R^{15}$ and $R^{16}$ are —C(O)—$R^1$, where $R^1$ is methyl. In some embodiments of compounds of formula (XXVII), each of $R^{23}$, $R^{24}$ and $R^{25}$ are —C(O)—$R^1$, where $R^1$ is methyl In some embodiments of compounds of formula (XXVI), each of $R^{13}$, $R^{14}$, $R^{15}$ and $R^{16}$ are —C(O)—$R^1$, where $R^1$ is ethyl. In some embodiments of compounds of formula (XXVII), each of $R^{23}$, $R^{24}$ and $R^{25}$ are —C(O)—$R^1$, where $R^1$ is ethyl.

In some embodiments of a compound of formula (XXVII), compound (80) is synthesized from compound (81) (prepared according to the methods of Tietze et al., ibid):

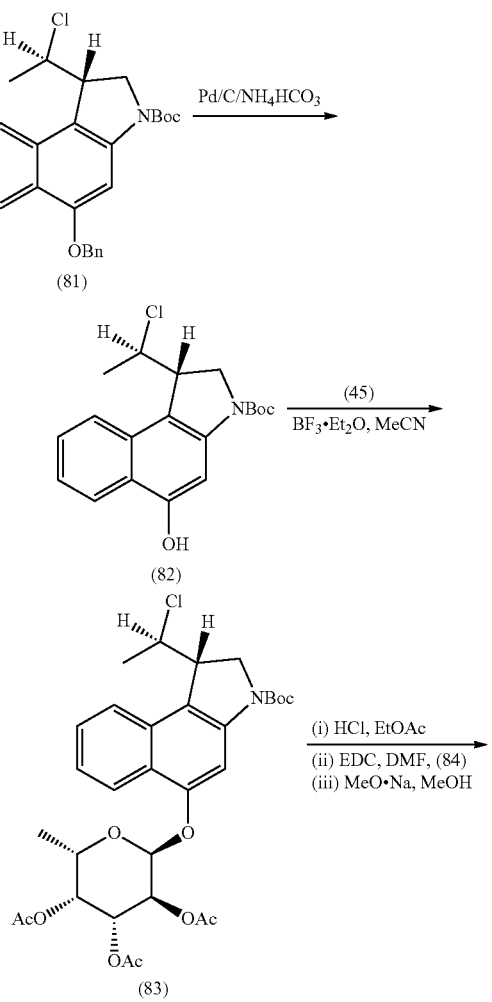

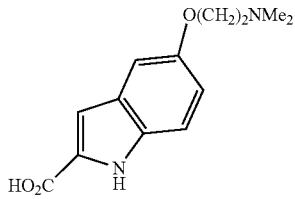

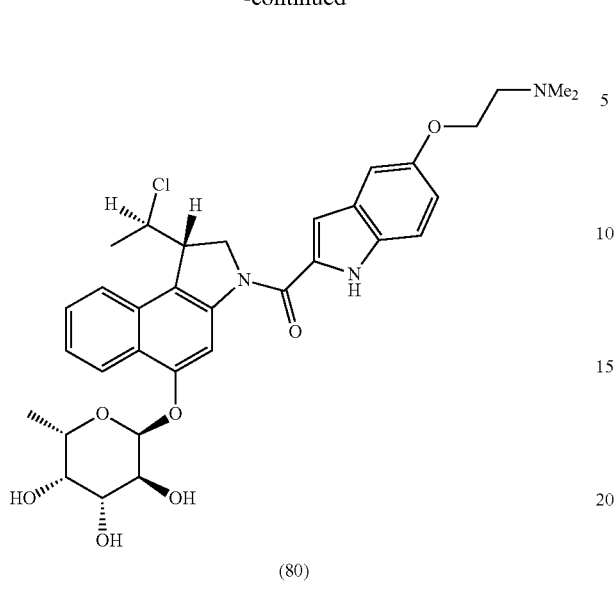

(80)

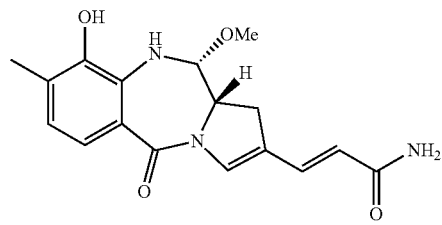

(84)

Yet other embodiments are directed to O-D-galactosyl and O-L-fucosyl conjugates of cytotoxic pyrrolo[2,1-c][1,4]benzodiazepines (PBDs) as senolytic agents. PBDs are a family of antitumor antibiotics that includes the natural product anthramycin (85). These compounds exert their cytotoxic effects by covalently bonding to the exocyclic $NH_2$ group of guanine residues in the minor groove of DNA through their N10-C11 imine functionality (see, e.g., Antonow and Thurston, Chem. Rev. 111 (2011) 2815-2864; and Mantaj et al., Angew. Chem. Int. Ed. 56 (2017) 462-488). PBD monomers show significant cytotoxicity and joining two PBD monomers through a linker generates PBD dimers capable of interstrand DNA cross-linking. SJG-136 (86) is one such dimer having high cytotoxic potency that has been used to construct antibody-drug conjugates with clinical utility.

(85)

Anthramycin

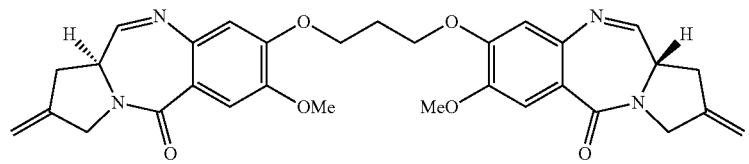

SJG-136

Kamal and coworkers have described β-galactoside analogs of both PBD monomers and dimers as anti cancer agents (e.g., see compounds (87) and (88) (Kamal et al., ChemMedChem 3 (2008) 794-802)).

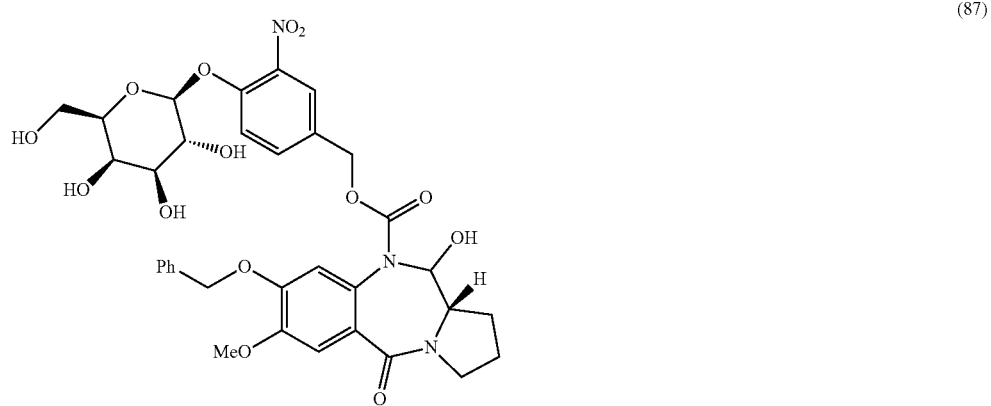
(87)

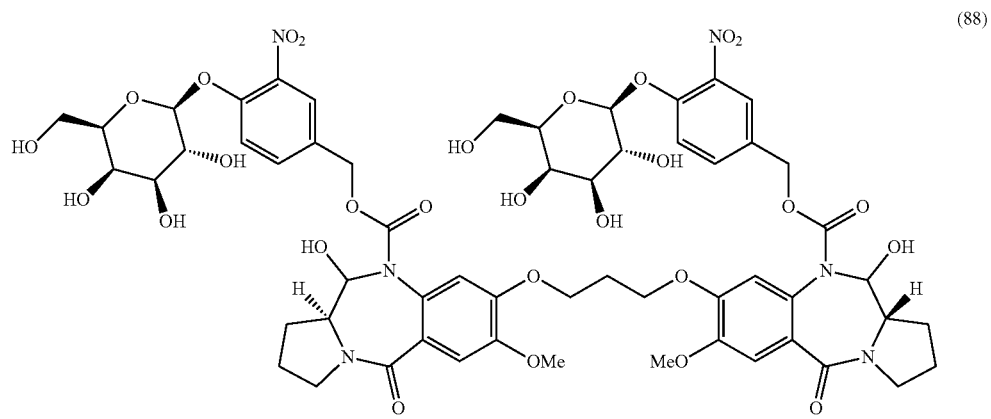
(88)

In some embodiments compounds of formula (XXVIII) or (XXIX) are senolytic agents:

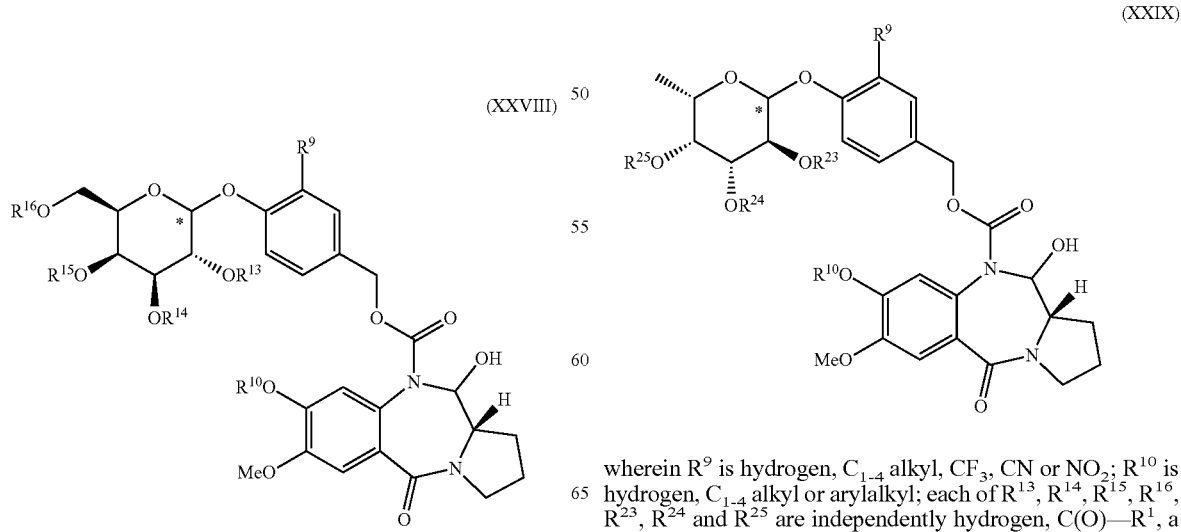

wherein $R^9$ is hydrogen, $C_{1-4}$ alkyl, $CF_3$, CN or $NO_2$; $R^{10}$ is hydrogen, $C_{1-4}$ alkyl or arylalkyl; each of $R^{13}$, $R^{14}$, $R^{15}$, $R^{16}$, $R^{23}$, $R^{24}$ and $R^{25}$ are independently hydrogen, C(O)—$R^1$, a moiety of formula (VI) or a moiety of formula (VII):

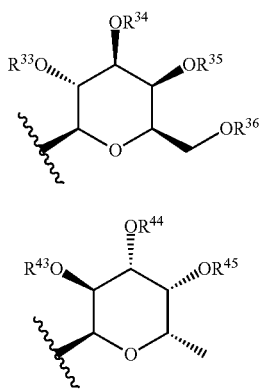

each $R^{33}$, $R^{34}$, $R^{35}$, $R^{36}$, $R^{43}$, $R^{44}$ and $R^{45}$ are independently hydrogen or C(O)—$R^2$, each $R^1$ is independently $C_{1-4}$ alkyl or phenyl, with the proviso that if one of $R^{13}$, $R^{14}$, $R^{15}$, or $R^{16}$ is a moiety of formula (VI) or formula (VII) then the remainder of $R^{13}$, $R^{14}$, $R^{15}$ and $R^{16}$ is hydrogen or C(O)—$R^1$; and each $R^2$ is independently $C_{1-4}$ alkyl or phenyl, with the proviso that if one of $R^{23}$, $R^{24}$ or $R^{25}$ is a moiety of formula (VI) or formula (VII) then the remainder of $R^{23}$, $R^{24}$ or $R^{25}$ is hydrogen or C(O)—$R^1$; provided that in a compound of formula (XXVIII) when $R^9$ is $NO_2$ and $R^{10}$ is benzyl, then each of $R^{13}$, $R^{14}$, $R^{15}$, $R^{16}$ are not simultaneously hydrogen or acetyl.

In some embodiments of compounds of formulae (XXVIII) or (XXIX), the anomeric carbon of the pyranose ring (labelled *) is of the S configuration and the compounds are respectively β-D-galactoside and α-L-fucoside conjugates of pyrrolo[2,1-c][1,4]benzodiazepine analogs.

In some embodiments of compounds of formula (XXVIII), each of $R^{13}$, $R^{14}$, $R^{15}$ and $R^{16}$ are hydrogen. In some embodiments of compounds of formula (XXIX), each of $R^{23}$, $R^{24}$ and $R^{25}$ are hydrogen.

In some embodiments of compounds of formula (XXVIII), each of $R^{13}$, $R^{14}$, $R^{15}$ and $R^{16}$ are independently —C(O)—$R^1$, wherein $R^1$ is $C_{1-4}$ alkyl or phenyl. In some embodiments of compounds of formula (XXIX), each of $R^{23}$, $R^{24}$ and $R^{25}$ are independently —C(O)—$R^1$, wherein $R^1$ is $C_{1-4}$ alkyl or phenyl.

In some embodiments of compounds of formula (XXVIII), each of $R^{13}$, $R^{14}$, $R^{15}$ and $R^{16}$ are —C(O)—$R^1$, where $R^1$ is methyl. In some embodiments of compounds of formula (XXIX), each of $R^{23}$, $R^{24}$ and $R^{25}$ are —C(O)—$R^1$, where $R^1$ is methyl In some embodiments of compounds of formula (XXVIII), each of $R^{13}$, $R^{14}$, $R^{15}$ and $R^{16}$ are —C(O)—$R^1$, where $R^1$ is ethyl. In some embodiments of compounds of formula (XXIX), each of $R^{23}$, $R^{24}$ and $R^{25}$ are —C(O)—$R^1$, where $R^1$ is ethyl.

In some embodiments, of a compound of formula (XXVIII), compound (89) is synthesized from compound (90) (prepared according to the methods of Kamal et al., ibid)

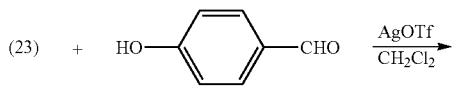

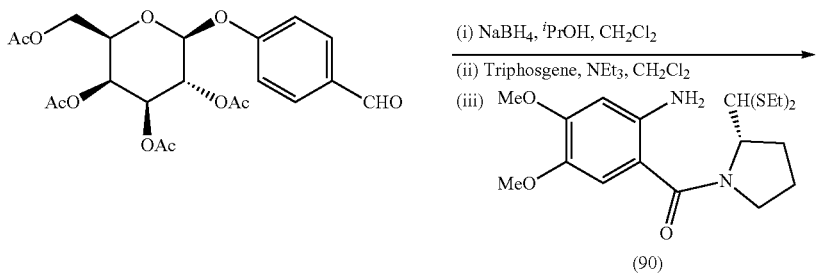

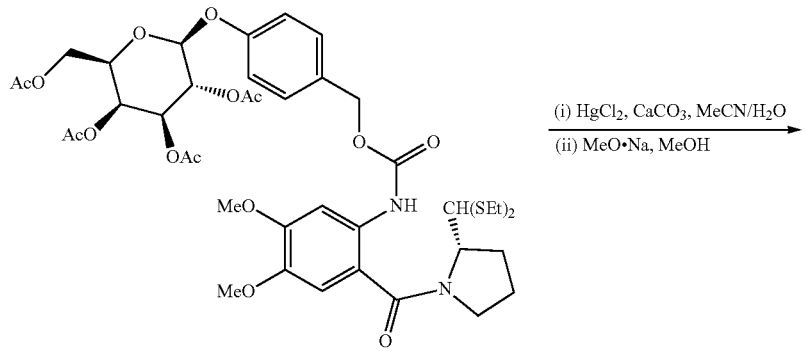

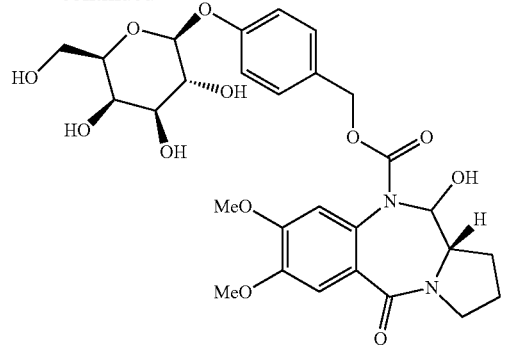

(89)

Specifically, as one embodiment of a compound of formula (XXIX), compound (91) is prepared from compound (90) using a comparable synthetic approach.

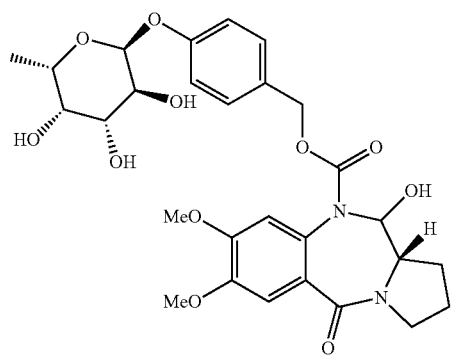

(91)

In still other embodiments, O-galactoside or O-fucoside conjugates of Akt inhibitors are senolytic agents. Akt inhibitors useful for the preparation of such conjugates are exemplified by compounds such as ipatasertib (or GDC-0068) (92), AZD5363 (93) and triciribine (94). In some embodiments, O-β-D-galactoside or O-α-L-fucoside conjugates of Akt inhibitors are senolytic agents.

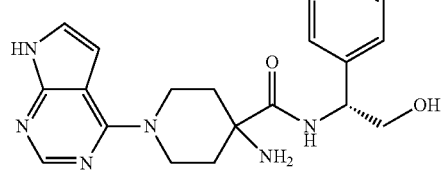

AZD5363 (93)

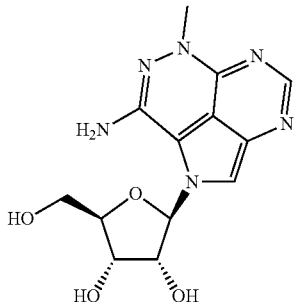

Triciribine (94)

Specific compounds are exemplified by compounds (95)-(100), wherein each $R^{46}$ is either hydrogen, acetyl or propionyl, prepared according to methods previously disclosed herein:

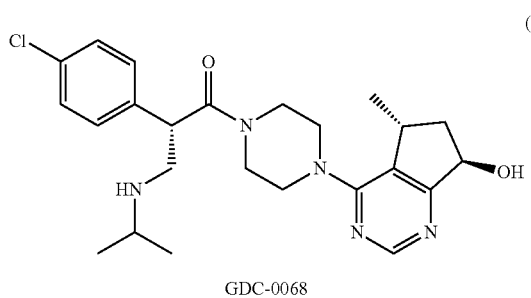

GDC-0068 (92)

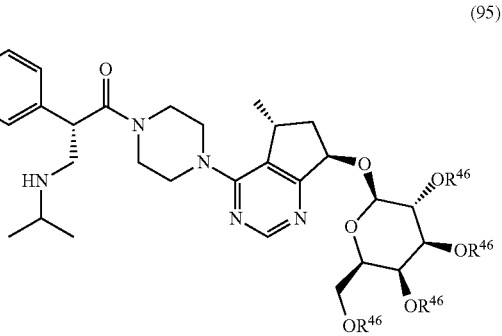

(95)

-continued

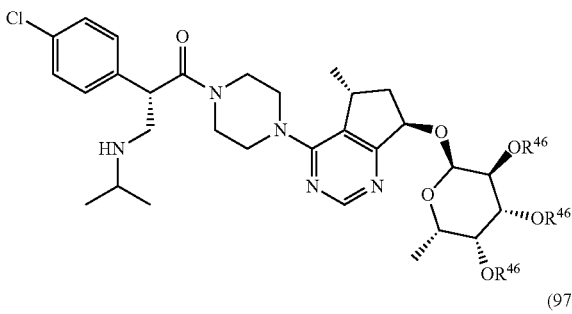

(96)

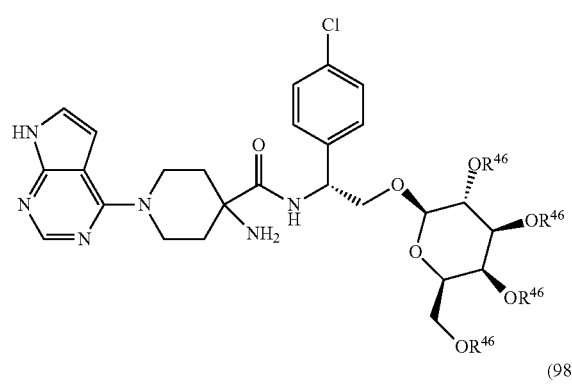

(97)

(98)

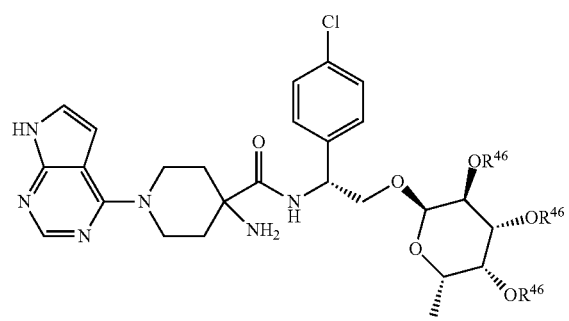

(99)

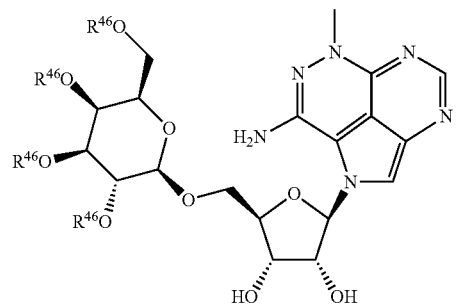

(100)

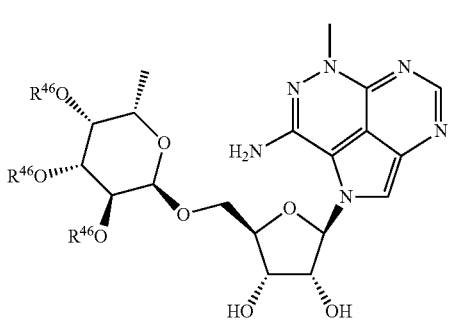

In some embodiments, a compound of Formula (I), exemplified by 5-fluorouridine-5'-O-β-D-galactopyranoside (FURGal) (101), is converted to a pro-apoptotic compound of Formula (II), specifically the cytotoxin 5-fluorouridine (FUR) (102) by the action of intracellular β-galactosidase enriched in senescent cells (i.e. SA-β-Gal):

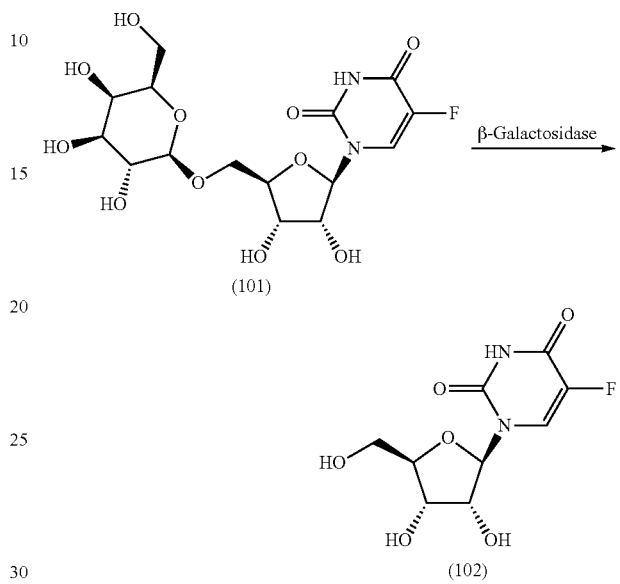

In another embodiment, a compound of Formula (I), exemplified by 5-fluorouridine-5'-O-α-L-fucopyranoside (FURFuc) (106), is converted to a pro-apoptotic compound of Formula (II), specifically the cytotoxin 5-fluorouridine (FUR) (102) by the action of intracellular α-fucosidase enriched in senescent cells:

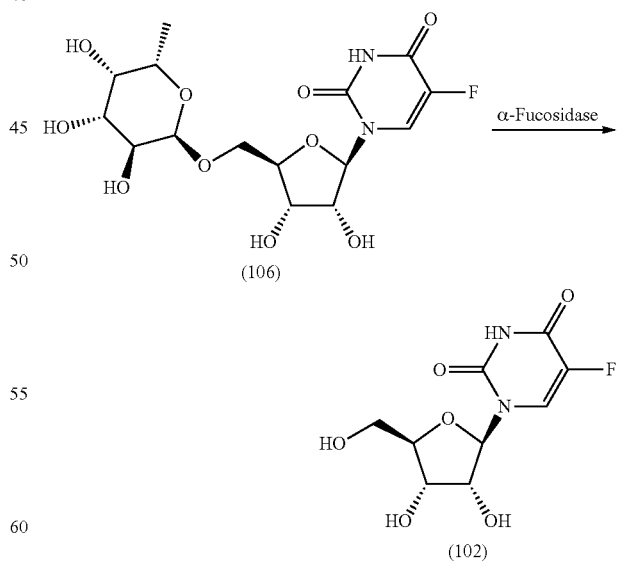

In yet further embodiments, O-galactoside or O-fucoside conjugates of proteasome inhibitors are senolytic agents. Proteasome inhibitors useful for the preparation of such conjugates are exemplified by compounds such as delanzomib (103). In some embodiments, the O-β-D-galactoside or O-α-L-fucoside conjugates (104) and (105) are senolytic agents.

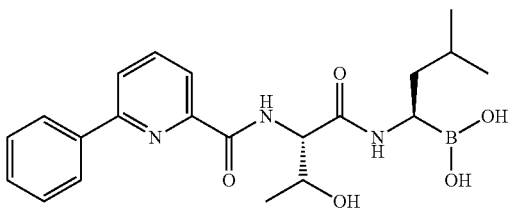

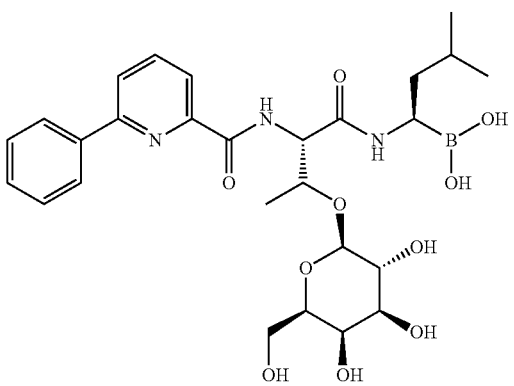

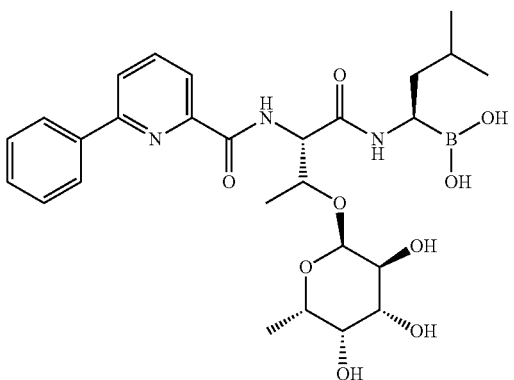

Methods for Characterizing and Identifying Senolytic Agents

Characterizing senolytic agents may be determined by using one or more cell-based assays and one or more animal models described herein or in the art and with which a person skilled in the art will be familiar. A senolytic agent may selectively kill one or more types of senescent cells (e.g., senescent preadipocytes, senescent endothelial cells, senescent fibroblasts, senescent neurons, senescent epithelial cells, senescent mesenchymal cells, senescent smooth muscle cells, senescent macrophages, or senescent chondrocytes). In certain embodiments, a senolytic agent is capable of selectively killing at least senescent fibroblasts.

Characterizing a compound as a senolytic agent can be accomplished using one or more cell-based assays and one or more animal models described herein or in the art. Those of skill in the art will readily appreciate that characterizing a compound as a senolytic agent and determining the level of killing by the compound can be accomplished by comparing the activity of a test agent with appropriate negative controls (e.g., vehicle or diluent only and/or a composition or compound known in the art not to kill senescent cells) and appropriate positive controls. In vitro cell-based assays for characterizing senolytic agents also include controls for determining the effect of the agent on non-senescent cells (e.g., quiescent cells or proliferating cells). A senolytic agent reduces (i.e., decreases) percent survival of a plurality of senescent cells (i.e., in some manner reduces the quantity of viable senescent cells in the animal or in the cell-based assay) compared with one or more negative controls. Conditions for a particular in vitro assay include temperature, buffers (including salts, cations, media), and other components, which maintain the integrity of the test agent and reagents used in the assay, are familiar to a person skilled in the art and/or which can be readily determined through routine experimentation.

The source of senescent cells for use in assays may be a primary cell culture, or culture-adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiable cell lines, transformed cell lines, and the like. In some embodiments, senescent cells are isolated from biological samples obtained from a host or subject who has a senescent cell associated disease or disorder. In other embodiments, non-senescent cells are used (e.g. primary cells obtained from a subject or a cell line adapted to grow in culture) and senescence is induced by methods described herein and in the art, such as by exposure to irradiation or a chemotherapeutic agent (e.g., doxorubicin). Biological samples may be, for example, blood samples, biopsy specimens, body fluids (e.g., lung lavage, ascites, mucosal washings, synovial fluid, etc.), bone marrow, lymph nodes, tissue explants, organ cultures, or any other tissues or cell preparations obtained from a subject. The biological samples may be a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject may be a human or non-human animal. By way of example, the senolytic effect of certain compounds of the present invention towards human fibroblasts in culture medium are characterized in Example 23 herein, and towards murine embryonic fibroblast cells in Example 24 herein. Examples 26 and 27 demonstrate that in vivo administration of senolytic compounds of the present invention lead to a reduction in senescent hepatocytes in mouse. Example 28 demonstrates that in vivo administration of a senolytic compound of the present invention lead to a reduction in senescent lung cells in mouse.

Transgenic animal models as described herein and in the art, may be used to determine killing or removal of senescent cells (see, e.g., Baker et al., supra; Nature, 479 (2011) 232-236; International Application No. WO/2012/177927; International Application No. WO 2013/090645). Exemplary transgenic animal models contain a transgene that includes a nucleic acid that allows for controlled clearance of senescent cells (e.g., p16INK4a positive senescent cells) as a positive control. The presence and level of senescent cells in the transgenic animals can be determined by measuring the level of a detectable label or labels that are expressed in senescent cells of the animal. The transgene nucleotide sequence includes a detectable label, for example, one or more of a red fluorescent protein; a green fluorescent protein; and one or more luciferases to detect clearance of senescent cells.

Animal models that are described herein or in the art include art-accepted models for determining the effectiveness of a senolytic agent to treat or prevent (i.e., reduce the likelihood of occurrence of) a particular senescence associated disease or disorder, such as atherosclerosis models, osteoarthritis models, COPD models, IPF models, etc. As described herein, pulmonary disease murine models, such as a bleomycin pulmonary fibrosis model, and a chronic cigarette smoking model are applicable for diseases such as COPD and may be routinely practiced by a person skilled in the art. Animal models for determining the effectiveness of a senolytic agent to treat and/or prevent (i.e., reduce the likelihood of occurrence of) chemotherapy and radiotherapy side effect models or to treat or prevent (i.e., reduce the likelihood of occurrence of) metastasis are described in International Application Nos. WO 2013/090645 and WO 2014/205244. Animal models for determining the effectiveness of agents for treating eye diseases, particularly age-related macular degeneration is also routinely used in the art (see, e.g., Pennesi et al., Mol. Aspects Med. 33 (2012) 487-509; Zeiss et al., Vet. Pathol. 47 (2010) 396-413; and Chavala et al., J. Clin. Invest. 123 (2013) 4170-4181).

By way of non-limiting example and as described herein, osteoarthritis animal models have been developed. Osteoarthritis may be induced in the animal, for example, by inducing damage to a joint, for example, in the knee by surgical severing, incomplete or total, of the anterior cruciate ligament. Osteoarthritis animal models may be used for assessing the effectiveness of a senolytic agent to treat or prevent (i.e., reducing the likelihood of occurrence of) osteoarthritis and cause a decrease in proteoglycan erosion and to induce (i.e., stimulate, enhance) collagen (such as collagen type 2) production, and to reduce pain in an animal that has ACL surgery. Immunohistology may be performed to examine the integrity and composition of tissues and cells in a joint. Immunochemistry and/or molecular biology techniques may also be performed, such as assays for determining the level of inflammatory molecules (e.g., IL-6) and assays for determining the level of senescence markers as noted above, using methods and techniques described herein, which may be routinely practiced by a person skilled in the art.

By way of another non-limiting example and as described herein, atherosclerosis animal models have been developed. Atherosclerosis may be induced in the animal, for example, by feeding animals a high fat diet or by using transgenic animals highly susceptible to developing atherosclerosis. Animal models may be used for determining the effectiveness of a senolytic agent to reduce the amount of plaque or to inhibit formation of plaque in an atherosclerotic artery, to reduce the lipid content of an atherosclerotic plaque (i.e., reduce, decrease the amount of lipid in a plaque), and to cause an increase or to enhance fibrous cap thickness of a plaque. Sudan staining may be used to detect the level of lipid in an atherosclerotic vessel. Immunohistology and immunochemistry and molecular biology assays (e.g., for determining the level of inflammatory molecules (e.g., IL-6), and for determining the level of senescence markers as noted above), may all be performed according to methods described herein, which are routinely practiced in the art.

In still another non-limiting example, and as described herein, mouse models in which animals are treated with bleomycin have been described (see, e.g., Peng et al., PLoS One 8(4) (2013) e59348. doi: 10.1371/journal-.pone.0059348; Mouratis et al., Curr. Opin. Pulm. Med. 17 (2011) 355-361) for determining the effectiveness of an agent for treating IPF. In pulmonary disease animal models (e.g., a bleomycin animal model, smoke-exposure animal model, or the like), respiratory measurements may be taken to determine elastance, compliance, static compliance, and peripheral capillary oxygen saturation ($SpO_2$). Immunohistology and immunochemistry and molecular biology assays (e.g., for determining the level of inflammatory molecules (e.g., IL-6), and for determining the level of senescence markers as noted above), may all be performed according to methods described herein, which are routinely practiced in the art.

Determining the effectiveness of a senolytic agent to selectively kill senescent cells as described herein in an animal model may be performed using one or more statistical analyses with which those skilled in the art will be familiar. By way of example, statistical analyses such as two-way analysis of variance (ANOVA) may be used for determining the statistical significance of differences between animal groups treated with an agent and those that are not treated with the agent (i.e., negative control group, which may include vehicle only and/or a non-senolytic agent). Statistical packages such as SPSS, MINITAB, SAS, Statistika, Graphpad, GLIM, Genstat, and BMDP are readily available and are routinely used by a person skilled in the animal model art.

Those of skill in the art will readily appreciate that characterizing a senolytic agent and determining the level of killing by the senolytic agent can be accomplished by comparing the activity of a test agent with appropriate negative controls (e.g., vehicle only and/or a composition, agent, or compound known in the art not to kill senescent cells) and appropriate positive controls. In vitro cell-based assays for characterizing the agent also include controls for determining the effect of the agent on non-senescent cells (e.g., quiescent cells or proliferating cells). A senolytic agent that is useful reduces (i.e., decreases) percent survival of senescent cells (i.e., in some manner reduces the quantity of viable senescent cells in the animal or in the cell-based assay) compared with one or more negative controls. Accordingly, a senolytic agent selectively kills senescent cells compared with killing of non-senescent cells (which may be referred to herein as selectively killing senescent cells over non-senescent cells).

In certain embodiments (either in an in vitro assay or in vivo (in a human or non-human animal)), the at least one senolytic agent kills at least 20% of the senescent cells and kills no more than 5% of non-senescent cells. In other embodiments (either in an in vitro assay or in vivo (in a human or non-human animal)), the at least one senolytic agent kills at least about 25%, 30%, 35%, 40%, 45%, 50%, 55%, 60%, or 65% of the senescent cells and kills no more than about 5% or 10% of non-senescent cells. In still other embodiments (either in an in vitro assay or in vivo (in a human or non-human animal)), the at least one senolytic agent kills at least about 30%, 35%, 40%, 45%, 50%, 55%, 60%, or 65% of the senescent cells and kills no more than about 5%, 10%, or 15% of non-senescent cells. In still other embodiments (either in an in vitro assay or in vivo (in a human or non-human animal)), the at least one senolytic agent kills at least about 40%, 45%, 50%, 55%, 60%, or 65% of the senescent cells and kills no more than about 5%, 10%, 15%, 20%, or 25% of non-senescent cells. In still other embodiments (either in an in vitro assay or in vivo (in a human or non-human animal)), the at least one senolytic agent kills at least about 50%, 55%, 60%, or 65% of the senescent cells and kills no more than about 5%, 10%, 15%, 20%, 25%, or 30% of non-senescent cells. Stated another way, a senolytic agent has at least 5-25, 10-50, 10-100 or 100-1000 times greater selectively for killing senescent cells than for non-senescent cells.

With respect to specific embodiments of the methods described herein for treating a senescence-associated disease or disorder, the percent senescent cells killed may refer to the percent senescent cells killed in a tissue or organ that comprises senescent cells that contribute to onset, progression, and/or exacerbation of the disease or disorder. By way of non-limiting example, tissues of the brain, tissues and parts of the eye, pulmonary tissue, cardiac tissue, arteries, joints, skin, and muscles may comprise senescent cells that may be reduced in percent as described above by the senolytic agents described herein and thereby provide a therapeutic effect. Moreover, selectively removing at least 20% or at least 25% of senescent cells from an affected tissue or organ can have a clinically significant therapeutic effect.

With respect to specific embodiments of the methods described herein, such as for example, treating a cardiovascular disease or disorder associated with arteriosclerosis, such as atherosclerosis, by administering a senolytic agent (i.e., in reference to vivo methods above), the percent senescent cells killed may refer to the percent senescent cells killed in an affected artery containing plaque versus non-senescent cells killed in the arterial plaque. In certain embodiments, in the methods for treating the cardiovascular disease, such as atherosclerosis, as described herein, the at least one senolytic agent kills at least 20% of the senescent cells and kills no more than 5% of non-senescent cells in the artery. In other embodiments, the senolytic agent selectively kills at least 25% of the senescent cells in the arteriosclerotic artery.

In some embodiments, with respect to the methods described herein for treating osteoarthritis by administering a senolytic agent, the percent senescent cells killed may refer to the percent senescent cells killed in an osteoarthritic joint versus non-senescent cells killed in the osteoarthritic joint. In certain embodiments, in the methods for treating osteoarthritis as described herein, the at least one senolytic agent kills at least 20% of the senescent cells and kills no more than 5% of non-senescent cells in the osteoarthritic joint. In other embodiments, the senolytic agent selectively kills at least 25% of the senescent cells in the osteoarthritic joint.

In some embodiments, with respect to the methods described herein for treating senescence associated pulmonary disease or disorder (e.g., COPD, IPF) by administering at least one senolytic agent, the percent senescent cells killed may refer to the percent senescent cells killed in affected pulmonary tissue versus non-senescent cells killed in the affected pulmonary tissue of the lung. In certain embodiments, in the methods for treating senescence associated pulmonary diseases and disorders as described herein, a senolytic agent kills at least 20% of the senescent cells and kills no more than 5% of non-senescent cells in the affected pulmonary tissue. In other embodiments, the senolytic agent selectively kills at least 25% of the senescent cells in the affected pulmonary tissue.

In certain embodiments, methods are provided for identifying (i.e., screening for) agents that are useful senolytic agents for treating or preventing (i.e., reducing the likelihood of occurrence of) a senescence associated disease or disorder. In some embodiments, a method for identifying a senolytic agent for treating such diseases and disorders, comprises inducing cells to senesce to provide established senescent cells. Methods for inducing cells to senesce are described herein and in the art and include, for example, exposure to radiation (e.g., 10 Gy is typically sufficient) or a chemotherapeutic agent (e.g., doxorubicin or other anthracycline). After exposure to the agent, the cells are cultured for an appropriate time and under appropriate conditions (e.g., media, temperature, $CO_2/O_2$ level appropriate for a given cell type or cell line) to allow senescence to be established. As discussed herein, senescence of cells may be determined by determining any number of characteristics, such as changes in morphology (as viewed by microscopy, for example); production of, for example, senescence-associated β-galactosidase (SA-β-gal), p16INK4a, p21, or any one or more SASP factors (e.g., IL-6, MMP3). A sample of the senescent cells is then contacted with a candidate agent (i.e., mixed with, combined, or in some manner permitting the cells and the agent to interact). Persons skilled in the art will appreciate that the assay will include the appropriate controls, negative and positive, either historical or performed concurrently. For example, a sample of control non-senescent cells that have been cultured similarly as the senescent cells but not exposed to a senescence inducing agent are contacted with the candidate agent. The level of survival of the senescent cells is determined and compared with the level of survival of the non-senescent cells. A senolytic agent is identified when the level of survival of the senescent cells is less than the level of survival of the non-senescent cells.

In some embodiments, the above described method to identify a senolytic agent may further comprise steps for identifying whether the senolytic agent is useful for treating osteoarthritis. The method may further comprise contacting the identified senolytic agent with cells capable of producing collagen; and determining the level of collagen produced by the cells. Embodiments, the cells are chondrocytes and the collagen is Type 2 collagen. The method may further comprise administering a candidate senolytic agent to a non-human animal with arthritic lesions in a joint and determining one or more of (a) the level of senescent cells in the joint; (b) physical function of the animal; (c) the level of one or more markers of inflammation; (d) histology of the joint; and (e) the level of Type 2 collagen produced, thereby determining therapeutic efficacy of the senolytic agent wherein one or more of the following is observed in the treated animal compared with an animal not treated with the senolytic agent: (i) a decrease in the level of senescent cells in the joint of the treated animal; (ii) improved physical function of the treated animal; (iii) a decrease in the level of one or more markers of inflammation in the treated animal; (iv) increased histological normalcy in the joint of the treated animal; and (v) an increase in the level of Type 2 collagen produced in the treated animal. As described herein and in the art, the physical function of the animal may be determined by techniques that determine the sensitivity of a leg to an induced or natural osteoarthritic condition, for example, by the animal's tolerance to bear weight on an affected limb or the ability of the animal to move away from an unpleasant stimulus, such as heat or cold. Determining the effectiveness of an agent to kill senescent cells as described herein in an animal model may be performed using one or more statistical analyses with which a skilled person will be familiar. Statistical analyses as described herein and routinely practiced in the art may be applied to analyze data.

In other embodiments, the above described method to identify a senolytic agent may further comprise steps for identifying whether the senolytic agent is useful for treating a cardiovascular disease caused by or associated with arteriosclerosis. Accordingly, the method may further comprise administering the senolytic candidate agent in non-human animals or in animal models for determining the effectiveness of an agent to reduce the amount of plaque, to inhibit formation of plaque in an atherosclerotic artery, to reduce the lipid content of an atherosclerotic plaque (i.e., reduce, decrease the amount of lipid in a plaque), and/or to cause an increase or to enhance fibrous cap thickness of a plaque. Sudan staining may be used to detect the level of lipid in an atherosclerotic vessel. Immunohistology, assays for determining the level of inflammatory molecules (e.g., IL-6), and/or assays for determining the level of senescence markers as noted above, may all be performed according to methods described herein and routinely practiced in the art.

In a specific embodiment, methods described herein for identifying a senolytic agent may further comprise administering a candidate senolytic agent to a non-human animal with atherosclerotic plaque and determining one or more of (a) the level of senescent cells in the artery; (b) physical function of the animal; (c) the level of one or more markers of inflammation; (d) histology of the affected blood vessel(s) (e.g., artery); and thereby determining therapeutic efficacy of the senolytic agent wherein one or more of the following is observed in the treated animal compared with an animal not treated with the senolytic agent: (i) a decrease in the level of senescent cells in the artery of the treated animal; (ii) improved physical function of the treated animal; (iii) a decrease in the level of one or more markers of inflammation in the treated animal; (iv) increased histological normalcy in the artery of the treated animal. As described herein and in the art, the physical function of the animal may be determined by measuring physical activity. Statistical analyses as described herein and routinely practiced in the art may be applied to analyze data.

In some embodiments, methods described herein for identifying a senolytic agent may comprise administering a candidate senolytic agent to a non-human animal pulmonary disease model such as a bleomycin model or a smoke-exposure animal model and determining one or more of (a) the level of senescent cells in a lung; (b) lung function of the animal; (c) the level of one or more markers of inflammation; (d) histology of pulmonary tissue, thereby determining therapeutic efficacy of the senolytic agent wherein one or more of the following is observed in the treated animal compared with an animal not treated with the senolytic agent: (i) a decrease in the level of senescent cells in the lungs and pulmonary tissue of the treated animal; (ii) improved lung function of the treated animal; (iii) a decrease in the level of one or more markers of inflammation in the treated animal; and (iv) increased histological normalcy in the pulmonary tissue of the treated animal. Respiratory measurements may be taken to determine elastance, compliance, static compliance, and peripheral capillary oxygen saturation ($SpO_2$). Lung function may be evaluated by determining any one of numerous measurements, such as expiratory reserve volume (ERV), forced vital capacity (FVC), forced expiratory volume (LEV) (e.g., LEV in one second, FEV1), FEV1/FEV ratio, forced expiratory flow 25% to 75%, and maximum voluntary ventilation (MVVpeak expiratory flow (PEF), slow vital capacity (SVC). Total lung volumes include total lung capacity (TEC), vital capacity (VC),), residual volume (RV), and functional residual capacity (FRC). Gas exchange across alveolar capillary membrane can be measured using diffusion capacity for carbon monoxide (DECO). Peripheral capillary oxygen saturation (SpO.sub.2) can also be measured. Statistical analyses as described herein and routinely practiced in the art may be applied to analyze data.

Methods of Treatment and Prevention of Senescence-Associated Diseases and Disorders Methods are provided herein for treating conditions, diseases, or disorders related to, associated with, or caused by cellular senescence, including age-related diseases and disorders in a subject in need thereof. A senescence-associated disease or disorder may also be called herein a senescent cell-associated disease or disorder. Senescence-associated diseases and disorders include, for example, age-related diseases and disorders induced by senescence; pulmonary diseases and disorders; neurological diseases and disorders (e.g., neurodegenerative diseases and disorders); eye diseases and disorders; metabolic diseases and disorders; cardiovascular diseases and disorders; inflammatory diseases and disorders; autoimmune diseases and disorders; dermatological diseases and disorders; skin conditions; age-related diseases; and transplant related diseases and disorders. A prominent feature of aging is a gradual loss of function, or degeneration that occurs at the molecular, cellular, tissue, and organismal levels. Age-related degeneration gives rise to well-recognized pathologies, such as sarcopenia, atherosclerosis and heart failure, osteoporosis, pulmonary insufficiency, renal failure, neurodegeneration (including macular degeneration, Alzheimer's disease, and Parkinson's disease), and many others. Although different mammalian species vary in their susceptibilities to specific age-related pathologies, collectively, age-related pathologies generally rise with approximately exponential kinetics beginning at about the mid-point of the species-specific life span (e.g., 50-60 years of age for humans) (see, e.g., Campisi, Annu. Rev. Physiol. 75 (2013) 685-705; Naylor et al., Clin. Pharmacol. Ther. 93 (2013) 105-116).

Examples of senescence-associated conditions, disorders, or diseases that may be treated by administering any one of the senolytic agents described herein according to the methods described herein include, aging-related diseases and disorders (e.g., kyphosis, renal dysfunction, frailty, hair loss, hearing loss, muscle fatigue, skin conditions, sarcopenia, and herniated intervertebral disc) and other age-related diseases that are induced by senescence (e.g., diseases/disorders resulting from irradiation, chemotherapy, smoking tobacco, eating a high fat/high sugar diet, and environmental factors); pulmonary diseases (e.g., idiopathic pulmonary fibrosis, chronic obstructive pulmonary disease (COPD), emphysema, obstructive bronchiolitis, asthma); proliferative diseases including cancer and metastasis; side effects associated with chemotherapeutic side or radiotherapy; fibrotic diseases and disorders (e.g., cystic fibrosis, renal fibrosis, liver fibrosis, pulmonary fibrosis, oral submucous fibrosis, cardiac fibrosis, and pancreatic fibrosis); cognitive diseases (e.g., mild cognitive impairment (MCI), Alzheimer's disease and other dementias; Huntington's disease); motor function diseases and disorders (e.g., Parkinson's disease, motor neuron dysfunction (MND); Huntington's disease); cerebrovascular disease; emphysema; osteoarthritis; benign prostatic hypertrophy; ophthalmic diseases or disorders (e.g., age-related macular degeneration, cataracts, glaucoma, vision loss, presbyopia); metabolic diseases and disorders (e.g., obesity, diabetes, metabolic syndrome); cardiovascular disease (e.g., atherosclerosis, cardiac diastolic dysfunction, aortic aneurysm, angina, arrhythmia, cardiomyopathy, congestive heart failure, coronary artery disease, myocardial infarction, endocarditis, hypertension, carotid artery disease, peripheral vascular diseases, cardiac stress resistance, cardiac fibrosis); inflammatory/autoimmune diseases and disorders (e.g., osteoarthritis, eczema, psoriasis, osteoporosis, mucositis, transplantation related diseases and disorders); dermatological diseases e.g. diabetic ulcer, wound healing and skin nevi. In certain embodiments, any one or more of the diseases or disorders described above or herein may be excluded.

In some embodiments, methods are provided for treating a senescence-associated disease or disorder by killing senescent cells (i.e., established senescent cells) associated with the disease or disorder in a subject who has the disease or disorder by administering a senolytic agent, wherein the disease or disorder is a disease of aging (e.g. frailty, muscle weakness, cognitive impairment); idiopathic pulmonary fibrosis; chronic obstructive pulmonary disease (COPD); renal or liver fibrosis; metastasis or other proliferative disorder; osteoarthritis; or atherosclerosis.

Age-Related Diseases and Disorders

A senolytic agent described herein selectively kills senescent cells. In this way, targeting senescent cells during the course of aging may be a preventative strategy. Accordingly, administration of a senolytic agent described herein to a subject may prevent comorbidity and delay mortality in an older subject. Further, selective killing of senescent cells may boost the immune system, extend the health span, and improve the quality of life in a subject.

A senolytic agent may also be useful for treating or preventing (i.e., reducing the likelihood of occurrence) of an age-related disease or disorder that occurs as part of the natural aging process or that occurs when the subject is exposed to a senescence inducing agent or factor (e.g., irradiation, chemotherapy, smoking tobacco, high-fat/high sugar diet, other environmental factors). An age-related disorder or disease or an age-sensitive trait may be associated with a senescence-inducing stimulus. The efficacy of a method of treatment described herein may be manifested by reducing the number of symptoms of an age-related disorder or age-sensitive trait associated with a senescence-inducing stimulus, decreasing the severity of one or more symptoms, or delaying the progression of an age-related disorder or age-sensitive trait associated with a senescence-inducing stimulus. In other embodiments, preventing an age-related disorder or age-sensitive trait associated with a senescence-inducing stimulus refers to preventing (i.e., reducing the likelihood of occurrence) or delaying onset of an age-related disorder or age-sensitive trait associated with a senescence-inducing stimulus, or reoccurrence of one or more age-related disorder or age-sensitive trait associated with a senescence-inducing stimulus. Age related diseases or conditions include, for example, renal dysfunction, kyphosis, herniated intervertebral disc, frailty, cognitive impairment, hair loss, hearing loss, vision loss (blindness or impaired vision), muscle fatigue, skin conditions, skin nevi, diabetes, metabolic syndrome, and sarcopenia. Vision loss refers to the absence of vision when a subject previously had vision. Various scales have been developed to describe the extent of vision and vision loss based on visual acuity. Age-related diseases and conditions also include dermatological conditions, for example without limitation, treating one or more of the following conditions: wrinkles, including superficial fine wrinkles; hyperpigmentation; scars; keloid; dermatitis; psoriasis; eczema (including seborrheic eczema); rosacea; vitiligo; ichthyosis vulgaris; dermatomyositis; and actinic keratosis. Frailty has been defined as a clinically recognizable state of increased vulnerability resulting from aging-associated decline in reserve and function across multiple physiologic systems that compromise a subject's ability to cope with every day or acute stressors. Frailty may be characterized by compromised energetics characteristics such as low grip strength, low energy, slowed walking speed, low physical activity, and/or unintentional weight loss. Studies have suggested that a patient may be diagnosed with frailty when three of five of the foregoing characteristics are observed (see, e.g., Fried et al., J. Gerontol. A Biol. Sci. Med, Sci. 56(3) (2001) M146-M156; Xue, Clin. Geriatr. Med. 27(1) (2001) 1-15). In certain embodiments, aging and diseases and disorders related to aging may be treated or prevented (i.e., the likelihood of occurrence of is reduced) by administering a senolytic agent. The senolytic agent may inhibit senescence of adult stem cells or inhibit accumulation, kill, or facilitate removal of adult stem cells that have become senescent. The importance of preventing senescence in stem cells to maintain regenerative capacity of tissues is discussed, e.g., in Park et al., J. Clin. Invest. 113 (2004) 175-179; and Sousa-Victor, Nature 506 (2014) 316-321.

Methods of measuring aging are known in the art. For example, aging may be measured in the bone by incident non-vertebral fractures, incident hip fractures, incident total fractures, incident vertebral fractures, incident repeat fractures, functional recovery after fracture, bone mineral density decrease at the lumbar spine and hip, rate of knee buckling, NSAID use, number of joints with pain, and osteoarthritis. Aging may also be measured in the muscle by functional decline, rate of falls, reaction time and grip strength, muscle mass decrease at upper and lower extremities, and dual tasking 10-meter gait speed. Further, aging may be measured in the cardiovascular system by systolic and diastolic blood pressure change, incident hypertension, major cardiovascular events such as myocardial infarction, stroke, congestive heart disease, and cardiovascular mortality. Additionally, aging may be measured in the brain by cognitive decline, incident depression, and incident dementia. Also, aging may be measured in the immune system by rate of infection, rate of upper respiratory infections, rate of flu-like illness, incident severe infections that lead to hospital admission, incident cancer, rate of implant infections, and rate of gastrointestinal infections. Other indications of aging may include, but not limited to, decline in oral health, tooth loss, rate of GI symptoms, change in fasting glucose and/or insulin levels, body composition, decline in kidney function, quality of life, incident disability regarding activities of daily living, and incident nursing home admission. Methods of measuring skin aging are known in the art and may include trans-epidermal water loss (TEWL), skin hydration, skin elasticity, area ratio analysis of crow's feet, sensitivity, radiance, roughness, spots, laxity, skin tone homogeneity, softness, and relief (variations in depth).

Administration of a senolytic agent described herein can prolong prolonging survival when compared to expected survival if a subject were not receiving treatment. Subjects in need of treatment include those who already have the disease or disorder as well as subjects prone to have or at risk of developing the disease or disorder, and those in which the disease, condition, or disorder is to be treated prophylactically. A subject may have a genetic predisposition for developing a disease or disorder that would benefit from clearance of senescent cells or may be of a certain age wherein receiving a senolytic agent would provide clinical benefit to delay development or reduce severity of a disease, including an age-related disease or disorder.

In other embodiments, a method is provided for treating a senescence-associated disease or disorder that further comprises identifying a subject who would benefit from treatment with a senolytic agent described herein (i.e., phenotyping; individualized treatment). This method comprises first detecting the level of senescent cells in the subject, such as in a particular organ or tissue of the subject. A biological sample may be obtained from the subject, for example, a blood sample, serum or plasma sample, biopsy specimen, body fluids (e.g., lung lavage, ascites, mucosal washings, synovial fluid, vitreous fluid, spinal fluid), bone marrow, lymph nodes, tissue explant, organ culture, or any other tissue or cell preparation from a subject. The level of senescent cells may be determined according to any of the in vitro assays or techniques described herein. For example, senescent cells may be detected by morphology (as viewed by microscopy, for example); production of senescence associated markers such as, senescence-associated β-galactosidase (SA-β-gal), p16INK4a, p21, PAI-1, or any one or more SASP factors (e.g., IL-6, MMP3). The senescent cells and non-senescent cells of the biological sample may also be used in an in vitro cell assay in which the cells are exposed to any one of the senolytic agents described herein to determine the capability of the senolytic agent to kill the subject's senescent cells without undesired toxicity to non-senescent cells. In addition, these methods may be used to monitor the level of senescent cells in the subject before, during, and after treatment with a senolytic agent. In certain embodiments, the presence of senescent cells, may be detected (e.g., by determining the level of a senescent cell marker expression of mRNA, for example), and the treatment course and/or non-treatment interval can be adjusted accordingly. Pulmonary Diseases and Disorders In some embodiments, methods are provided for treating or preventing (i.e., reducing the likelihood of occurrence of) a senescence-associated disease or disorder that is a pulmonary disease or disorder by killing senescent cells (i.e., established senescent cells) associated with the disease or disorder in a subject who has the disease or disorder by administering senolytic agents described herein. Senescence associated pulmonary diseases and disorders include, for example, idiopathic pulmonary fibrosis (IPF), chronic obstructive pulmonary disease (COPD), asthma, cystic fibrosis, bronchiectasis, and emphysema.

COPD is a lung disease defined by persistently poor airflow resulting from the breakdown of lung tissue (emphysema) and the dysfunction of the small airways (obstructive bronchiolitis). Primary symptoms of COPD include shortness of breath, wheezing, chest tightness, chronic cough, and excess sputum production. Elastase from cigarette smoke-activated neutrophils and macrophages disintegrates the extracellular matrix of alveolar structures, resulting in enlarged air spaces and loss of respiratory capacity (see, e.g., Shapiro et al., Am. J. Respir. Cell Mol. Biol. 32 (2005) 367-372). COPD is most commonly caused by tobacco smoke (including cigarette smoke, cigar smoke, secondhand smoke, pipe smoke), occupational exposure (e.g., exposure to dust, smoke or fumes), and pollution, occurring over decades thereby implicating aging as a risk factor for developing COPD.

The processes involved in causing lung damage include, for example, oxidative stress produced by the high concentrations of free radicals in tobacco smoke; cytokine release due to inflammatory response to irritants in the airway; and impairment of anti-protease enzymes by tobacco smoke and free radicals, allowing proteases to damage the lungs. Genetic susceptibility can also contribute to the disease. In about 1% percent of people with COPD, the disease results from a genetic disorder that causes low level production of alpha-1-antitrypsin in the liver. The enzyme is normally secreted into the bloodstream to help protect the lungs.

Pulmonary fibrosis is a chronic and progressive lung disease characterized by stiffening and scarring of the lung, which may lead to respiratory failure, lung cancer, and heart failure. Fibrosis is associated with repair of epithelium. Fibroblasts are activated, production of extracellular matrix proteins is increased, and transdifferentiation to contractile myofibroblasts contribute to wound contraction. A provisional matrix plugs the injured epithelium and provides a scaffold for epithelial cell migration, involving an epithelial-mesenchymal transition (EMF). Blood loss associated with epithelial injury induces platelet activation, production of growth factors, and an acute inflammatory response. Normally, the epithelial barrier heals and the inflammatory response resolves. However, in fibrotic disease the fibroblast response continues, resulting in unresolved wound healing. Formation of fibroblastic foci is a feature of the disease, reflecting locations of ongoing fibrogenesis. As the name connotes, the etiology of IPF is unknown. The involvement of cellular senescence in IPF is suggested by the observations that the incidence of the disease increases with age and that lung tissue in IPF patients is enriched for SA-β-Gal-positive cells and contains elevated levels of the senescence marker p21 (see, e.g., Minagawa et al., Am. J. Physiol. Lung Cell. Mol. Physiol. 300 (2011) L391-L401; see also, e.g., Naylor et al., supra). Short telomeres are a risk factor common to both IPF and cellular senescence (see, e.g., Alder et al., Proc. Natl. Acad. Sci. USA 105 (2008) 13051-13056). Without wishing to be bound by theory, the contribution of cellular senescence to IPF is suggested by the report that SASP components of senescent cells, such as IL-6, IL-8, and IL-1β, promote fibroblast-to-myofibroblast differentiation and epithelial-mesenchymal transition, resulting in extensive remodeling of the extracellular matrix of the alveolar and interstitial spaces (see, e.g., Minagawa et al., supra).

Subjects at risk of developing pulmonary fibrosis include those exposed to environmental or occupational pollutants, such as asbestosis and silicosis; who smoke cigarettes; having some typical connective tissue diseases such as rheumatoid arthritis, SEE and scleroderma; having other diseases that involve connective tissue, such as sarcoidosis and Wegener's granulomatosis; having infections; taking certain medications (e.g., amiodarone, bleomycin, busulfan, methotrexate, and nitrofurantoin); those subject to radiation therapy to the chest; and those whose family member has pulmonary fibrosis.

Symptoms of COPD may include any one of shortness of breath, especially during physical activities; wheezing; chest tightness; having to clear your throat first thing in the morning because of excess mucus in the lungs; a chronic cough that produces sputum that may be clear, white, yellow or greenish; blueness of the lips or fingernail beds (cyanosis); frequent respiratory infections; lack of energy; unintended weight loss (observed in later stages of disease). Subjects with COPD may also experience exacerbations, during which symptoms worsen and persist for days or longer. Symptoms of pulmonary fibrosis are known in the art and include shortness of breath, particularly during exercise; dry, hacking cough; fast, shallow breathing; gradual unintended weight loss; tiredness; aching joints and muscles; and clubbing (widening and rounding of the tips of the fingers or toes).

Subjects suffering from COPD or pulmonary fibrosis can be identified using standard diagnostic methods routinely practiced in the art. Monitoring the effect of one or more senolytic agents administered to a subject who has or who is at risk of developing a pulmonary disease may be performed using the methods typically used for diagnosis. Generally, one or more of the following exams or tests may be performed: physical exam, patient's medical history, patient's family's medical history, chest X-ray, lung function tests (such as spirometry), blood test (e.g., arterial blood gas analysis), bronchoalveolar lavage, lung biopsy, CT scan, and exercise testing.

Other pulmonary diseases or disorders that may be treated by using a senolytic agent include, for example, emphysema, asthma, bronchiectasis, and cystic fibrosis (see, e.g., Fischer et al., Am J Physiol Lung Cell Mol Physiol. 304(6) (2013) L394-400). These diseases may also be exacerbated by tobacco smoke (including cigarette smoke, cigar smoke, secondhand smoke, pipe smoke), occupational exposure (e.g., exposure to dust, smoke or fumes), infection, and/or pollutants that induce cells into senescence and thereby contribute to inflammation. Emphysema is sometimes considered as a subgroup of COPD.

Bronchiectasis results from damage to the airways that causes them to widen and become flabby and scarred. Bronchiectasis usually is caused by a medical condition that injures the airway walls or inhibits the airways from clearing mucus. Examples of such conditions include cystic fibrosis and primary ciliary dyskinesia (PCD). When only one part of the lung is affected, the disorder may be caused by a blockage rather than a medical condition.

The methods described herein for treating or preventing (i.e., reducing the likelihood or occurrence of) a senescence associated pulmonary disease or disorder may also be used for treating a subject who is aging and has loss (or degeneration) of pulmonary function (i.e., declining or impaired pulmonary function compared with a younger subject) and/or degeneration of pulmonary tissue. The respiratory system undergoes various anatomical, physiological and immunological changes with age. The structural changes include chest wall and thoracic spine deformities that can impair the total respiratory system compliance resulting in increased effort to breathe. The respiratory system undergoes structural, physiological, and immunological changes with age. An increased proportion of neutrophils and lower percentage of macrophages can be found in bronchoalveolar lavage (BAL) of older adults compared with younger adults. Persistent low grade inflammation in the lower respiratory tract can cause proteolytic and oxidant-mediated injury to the lung matrix resulting in loss of alveolar unit and impaired gas exchange across the alveolar membrane seen with aging. Sustained inflammation of the lower respiratory tract may predispose older adults to increased susceptibility to toxic environmental exposure and accelerated lung function decline. (See, for example, Sharma et al., Clinical Interventions in Aging 1 (2006) 253-260). Oxidative stress exacerbates inflammation during aging (see, e.g., Brod, Inflamm. Res. 49 (2000) 561-570; Hendel et al., Cell Death and Differentiation 17 (2010) 596-606). Alterations in redox balance and increased oxidative stress during aging precipitate the expression of cytokines, chemokines, and adhesion molecules, and enzymes (see, e.g., Chung et al., Ageing Res. Rev. 8 (2009) 18-30). Constitutive activation and recruitment of macrophages, T cells, and mast cells foster release of proteases leading to extracellular matrix degradation, cell death, remodeling, and other events that can cause tissue and organ damage during chronic inflammation (see, e.g., Demedts et al., Respir. Res. 7 (2006) 53-63). By administering a senolytic agent to an aging subject (which includes a middle-aged adult who is asymptomatic), the decline in pulmonary function may be decelerated or inhibited by killing and removing senescent cells from the respiratory tract.

The effectiveness of a senolytic agent can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of the treatment of a senolytic agent or pharmaceutical composition comprising the agent can be analyzed using techniques known in the art, such as comparing symptoms of patients suffering from or at risk of the pulmonary disease that have received the treatment with those of patients without such a treatment or with placebo treatment. In addition, methods and techniques that evaluate mechanical functioning of the lung, for example, techniques that measure lung capacitance, elastance, and airway hypersensitivity may be performed. To determine lung function and to monitor lung function throughout treatment, any one of numerous measurements may be obtained, expiratory reserve volume (ERV), forced vital capacity (FVC), forced expiratory volume (FEV) (e.g., FEV in one second, FEV1), FEV1/FEV ratio, forced expiratory flow 25% to 75%, and maximum voluntary ventilation (MW), peak expiratory flow (PEF), slow vital capacity (SVC). Total lung volumes include total lung capacity (TEC), vital capacity (VC), residual volume (RV), and functional residual capacity (FRC). Gas exchange across alveolar capillary membrane can be measured using diffusion capacity for carbon monoxide (DECO). Peripheral capillary oxygen saturation ($SpO_2$) can also be measured; normal oxygen levels are typically between 95% and 100%. An $SpO_2$ level below 90% suggests the subject has hypoxemia. Values below 80% are considered critical and requiring intervention to maintain brain and cardiac function and avoid cardiac or respiratory arrest.

Metastasis

In some embodiments, methods are provided for treating or preventing (i.e., reducing the likelihood of occurrence or development of) a senescent cell associated disease (or disorder or condition), which is metastasis. The senolytic agents described herein may also be used according to the methods described herein for treating or preventing (i.e., reducing the likelihood of occurrence of) metastasis (i.e., the spreading and dissemination of cancer or tumor cells) from one organ or tissue to another organ or tissue in the body.

A senescent cell-associated disease or disorder includes metastasis, and a subject who has a cancer may benefit from administration of a senolytic agent as described herein for inhibiting metastasis. Such a senolytic agent when administered to a subject who has a cancer according to the methods described herein may inhibit tumor proliferation. Metastasis of a cancer occurs when the cancer cells (i.e., tumor cells) spread beyond the anatomical site of origin and initial colonization to other areas throughout the body of the subject. Tumor proliferation may be determined by tumor size, which can be measured in various ways familiar to a person skilled in the art, such as by PET scanning, MRI, CAT scan, biopsy, for example. The effect of the therapeutic agent on tumor proliferation may also be evaluated by examining differentiation of the tumor cells.

As used herein and in the art, the terms cancer or tumor are clinically descriptive terms that encompass diseases typically characterized by cells exhibiting abnormal cellular proliferation. The term cancer is generally used to describe a malignant tumor or the disease state arising from the tumor. Alternatively, an abnormal growth may be referred to in the art as a neoplasm. The term tumor, such as in reference to a tissue, generally refers to any abnormal tissue growth that is characterized, at least in part, by excessive and abnormal cellular proliferation. A tumor may be metastatic and capable of spreading beyond its anatomical site of origin and initial colonization to other areas throughout the body of the subject. A cancer may comprise a solid tumor or may comprise a "liquid" tumor (e.g., leukemia and other blood cancers).

Cells are induced to senesce by cancer therapies, such as radiation and certain chemotherapy drugs. The presence of senescent cells increases secretion of inflammatory molecules, promotes tumor progression, which may include promoting tumor growth and increasing tumor size, promoting metastasis, and altering differentiation. When senescent cells are destroyed, tumor progression is significantly inhibited, resulting in tumors of small size and with little or no observed metastatic growth (see, e.g., International Publication No. WO 2013/090645).

In some embodiments, methods are provided for preventing (i.e., reducing the likelihood of occurrence of), inhibiting, or retarding metastasis in a subject who has a cancer by administering a senolytic agent as described herein. In other embodiments, the senolytic agent is administered on one or more days within a treatment window (i.e., treatment course) of no longer than 7 days or 14 days. In still other embodiments, the treatment course is no longer than 2, 3, 4, 5, 6, 7, 8, 9, 10, 11, 12, 13, 14, 15, 16, 17, 18, 19, 20, or no longer than 21 days. In still other embodiments, the treatment course is a single day. In still other embodiments, the senolytic agent is administered on two or more days within a treatment window of no longer than 7 days or 14 days.

Because cells may be induced to senesce by cancer therapies, such as radiation and certain chemotherapy drugs (e.g., doxorubicin; paclitaxel; gemcitabine; pomalidomide; lenalidomide), a senolytic agent described herein may be administered after the chemotherapy or radiotherapy to kill (or facilitate killing) of these senescent cells. As discussed herein and understood in the art, establishment of senescence, such as shown by the presence of a senescence-associated secretory phenotype (SASP), occurs over several days; therefore, administering a senolytic agent to kill senescent cells, and thereby reduce the likelihood of occurrence or reduce the extent of metastasis, is initiated when senescence has been established. As discussed herein, the following treatment courses for administration of the senolytic agent may be used in methods described herein for treating or preventing (i.e., reducing the likelihood of occurrence, or reducing the severity) a chemotherapy or radiotherapy side effect.

In certain embodiments, when chemotherapy or radiotherapy is administered in a treatment cycle of at least one day on-therapy (i.e., chemotherapy or radiotherapy)) followed by at least 3, 4, 5, 6, 7, 8, 9, 10, 11, 12, 13, 14 (or about 2 weeks), 15, 16, 17, 18, 19, 20, 21 (or about 3 weeks) days, or about 4 weeks (about one month) off-therapy (i.e., off chemo- or radio-therapy), the senolytic agent is administered on one or more days during the off-therapy time interval (time period) beginning on or after the second day of the off-therapy time interval and ending on or before the last day of the off-therapy time interval. By way of illustrative example, if n is the number of days off-therapy, then the senolytic agent is administered on at least one day and no more than n−1 days of the off-therapy time interval. In some embodiments when chemotherapy or radiotherapy is administered in a treatment cycle of at least one day on-therapy (i.e., chemotherapy or radiotherapy) followed by at least one week off-therapy, the senolytic agent is administered on one or more days during the off-therapy time interval beginning on or after the second day of the off-therapy time interval and ending on or before the last day of the off-therapy time interval.

A chemotherapy may be referred to as a chemotherapy, chemotherapeutic, or chemotherapeutic drug. Many chemotherapeutics are compounds referred to as small organic molecules. Chemotherapy is a term that is also used to describe a combination of chemotherapeutic drugs that are administered to treat a particular cancer. As understood by a person skilled in the art, a chemotherapy may also refer to a combination of two or more chemotherapeutic molecules that are administered coordinately and which may be referred to as combination chemotherapy. Numerous chemotherapeutic drugs are used in the oncology art and include, without limitation, alkylating agents; antimetabolites; anthracyclines, plant alkaloids; and topoisomerase inhibitors.

A cancer that may metastasize may be a solid tumor or may be a liquid tumor (e.g., a blood cancer, for example, a leukemia). Cancers that are liquid tumors are classified in the art as those that occur in blood, bone marrow, and lymph nodes and include generally, leukemias (myeloid and lymphocytic), lymphomas (e.g., Hodgkin lymphoma), and melanoma (including multiple myeloma). Leukemias include for example, acute lymphoblastic leukemia (ALL), acute myeloid leukemia (AML), chronic lymphocytic leukemia (CLL), chronic myelogenous leukemia (CML), and hairy cell leukemia. Cancers that are solid tumors and occur in greater frequency in humans include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer (including squamous cell skin cancer), renal cancer, head and neck cancers, throat cancer, squamous carcinomas that form on the moist mucosal linings of the nose, mouth, throat, etc.), bladder cancer, osteosarcoma (bone cancer), cervical cancer, endometrial cancer, esophageal cancer, liver cancer, and kidney cancer. In certain specific embodiments, the senescent cell-associated disease or disorder treated or prevented (i.e., likelihood of occurrence or development is reduced) by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

The methods described herein are also useful for inhibiting, retarding or slowing progression of metastatic cancer of any one of the types of tumors described in the medical art. Types of cancers (tumors) include the following: adrenocortical carcinoma, childhood adrenocortical carcinoma, aids-related cancers, anal cancer, appendix cancer, basal cell carcinoma, childhood basal cell carcinoma, bladder cancer, childhood bladder cancer, bone cancer, brain tumor, childhood astrocytomas, childhood brain stem glioma, childhood central nervous system atypical teratoid/rhabdoid tumor, childhood central nervous system embryonal tumors, childhood central nervous system germ cell tumors, childhood craniopharyngioma brain tumor, childhood ependymoma brain tumor, breast cancer, childhood bronchial tumors, carcinoid tumor, childhood carcinoid tumor, gastrointestinal carcinoid tumor, carcinoma of unknown primary, childhood carcinoma of unknown primary, childhood cardiac (heart) tumors, cervical cancer, childhood cervical cancer, childhood chordoma, chronic myeloproliferative disorders, colon cancer, colorectal cancer, childhood colorectal cancer, extrahepatic bile duct cancer, ductal carcinoma in situ (DCIS), endometrial cancer, esophageal cancer, childhood esophageal cancer, childhood esthesioneuroblastoma, eye cancer, malignant fibrous histiocytoma of bone, gallbladder cancer, gastric (stomach) cancer, childhood gastric (stomach) cancer, gastrointestinal stromal tumors (GIST), childhood gastrointestinal stromal tumors (GIST), childhood extracranial germ cell tumor, extragonadal germ cell tumor, gestational trophoblastic tumor, glioma, head and neck cancer, childhood head and neck cancer, hepatocellular (liver) cancer, hypopharyngeal cancer, kidney cancer, renal cell kidney cancer, Wilms tumor, childhood kidney tumors, Langerhans cell histiocytosis, laryngeal cancer, childhood laryngeal cancer, leukemia, acute lymphoblastic leukemia (ALL), acute myeloid leukemia (AML), chronic lymphocytic leukemia (CLL), chronic myelogenous leukemia (CML), hairy cell leukemia, lip cancer, liver cancer (primary), childhood liver cancer (primary), lobular carcinoma in situ (LCIS), lung cancer, non-small cell lung cancer, small cell lung cancer, lymphoma, aids-related lymphoma, Burkitt lymphoma, cutaneous T-cell lymphoma, Hodgkin lymphoma, non-Hodgkin lymphoma, primary central nervous system lymphoma (CNS), melanoma, childhood melanoma, intraocular (eye) melanoma, Merkel cell carcinoma, malignant mesothelioma, childhood malignant mesothelioma, metastatic squamous neck cancer with occult primary, midline tract carcinoma involving the NUT gene, mouth cancer, childhood multiple endocrine neoplasia syndromes, mycosis fungoides, myelodysplastic syndromes, myelodysplastic neoplasms, myeloproliferative neoplasms, multiple myeloma, nasal cavity cancer, nasopharyngeal cancer, childhood nasopharyngeal cancer, neuroblastoma, oral cancer, childhood oral cancer, oropharyngeal cancer, ovarian cancer, childhood ovarian cancer, epithelial ovarian cancer, low malignant potential tumor ovarian cancer, pancreatic cancer, childhood pancreatic cancer, pancreatic neuroendocrine tumors (islet cell tumors), childhood papillomatosis, paraganglioma, paranasal sinus cancer, parathyroid cancer, penile cancer, pharyngeal cancer, pheochromocytoma, pituitary tumor, plasma cell neoplasm, childhood pleuropulmonary blastoma, prostate cancer, rectal cancer, renal pelvis transitional cell cancer, retinoblastoma, salivary gland cancer, childhood salivary gland cancer, Ewing sarcoma family of tumors, Kaposi Sarcoma, osteosarcoma, rhabdomyosarcoma, childhood rhabdomyosarcoma, soft tissue sarcoma, uterine sarcoma, Sezary syndrome, childhood skin cancer, nonmelanoma skin cancer, small intestine cancer, squamous cell carcinoma, childhood squamous cell carcinoma, testicular cancer, childhood testicular cancer, throat cancer, thymoma and thymic carcinoma, childhood thymoma and thymic carcinoma, thyroid cancer, childhood thyroid cancer, ureter transitional cell cancer, urethral cancer, endometrial uterine cancer, vaginal cancer, vulvar cancer, and Waldenstrom macroglobulinemia.

Chemotherapy and Radiotherapy Side Effects

In other embodiments, the senescence cell associated disorder or condition is a chemotherapeutic side effect or a radiotherapy side effect. Examples of chemotherapeutic agents that induce non-cancer cells to senesce include anthracyclines (such as doxorubicin, daunorubicin); taxols (e.g., paclitaxel); gemcitabine; pomalidomide; and lenalidomide. One or more of the senolytic agents administered as described herein may be used for treating and/or preventing (i.e., reducing the likelihood or occurrence of) a chemotherapeutic side effect or a radiotherapy side effect. Removal or destruction of senescent cells may ameliorate acute toxicity, including acute toxicity comprising energy imbalance, of a chemotherapy or radiotherapy. Acute toxic side effects include but are not limited to gastrointestinal toxicity (e.g., nausea, vomiting, constipation, anorexia, diarrhea), peripheral neuropathy, fatigue, malaise, low physical activity, hematological toxicity (e.g., anemia), hepatotoxicity, alopecia (hair loss), pain, infection, mucositis, fluid retention, dermatological toxicity (e.g., rashes, dermatitis, hyperpigmentation, urticaria, photosensitivity, nail changes), mouth (e.g., oral mucositis), gum or throat problems, or any toxic side effect caused by a chemotherapy or radiotherapy. For example, toxic side effects caused by radiotherapy or chemotherapy may be ameliorated by the methods described herein. Accordingly, in certain embodiments, methods are provided herein for ameliorating (reducing, inhibiting, or preventing occurrence (i.e., reducing the likelihood of occurrence)) acute toxicity or reducing severity of a toxic side effect (i.e., deleterious side effect) of a chemotherapy or radiotherapy or both in a subject who receives the therapy, wherein the method comprises administering to the subject an agent that selectively kills, removes, or destroys or facilitates selective destruction of senescent cells. Administration of senolytic agents described herein for treating or reducing the likelihood of occurrence, or reducing the severity of a chemotherapy or radiotherapy side effect may be accomplished by the same treatment courses described above for treatment/prevention of metastasis. As described for treating or preventing (i.e., reducing the likelihood of occurrence of) metastasis, the senolytic agent is administered during the off-chemotherapy or off-radiotherapy time interval or after the chemotherapy or radiotherapy treatment regimen has been completed.

In more specific embodiments, the acute toxicity is an acute toxicity comprising energy imbalance and may comprise one or more of weight loss, endocrine change(s) (e.g., hormone imbalance, change in hormone signaling), and change(s) in body composition. In certain embodiments, an acute toxicity comprising energy imbalance relates to decreased or reduced ability of the subject to be physically active, as indicated by decreased or diminished expenditure of energy than would be observed in a subject who did not receive the medical therapy. By way of non-limiting example, such an acute toxic effect that comprises energy imbalance includes low physical activity. In other embodiments, energy imbalance comprises fatigue or malaise.

In some embodiments, a chemotherapy side effect to be treated or prevented (i.e., likelihood of occurrence is reduced) by a senolytic agent described herein is cardiotoxicity. A subject who has a cancer that is being treated with an anthracycline (such as doxorubicin, daunorubicin) may be treated with one or more senolytic agents described herein that reduce, ameliorate, or decrease the cardiotoxicity of the anthracycline. As is well understood in the medical art, because of the cardiotoxicity associated with anthracyclines, the maximum lifetime dose that a subject can receive is limited even if the cancer is responsive to the drug. Administration of one or more of the senolytic agents may reduce the cardiotoxicity such that additional amounts of the anthracycline can be administered to the subject, resulting in an improved prognosis related to cancer disease. In some embodiments, the cardiotoxicity results from administration of an anthracycline, such as doxorubicin. Doxorubicin is an anthracycline topoisomerase inhibitor that is approved for treating patients who have ovarian cancer after failure of a platinum based therapy; Kaposi's sarcoma after failure of primary systemic chemotherapy or intolerance to the therapy; or multiple myeloma in combination with bortezomib in patients who have not previously received bortezomib or who have received at least one prior therapy. Doxorubicin may cause myocardial damage that could lead to congestive heart failure if the total lifetime dose to a patient exceeds 550 mg/m$^2$. Cardiotoxicity may occur at even lower doses if the patient also receives mediastinal irradiation or another cardiotoxic drug.

In other embodiments, a senolytic agent described herein may be used in the methods as provided herein for ameliorating chronic or long-term side effects. Chronic toxic side effects typically result from multiple exposures to or administrations of a chemotherapy or radiotherapy over a longer period of time. Certain toxic effects appear long after treatment (also called late toxic effects) and result from damage to an organ or system by the therapy. Organ dysfunction (e.g., neurological, pulmonary, cardiovascular, and endocrine dysfunction) has been observed in patients who were treated for cancers during childhood (see, e.g., Hudson et al., JAMA 309 92013) 2371-2381). Without wishing to be bound by any particular theory, by destroying senescent cells, particular normal cells that have been induced to senescence by chemotherapy or radiotherapy, the likelihood of occurrence of a chronic side effect may be reduced, or the severity of a chronic side effect may be reduced or diminished, or the time of onset of a chronic side effect may be delayed. Chronic and/or late toxic side effects that occur in subjects who received chemotherapy or radiation therapy include by way of non-limiting example, cardiomyopathy, congestive heart disease, inflammation, early menopause, osteoporosis, infertility, impaired cognitive function, peripheral neuropathy, secondary cancers, cataracts and other vision problems, hearing loss, chronic fatigue, reduced lung capacity, and lung disease.

In addition, by killing or removing senescent cells in a subject who has a cancer by administering a senolytic agent, the sensitivity to the chemotherapy or the radiotherapy may be enhanced in a clinically or statistically significant manner than if the senolytic agent was not administered. In other words, development of chemotherapy or radiotherapy resistance may be inhibited when a senolytic agent is administered to a subject treated with the respective chemotherapy or radiotherapy.

Neurological Diseases and Disorders

Senescence-associated diseases or disorders treatable by administering a senolytic agent described herein include neurological diseases or disorders. Such senescence-associated diseases and disorders include Parkinson's disease, Alzheimer's disease (and other dementias), motor neuron dysfunction (MND), mild cognitive impairment (MCI), Huntington's disease and diseases and disorders of the eyes, such as age-related macular degeneration. Other diseases of the eye that are associated with increasing age are glaucoma, vision loss, presbyopia, and cataracts.

Parkinson's disease (PD) is the second most common neurodegenerative disease. It is a disabling condition of the brain characterized by slowness of movement (bradykinesia), shaking, stiffness and in the later stages, loss of balance. Many of these symptoms are due to the loss of certain nerves in the brain, which results in the lack of dopamine. This disease is characterized by neurodegeneration, such as the loss of about 50% to 70% of the dopaminergic neurons in the substantia nigra pars comp acta, a profound loss of dopamine in the striatum and/or the presence of intracytoplasmic inclusions (Lewy bodies), which are composed mainly of alpha-synuclein and ubiquitin. Parkinson's disease also features locomotor deficits, such as tremor, rigidity, bradykinesia and/or postural instability. Subjects at risk of developing Parkinson's disease include those having a family history of Parkinson's disease and those exposed to pesticides (e.g., rotenone or paraquat), herbicides (e.g., agent orange), or heavy metals. Senescence of dopamine-producing neurons is thought to contribute to the observed cell death in PD through the production of reactive oxygen species (see, e.g., Cohen et al., J. Neural Transm. Suppl. 19 (1983) 89-103); therefore, the methods and senolytic agents described herein are useful for treatment and prophylaxis of Parkinson's disease.

Methods for detecting, monitoring or quantifying neurodegenerative deficiencies and/or locomotor deficits associated with Parkinson's diseases are known in the art, such as histological studies, biochemical studies, and behavioral assessment (see, e.g., U.S. Application Publication No. 2012/0005765). Symptoms of Parkinson's disease are known in the art and include, but are not limited to, difficulty starting or finishing voluntary movements, jerky, stiff movements, muscle atrophy, shaking (tremors), and changes in heart rate, but normal reflexes, bradykinesia, and postural instability. There is a growing recognition that people diagnosed with Parkinson's disease may have cognitive impairment, including mild cognitive impairment, in addition to their physical symptoms.

Alzheimer's disease (AD) is a neurodegenerative disease that shows a slowly progressive mental deterioration with failure of memory, disorientation, and confusion, leading to profound dementia. Age is the single greatest predisposing risk factor for developing AD, which is the leading cause of dementia in the elderly (see, e.g., Hebert, et al., Arch. Neural. 60 (2003) 1119-1122). Early clinical symptoms show remarkable similarity to mild cognitive impairment (see below). As the disease progresses, impaired judgment, confusion, behavioral changes, disorientation, and difficulty in walking and swallowing occur.

Alzheimer's disease is characterized by the presence of neurofibrillary tangles and amyloid (senile) plaques in histological specimens. The disease predominantly involves the limbic and cortical regions of the brain. The argyrophilic plaques containing the amyloidogenic Aβ fragment of amyloid precursor protein (APP) are scattered throughout the cerebral cortex and hippocampus. Neurofibrillary tangles are found in pyramidal neurons predominantly located in the neocortex, hippocampus, and nucleus basalis of Meynert. Other changes, such as granulovacuolar degeneration in the pyramidal cells of the hippocampus and neuron loss and gliosis in the cortex and hippocampus, are observed. Subjects at risk of developing Alzheimer's disease include those of advanced age, those with a family history of Alzheimer's disease, those with genetic risk genes (e.g., ApoE4) or deterministic gene mutations (e.g., APP, PS1, or PS2), and those with history of head trauma or heart/vascular conditions (e.g., high blood pressure, heart disease, stroke, diabetes, high cholesterol, etc.).

A number of behavioral and histopathological assays are known in the art for evaluating Alzheimer's disease phenotype, for characterizing therapeutic agents, and assessing treatment. Histological analyses are typically performed postmortem. Histological analysis of Aβ levels may be performed using Thioflavin-S, Congo red, or anti-Aβ staining (e.g., 4G8, 10D5, or 6E10 antibodies) to visualize Aβ deposition on sectioned brain tissues (see, e.g., Holcomb et al., Nat. Med. 4 (1998) 97-100; Borchelt et al., Neuron 19 (1997) 939-945; Dickson et al., Am. J. Path. 132 (1998) 86-101). In vivo methods of visualizing Aβ deposition in transgenic mice have been also described. FSB ((trans, trans)-1-bromo-2,5-his-(3-hydroxycarbonyl-4-hydroxy) styrylbenzene) and PET tracer $^{11}$C-labelled Pittsburgh Compound-μ (PIB) bind to AP plaques (see, e.g., Skovronsky et al., Proc. Natl. Acad. Sci. USA 97 (2000) 7609-7614; Klunk et al., Ann. Neurol. 55 (2004) 306-319). $^{19}$F-containing amyloidophilic Congo red-type compound FSB ((E,E)-1-fluoro-2,5-his-(3-hydroxycarbonyl-4-hydroxy)styrylbenzene) allows visualization of Aβ plaques by MRI (see, e.g., Higuchi et al., Nature Neurosci. 8 (2005) 527-533). Radiolabeled, putrescine-modified amyloid-beta peptide labels amyloid deposits in vivo in a mouse model of Alzheimer's disease (see, e.g., Wengenack et al., Nat. Biotechnol. 18 (2000) 868-872).

Increased glial fibrillary acidic protein (GFAP) by astrocytes is a marker for astroglial activation and gliosis during neurodegeneration. AP plaques are associated with GFAP-positive activated astrocytes, and may be visualized via GFAP staining (see, e.g., Nagele et al., Neurobiol. Aging 25 (2004) 663-674; Mandybur et al., Neurology 40 (1990) 635-639; Liang et al., J. Biol. Chem. 285 (2010) 27737-27744). Neurofibrillary tangles may be identified by immunohistochemistry using thioflavin-S fluorescent microscopy and Galiyas silver stains (see, e.g., Gotz et al., J. Biol. Chem. 276 (2001) 529-534; U.S. Pat. No. 6,664,443). Axon staining with electron microscopy and axonal transport studies may be used to visualize neuronal degeneration (see, e.g., Ishihara et al., Neuron 24 (1999) 751-762).

Subjects suffering from Alzheimer's disease can be identified using standard diagnostic methods known in the art for Alzheimer's disease. Generally, diagnosis of Alzheimer's disease is based on symptoms (e.g., progressive decline in memory function, gradual retreat from and frustration with normal activities, apathy, agitation or irritability, aggression, anxiety, sleep disturbance, dysphoria, aberrant motor behavior, disinhibition, social withdrawal, decreased appetite, hallucinations, dementia), medical history, neuropsychological tests, neurological and/or physical examination of a patient. Cerebrospinal fluid may also be tested for various proteins that have been associated with Alzheimer pathology, including tau, amyloid beta peptide, and AD7C-NTP. Genetic testing is also available for early-onset familial Alzheimer disease (eFAD), an autosomal-dominant genetic disease. Clinical genetic testing is available for individuals with AD symptoms or at-risk family members of patients with early-onset disease. In the U.S., mutations for PS2, and APP may be tested in a clinical or federally approved laboratory under the Clinical Laboratory Improvement Amendments. A commercial test for PS1 mutations is also available (Elan Pharmaceuticals).

Zhang et al have reported that, in the brains of patients with AD and in AD mouse models, Aβ plaque-associated Olig2- and NG2-expressing oligodendrocyte progenitor cells (OPCs), but not astrocytes, microglia, or oligodendrocytes, exhibit a senescence-like phenotype characterized by the upregulation of p21/CDKN1A, p16/INK4/CDKN2A proteins, and senescence-associated β-galactosidase activity (see Nature Neurosci. 22 (2019) 719-728). Molecular interrogation of the Aβ plaque environment revealed elevated levels of transcripts encoding proteins involved in OPC function, replicative senescence, and inflammation. Direct exposure of cultured OPCs to aggregating Aβ triggered cell senescence. Treatment of AD mice with a senolytic cocktail comprising dasatinib plus quercetin selectively removed senescent cells from the plaque environment, reduced neuroinflammation, lessened Aβ load, and ameliorated cognitive deficits. These findings suggest a role for Aβ-induced OPC cell senescence in neuroinflammation and cognitive deficits in AD, and a potential therapeutic benefit of senolytic treatments.

The effectiveness of one or more senolytic agents described herein and monitoring of a subject who receives one or more senolytic agents can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of administering one or more senolytic agents can be analyzed using techniques known in the art, such as comparing symptoms of patients suffering from or at risk of Alzheimer's disease that have received the treatment with those of patients without such a treatment or with placebo treatment.

Mild Cognitive Impairment (MCI) is a brain-function syndrome involving the onset and evolution of cognitive impairments beyond those expected based on age and education of the individual, but which are not significant enough to interfere with the of the daily activities individual. MCI is an aspect of cognitive aging that is considered to be a transitional state between normal aging and the dementia into which it may convert (see, Pepeu, Dialogues in Clinical Neuroscience 6 (2004) 369-377). MCI that primarily affects memory is known as "amnestic MCI." A person with amnestic MCI may start to forget important information that he or she would previously have recalled easily, such as recent events. Amnestic MCI is frequently seen as prodromal stage of Alzheimer's disease. MCI that affects thinking skills other than memory is known as "non-amnestic MCI." This type of MCI affect thinking skills such as the ability to make sound decisions, judge the time or sequence of steps needed to complete a complex task, or visual perception. Individuals with non-amnestic MCI are believed to be more likely to convert to other types of dementias (e.g., dementia with Lewy bodies).

Persons in the medical art have a growing recognition that people diagnosed with Parkinson's disease may have MCI in addition to their physical symptoms. Recent studies show 20-30% of people with Parkinson's disease have MCI and that their MCI tends to be non-amnestic. Parkinson's disease patients with MCI sometimes go on to develop full blown dementia (Parkinson's disease with dementia).

Methods for detecting, monitoring, quantifying or assessing neuropathological deficiencies associated with MCI are known in the art, including astrocyte morphological analyses, release of acetylcholine, silver staining for assessing neurodegeneration, and PiB PET imaging to detect beta amyloid deposits (see, e.g., U.S. Application Publication No. 2012/0071468; Pepeu, (2004), supra). Methods for detecting, monitoring, quantifying or assessing behavioral deficiencies associated with MCI are also known in the art, including eight-arm radial maze paradigm, non-matching-to-sample task, allocentric place determination task in a water maze, Morris maze test, visuospatial tasks, delayed response spatial memory task, and the olfactory novelty test.

Motor Neuron Dysfunction (MND) is a group of progressive neurological disorders that destroy motor neurons, the cells that control essential voluntary muscle activity such as speaking, walking, breathing and swallowing. It is classified according to whether degeneration affects upper motor neurons, lower motor neurons, or both. Examples of MNDs include, but are not limited to Amyotrophic Lateral Sclerosis (ALS), also known as Lou Gehrig's Disease, progressive bulbar palsy, pseudobulbar palsy, primary lateral sclerosis, progressive muscular atrophy, lower motor neuron disease, and spinal muscular atrophy (SMA) (e.g., SMA1 also called Werdnig-Hoffmann Disease, SMA2, SMA3 also called Kugelberg-Weiander Disease, and Kennedy's disease), post-polio syndrome, and hereditary spastic paraplegia. In adults, the most common MND is amyotrophic lateral sclerosis (ALS), which affects both upper and lower motor neurons. It can affect the arms, legs, or facial muscles. Primary lateral sclerosis is a disease of the upper motor neurons, while progressive muscular atrophy affects only lower motor neurons in the spinal cord. In progressive bulbar palsy, the lowest motor neurons of the brain stem are most affected, causing slurred speech and difficulty chewing and swallowing. There are almost always mildly abnormal signs in the arms and legs. Patients with MND exhibit a phenotype of Parkinson's disease (e.g., having tremor, rigidity, bradykinesia, and/or postural instability). Methods for detecting, monitoring or quantifying locomotor and/or other deficits associated with Parkinson's diseases, such as MND, are known in the art (see, e.g., U.S. Application Publication No. 2012/0005765).

Methods for detecting, monitoring, quantifying or assessing motor deficits and histopathological deficiencies associated with MND are known in the art, including histopathological, biochemical, and electrophysiological studies and motor activity analysis (see, e.g., Rich et al., J. Neurophysiol. 88 (2002) 3293-3304; Appel et al., Proc. Natl. Acad. Sci. USA 88 (1991) 647-651). Histopathologically, MNDs are characterized by death of motor neurons, progressive accumulation of detergent-resistant aggregates containing SOD1 and ubiquitin and aberrant neurofilament accumulations in degenerating motor neurons. In addition, reactive astroglia and microglia are often detected in diseased tissue. Patients with an MND show one or more motor deficits, including muscle weakness and wasting, uncontrollable twitching, spasticity, slow and effortful movements, and overactive tendon reflexes.

Ophthalmic Diseases and Disorders

In certain embodiments, a senescence-associated disease or disorder is an ocular disease, disorder, or condition, for example, presbyopia, macular degeneration, or cataracts. In other certain embodiments, the senescence-associated disease or disorder is glaucoma. Macular degeneration is a neurodegenerative disease that causes the loss of photoreceptor cells in the central part of retina, called the macula. Macular degeneration generally is classified into two types: dry type and wet type. The dry form is more common than the wet, with about 90% of age-related macular degeneration (ARMD or AMD) patients diagnosed with the dry form. The wet form of the disease usually leads to more serious vision loss. While the exact causes of age-related macular degeneration are still unknown, the number of senescent retinal pigmented epithelial (RPE) cells increases with age. Age and certain genetic factors and environmental factors are risk factors for developing ARMD (see, e.g., Lyengar et al., Am. J. Hum. Genet. 74 (2004) 20-39; Kenealy et al., Mol. Ms. 10 (2004) 57-61; Gorin et al., Mol. Ms. 5 (1999) 29). Environment predisposing factors include omega-3 fatty acids intake (see, e.g., Christen et al., Arch. Ophthalmol. 129 (2011) 921-929); estrogen exposure (see, e.g., Feshanich et al., Arch. Ophthalmol. 126(4) (2008) 519-524); and increased serum levels of vitamin D (see, e.g., Millen, et al., Arch. Ophthalmol. 129(4) (2011) 481-89). Genetic predisposing risk factors include reduced levels Dicer1 (enzyme involved in maturation of micro RNA) in eyes of patients with dry AMD, and decreased micro RNAs contributes to a senescent cell profile.

Dry ARMD is associated with atrophy of RPE layer, which causes loss of photoreceptor cells. The dry form of ARMD may result from aging and thinning of macular tissues and from deposition of pigment in the macula. Senescence appears to inhibit both replication and migration of RPE, resulting in permanent RPE depletion in the macula of dry AMD patients (see, e.g., Iriyama et al., J. Biol. Chem. 283 (2008) 11947-11953). With wet ARMD, new blood vessels grow beneath the retina and leak blood and fluid. This abnormal leaky choroidal neovascularization causes the retinal cells to die, creating blind spots in central vision. Different forms of macular degeneration may also occur in younger patients. Non-age related etiology may be linked to heredity, diabetes, nutritional deficits, head injury, infection, or other factors.

Declining vision noticed by the patient or by an ophthalmologist during a routine eye exam may be the first indicator of macular degeneration. The formation of exudates, or "drusen," underneath the Bruch's membrane of the macula is often the first physical sign that macular degeneration may develop. Symptoms include perceived distortion of straight lines and, in some cases, the center of vision appears more distorted than the rest of a scene; a dark, blurry area or "white-out" appears in the center of vision; and/or color perception changes or diminishes. Diagnosing and monitoring of a subject with macular degeneration may be accomplished by a person skilled in the ophthalmic art according to art-accepted periodic eye examination procedures and report of symptoms by the subject.

Presbyopia is an age-related condition where the eye exhibits a progressively diminished ability to focus on near objects as the speed and amplitude of accommodation of a normal eye decrease with advancing age. Loss of elasticity of the crystalline lens and loss of contractility of the ciliary muscles have been postulated as its cause (see, e.g., Heys et al., Mol. Vis. 10 (2004) 956-963; Petrash, Invest. Ophthalmol. Vts. Sci. 54 (2013) ORSF54-ORSF59). Age-related changes in the mechanical properties of the anterior lens capsule and posterior lens capsule suggest that the mechanical strength of the posterior lens capsule decreases significantly with age (see, e.g., Krag et al., Invest. Ophthalmol. Vis. Sci. 44 (2003) 691-696; Krag et al., Invest. Ophthalmol. Vis. Sci. 38 (1997) 357-363).

The laminated structure of the capsule also changes and may result, at least in part, from a change in the composition of the tissue (see, e.g., Krag et al., 1997, supra, and references cited therein). The major structural component of the lens capsule is basement membrane type IV collagen that is organized into a three-dimensional molecular network (see, e.g., Cummings et al., Connect. Tissue Res. 55 (2014) 8-12; Veis et al., Coll. Relat. Res. 1 (1981) 269-286). Type IV collagen is composed of six homologous a chains (a 1-6) that associate into heterotrimeric collagen IV protomers with each comprising a specific chain combination of a 112, a 345, or a 556 (see, e.g., Khoshnoodi et al., Microsc. Res. Tech. 71 (2008) 357-370). Protomers share structural similarities of a triple-helical collagenous domain with the triplet peptide sequence of Gly-X-Y (Timpl et al., Eur. J. Biochem. 95 (1979) 255-263), ending in a globular C-terminal region termed the non-collagenous 1 (NC1) domain. The N-termini are composed of a helical domain termed the 7S domain (see, e.g., Risteli et al., Eur. J. Biochem. 108 (1980) 239-250), which is also involved in protomer-protomer interactions.

Research has suggested that collagen IV influences cellular function which is inferred from the positioning of basement membranes underneath epithelial layers, and data support the role of collagen IV in tissue stabilization (see, e.g., Cummings et al., supra). Posterior capsule opacification (PCO) develops as a complication in approximately 20-40% of patients in subsequent years after cataract surgery (see, e.g., Awasthi et al., Arch. Ophthalmol. 127 (2009) 555-562). PCO results from proliferation and activity of residual lens epithelial cells along the posterior capsule in a response akin to wound healing. Growth factors, such as fibroblast growth factor, transforming growth factor-β, epidermal growth factor, hepatocyte growth factor, insulin-like growth factor, and interleukins IL-1 and IL-6 may also promote epithelial cell migration, (see, e.g., Awasthi et al, supra; Raj et al., supra). As discussed herein, production of these factors and cytokines by senescent cells contribute to the SASP. In contrast, in vitro studies show that collagen IV promotes adherence of lens epithelial cells (see, e.g., Olivero et al., Invest. Ophthalmol. Vis. Sci. 34 (1993) 2825-2834). Adhesion of the collagen IV, fibronectin, and laminin to the intraocular lens inhibits cell migration and may reduce the risk of PCO (see, e.g., Raj et al, Int. J. Biomed. Sci. 3 (2007) 237-250).

Without wishing to be bound by any particular theory, selective killing of senescent cells by the senolytic agents described herein may slow or impede (delay, inhibit, retard) the disorganization of the type IV collagen network. Removal of senescent cells and thereby removing the inflammatory effects of SASP may decrease or inhibit epithelial cell migration and may also delay (suppress) the onset of presbyopia or decrease or slow the progressive severity of the condition (such as slow the advancement from mild to moderate or moderate to severe). The senolytic agents described herein may also be useful for post-cataract surgery to reduce the likelihood of occurrence of PCO.

While no direct evidence for the involvement of cellular senescence with the development of cataracts has been obtained from human studies, BubR1 hypomorphic mice develop posterior subcapsular cataracts bilaterally early in life, suggesting that senescence may play a role (see, e.g., Baker et al., Nat. Cell Biol. 10 (2008) 825-836). Cataracts are a clouding of the lens of an eye, causing blurred vision, and if left untreated can result in blindness. Surgery is effective and routinely performed to remove cataracts. Administration of one or more of the senolytic agents described herein may result in decreasing the likelihood of occurrence of a cataract or may slow or inhibit progression of a cataract. The presence and severity of a cataract can be monitored by eye exams using methods routinely performed by a person skilled in the ophthalmology art.

In certain embodiments, at least one senolytic agent described herein may be administered to a subject who is at risk of developing presbyopia, cataracts, or macular degeneration. Treatment with a senolytic agent may be initiated when a human subject is at least 40 years of age to delay or inhibit onset or development of cataracts, presbyopia, and macular degeneration. Because almost all humans develop presbyopia, in certain embodiments, the senolytic agent may be administered in a manner as described herein to a human subject after the subject reaches the age of 40 to delay or inhibit onset or development of presbyopia.

In certain embodiments, the senescence associated disease or disorder is glaucoma. Glaucoma is a broad term used to describe a group of diseases that causes visual field loss, often without any other prevailing symptoms. The lack of symptoms often leads to a delayed diagnosis of glaucoma until the terminal stages of the disease. Even if subjects afflicted with glaucoma do not become blind, their vision is often severely impaired. Normally, clear fluid flows into and out of the front part of the eye, known as the anterior chamber. In individuals who have open/wide-angle glaucoma, this fluid drains too slowly, leading to increased pressure within the eye. If left untreated, this high pressure subsequently damages the optic nerve and can lead to complete blindness. The loss of peripheral vision is caused by the death of ganglion cells in the retina. Ganglion cells are a specific type of projection neuron that connects the eye to the brain. When the cellular network required for the outflow of fluid was subjected to SA-β-Gal staining, a fourfold increase in senescence has been observed in glaucoma patients (see, e.g., Liton et al., Exp. Gerontol. 40 (2005) 745-748).

For monitoring the effect of a therapy on inhibiting progression of glaucoma, standard automated perimetry (visual field test) is the most widely used technique. In addition, several algorithms for progression detection have been developed (see, e.g., Wesselink et al., Arch. Ophthalmol. 127(3) (2009) 270-274, and references therein). Additional methods include gonioscopy (examines the trabecular meshwork and the angle where fluid drains out of the eye); imaging technology, for example scanning laser tomography (e.g., HRT3), laser polarimetry (e.g., GDX), and ocular coherence tomography); ophthalmoscopy; and pachymeter measurements that determine central corneal thickness.

Metabolic Diseases or Disorders

Senescence-associated diseases or disorders treatable by administering a senolytic agent include metabolic diseases or disorders. Such senescent cell associated diseases and disorders include diabetes, metabolic syndrome, diabetic ulcers, and obesity.

Diabetes is characterized by high levels of blood glucose caused by defects in insulin production, insulin action, or both. The great majority (90 to 95%) of all diagnosed cases of diabetes in adults are type 2 diabetes, characterized by the gradual loss of insulin production by the pancreas. Diabetes is the leading cause of kidney failure, nontraumatic lower-limb amputations, and new cases of blindness among adults in the U.S. Diabetes is a major cause of heart disease and stroke and is the seventh leading cause of death in the U.S. (see, e.g., Centers for Disease Control and Prevention, National diabetes fact sheet: national estimates and general information on diabetes and pre-diabetes in the United States, 2011 ("Diabetes fact sheet")). Senolytic agents described herein may be used for treating type 2 diabetes, particularly age-, diet- and obesity-associated type 2 diabetes.

Involvement of senescent cells in metabolic disease, such as obesity and type 2 diabetes, has been suggested as a response to injury or metabolic dysfunction (see, e.g., Tchkonia et al., Aging Cell 9 (2010) 667-684). Fat tissue from obese mice showed induction of the senescence markers SA-β-Gal, p53, and p21 (see, e.g., Tchkonia et al., supra; Minamino et al., Nat. Med. 15 (2009) 1082-1087). A concomitant up-regulation of pro-inflammatory cytokines, such as tumor necrosis factor-α and Ccl2/MCP1, was observed in the same fat tissue (see, e.g., Minamino et al., supra). Induction of senescent cells in obesity potentially has clinical implications because pro-inflammatory SASP components are also suggested to contribute to type 2 diabetes (see, e.g., Tchkonia et al., supra). A similar pattern of up-regulation of senescence markers and SASP components are associated with diabetes, both in mice and in humans (see, e.g., Minamino et al., supra). Accordingly, the methods described herein that comprise administering a senolytic agent may be useful for treatment or prophylaxis of type 2 diabetes, as well as obesity and metabolic syndrome. Without wishing to be bound by theory, contact of senescent pre-adipocytes with a senolytic agent thereby killing the senescent pre-adipocytes may provide clinical and health benefit to a person who has any one of diabetes, obesity, or metabolic syndrome.

Subjects suffering from type 2 diabetes can be identified using standard diagnostic methods known in the art for type 2 diabetes. Generally, diagnosis of type 2 diabetes is based on symptoms (e.g., increased thirst and frequent urination, increased hunger, weight loss, fatigue, blurred vision, slow-healing sores or frequent infections, and/or areas of darkened skin), medical history, and/or physical examination of a patient. Subjects at risk of developing type 2 diabetes include those who have a family history of type 2 diabetes and those who have other risk factors such as excess weight, fat distribution, inactivity, race, age, prediabetes, and/or gestational diabetes.

The effectiveness of a senolytic agent can readily be determined by a person skilled in the medical and clinical arts. One or any combination of diagnostic methods, including physical examination, assessment and monitoring of clinical symptoms, and performance of analytical tests and methods, such as those described herein, may be used for monitoring the health status of the subject. A subject who is receiving one or more senolytic agents described herein for treatment or prophylaxis of diabetes can be monitored, for example, by assaying glucose and insulin tolerance, energy expenditure, body composition, fat tissue, skeletal muscle, and liver inflammation, and/or lipotoxicity (muscle and liver lipid by imaging in vivo and muscle, liver, bone marrow, and pancreatic β-cell lipid accumulation and inflammation by histology). Other characteristic features or phenotypes of type 2 diabetes are known and can be assayed as described herein and by using other methods and techniques known and routinely practiced in the art.

Obesity and obesity-related disorders are used to refer to conditions of subjects who have a body mass that is measurably greater than ideal for their height and frame. Body Mass Index (BMI) is a measurement tool used to determine excess body weight, and is calculated from the height and weight of a subject. A human is considered overweight when the person has a BMI of 25-29; a person is considered obese when the person has a BMI of 30-39, and a person is considered severely obese when the person has a BMI of >40. Accordingly, the terms obesity and obesity-related refer to human subjects with body mass index values of greater than 30, greater than 35, or greater than 40. A category of obesity not captured by BMI is called "abdominal obesity" in the art, which relates to the extra fat found around a subject's middle, which is an important factor in health, even independent of BMI. The simplest and most often used measure of abdominal obesity is waist size. Generally abdominal obesity in women is defined as a waist size 35 inches or higher, and in men as a waist size of 40 inches or higher. More complex methods for determining obesity require specialized equipment, such as magnetic resonance imaging or dual energy X-ray absorptiometry machines.

A condition or disorder associated with diabetes and senescence is a diabetic ulcer (i.e., diabetic wound). An ulcer is a breakdown in the skin, which may extend to involve the subcutaneous tissue or even muscle or bone. These lesions occur, particularly, on the lower extremities. Patients with diabetic venous ulcer exhibit elevated presence of cellular senescence at sites of chronic wounds (see, e.g., Stanley et al., J. Vas. Surg. 33 (2001) 1206-1211). Chronic inflammation is also observed at sites of chronic wounds, such as diabetic ulcers (see, e.g., Goren et al., Am. J. Pathol. 168 (2006) 65-77) suggesting that the proinflammatory cytokine phenotype of senescent cells has a role in the pathology.

Subjects who have type 2 diabetes or who are at risk of developing type 2 diabetes may have metabolic syndrome. Metabolic syndrome in humans is typically associated with obesity and characterized by one or more of cardiovascular disease, liver steatosis, hyperlipidemia, diabetes, and insulin resistance. A subject with metabolic syndrome may present with a cluster of metabolic disorders or abnormalities which may include, for example, one or more of hypertension, type-2 diabetes, hyperlipidemia, dyslipidemia (e.g., hypertriglyceridemia, hypercholesterolemia), insulin resistance, liver steatosis (steatohepatitis), hypertension, atherosclerosis, and other metabolic disorders.

Renal Dysfunction

Nephrological pathologies, such as glomerular disease, arise in the elderly and may be treated by the administration of senolytic compounds described herein. Glomerulonephritis is characterized by inflammation of the kidney and by the expression of two proteins, IL1α and IL1β (see, e.g., Niemir et al., Kidney Int. 52 (1997) 393-403). IL1α and IL1β are considered master regulators of SASP (see, e.g., Coppe et al., PLoS. Biol. 6 (2008) 2853-2868). Glomerular disease is associated with elevated presence of senescent cells, especially in fibrotic kidneys (see, e.g., Sis et al., Kidney Int. 71 (2007) 218-226).

Dermatological Diseases or Disorders

Senescence-associated diseases or disorders treatable by administering a senolytic agent described herein include dermatological diseases or disorders. Such senescent cell associated diseases and disorders include psoriasis and eczema, which are also inflammatory diseases and are discussed in greater detail above. Other dermatological diseases and disorders that are associated with senescence include rhytides (wrinkles due to aging); pruritis (linked to diabetes and aging); dysesthesia (chemotherapy side effect that is linked to diabetes and multiple sclerosis); psoriasis (as noted) and other papulosquamous disorders, for example, erythroderma, lichen planus, and lichenoid dermatosis; atopic dermatitis (a form of eczema and associated with inflammation); eczematous eruptions (often observed in aging patients and linked to side effects of certain drugs). Other dermatological diseases and disorders associated with senescence include eosinophilic dermatosis (linked to certain kinds of hematologic cancers); reactive neutrophilic dermatosis (associated with underlying diseases such as inflammatory bowel syndrome); pemphigus (an autoimmune disease in which autoantibodies form against desmoglein); pemphigoid and other immunobullous dermatosis (autoimmune blistering of skin); fibrohistiocytic proliferations of skin, which is linked to aging; and cutaneous lymphomas that are more common in older populations. Another dermatological disease that may be treatable according to the methods described herein includes cutaneous lupus, which is a symptom of lupus erythematosus. Late onset lupus may be linked to decreased (i.e., reduced) function of T-cell and B-cells and cytokines (immunosenescence) associated with aging.

Inflammatory and Autoimmune Diseases and Disorders

In certain embodiments, a senescence-associated disease or disorder is an inflammatory disease or disorder, such as by way of non-limiting example, osteoarthritis, that may be treated or prevented (i.e., likelihood of occurrence is reduced) according to the methods described herein that comprise administration of a senolytic agent. Other inflammatory or autoimmune diseases or disorders that may be treated by administering a senolytic agent such as the inhibitors and antagonists described herein include osteoporosis, psoriasis, oral mucositis, rheumatoid arthritis, inflammatory bowel disease, eczema, kyphosis, herniated intervertebral disc, and the pulmonary diseases, COPD and idiopathic pulmonary fibrosis.

Osteoarthritis degenerative joint disease is characterized by fibrillation of the cartilage at sites of high mechanical stress, bone sclerosis, and thickening of the synovium and the joint capsule. Fibrillation is a local surface disorganization involving splitting of the superficial layers of the cartilage. The early splitting is tangential with the cartilage surface, following the axes of the predominant collagen bundles. Collagen within the cartilage becomes disorganized, and proteoglycans are lost from the cartilage surface. In the absence of protective and lubricating effects of proteoglycans in a joint, collagen fibers become susceptible to degradation, and mechanical destruction ensues. Predisposing risk factors for developing osteoarthritis include increasing age, obesity, previous joint injury, overuse of the joint, weak thigh muscles, and genetics. Symptoms of osteoarthritis include sore or stiff joints, particularly the hips, knees, and lower back, after inactivity or overuse; stiffness after resting that goes away after movement; and pain that is worse after activity or toward the end of the day. Osteoarthritis may also affect the neck, small finger joints, the base of the thumb, ankle, and big toe. Chronic inflammation is thought to be the main age-related factor that contributes to osteoarthritis. In combination with aging, joint overuse and obesity appear to promote osteoarthritis.

By selectively killing senescent cells a senolytic agent prevents (i.e., reduces the likelihood of occurrence), reduces or inhibits loss or erosion of proteoglycan layers in a joint, reduces inflammation in the affected joint, and promotes (i.e., stimulates, enhances, induces) production of collagen (e.g., type 2 collagen). Removal of senescent cells causes a reduction in the amount (i.e., level) of inflammatory cytokines, such as IL-6, produced in a joint and inflammation is reduced. Methods are provided herein for treating osteoarthritis, for selectively killing senescent cells in an osteoarthritic joint of a subject, and/or inducing collagen (such as Type 2 collagen) production in the joint of a subject by administering at least one senolytic agent (which may be combined with at least one pharmaceutically acceptable excipient to form a pharmaceutical composition) to the subject. A senolytic agent also may be used for decreasing (inhibiting, reducing) production of metalloproteinase 13 (MMP-13), which degrades collagen in a joint, and for restoring proteoglycan layer or inhibiting loss and/or degradation of the proteoglycan layer. Treatment with the senolytic agent thereby also prevents (i.e., reduces likelihood of occurrence of), inhibits, or decreases erosion, or slows (i.e., decreases rate) erosion of the bone. As described in detail herein, in certain embodiments, the senolytic agent is administered directly to an osteoarthritic joint (e.g., by intra-articularly, topical, transdermal, intradermal, or subcutaneous delivery). Treatment with a senolytic agent can also restore, improve, or inhibit deterioration of strength of a joint. In addition, the methods comprising administering a senolytic agent can reduce joint pain and are therefore useful for pain management of osteoarthritic joints.

The effectiveness of one or more senolytic agents for treatment or prophylaxis of osteoarthritis in a subject and monitoring of a subject who receives one or more senolytic agents can readily be determined by a person skilled in the medical and clinical arts. One or any combination of diagnostic methods, including physical examination (such as determining tenderness, swelling or redness of the affected joint), assessment and monitoring of clinical symptoms (such as pain, stiffness, mobility), and performance of analytical tests and methods described herein and practiced in the art (e.g., determining the level of inflammatory cytokines or chemokines; X-ray images to determine loss of cartilage as shown by a narrowing of space between the bones in a joint; magnetic resonance imaging (MRI), providing detailed images of bone and soft tissues, including cartilage), may be used for monitoring the health status of the subject. The effects of the treatment of one or more senolytic agents can be analyzed by comparing symptoms of patients suffering from or at risk of an inflammatory disease or disorder, such as osteoarthritis, who have received the treatment with those of patients who have not received such a treatment or who have received a placebo treatment.

In certain embodiments, senolytic agents may be used for treating and/or preventing (i.e., decreasing or reducing the likelihood of occurrence) rheumatoid arthritis (RA). Dysregulation of innate and adaptive immune responses characterize rheumatoid arthritis (RA), which is an autoimmune disease the incidence of which increases with age. Rheumatoid arthritis is a chronic inflammatory disorder that typically affects the small joints in hands and feet. Whereas osteoarthritis results from, at least in part, wear and tear of a joint, rheumatoid arthritis affects the lining of joints, resulting in a painful swelling that can lead to bone erosion and joint deformity. RA can sometimes also affect other organs of the body, such as the skin, eyes, lungs and blood vessels. RA can occur in a subject at any age; however, RA usually begins to develop after age 40. The disorder is much more common in women. In certain embodiments of the methods described herein, RA is excluded.

Chronic inflammation may also contribute to other age-related or aging related diseases and disorders, such as kyphosis and osteoporosis. Kyphosis is a severe curvature in the spinal column, and it is frequently seen with normal and premature aging (see, e.g., Katzman et al., J. Orthop. Sports Phys. Ther. 40 (2010) 352-360). Age-related kyphosis often occurs after osteoporosis weakens spinal bones to the point that they crack and compress. A few types of kyphosis target infants or teens. Severe kyphosis can affect lungs, nerves, and other tissues and organs, causing pain and other problems. Kyphosis has been associated with cellular senescence. Characterizing the capability of a senolytic agent for treating kyphosis may be determined in pre-clinical animal models used in the art. By way of example, TTD mice develop kyphosis (see, e.g., de Boer et al., Science 296 (2002) 1276-1279); other mice that may be used include BubR1$^{H/H}$ mice, which are also known to develop kyphosis (see, e.g., Baker et al., Nature 479 (2011) 232-236). Kyphosis formation is visually measured over time. The level of senescent cells decreased by treatment with the senolytic agent can be determined by detecting the presence of one or more senescent cell associated markers such as by SA-β-Gal staining.

Osteoporosis is a progressive bone disease that is characterized by a decrease in bone mass and density that may lead to an increased risk of fracture, which may be treated or prevented by administration of the senolytic agents described herein. Bone mineral density (BMD) is reduced, bone microarchitecture deteriorates, and the amount and variety of proteins in bone are altered. Osteoporosis is typically diagnosed and monitored by a bone mineral density test. Post-menopausal women or women who have reduced estrogen are most at risk. While both men and women over 75 are at risk, women are twice as likely to develop osteoporosis than men. The level of senescent cells decreased by treatment with the senolytic agent can be determined by detecting the presence of one or more senescent cell associated markers such as by SA-β-Gal staining.

In still other embodiments, an inflammatory/autoimmune disorder that may be treated or prevented (i.e., likelihood of occurrence is reduced) with the senolytic agents described herein includes irritable bowel syndrome (IBS) and inflammatory bowel diseases, such as ulcerative colitis and Crohn's disease. Inflammatory bowel disease (IBD) involves chronic inflammation of all or part of the digestive tract. In addition to life-threatening complications arising from IBD, the disease can be painful and debilitating. Ulcerative colitis is an inflammatory bowel disease that causes long-lasting inflammation in part of the digestive tract. Symptoms usually develop over time, rather than suddenly. Ulcerative colitis usually affects only the innermost lining of the large intestine (colon) and rectum. Crohn's disease is an inflammatory bowel disease that causes inflammation anywhere along the lining of your digestive tract, and often extends deep into affected tissues. This can lead to abdominal pain, severe diarrhea and malnutrition. The inflammation caused by Crohn's disease can involve different areas of the digestive tract. Diagnosis and monitoring of the diseases are performed according to methods and diagnostic tests routinely practiced in the art, including blood tests, colonoscopy, flexible sigmoidoscopy, barium enema, CT scan, MRI, endoscopy, and small intestine imaging.

Other inflammatory or autoimmune diseases that may be treated or prevented (i.e., likelihood of occurrence is reduced) by using a senolytic agent include eczema, psoriasis, osteoporosis, and pulmonary diseases (e.g., chronic obstructive pulmonary disease (COPD), idiopathic pulmonary fibrosis (IPF), asthma), inflammatory bowel disease, and mucositis (including oral mucositis, which in some instances is induced by radiation). Certain fibrosis or fibrotic conditions of organs such as renal fibrosis, liver fibrosis, pancreatic fibrosis, cardiac fibrosis, skin wound healing, and oral submucous fibrosis may be treated with the senolytic agents described herein.

In certain embodiments, the senescent cell associated disorder is an inflammatory disorder of the skin, such as by way of a non-limiting examples, psoriasis and eczema that may be treated or prevented (i.e., likelihood of occurrence is reduced) according to the methods described herein that comprise administration of a senolytic agent. Psoriasis is characterized by abnormally excessive and rapid growth of the epidermal layer of the skin. A diagnosis of psoriasis is usually based on the appearance of the skin. Skin characteristics typical for psoriasis are scaly red plaques, papules, or patches of skin that may be painful and itch. In psoriasis, cutaneous and systemic overexpression of various proinflammatory cytokines is observed such as IL-6, a key component of the SASP. Eczema is an inflammation of the skin that is characterized by redness, skin swelling, itching and dryness, crusting, flaking, blistering, cracking, oozing, or bleeding. The effectiveness of senolytic agents for treatment of psoriasis and eczema and monitoring of a subject who receives such a senolytic agent can be readily determined by a person skilled in the medical or clinical arts. One or any combination of diagnostic methods, including physical examination (such as skin appearance), assessment of monitoring of clinical symptoms (such as itching, swelling, and pain), and performance of analytical tests and methods described herein and practiced in the art (i.e., determining the level of pro-inflammatory cytokines).

Other immune disorders or conditions that may be treated or prevented (i.e., likelihood of occurrence is reduced) with senolytic agents described herein include conditions resulting from a host immune response to an organ transplant (e.g., kidney, bone marrow, liver, lung, or heart transplant), such as rejection of the transplanted organ. Senolytic agents described herein may also be used for treating or reducing the likelihood of occurrence of graft-vs-host disease.

Cardiovascular Diseases and Disorders

In other embodiments, the senescence-associated disease or disorder treated by the methods described herein is a cardiovascular disease. The cardiovascular disease may be any one or more of angina, arrhythmia, atherosclerosis, cardiomyopathy, congestive heart failure, coronary artery disease (CAD), carotid artery disease, endocarditis, heart attack (coronary thrombosis, myocardial infarction [MI]), high blood pressure/hypertension, aortic aneurysm, brain aneurysm, cardiac fibrosis, cardiac diastolic dysfunction, hypercholesterolemia/hyperlipidemia, mitral valve prolapse, peripheral vascular disease (e.g., peripheral artery disease (PAD)), cardiac stress resistance and stroke.

In certain embodiments, methods are provided for treating senescence-associated cardiovascular disease that is associated with or caused by arteriosclerosis (i.e., hardening of the arteries). The cardiovascular disease may be any one or more of atherosclerosis (e.g., coronary artery disease (CAD) and carotid artery disease); angina, congestive heart failure, and peripheral vascular disease (e.g., peripheral artery disease (PAD)). The methods for treating a cardiovascular disease that is associated with or caused by arteriosclerosis may reduce the likelihood of occurrence of high blood pressure/hypertension, angina, stroke, and heart attack (i.e., coronary thrombosis, myocardial infarction (MI)). In certain embodiments, methods are provided for stabilizing atherosclerotic plaque(s) in a blood vessel (e.g., artery) of a subject, thereby reducing the likelihood of occurrence or delaying the occurrence of a thrombotic event, such as stroke or myocardial infraction. In certain embodiments, these methods comprising administration of a senolytic agent, reduce (i.e., cause decrease of) the lipid content of an atherosclerotic plaque in a blood vessel (e.g., artery) of the subject and/or increase the fibrous cap thickness (i.e., cause an increase, enhance or promote thickening of the fibrous cap).

Atherosclerosis is characterized by patchy intimal plaques (atheromas) that encroach on the lumen of medium-sized and large arteries; the plaques contain lipids, inflammatory cells, smooth muscle cells, and connective tissue. Atherosclerosis can affect large and medium-sized arteries, including the coronary, carotid, and cerebral arteries, the aorta and its branches, and major arteries of the extremities. In some embodiments, methods are provided for inhibiting the formation of atherosclerotic plaques (or reducing, diminishing, causing decrease in formation of atherosclerotic plaques) by administering a senolytic agent. In other embodiments, methods are provided for reducing (decreasing, diminishing) the amount (i.e., level) of plaque. Reduction in the amount of plaque in a blood vessel (e.g., artery) may be determined, for example, by a decrease in surface area of the plaque, or by a decrease in the extent or degree (e.g., percent) of occlusion of a blood vessel (e.g., artery), which can be determined by angiography or other visualizing methods used in the cardiovascular art. Also provided herein are methods for increasing the stability (or improving, promoting, enhancing stability) of atherosclerotic plaques that are present in one or more blood vessels (e.g., one or more arteries) of a subject, which methods comprise administering to the subject any one of the senolytic agents described herein.

Subjects suffering from cardiovascular disease can be identified using standard diagnostic methods known in the art for cardiovascular disease. Generally, diagnosis of atherosclerosis and other cardiovascular disease is based on symptoms (e.g., chest pain or pressure (angina), numbness or weakness in arms or legs, difficulty speaking or slurred speech, drooping muscles in face, leg pain, high blood pressure, kidney failure and/or erectile dysfunction), medical history, and/or physical examination of a patient. Diagnosis may be confirmed by angiography, ultrasonography, or other imaging tests. Subjects at risk of developing cardiovascular disease include those having any one or more of predisposing factors, such as a family history of cardiovascular disease and those having other risk factors (i.e., predisposing factors) such as high blood pressure, dyslipidemia, high cholesterol, diabetes, obesity and cigarette smoking, sedentary lifestyle, and hypertension. In certain embodiments, the cardiovascular disease that is a senescent cell associated disease/disorder is atherosclerosis.

The effectiveness of one or more senolytic agents for treating or preventing (i.e., reducing or decreasing the likelihood of developing or occurrence of) a cardiovascular disease (e.g., atherosclerosis) can readily be determined by a person skilled in the medical and clinical arts. One or any combination of diagnostic methods, including physical examination, assessment and monitoring of clinical symptoms, and performance of analytical tests and methods described herein and practiced in the art (e.g., angiography, electrocardiography, stress test, non-stress test), may be used for monitoring the health status of the subject. The effects of the treatment of a senolytic agent or pharmaceutical composition comprising the same can be analyzed using techniques known in the art, such as comparing symptoms of patients suffering from or at risk of cardiovascular disease that have received the treatment with those of patients without such a treatment or with placebo treatment.

Combination Therapy

The senolytic agents and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration one or more symptoms or disorders described herein.

For example, a senolytic agent may be administered in combination with, or subsequent to, administration of a chemotherapeutic agent. In one embodiment, a tumor is treated with a chemotherapeutic agent that induces a state of senescence in the tumor cells and a co-administered senolytic agent kills the senescent tumors cells. Examples of chemotherapeutics useful for treatment of tumors in combination with senolytic compounds include topoisomerase inhibitors such as doxorubicin, CDK4/6 inhibitors such as palbociclib and PARP inhibitors such as olaparib (for example, see Fleury et al, Nature Communications, 10 (2019) 2556).

It should be understood that any suitable combination of the compounds and pharmaceutical compositions provided herein with one or more of the above therapeutic agents and optionally one or more further pharmacologically active substances are considered to be within the scope of the present disclosure. In some embodiments, the compounds and pharmaceutical compositions provided herein are administered prior to or subsequent to the one or more additional active ingredients.

Pharmaceutical Compositions and Methods of Administration

Also provided herein are pharmaceutical compositions that comprise a senolytic agent as described herein and at least one pharmaceutically acceptable excipient, which may also be called a pharmaceutically suitable excipient or carrier (i.e., a non-toxic material that does not interfere with the activity of the active ingredient). A pharmaceutical composition may be a sterile aqueous or non-aqueous solution, suspension or emulsion (e.g., a microemulsion). The excipients described herein are examples and are in no way limiting. An effective amount or therapeutically effective amount refers to an amount of the one or more senolytic agents administered to a subject, either as a single dose or as part of a series of doses, which is effective to produce a desired therapeutic effect.

When two or more senolytic agents are administered to a subject for treatment of a disease or disorder described herein, each of the senolytic agents may be formulated into separate pharmaceutical compositions. A pharmaceutical preparation may be prepared that comprises each of the separate pharmaceutical compositions (which may be referred to for convenience, for example, as a first pharmaceutical composition and a second pharmaceutical composition comprising each of the first and second senolytic agents, respectively). Each of the pharmaceutical compositions in the preparation may be administered at the same time (i.e., concurrently) and via the same route of administration or may be administered at different times by the same or different administration routes. Alternatively, two or more senolytic agents may be formulated together in a single pharmaceutical composition.

Pharmacokinetics of a senolytic agent (or one or more metabolites thereof) that is administered to a subject may be monitored by determining the level of the senolytic agent in a biological fluid, for example, in the blood, blood fraction (e.g., serum), and/or in the urine, and/or other biological sample or biological tissue from the subject. Any method practiced in the art and described herein to detect the agent may be used to measure the level of the senolytic agent during a treatment course.

The dose of a senolytic agent described herein for treating a senescence cell associated disease or disorder may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. In addition to the factors described herein and above related to use of the senolytic agent for treating a senescence-associated disease or disorder, suitable duration and frequency of administration of the senolytic agent may also be determined or adjusted by such factors as the condition of the patient, the type and severity of the patient's disease, the particular form of the active ingredient, and the method of administration. Optimal doses of an agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a senolytic agent (including when administered for prophylactic benefit) described herein are well within the skill of a person skilled in the relevant art. When two or more senolytic agents are administered to treat a senescence-associated disease or disorder, the optimal dose of each senolytic agent may be different, such as less, than when either agent is administered alone as a single agent therapy. In certain embodiments, two senolytic agents in combination make act synergistically or additively, and either agent may be used in a lesser amount than if administered alone. An amount of a senolytic agent that may be administered per day may be, for example, between about 0.01 mg/kg and 100 mg/kg (e.g., between about 0.1 to 1 mg/kg, between about 1 to 10 mg/kg, between about 10-50 mg/kg, between about 50-100 mg/kg body weight. In other embodiments, the amount of a senolytic agent that may be administered per day is between about 0.01 mg/kg and 1000 mg/kg, between about 100-500 mg/kg, or between about 500-1000 mg/kg body weight. The optimal dose (per day or per course of treatment) may be different for the senescence-associated disease or disorder to be treated and may also vary with the administrative route and therapeutic regimen.

Pharmaceutical compositions comprising a senolytic agent can be formulated in a manner appropriate for the delivery method by using techniques routinely practiced in the art. The composition may be in the form of a solid (e.g., tablet, capsule), semi-solid (e.g., gel), liquid, or gas (aerosol). In other certain specific embodiments, the senolytic agent (or pharmaceutical composition comprising same) is administered as a bolus infusion. In certain embodiments when the senolytic agent is delivered by infusion, the senolytic agent is delivered to an organ or tissue comprising senescent cells to be killed via a blood vessel in accordance with techniques routinely performed by a person skilled in the medical art.

Pharmaceutical acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in Remington: The Science and Practice of Pharmacy (Gennaro, $21^{st}$ Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate. A composition described herein may be lyophilized or otherwise formulated as a lyophilized product using one or more appropriate excipient solutions for solubilizing and/or diluting the agent (s) of the composition upon administration. In other embodiments, the agent may be encapsulated within liposomes using technology known and practiced in the art. Pharmaceutical compositions may be formulated for any appropriate manner of administration described herein and in the art.

A pharmaceutical composition may be delivered to a subject in need thereof by any one of several routes known to a person skilled in the art. By way of non-limiting example, the composition may be delivered orally, intravenously, intraperitoneally, by infusion (e.g., a bolus infusion), subcutaneously, enteral, rectal, intranasal, by inhalation, buccal, sublingual, intramuscular, transdermal, intradermal, topically, intraocular, vaginal, rectal, or by intracranial injection, or any combination thereof. In certain embodiments, administration of a dose, as described above, is via intravenous, intraperitoneal, directly into the target tissue or organ, or subcutaneous route. In certain embodiments, a delivery method includes drug-coated or permeated stents for which the drug is the senolytic agent. Formulations suitable for such delivery methods are described in greater detail herein.

In certain embodiments, a senolytic agent (which may be combined with at least one pharmaceutically acceptable excipient to form a pharmaceutical composition) is administered directly to the target tissue or organ comprising senescent cells that contribute to the manifestation of the disease or disorder. In specific embodiments when treating osteoarthritis, the at least one senolytic agent is administered directly to an osteoarthritic joint (i.e., intra-articularly) of a subject in need thereof. In other specific embodiments, a senolytic agent(s) may be administered to the joint via topical, transdermal, intradermal, or subcutaneous route. In other certain embodiments, methods are provided herein for treating a cardiovascular disease or disorder associated with arteriosclerosis, such as atherosclerosis by administering directly into an artery. In other embodiments, a senolytic agent (which may be combined with at least one pharmaceutically acceptable excipient to form a pharmaceutical composition) for treating a senescent-associated pulmonary disease or disorder may be administered by inhalation, intranasally, by intubation, or intrathecally, for example, to provide the senolytic agent more directly to the affected pulmonary tissue. By way of another non-limiting example, the senolytic agent (or pharmaceutical composition comprising the senolytic agent) may be delivered directly to the eye either by injection (e.g., intraocular or intravitreal) or by conjunctival application underneath an eyelid of a cream, ointment, gel, or eye drops. In more particular embodiments, the senolytic agent or pharmaceutical composition comprising the senolytic agent may be formulated as a timed release (also called sustained release, controlled release) composition or may be administered as a bolus infusion.

A pharmaceutical composition (e.g., for oral administration or for injection, infusion, subcutaneous delivery, intramuscular delivery, intraperitoneal delivery or other method) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In other embodiments, for treatment of an ophthalmological condition or disease, a liquid pharmaceutical composition may be applied to the eye in the form of eye drops. A liquid pharmaceutical composition may be delivered orally.

For oral formulations, at least one of the senolytic agents described herein can be used alone or in combination with appropriate additives to make tablets, powders, granules or capsules, and if desired, with diluents, buffering agents, moistening agents, preservatives, coloring agents, and flavoring agents. The compounds may be formulated with a buffering agent to provide for protection of the compound from low pH of the gastric environment and/or an enteric coating. A senolytic agent included in a pharmaceutical composition may be formulated for oral delivery with a flavoring agent, e.g., in a liquid, solid or semi-solid formulation and/or with an enteric coating.

A pharmaceutical composition comprising any one of the senolytic agents described herein may be formulated for sustained or slow release (also called timed release or controlled release). Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active agent contained within a sustained release formulation depends upon the site of implantation, the rate and expected duration of release, and the nature of the condition, disease or disorder to be treated or prevented.

In certain embodiments, the pharmaceutical compositions comprising a senolytic agent are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated (intradermally or subcutaneously). The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, thimerosal, and combinations thereof.

Pharmaceutical compositions comprising a senolytic agent can be formulated as emulsions for topical application. An emulsion contains one liquid distributed the body of a second liquid. The emulsion may be an oil-in-water emulsion or a water-in-oil emulsion. Either or both of the oil phase and the aqueous phase may contain one or more surfactants, emulsifiers, emulsion stabilizers, buffers, and other excipients. The oil phase may contain other oily pharmaceutically approved excipients. Suitable surfactants include, but are not limited to, anionic surfactants, non-ionic surfactants, cationic surfactants, and amphoteric surfactants. Compositions for topical application may also include at least one suitable suspending agent, antioxidant, chelating agent, emollient, or humectant.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays may be delivered from pressurized packs, for example, via a specially shaped closure. Oil-in-water emulsions can also be used in the compositions, patches, bandages and articles. These systems are semi solid emulsions, micro-emulsions, or foam emulsion systems.

Controlled or sustained release transdermal or topical formulations can be achieved by the addition of time-release additives, such as polymeric structures, matrices, that are available in the art. For example, the compositions may be administered through use of hot-melt extrusion articles, such as bioadhesive hot-melt extruded film. The formulation can comprise a cross-linked polycarboxylic acid polymer formulation. A cross-linking agent may be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the active agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

A polymer formulation can also be utilized to provide controlled or sustained release. Bioadhesive polymers described in the art may be used. By way of example, a sustained-release gel and the compound may be incorporated in a polymeric matrix, such as a hydrophobic polymer matrix. Examples of a polymeric matrix include a microparticle. The microparticles can be microspheres, and the core may be of a different material than the polymeric shell. Alternatively, the polymer may be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the senolytic agent. The matrices can be formed by solvent evaporation, spray drying, solvent extraction and other methods known to those skilled in the art.

Kits with unit doses of one or more of the agents described herein, usually in oral or injectable doses, are provided. Such kits may include a container containing the unit dose, an informational package insert describing the use and attendant benefits of the drugs in treating the senescent cell associated disease, and optionally an appliance or device for delivery of the composition.

All references and patent documents are hereby incorporated in their entirety for all purposes.

EXAMPLES

Example 1: Preparation of (E)-3-(4-(((((9H-fluoren-9-yl)methoxy)carbonyl)(2-(2-methyl-1H-indol-3-yl)ethyl)amino)methyl)phenyl)acrylic Acid (29)

(29)

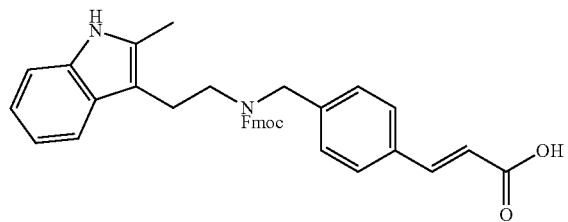

2-(2-Methyl-1H-indol-3-yl)ethan-1-amine (28) (400 mg, 2.2 mmol) was dissolved in a mixture of THF:Dichloroethane:methanol (5:5:0.5). To this solution was added (E)-3-(4-formylphenyl)acrylic acid (27) (367 mg, 2.09 mmol, 0.95 equiv), triacetoxyborohydride (2320 mg, 11 mmol, 5.0 equiv) and 3 drops of acetic acid. The mixture was allowed to stir overnight, and the volatiles were removed under vacuum. LC/MS showed the presence the desired product. Water was added and a solid precipitated out of solution. After adjusting the pH to 7 with dilute NaHCO$_3$, the aqueous solution was washed with ethyl acetate. The white solid was filtered and washed with water, ether, and hexane to give (E)-3-(4-(((2-(2-methyl-1H-indol-3-yl)ethyl)amino)methyl) phenyl)acrylic acid as a light yellow solid. (620 mg, 81% yield). LC/MS: RT=2.41 min; m/z=335.4 [M+H]$^+$.

The preceding product (E)-3-(4-(((2-(2-methyl-1H-indol-3-yl)ethyl)amino)methyl)phenyl)acrylic acid (260 mg, 0.77 mmol, 1.0 equiv) and sodium bicarbonate (245 mg, 2.92 mmol, 3.8 equiv) was suspended in dioxane:water (3:1) (5.1 mL, 0.15M). Fmoc chloride was added portion wise (230 mg, 0.89 mmol, 1.15 equiv) at 0° C. The reaction mixture was allowed to warm to room temperature. Analysis by LC/MS showed the desired product. Dilute HCl was added to pH 2. The aqueous solution was extracted twice with ethyl acetate. The combined organic layers were washed with brine, dried over sodium sulfate and concentrated to give an orange solid. The crude product was subjected to normal phase purification eluting with 10-100% ethyl acetate in hexane. The product fractions were combined and concentrated to dryness to give (E)-3-(4-(((((9H-fluoren-9-yl) methoxy)carbonyl)(2-(2-methyl-1H-indol-3-yl)ethyl) amino)methyl)phenyl)acrylic acid (29) as an off white solid. (240 mg, 56% yield). LC/MS: RT=3.91 min; m/z=557.6 [M+H]$^+$.

Example 2: Preparation of 2-(4-(((((9H-fluoren-9-yl)methoxy)carbonyl)((1-methyl-1H-indol-3-yl) methyl)amino)methyl)piperidin-1-yl)pyrimidine-5-carboxylic Acid (110)

(110)

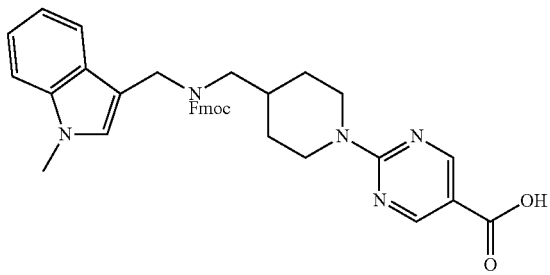

Tert-butyl (piperidin-4-ylmethyl)carbamate (1400 mg, 6.5 mmol, 1.0 equiv) and methyl 2-chloropyrimidine-5-carboxylate (1180 mg. 6.8 mmol, 1.05 equiv) in dioxane (28.0 mL, 0.23 M) were treated with cesium carbonate (5.27 g, 16.2 mmol, 2.5 equiv) and Pd(dba)$_2$acetone (440 mg, 0.48 mmol, 0.075 equiv) was added. The solution was purged with nitrogen (3×). Xantphos (558 mg, 0.96 mmol, 0.15 equiv) was then added in one portion. The suspension turned from dark red to yellow green within a few minutes. It was then heated at 70° C. for 30 min, at which time LC/MS analysis showed the presence of the desired product. The mixture was cooled to room temperature and filtered through a pad of Celite, washing with dichloromethane (20 mL, 3×). The solvent was concentrated to dryness and the residue subjected to normal phase purification eluting with hexane: ethyl acetate (40-100%). The product fractions were collected, combined, and concentrated to give 2-[4-(tert-butoxycarbonylamino-methyl)-piperidin-1-yl]-pyrimidine-carboxylic acid methyl ester as an off-white solid. (1650 mg). LC/MS: RT=3.23 min; m/z=351.6 [M+H]$^+$.

2-[4-(tert-Butoxycarbonylamino-methyl)-piperidin-1-yl]-pyrimidine-5-carboxylic acid methyl ester (1.65 g, 4.7 mmol) was dissolved in THF (10 mL). 4N HCl/dioxane (9.4 mL, 37.6 mmol, 8.0 equiv) was added and the solution was heated at 60° C. for 2 h, during which time, a solid precipitated. The hydrochloride precipitate was filtered, washed with ether/hexane (3×) and dried to afford 2-(4-aminomethyl-piperidin-1-yl)-pyrimidine-5-carboxylic acid methyl ester hydrochloride salt as a white solid (1.08 g). LC/MS: RT=1.88 min; m/z=251.4 [M+H]$^+$.

To 2-(4-Aminomethyl-piperidin-1-yl)-pyrimidine-5-carboxylic acid methyl ester (1080 mg, 3.77 mmol, 1.0 equiv) and triethylamine (1.5 mL, 10.5 mmol, 2.5 equiv) in THF: DCE (1:1) 5% methanol 18 mL) was added 1-methyl-1H-indole-3-carbaldehyde (600 mg, 3.77 mmol, 0.95 equiv) in one portion. Sodium triacetoxyborohyride was added (6300 mg, 30.6 mmol, 8.0 equiv) plus 4 drops of acetic acid. NMP (1.8 mL) was added and the mixture was stirred at room temperature for 2 days. LC/MS analysis showed the formation of the desired product. Water was added, the pH was adjusted to 7 with sodium bicarbonate, and the white solid was filtered and washed with water and ethyl acetate. The product was dried under high vacuum to give methyl 2-(4-((((1-methyl-1H-indol-3-yl)methyl)amino)methyl)piperidin-1-yl)pyrimidine-5-carboxylate as white solid (1300 mg). This material was used without further purification for the next step. LC/MS: RT=2.67 min; m/z=394.5 [M+H]$^+$.

Crude methyl 2-(4-((((1-methyl-1H-indol-3-yl)methyl) amino)methyl)piperidin-1-yl)-pyrimidine-5-carboxylate (1300 mg, 3.3 mmol, 1.0 equiv) and sodium hydroxide (1058 mg, 26.4 mmol, 8.0 equiv) was suspended in dioxane: water (3:1) (10.0 mL). The solution was heated at 70° C. for 2 h. LC/MS analysis showed complete reaction. The solvent was concentrated to remove excess alcohol, and the mixture was acidified to pH 5 and washed with water followed by hexane. The grey solid was dried under high vacuum to afford pure 2-(4-((((1-methyl-1H-indol-3-yl)methyl)amino) methyl)piperidin-1-yl)pyrimidine-5-carboxylic acid (220 mg). LC/MS: RT=2.41 min; m/z=380.6 [M+H]$^+$.

2-(4-((((1-methyl-1H-indol-3-yl)methyl)amino)methyl) piperidin-1-yl)pyrimidine-5-carboxylic acid (200 mg, 0.52 mmol, 1.0 equiv) and sodium bicarbonate (165 mg, 1.9 mmol, 3.8 equiv) were suspended in dioxane:water (3:1) (1.4 mL). Fmoc chloride (136 mg, 0.5 mmol, 1.0 equiv) was added portion-wise until the solution was clear. LC/MS analysis showed the desired product. The pH of the solution was adjusted to 2 and ethyl acetate was added. The mixture was extracted with water (3×) and washed with brine. The combined organic layers were dried with sodium sulfate, concentrated to dryness to give a white foam which was triturated with dichloromethane methanol-hexane (1:5, 3×). Thorough drying afforded the title compound 2-(4-(((((9H-fluoren-9-yl)methoxy)carbonyl)((1-methyl-1H-indol-3-yl) methyl)amino)-methyl)piperidin-1-yl)pyrimidine-5-carboxylic acid (110) as a white foam (200 mg). LC/MS: RT=3.96 min; m/z=602.3 [M+H]$^+$.

Example 3: Preparation of (2R,3S,4S,5R,6S)-2-(Acetoxymethyl)-6-(aminooxy)tetrahydro-2H-pyran-3,4,5-triyl Triacetate (24)

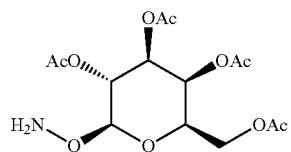

(24)

(2R,3S,4S,5R,6R)-2-(acetoxymethyl)-6-bromotetrahydro-2H-pyran-3,4,5-triyl triacetate (23) (6600 mg, 16.05 mmol, 1.0 equiv) was dissolved in dichloromethane (80 mL). To this solution was added 2-hydroxyisoindoline-1,3-dione (2600 mg, 16.05 mmol, 1.0 equiv). Tetrabutylammonium hydrogen sulfate (1090 mg, 3.21 mmol, 0.2 equiv) in 1M sodium carbonate (32.0 mL, 32 mmol, 2.0 equiv) was added slowly at ice bath temperature. The mixture was stirred at room temperature overnight. TLC analysis showed a new spot at lower rf compared to starting material with PMA stain. Water was added and the mixture was extracted with dichloromethane (3×). The combined organic layers were washed with water and brine, then dried over sodium sulfate and concentrated to afford a red solid. The crude product was subjected to normal phase purification eluting with 20-70% ethyl acetate:hexane. The product fractions were collected, combined and concentrated to give pure (2R,3S,4S,5R,6S)-2-(acetoxymethyl)-6-((1,3-dioxoisoindolin-2-yl)oxy)tetrahydro-2H-pyran-3,4,5-triyl triacetate as white foam. (2000 mg, 55%). LC/MS: RT=2.96 min; m/z=494.4 [M+H]$^+$.

(2R,3S,4S,5R,6S)-2-(Acetoxymethyl)-6-((1,3-dioxoisoindolin-2-yl)oxy)tetrahydro-2H-pyran-3,4,5-triyl triacetate (2000 mg, 4.05 mmol, 1.0 equiv) was dissolved in methanol (35 mL, 0.1M). Hydrazine hydrate (0.20 mL, 4.25 mmol, 1.05 equiv) was added slowly. After five minutes LC/MS analysis showed the desired product. Dichloromethane (125 mL) was added and the solution was washed with saturated NaHCO$_3$ (3×). The combined organic layers were washed with water and brine, dried over sodium sulfate and concentrated to give a solid (2000 mg). The product was subjected to normal phase purification eluting 30-90% ethyl acetate:hexane. The product fractions were collected, combined and concentrated to afford the title compound (2R,3S,4S,5R,6S)-2-(acetoxymethyl)-6-(aminooxy)tetrahydro-2H-pyran-3,4,5-triyl triacetate (24) as a white foam. (1170 mg, 79% yield). LC/MS: RT=1.98 min; m/z=364.3 [M+H]$^+$.

Example 4: Preparation of (2S,3S,4R,5R,6S)-2-(Aminooxy)-6-methyltetrahydro-2H-pyran-3,4,5-triyl Triacetate (32)

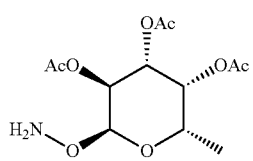

(32)

(3S,4R,5R,6S)-2-Hydroxy-6-methyltetrahydro-2H-pyran-3,4,5-triyl triacetate (5000 mg, 17 mmol) was dissolved in THF (100.0 mL). DAST (18.0 mL, 137 mmol, 8.0 equiv) was added at −30° C. cooling with a dry ice-methanol bath. The reaction mixture was allowed to warm to room temperature, stirring at this temperature for 1 h. Another portion of DAST (4 mL) was added at −30° C. and again was allowed to warm to room temperature and stirred for 1 h. LC/MS analysis indicated that the reaction was complete. Methanol was added at −20° C., and the solvent was evaporated. NaHCO$_3$ was added and the solution was extracted with dichloromethane (3×). The combined organic layers were washed with water. Dilute HCl was added to decompose the residual DAST and the solution was extracted with ethyl acetate (2×). The combined organic layers were washed with brine, dried over sodium sulfate and concentrated to give the crude product as an oil (4000 mg). This brown oil was subjected to normal phase purification eluting with hexane-ethyl acetate (0 to 40%). The product fractions were collected, combined and concentrated to give (3S,4R,5R,6S)-2-fluoro-6-methyltetrahydro-2H-pyran-3,4,5-triyl triacetate (30) as white foam solid. (2000 mg). LC/MS: RT=2.45 min; m/z=310 [M+H$_2$O]$^+$.

(3S,4R,5R,6S)-2-Fluoro-6-methyltetrahydro-2H-pyran-3,4,5-triyl triacetate (30) (1800 mg, 6.16 mmol, 1.0 equiv) was dissolved in acetonitrile (30 mL). N-hydroxyphathalimide (1100 mg, 6.78 mmol, 1.1 equiv) was added followed by TEA (1.15 mL, 6.78 mmol, 1.05 equiv). BF$_3$:Et$_2$O (1.1 mL, 6.78 mmol, 1.05 equiv) was added dropwise, and the reaction was stirred for 1 h, at which time LC/MS analysis showed the presence of the desired product. The mixture was poured into 10% NaHCO$_3$/EtOAc. The layers were shaken and separated and the organic layer was washed with sodium bicarbonate (2×), water, and brine. The organic layer was dried over sodium sulfate and concentrated to give a dark oil. The crude product was subjected to normal phase purification eluting with hexane:ethyl acetate (0 to 50%). The product fractions were collected and combined (less polar product-fractions 55-64, 1.0 g; more polar product—fractions 91-105, 500 mg). The less polar product is the desired α-anomer of (2S,3S,4R,5R,6S)-2-((1,3-dioxolsoindolin-2-yl)oxy)-6-methyltetrahydro-2H-pyran-3,4,5-triyl triacetate (31). The more polar product is the undesired β-anomer. LC/MS: RT=3.02 min and 3.28 min; m/z=436.5 [M+H]$^+$.

(2S,3S,4R,5R,6S)-2-((1,3-Dioxoisoindolin-2-yl)oxy)-6-methyltetrahydro-2H-pyran-3,4,5-triyl triacetate (31) (350 mg, 0.8 mmol, 1.0 equiv) was dissolved in methanol (8.0 mL). Hydrazine hydrate (65%, 0.066 mL, 0.8 mmol, 1.0 equiv) was added slowly at ice bath temperature. LC/MS analysis showed complete reaction within a few minutes. The white precipitate was filtered off. The reaction was diluted with dichloromethane and filtered a second time. The filtered solution was washed with NaHCO$_3$ (3×). The organic layer was washed with brine, dried over sodium sulfate, and concentrated to give the desired (2S,3S,4R,5R,6S)-2-(aminooxy)-6-methyltetrahydro-2H-pyran-3,4,5-triyl triacetate (32) as white foam solid (500 mg). LC/MS: RT=2.2 min; m/z=306.6 [M+H]$^+$.

Example 5: Preparation of (E)-3-(4-(((2-(2-Methyl-1H-indol-3-yl)ethyl)amino)methyl)phenyl)-N-(((2S,3R,4S,5R,6R)-3,4,5-trihydroxy-6-(hydroxymethyl)tetrahydro-2H-pyran-2-yl)oxy)acrylamide (26)

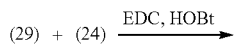

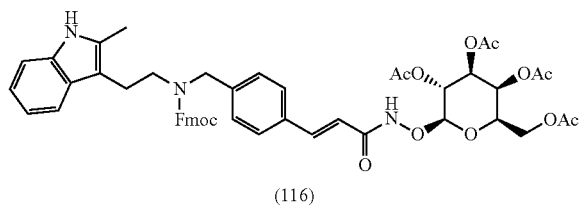

1-(3-Dimethyl aminopropyl)-3-ethylcarbodiimide hydrochloride (EDC. HCl) (114 mg, 0.59 mmol, 1.33 equiv) and 1-hydroxybenzotriazole (HOBt) (91 mg, 0.59 mmol, 1.33 equiv) were added to a solution of (E)-3-(4-(((((9H-fluoren-9-yl)methoxy)carbonyl)(2-(2-methyl-1H-indol-3-yl)ethyl)amino)methyl)phenyl)acrylic acid (29) (250 mg, 0.449 mmol, 1.0 equiv) in N,N-dimethylformamide (DMF) (1.4 mL) and stirred at room temperature for 30 min. Then (2R,3S,4S,5R,6S)-2-(acetoxymethyl)-6-(aminooxy)tetrahydro-2H-pyran-3,4,5-triyl triacetate (24) (244 mg, 0.67 mmol, 1.5 equiv) and DIPEA (0.078 mL, 0.449 mmol, 1.4 equiv) were added to the mixture at ice bath temperature. The mixture was stirred at room temperature overnight. LC/MS analysis showed the desired product. The mixture was quenched with cold saturated NH₄Cl solution. The white precipitate thus formed was filtered and washed with water (2×). The white solid was re-dissolved in ethyl acetate, washed with water, NaHCO₃, and brine. The combined organic layers were dried over sodium sulfate and concentrated to give pure (2S,3R,4S,5S,6R)-2-(((E)-3-(4-(((((9H-fluoren-9-yl)methoxy)carbonyl)(2-(2-methyl-1H-indol-3-yl)ethyl)amino)methyl)phenyl)acrylamido)oxy)-6-(acetoxymethyl)tetrahydro-2H-pyran-3,4,5-triyl triacetate (116) as light yellow, foamy solid. (320 mg, 79% yield). LC/MS: RT=6.95 min; m/z=902.7 [M+H]$^+$.

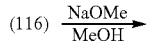

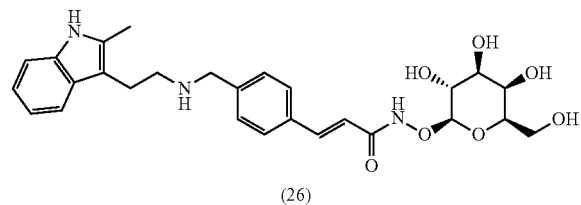

(2S,3R,4S,5S,6R)-2-(((E)-3-(4-(((((9H-Fluoren-9-yl)methoxy)carbonyl)(2-(2-methyl-1H-indol-3-yl)ethyl)amino)methyl)phenyl)acrylamido)oxy)-6-(acetoxymethyl)tetrahydro-2H-pyran-3,4,5-triyl triacetate (116) (150 mg, 0.166 mmol, 1.0 equiv) was dissolved in methanol (3.0 mL) and 25% sodium methoxide in methanol (0.1 mL, 0.49 mmol, 3.0 equiv) was added slowly at ice bath temperature. LC/MS showed the desired product after 20 min. The reaction was quenched by the addition of 10% acetic acid. The water was removed and replaced by methanol. Filtration twice removed the insoluble salts and the crude product after solvent removal was subject to HPLC purification for final analyses. The title compound (E)-3-(4-(((2-(2-methyl-1H-indol-3-yl)ethyl)amino)methyl)phenyl)-N-(((2S,3R,4S,5R,6R)-3,4,5-trihydroxy-6-(hydroxymethyl)tetrahydro-2H-pyran-2-yl)oxy)acrylamide (26) was isolated as a white solid. LC/MS: RT=1.28 min; m/z=512.5 [M+H]$^+$. $^1$H NMR (500 MHz, Methanoic): δ 7.59-7.45 (m, 3H), 7.40 (d, J=7.8 Hz, 1H), 7.31 (d, J=7.9 Hz, 2H), 7.25 (d, J=8.1 Hz, 1H), 7.02 (t, J=7.5 Hz, 1H), 6.94 (t, J=7.2 Hz, 1H), 6.50 (J=15.8 Hz, 1H), 4.56 (d, J=8.0 Hz, 1H), 3.85 (m, 4H), 3.78-3.67 (m, 2H), 3.65-3.60 (m, 1H), 3.57 (dd, J=9.6, 3.4 Hz, 1H), 2.97 (dd, J=7.9, 5.8 Hz, 2H), 2.90 (t, J=7.3 Hz, 2H), 2.36 (s, 3H).

Example 6: Preparation of (2R,3S,4S,5R,6S)-2-(Acetoxymethyl)-6-(((E)-3-(4-(((2-(2-methyl-1H-indol-3yl)ethyl)amino)methyl)phenyl)acrylamido)oxy)tetrahydro-2H-pyran-3,4,5-triyl Triacetate (113)

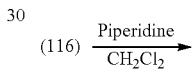

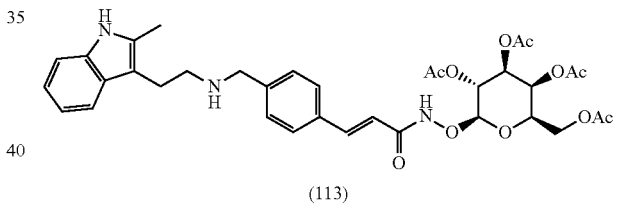

(2S,3R,4S,5S,6R)-2-(((E)-3-(4-(((((9H-Fluoren-9-yl)methoxy)carbonyl)(2-(2-methyl-1H-indol-3-yl)ethyl)amino)methyl)phenyl)acrylamido)oxy)-6-(acetoxymethyl)tetrahydro-2H-pyran-3,4,5-triyl triacetate (116) (745 mg, 0.825 mmol, 1.0 equiv) was dissolved in dichloromethane (5 mL). Piperidine (10% in DCM) (7.0 mL, 8.2 mmol, 10.0 equiv) was added and the mixture was stirred at room temperature for 3 h. LC/MS analysis showed the reaction was complete. EtOAc was added (200 mL) and the solution was washed with NaHCO₃ (2×). The organic layers were washed with brine, dried over sodium sulfate and concentrated to dryness to give the crude product. The title compound (2R,3S,4S,5R,6S)-2-(acetoxymethyl)-6-(((E)-3-(4-(((2-(2-methyl-1H-indol-3-yl)ethyl)amino)methyl)phenyl)acrylamido)oxy tetrahydro-2H-pyran-3,4,5-triyl triacetate (113) was isolated as its white hydrochloride salt after HPLC purification using an HCl-containing buffer (550 mg, 80% yield). LC/MS: RT=4.38 min; m/z=680.7 [M+H]$^+$. $^1$H NMR (500 MHz, Methanoic): δ 7.61-7.48 (m, 3H), 7.40 (dt, J=7.8 Hz, 1.0 Hz, 1H), 7.33 (d, J=7.9 Hz, 2H), 7.25 (d, J=8.0 Hz, 1H), 7.02 (t, J=7.5 Hz, 1H), 6.95 (t, J=7.4 Hz, 1H), 6.48 (d, j=16.1 Hz, 1H), 5.43 (d, J=3.3 Hz, 1H), 5.32-5.19 (m, 2H), 5.02 (d, J=8.0 Hz, 1H), 4.27-4.13 (m, 3H), 3.89 (s, 2H), 3.11 (t, 7=5.7 Hz, 1H), 3.02-2.87 (m, 4H), 2.37 (s, 3H), 2.15 (s, 3H), 2.13 (s, 3H), 2.03 (s, 3H), 1.98 (s, 3H).

Example 7: Preparation of (E)-3-(4-(((2-(2-Methyl-1H-indol-3-yl)ethyl)amino)methyl)phenyl)-N-(((2S,3S,4R,5S,6S)-3,4,5-trihydroxy-6-methyltetrahydro-2H-pyran-2-yl)oxy)acrylamide (35)

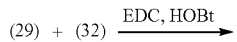

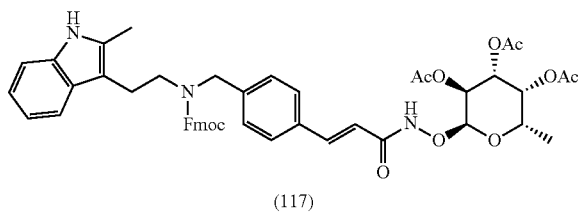

EDC (430 mg, 2.2 mmol, 1.4 equiv) and HOBt (344 mg, 2.2 mmol, 1.4 equiv) was added to (29) (900 mg, 1.6 mmol, 1.0 equiv) in DMF (8.0 mL). The mixture was stirred for 10 min. Compound (32) (500 mg, 1.63 mmol, 1.05 equiv) was added, followed by addition of DIEA (418 μL, 1.5 equiv) at ice bath temperature. The reaction was stirred at room temperature overnight. LC/MS analysis showed the desired product. Saturated ammonium chloride solution was added (20 mL) as a white solid precipitated. The solid was filtered, washed with water (2×), and dried to give a white solid (1.30 g). The solid was purified by normal phase chromatography eluting with hexane-ethyl acetate (20-75%). The product fractions were collected, combined, and the solvents were concentrated to give (2S,3S,4R,5R,6S)-2-(((E)-3-(4-(((((9H-fluoren-9-yl)methoxy)carbonyl)(2-(2-methyl-1H-indol-3-yl)ethyl)amino)methyl)phenyl)acrylamido)oxy)-6-methyltetrahydro-2H-pyran-3,4,5-triyl triacetate (117) as an off-white solid (650 mg). LC/MS: RT=3.89 min; m/z=844.5 [M+H]$^+$.

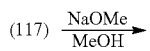

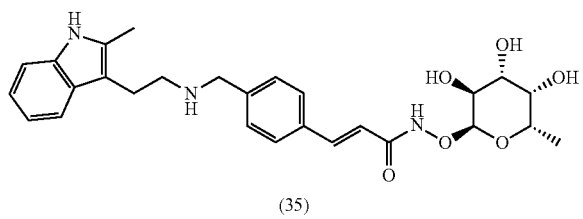

(2S,3S,4R,5R,6S)-2-(((E)-3-(4-(((((9H-Fluoren-9-yl)methoxy)carbonyl)(2-(2-methyl-1H-indol-3-yl)ethyl)amino)methyl)phenyl)acrylamido)oxy)-6-methyltetrahydro-2H-pyran-3,4,5-triyl triacetate (117) (150 mg, 0.17 mmol, 1.0 equiv) and sodium methoxide (25%) (0.085 mL, 2.6 equiv) in methanol (1.0 mL) were mixed at ice bath temperature. The mixture was stirred at room temperature for 2 h. 1N HCl (1.0 equiv) was added and the solution was concentrated to dryness and the residue subjected to HPLC purification, with the title compound (E)-3-(4-(((2-(2-methyl-1H-indol-3-yl)ethyl)amino)methyl)phenyl)-N-(((2S,3S,4R,5S,6S)-3,4,5-trihydroxy-6-methyltetrahydro-2H-pyran-2-yl)oxy)acrylamide (35) being isolated as a white solid (70 mg). LC/MS: RT=1.35 min; m/z=496.5 [M+H]$^+$. $^1$H NMR (500 MHz, Methanoic): δ 7.69 (d, J=8.5 Hz, 3H), 7.53 (d, J=8.2 Hz, 2H), 7.43 (d, J=7.8 Hz, 1H), 7.28 (d, J=8.0 Hz, 1H) 7.08-6.97 (m, 2H), 6.59 (d, 7=15.8 Hz, 1H), 4.57 (d, J=7.9 Hz, 1H), 4.28 (s, 2H), 3.74 (q, J=6.4 Hz, 1H), 3.68-3.61 (m, 2H), 3.57 (dd, J=9.7, 3.3 Hz, 1H), 3.30-3.22 (m, 2H), 3.14 (dd, J=9.3, 6.6 Hz, 2H), 2.42 (s, 3H), 1.33 (d, J=6.4 Hz, 3H).

Example 8: Preparation of (2S,3R,4R,5S,6S)-2-Methyl-6-(((E)-3-(4-(((2-(2-methyl-1H-indol-3-yl)ethyl)amino)methyl)phenyl)acrylamido)oxy)tetrahydro-2H-pyran-3,4,5-triyl triacetate (119)

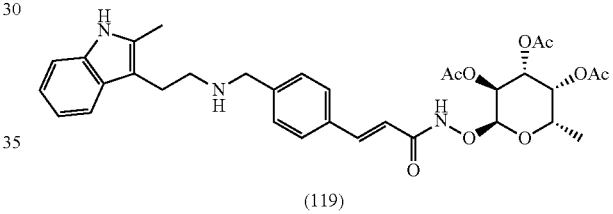

To compound (117) (640 mg, 0.75 mmol, 1.0 eq) in DCM:DMF (1:1) (10 mL) was added 50% triethyl amine/DCM (10.0 mL). The mixture was stirred overnight at room temperature. LC/MS analysis showed the presence of the desired product and starting material. The solvent was concentrated. The residue was taken up in 50% TEA/DCM (5 mL) and DMF (2.0 mL), and the mixture was stirred for 4 h. LC/MS now showed that the starting material had been consumed. The solvents were was removed under reduced pressure. The residue was triturated with hexane to remove the bulk of the 9-methylene-9H-fluorene. Saturated ammonium chloride solution and ethyl acetate were added, and the organic layer was washed with water (3×) followed by brine, and dried over sodium sulfate. The solvent was removed and the residue was purified by HPLC using a buffer containing HCl, and the title compound (2S,3R,4R,5S,6S)-2-methyl-6-(((E)-3-(4-(((2-(2-methyl-1H-indol-3-yl)ethyl)amino)methyl)phenyl)acrylamido)oxy)tetrahydro-2H-pyran-3,4,5-triyl triacetate (119) being isolated as its hydrochloride salt as a white solid. LC/MS: RT=1.89 min; m/z=622.4 [M+H]$^+$. $^1$H NMR (500 MHz, Methanoic): δ 7.73-7.61 (m, 3H), 7.54 (d, J=8.1 Hz, 2H), 7.44 (d, J=7.8 Hz, 1H), 7.28 (d, J=8.0 Hz, 1H), 7.06 (t, J=7.5 Hz, 1H), 7.00 (t, J=7.4 Hz, 1H), 6.55 (d, J=15.9 Hz, 1H), 5.48-5.31 (m, 3H), 5.16 (dd, 7=11.3, 3.9 Hz, 1H), 4.63 (s, 1H), 4.28 (s, 2H), 3.26 (dd, J=9.5, 6.5 Hz, 2H), 3.14 (dd, J=9.3, 6.5 Hz, 2H), 2.42 (s, 3H), 2.18 (s, 3H), 2.16 (s, 3H), 2.01 (s, 3H), 1.20 (d, J=6.5 Hz, 3H).

Example 9: Preparation of (2S,3R,4S,5S,6R)-2-((2-(4-(((((9H-Fluoren-9-yl)methoxy)carbonyl)((1-methyl-1H-indol-3-yl)methylaminomethyl)piperidin-1-yl)pyrimidine-5-carboxamido)oxy)-6-(acetoxymethyl)tetrahydro-2H-pyran-3,4,5-triyl Triacetate (111)

(110) + (24) $\xrightarrow{\text{EDC, HOBt}}$

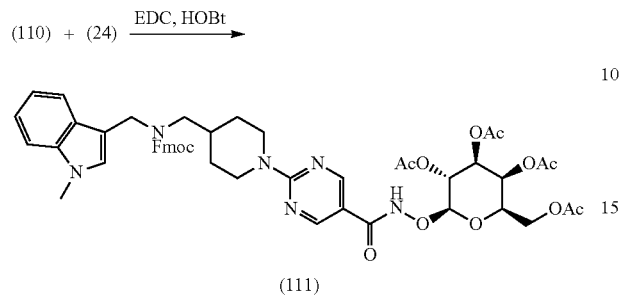

(111)

EDC (76 mg, 0.40 mmol, 1.4 equiv) and HOBt (61 mg, 0.4 mmol, 1.4 equiv) were added to 2-(4-{[(9H-Fluoren-9-ylmethoxycarbonyl)-(1-methyl-1H-indol-3-ylmethyl)-amino]-methyl}-piperidin-1-yl)-pyrimidine-5-carboxylic acid (110) (170 mg, 0.28 mmol, 1.0 equiv) in DMF (0.5 mL). The solution was stirred for 10 min, after which time compound (24) (148 mg, 0.45 mmol, 1.5 equiv) was added followed by DIEA (80 µL, 1.5 equiv) at ice bath temperature. The solution was stirred at room temperature overnight. LC/MS analysis showed the formation of the desired product. Saturated ammonium chloride solution was added (2.0 mL), and a white solid precipitated. The precipitate was washed with water (2x). The solid was filtered and dried to afford (2S,3R,4S,5S,6R)-2-((2-(4-(((((9H-fluoren-9-yl)methoxy)carbonyl)((1-methyl-1H-indol-3-yl)methyl)amino)methyl)piperidin-1-yl)pyrimidine-5-carboxamido)oxy)-6-(acetoxymethyl)tetrahydro-2H-pyran-3,4,5-triyl triacetate (111) as white solid (260 mg), which was used without further purification in the following step. LC/MS: RT=7.07 min; m/z=947.9 [M+H]$^+$.

Example 10: Preparation of 2-(4-((((l-Methyl-1H-indol-3-yl)methyl)amino)methyl)piperidin-1-yl)-N-(((2S,3R,4S,5R,6R)-3,4,5-trihydroxy-6-(hydroxymethyl)tetrahydro-2H-pyran-2-yl)oxy)pyrimidine-5-carboxamide (112)

(111) $\xrightarrow{\text{NaOMe}}_{\text{MeOH}}$

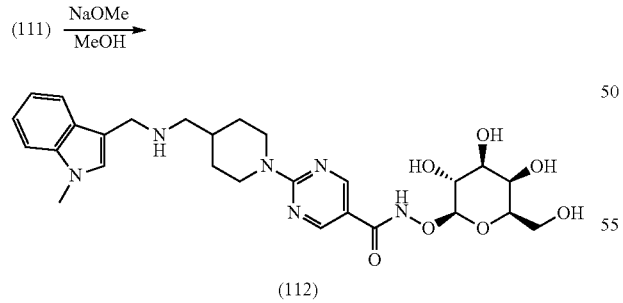

(112)

Compound (111) (170 mg, 0.18 mmol) was dissolved in methanol (1.79 mL), and 25% sodium methoxide in methanol (0.040 mL, 1.0 equiv) was added slowly at ice bath temperature. After stirring at room temperature for 2 h, the Fmoc protecting group was not entirely removed. Another 0.2 equiv of sodium methoxide was added at ice bath temperature, and the reaction went to completion within 20 min. HCl/dioxane (IN, 1.2 equiv) was added to adjust the pH to 5~6. The solvent was concentrated to dryness and the residue subjected to HPLC purification to afford the title compound 2-(4-((((1-methyl-1H-indol-3-yl)methyl)amino)methyl)piperidin-1-yl)-N-(((2S,3R,4S,5R,6R)-3,4,5-trihydroxy-6-(hydroxymethyl)tetrahydro-2H-pyran-2-yl)oxy)pyrimidine-5-carboxamide (112) (80 mg). LC/MS: RT=1.33 min; m/z=557.3 [M+H]$^+$. $^1$H NMR (500 MHz, Methanoic): δ 8.72 (s, 2H), 7.75 (m, 1H), 7.47 (m, 2H), 7.29 (m, 1H), 7.20 (m, 1H), 4.95-4.91 (m, 2H), 4.60 (d, J=7.8 Hz, 1H), 4.45, (s 2H), 3.88-3.81 (m, 5H), 3.77 (dd, J=11.3, 4.6 Hz, 1H), 3.71 (dd, J=9.6, 8.0 Hz, 1H), 3.64 (m, 1H), 3.57 (m, 1H), 3.05-2.96 (m, 4H), 2.10 (m, 1H), 2.06 (s, 2H), 1.92-1.85 (m, 2H), 1.26 (m, 2H).

Example 11: Preparation of (2R,3S,4S,5R,6S)-2-(Acetoxymethyl)-6-((2-(4-((((1-methyl-1H-indol-3-yl)methyl)amino)methyl)piperidin-1-yl)pyrimidine-5-carboxamido)oxy)tetrahydro-2H-pyran-3,4,5-triyl Triacetate (114)

(111) $\xrightarrow{\text{Piperidine}}_{\text{CH}_2\text{Cl}_2}$

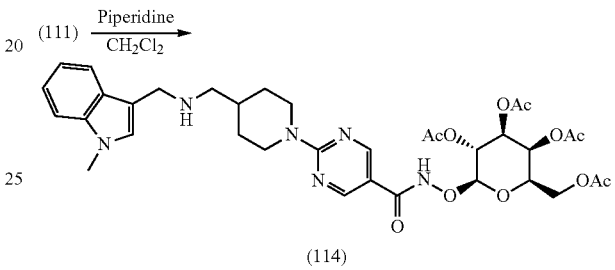

(114)

Compound (111) (88 mg, 0.092 mmol) was dissolved in dichloromethane (0.1 mL). Piperidine (20% in DCM) (0.47 mmol, 1.1 mmol, 12.0 equiv) was added. The mixture was stirred at room temperature for 6 h. LC/MS analysis showed that the reaction was complete. IN HCl/dioxane (1.0 equiv) was added. The solution was concentrated to dryness and the crude residue was subjected to HPLC purification to yield 60 mg of the title compound (2R,3S,4S,5R,6S)-2-(acetoxymethyl)-6-((2-(4-((((1-methyl-1H-indol-3-yl)methyl)amino)methyl)piperidin-1-yl)pyrimidine-5-carboxamido)oxy)tetrahydro-2H-pyran-3,4,5-triyl triacetate (114). LC/MS: RT=1.89 min; m/z=725.3 [M+H]$^+$. $^1$H NMR (500 MHz, Methanoic): δ 8.64 (s, 2H), 7.69 (m, 1H), 7.40 (m, 1H), 7.31 (s, 1H), 7.23 (m, 1H), 7.13 (m, 1H), 5.42 (d, J=3.5 Hz, 1H), 5.34 (m, 1H), 5.21 (m, 1H), 5.07 (d, J=8.3 Hz, 1H), 4.81 (d, J=13.3 Hz, 2H), 4.26-4.13 (m, 5H), 3.82 (s, 3H), 2.94 (t, J=12.8 Hz, 2H), 2.77 (d, J=6.8 Hz, 2H), 2.13 (s, 3H), 2.11 (s, 3H), 2.02 (s, 3H), 1.97 (s, 3H), 1.85 (d, J=11.6 Hz, 2H), 1.19 (m, 2H).

Example 12: Preparation of (2S,3R,4R,5S,6S)-2-Methyl-6-((2-(4-((((1-methyl-1H-indol-3-yl)methyl)amino)methyl)piperidin-1-yl)pyrimidine-5-carboxamido)oxy)tetrahydro-2H-pyran-3,4,5-triyl Triacetate (115)

(110) + (32) $\xrightarrow{\text{(i) EDC, HOBt}}_{\text{(ii) NEt}_2{}^i\text{Pr}}$

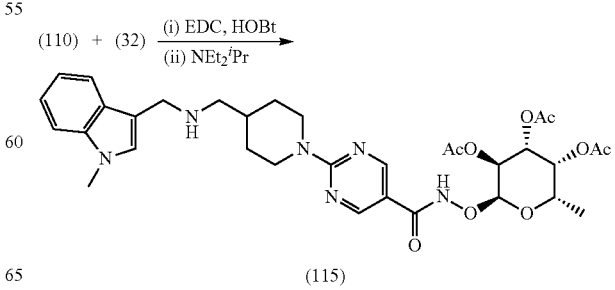

(115)

EDC (54 mg, 0.28 mmol) and HOBt (42 mg, 0.28 mmol, 1.05 equiv) were added to a solution of compound (110) (96 mg, 0.31 mmol, 1.4 equiv) in DMF (0.5 mL). The solution was stirred at room temperature for 15 min, at which time compound (32) (96 mg, 0.37 mmol, 1.4 eq) was added in one portion. DIEA (1.5 eq, 0.073 mL) was added at ice bath temperature and the mixture was stirred at room temperature for 1 h. LC/MS analysis showed the presence of the desired product. Saturated ammonium chloride solution was added to the reaction, and a yellow solid was filtered off and washed with water. Ethyl acetate was added to the solution and it was washed with brine (2×). The combined organic layers were dried over sodium sulfate and concentrated to give (2S,3R,4R,5S,6S)-2-methyl-6-((2-(4-((((1-methyl-1H-indol-3-yl)methyl)amino)methyl)piperidin-1-yl)pyrimidine-5-carboxamido)oxy)tetrahydro-2H-pyran-3,4,5-triyl triacetate (115) as a foam solid (200 mg) which was used as such without purification in the next reaction. LC/MS: RT=6.83 min; m/z=889.9 [M+H]⁺.

Example 13: Preparation of 2-(4-((((1-Methyl-1H-indol-3-yl)methyl)amino)methyl)piperidin-1-yl)-N-(((2S,3S,4R,5S,6S)-3,4,5-trihydroxy-6-methyltetrahydro-2H-pyran-2-yl)oxy)pyrimidine-5-carboxamide (120)

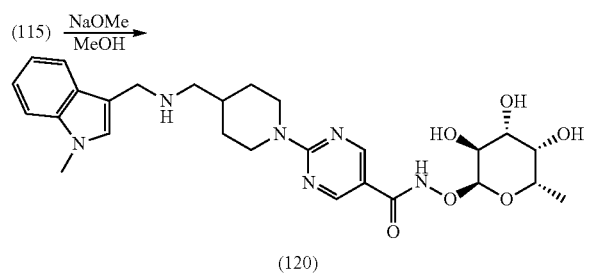

Compound (115) (70 mg, 0.079 mmol, 1.0 equiv) and sodium methoxide (25%) (2.0 equiv) were dissolved in methanol (0.8 mL) at ice bath temperature. The mixture was stirred at room temperature 2 h. 1N HCl (1.0 equiv) was added and the solution was concentrated to dryness and the residue subjected to HPLC purification to afford the title compound (120). LC/MS: RT=3.05 min; m/z=541.3 [M+H]⁺. ¹H NMR (500 MHz, Methanoic): δ 8.71 (s, 2H), 7.74 (d, J=8.0 Hz, 1H), 7.51-7.43 (m, 2H), 7.30 (m, 1H), 7.21 (m, 1H), 4.93 (d, J=3D Hz, 1H), 4.59 (d, J=7.9 Hz, 1H), 4.45 (s, 2H), 3.87 (s, 3H), 3.77-3.71 (m, 1H), 3.68-3.61 (m, 2H), 3.57 (m, 1H), 3.05-2.95 (m, 4H), 2.09 (m, 1H), 1.88 (d, J=12.4 Hz, 2H), 1.33 (d, J=6.5 Hz, 3H), 1.26 (m, 2H).

Example 14: Preparation of (2S,3R,4R,5S,6S)-2-Methyl-6-(((E)-3-(4-(((2-(2-methyl-1H-indol-3-yl)ethyl)amino)methyl)phenyl)acrylamido)oxy)tetrahydro-2H-pyran-3,4,5-triyl Tripropionate (121)

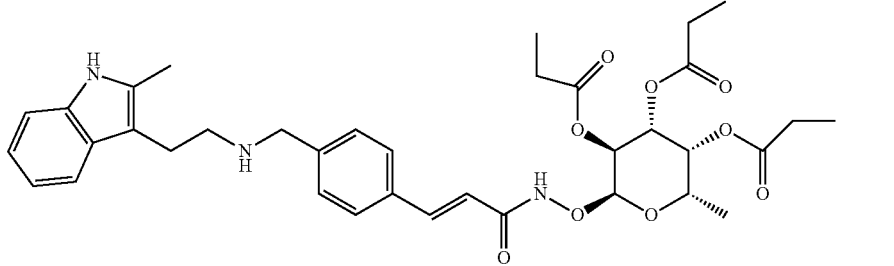

L-Fucose (3000 mg, 18.2 mmol, 1.0 equiv) was stirred in mixture of pyridine (9.0 mL) and propionic anhydride (27.0 mL). The solution was heated at 80° C. for 2 days at which time more propionic anhydride (5.0 mL) was added, and stirring was continued for one more day. The mixture was concentrated to dryness, ethyl acetate (80 mL) and water (30 mL) were added and the aqueous layer was further extracted twice. The combined organic layers were washed with dilute 1 N HCl followed by brine. The solution was dried over sodium sulfate, and the solution was concentrated to dryness to give (2R,3S,4R,5R,6S)-6-methyltetrahydro-2H-pyran-2,3,4,5-tetrayl tetrakis(propionoate), as a brown oil (10 g). LC/MS: RT=3.3 min; m/z=467.5 [M+79]⁺.

Acetic acid (1.8 mL, 28.8 mmol, 1.4 equiv) was added to a solution of ethylenediamine (1.78 mL, 24.7 mmol, 1.2 equiv) in THF (200 mL). A solid precipitated and (2R,3S,4R,5R,6S)-6-methyltetrahydro-2H-pyran-2,3,4,5-tetrayl tetrakis(propionoate) (8 g, 20.66 mmol, 1.0 equiv) was added in one portion. The reaction mixture was stirred at room temperature overnight, at which time, LC/MS analysis showed mainly unreacted starting material. The reaction was worked up and re-subjected to the same reaction conditions, stirring at room temperature overnight. A second lot was repeated at the same scale. LC/MS analysis showed that the reaction was complete. Water was added and the two layers were separated. Dilute HCl (2%) and ethyl acetate were added and the organic layer was washed with water twice followed by brine. The solution was dried over sodium sulfate and the solvent was removed to give (2R,3S,4R,5R,6S)-2-hydroxy-6-methyltetrahydro-2H-pyran-3,4,5-triyl tripropionate as a white sticky solid. (5.8 g). LC/MS: RT=2.6 min; m/z=350.1 [M+18], (2R,3S,4R,5R,6S)-2-hydroxy-6-methyltetrahydro-2H-pyran-3,4,5-triyl tripropionate (3.0 g, 9.03 mmol, 1.0 equiv) was dissolved in THF (150 mL). The solution was purged with nitrogen for 5 min and the solution was cooled to −50° C. DAST (5.0 mL) was added dropwise via a plastic pipette. The solution was allowed to warm to 0° C. TLC analysis showed mostly starting material. Another portion of DAST (2.0 mL) was added at −50° C. (1.5 equiv), and the temperature was warmed to 0° C. TLC analysis showed a less polar spot and a small amount of starting material. Additional DAST was added twice (3.0 ml, 3.0 mL each) as before and the reaction was allowed to stir until the starting material was totally consumed (approx. 8 h total). The solution was cooled to −30° C., methanol (15 mL) was added slowly, and the mixture was allowed to warm to room temperature. Cold NaHCO$_3$ solution was added and the mixture was dilute with dichloromethane. The organic layer was separated and washed with 1N HCl (2×) followed by brine. The solution was dried over sodium sulfate and the solvent was removed to give a yellow oil (4.1 g). TLC analysis showed that the product was impure. The crude product was subjected to normal phase purification eluting with a gradient of 100% hexane to 15% ethyl acetate in hexane over 60 min. The product fractions were collected and the solvent was removed to give pure (2S,3S,4R,5R,6S)-2-fluoro-6-methyltetrahydro-2H-pyran-3,4,5-triyl tripropionate as a colorless oil (2.4 g). LC/MS: RT=3.2 min; m/z=413.1 [M+79]$^+$.

(2S,3S,4R,5R,6S)-2-fluoro-6-methyltetrahydro-2H-pyran-3,4,5-triyl tripropionate (1500 mg, 4.49 mmol, 1.0 equiv) was dissolved in acetonitrile (15 mL). N-hydroxyphathlimide (915 mg, 5.61 mmol, 1.25 equiv) was added followed by addition of triethylamine (0.81 mL, 5.61 mmol, 1.25 equiv). The solution turned dark red. BF$_3$-etherate (1.03 mL, 8.08 mmol, 1.8 equiv) was added and the solution turned clear. It was stirred at room temperature for 1 hr. LC/MS showed desired product. A cold solution of NaHCO$_3$ was added and it was extracted twice with ethyl acetate. The solution turned dark red. The combined organic layers were washed twice with NaHCO$_3$ until no more color was detected. The organic solvents were dried over sodium sulfate. The solvent was concentrated to give as yellow oil (2000 mg). The crude mixture was subjected to normal phase purification using a 25 g silica gel column, eluting with a gradient of 100% hexane to 25% ethyl acetate in hexane over 40 minutes. The product fractions were collected as 2 peaks. Peak #1 (normal phase, less polar) LC/MS (reverse phase): RT=3.56 min; m/z=478.4 [M+H]$^+$. Peak #2 (normal phase, more polar) LC/MS (reverse phase): RT=3.31 min; m/z=478.4 [M+H]$^+$. Peak #1 was determined to be the desired alpha isomer, (2S,3S,4R,5R,6S)-2-((1,3-dioxoisoindolin-2-yl)oxy)-6-methyltetrahydro-2H-pyran-3,4,5-triyl tripropionate, by comparison of its $^1$H NMR spectrum with the literature characterized triacetoxy analog (31). It was isolated as a white solid (500 mg).

(2S,3S,4R,5R,6S)-2-((1,3-Dioxoisoindolin-2-yl)oxy)-6-methyltetrahydro-2H-pyran-3,4,5-triyl tripropionate (500 mg, 1.04 mmol, 1.0 eq) was dissolved in methanol (10 mL). Hydrazine hydrate (65%, 0.090 mL, 1.04 mmol, 1.0 equiv) was added dropwise at ice bath temperature. The mixture was stirred for 30 minutes and the solution went from clear to cloudy. LC/MS showed the reaction was complete. Dichloromethane (15 mL) was added and the mixture was extracted twice with cold saturated aqueous NaHCO$_3$. The combined organic layers were washed with brine and dried over sodium sulfate. The solvent was concentrated to give (2S,3S,4R,5R,6S)-2-(aminooxy)-6-methyltetrahydro-2H-pyran-3,4,5-triyl tripropionate as a white solid (280 mg). LC/MS: RT=2.34 min; m/z=348.4 [M+H]$^+$.

(E)-3-(4-(((((9H-Fluoren-9-yl)methoxy)carbonyl)(2-(2-methyl-1H-indol-3-yl)ethyl)amino)methyl)phenyl)acrylic acid (29) (281 mg, 0.503 mmol, 1.0 equiv) was dissolved in DMF (1.5 mL). EDC (124 mg, 0.653 mmol, 1.3 equiv) and 1-hydroxybenzotriazole (100 mg, 0.65 mmol, 1.3 equiv) was added and the mixture stirred for 10 minutes. (2S,3S,4R,5R,6S)-2-(Aminooxy)-6-methyltetrahydro-2H-pyran-3,4,5-triyl tripropionate (226 mg, 0.503 mmol, 1.0 equiv) was added followed by addition of DIPEA (1.4 eq). After stirring at room temperature for 2 hr, LC/MS showed the desired product. Saturated NH$_4$Cl solution was added then ethyl acetate was added and the organic phase was extracted twice with NaHCO$_3$. The combined organic layers were washed with brine and the solvent was concentrated to give a light yellow foam. (490 mg). The product was purified using normal phase purification on a 40 g silica gel column eluting with a gradient of 100% hexane to 50% ethyl acetate in hexane over 45 minutes. The product fractions were collected and the solvent was concentrated to afford (2S,3S,4R,5R,6S)-2-(((E)-3-(4-(((((9H-fluoren-9-yl)methoxy)carbonyl)(2-(2-methyl-1H-indol-3-yl)ethyl)amino)methyl)phenyl)acrylamido)oxy)-6-methyltetrahydro-2H-pyran-3,4,5-triyl tripropionate as a white foamy solid. (200 mg). LC/MS: RT=7.48 min; m/z=886.7 [M+H]$^+$.

(2S,3S,4R,5R,6S)-2-(((E)-3-(4-(((((9H-Fluoren-9-yl)methoxy)carbonyl)(2-(2-methyl-1H-indol-3-yl)ethyl)amino)methyl)phenyl)acrylamido)oxy)-6-methyltetrahydro-2H-pyran-3,4,5-triyl tripropionate (200 mg, 0.225 mmol, 1.0 equiv) was dissolved in 50% NEt$_3$ in DCM/DMF. The solution was stirred at room temperature for 3 days to remove the Fmoc protecting group. LC/MS showed the reaction was complete. The solvent was concentrated, saturated NH$_4$Cl solution was added then the mixture extracted twice with ethyl acetate. The combined organic layers were dried over sodium sulfate. The crude mixture was triturated twice with hexane. The final product was concentrated to give a white foamy solid. (138 mg). This solid was purified by HPLC using a buffer containing HCl, and the title compound (2S,3R,4R,5S,6S)-2-methyl-6-(((E)-3-(4-(((2-(2-methyl-1H-indol-3-yl)ethyl)amino)methyl)phenyl)acrylamido)oxy tetrahydro-2H-pyran-3,4,5-triyl tripropionate (121) was isolated as its hydrochloride salt as a white solid. LC/MS: RT=4.98 min; m/z=664.7 [M+H]$^+$. $^1$H NMR (500 MHz, Methanoic): δ 7.70-7.68 (m, 3H), 7.53 (d, J=7.9 Hz, 2H), 7.47-7.40 (m, 1H), 7.28 (dt, J=8.0, 1.0 Hz, 1H), 7.06 (ddd, J=8.2, 7.1, 1.2 Hz, 1H), 7.03-6.97 (m, 1H), 6.55 (d, J=15.8 Hz, 1H), 5.49-5.43 (m, 1H), 5.43-5.39 (m, 1H), 5.38-5.31 (m, 1H), 5.24-5.17 (m, 1H), 4.66 (s, 1H), 4.28 (s, 2H), 3.29-3.23 (m, 2H), 3.17-3.10 (m, 2H), 2.55-2.46 (m, 3H), 2.42 (s, 3H), 2.34-2.20 (m, 2H), 1.25-1.14 (m, 9H), 1.10 (t, 7=7.6 Hz, 3H).

Example 15: Preparation of (2S,3R,4R,5S,6S)-2-Methyl-6-(((E)-3-(4-(((2-(2-methyl-1H-indol-3-yl)ethyl)amino)methyl)phenyl)acrylamido)oxy)tetrahydro-2H-pyran-3,4,5-triyl tris(2-methylpropanoate) (122)

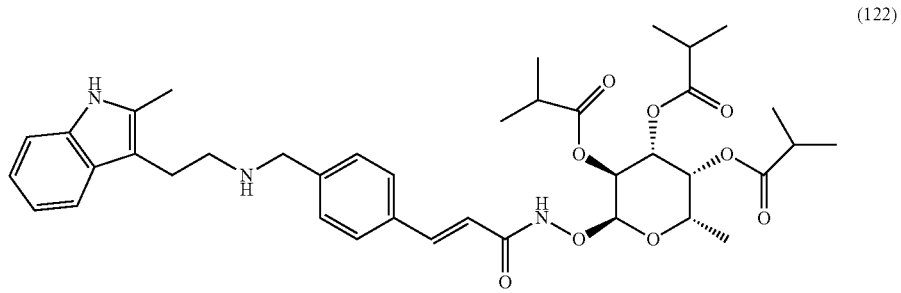 [SMILES: Cc1[nH]c2ccccc2c1CCNCc1ccc(/C=C/C(=O)NO[C@@H]2O[C@@H](C)[C@@H](OC(=O)C(C)C)[C@@H](OC(=O)C(C)C)[C@@H]2OC(=O)C(C)C)cc1]

(122)

L-Fucose (3 g, 18.4 mmol, 1.0 equiv) was dissolved pyridine (13 mL) and chloroform (19.5 mL). Under a nitrogen atmosphere, isobutyryl chloride (13.14 mL, 123.8 mmol, 6.7 equiv) was added via syringe slowly at ice bath temperature. The reaction mixture was allowed to rise to room temperature and then stirred for 48 h. The solution was concentrated to dryness under high vacuum and then quenched with 2M HCl (15 mL). Ethyl acetate (200 mL) was added and the solution was washed with water twice. The organic layer was washed once more with 2M HCl (20 mL) followed by saturated sodium bicarbonate solution (30 mL) and then water (30 mL). The organic layers were dried over sodium sulfate solution. The solvent was removed to afford (2S,3S,4R,5R,6S)-6-methyltetrahydro-2H-pyran-2,3,4,5-tetrayl tetrakis(2-methylpropanoate), as a pale yellow oil (9.8 g). LC/MS: RT=3.93 min; m/z=462.8 [M+18], Acetic acid (1.5 mL, 24 mmol, 1.4 equiv) was added to a solution of ethylenediamine (1.6 mL, 20.5 mmol, 1.2 equiv) in THF (200 mL). To the suspension of precipitated solid was added (2S,3S,4R,5R,6S)-6-methyltetrahydro-2H-pyran-2,3,4,5-tetrayl tetrakis(2-methylpropanoate) (8 g, 20.66 mmol, 1.0 equiv) in one portion. The mixture was stirred at room temperature overnight. The next day, LC/MS analysis showed largely unreacted starting material. The reaction was worked up and resubmitted to the same reaction conditions, this time stirring for a total of five days at which time water was added. The layers were separated, and dilute HCl (2%) was added followed by ethyl acetate (200 mL). After shaking, the layers were separated and the organic layer was washed twice with water. The organic layer was further washed with brine and dried over sodium sulfate. The solvent was removed to afford (2R,3S,4R,5R,6S)-2-hydroxy-6-methyltetrahydro-2H-pyran-3,4,5-triyl tris(2-methylpropanoate) as a yellow oil. The crude product was dry loaded onto an 80 g silica gel column and was purified using a gradient of 100% hexane to 30% ethyl acetate in hexane over 1 hour. The product fractions were collected and concentrated to give (2R,3S,4R,5R,6S)-2-hydroxy-6-methyltetrahydro-2H-pyran-3,4,5-triyl tris(2-methylpropanoate), as a colorless oil. (2.89 g). LC/MS: RT=3.19 min; m/z=392.5 [M+18], To a solution of (2R,3S,4R,5R,6S)-2-hydroxy-6-methyltetrahydro-2H-pyran-3,4,5-triyl tris(2-methylpropanoate) (2.4 g, 6.4 mmol, 1.0 equiv) in dichloromethane (60 mL) was added DAST (3.69 mL, 27.5 mmol, 4.3 equiv) dropwise in 3 portions over 30 min at 0° C. The mixture was stirred at this temperature for an additional 30 min. TLC analysis indicated the absence of starting material. The reaction mixture was cooled to −20° C. and methanol (5.0 mL) was added slowly. The mixture was stirred an addition 15 min, at which time dichloromethane was added and the mixture was poured into a cold solution of sodium bicarbonate. The separated organic layer was washed twice with IN HCl followed by saturated sodium bicarbonate solution and finally with brine. After drying over sodium sulfate, the solvent was removed to afford a yellow oil (2.5 g). The crude product was subjected to normal phase purification using a 25 g silica gel column, eluting with a gradient of 100% hexane to 25% ethyl acetate in hexane. The product fractions were collected and the solvent was removed to give (2RS,3S,4R,5R,6S)-2-fluoro-6-methyltetrahydro-2H-pyran-3,4,5-triyl tris(2-methylpropanoate) as a white foam (2.0 g). LC/MS: RT=3.64, 3.78 min; m/z=377.5 [M+H]$^+$.

To a solution of (2RS,3S,4R,5R,6S)-2-fluoro-6-methyltetrahydro-2H-pyran-3,4,5-triyl tris(2-methylpropanoate) (2000 mg, 5.3 mmol, 1.0 equiv) and N-hydroxyphathlimide (1100 mg, 6.89 mmol, 1.3 equiv) in acetonitrile (4.0 mL) was added triethylamine (0.98 mL, 6.8 mmol, 1.3 equiv). BF$_3$.Et$_2$O (2.1 mL, 15.9 mmol, 3.0 equiv) was slowly added via syringe. The solution turned from red to a clear light yellow color. After 30 min, LC/MS analysis showed the reaction was complete, affording two isomeric products. Dichloromethane was added and the solution was poured into a cold solution of sodium bicarbonate. The organic layer was separated and washed twice with aqueous sodium bicarbonate until colorless. The solution was then washed with brine and dried over sodium sulfate. The solution was concentrated to dryness to give 2500 mg crude (2RS,3S,4R,5R,6S)-2-((1,3-dioxoisoindolin-2-yl)oxy)-6-methyltetrahydro-2H-pyran-3,4,5-triyl tris(2-methylpropanoate). The product was purified by normal phase column chromatography (on a 40 g silica gel column) using a gradient of 100% hexane to 25% ethyl acetate in hexane over 40 min. The product fractions were collected as 2 peaks. Peak #1 (normal phase, less polar) LC/MS (reverse phase): RT=4.04 min; m/z=520.6 [M+H]$^+$. Peak #2 (normal phase, more polar) LC/MS (reverse phase): RT=3.74 min; m/z=520.6 [M+H]$^+$.

Peak #1 was determined to be the desired alpha isomer, (2S,3S,4R,5R,6S)-2-((1,3-dioxoisoindolin-2-yl)oxy)-6-methyltetrahydro-2H-pyran-3,4,5-triyl tris(2-methylpropanoate), by comparison of its $^1$H NMR spectrum with the literature characterized triacetoxy analog (31). It was isolated as a white solid (1400 mg). Peak #2 was determined to be the beta isomer, (2R,3S,4R,5R,6S)-2-((1,3-dioxoisoindolin-2-yl)oxy)-6-methyltetrahydro-2H-pyran-3,4,5-triyl tris(2-methylpropanoate). It was isolated as a white solid (500 mg).

(2R,3S,4R,5R,6S)-2-((1,3-Dioxoisoindolin-2-yl)oxy)-6-methyltetrahydro-2H-pyran-3,4,5-triyl tris(2-methylpropanoate) (900 mg, 2.3 mmol, 1.0 equiv) was dissolved in methanol (20 mL). Hydrazine hydrate (65%, 2.3 mL, 2.3 mmol, 1.0 equiv) was added dropwise at ice bath temperature and the reaction mixture was stirred for 30 min. The solution turned from clear to cloudy. LC/MS analysis showed that the reaction was complete. Dichloromethane (25 mL) was added and the separated organic layer was washed twice with cold saturated NaHCO₃ solution. The organic layer was washed with brine and dried over sodium sulfate. The solvent was removed to afford (2S,3S,4R,5R,6S)-2-(aminooxy)-6-methyltetrahydro-2H-pyran-3,4,5-triyl tris(2-methylpropanoate) as a white solid (750 mg). LC/MS: RT=2.87 min; m/z=390.5 [M+H]⁺. (E)-3-(4-(((((9H-Fluoren-9-yl)methoxy)carbonyl)(2-(2-methyl-1H-indol-3-yl)ethyl)amino)methyl)phenyl)acrylic acid (29) (300 mg, 0.53 mmol, 1.0 equiv) was dissolved in DMF (1.5 mL). EDC (124 mg, 0.653 mmol, 1.3 equiv) and 1-hydroxybenzotriazole (100 mg, 0.65 mmol, 1.3 equiv) was added. The reaction mixture was stirred for 10 min, after which time (2S,3S,4R,5R,6S)-2-(aminooxy)-6-methyltetrahydro-2H-pyran-3,4,5-triyl tris(2-methylpropanoate) (247 mg, 0.53 mmol, 1.0 equiv) was added followed by DIPEA (1.4 equiv). The mixture was stirred at room temperature for 2 h. LC/MS analysis showed the formation of the desired product. Ethyl acetate was added and the mixture was washed twice with saturated NH₄Cl solution. The ethyl acetate layer was washed twice with aqueous NaHCO₃, and finally with brine. The solvent was removed to give a light yellow foam (590 mg). The product was purified using normal phase purification using a 10 g silica gel column, eluting with a gradient of 100% hexane to 30% ethyl acetate in hexane over 45 min. The product fractions were collected and the solvent was removed to afford (2S,3S,4R,5R,6S)-2-(((E)-3-(4-(((((9H-fluoren-9-yl)methoxy)carbonyl)(2-(2-methyl-1H-indol-3-yl)ethyl)amino)methyl)phenyl)acrylamido)oxy)-6-methyltetrahydro-2H-pyran-3,4,5-triyl tris(2-methylpropanoate) as a white foam (250 mg). LC/MS: RT=8.13 min; m/z=829.1 [M+H]⁺.

(2S,3S,4R,5R,6S)-2-(((E)-3-(4-(((((9H-Fluoren-9-yl)methoxy)carbonyl)(2-(2-methyl-1H-indol-3-yl)ethyl)amino)methyl)phenyl)acrylamido)oxy)-6-methyltetrahydro-2H-pyran-3,4,5-triyl tris(2-methylpropanoate) (250 mg, 0.26 mmol, 1.0 eq) was dissolved in DMF (1.0 mL). Triethylamine (1.0 mL) was added and it was stirring room temperature overnight to remove the Fmoc protecting group. LC/MS showed the desired product. The mixture was titurated with hexane, ethyl acetate was added and the mixture was extracted twice with saturated NH₄Cl. The combined organic layers were washed with brine and dried over sodium sulfate. The solvent was concentrated to give a yellow foam. (300 mg). This residue was titurated with hexane/DCM (10%). The crude product was concentrated and dried to give an orange solid (180 mg). This solid was purified by HPLC using a buffer containing HCl, and the title compound (2S,3R,4R,5S,6S)-2-methyl-6-(((E)-3-(4-(((2-(2-methyl-1H-indol-3-yl)ethyl)amino)methyl)phenyl)acrylamido)oxy)tetrahydro-2H-pyran-3,4,5-triyl tris(2-methylpropanoate) (122) was isolated as its hydrochloride salt as a white solid. LC/MS: RT=5.67 min; m/z=706.9 [M+H]⁺. ¹H NMR (500 MHz, Methanoic): δ 7.72-7.61 (m, 3H), 7.53 (d, J=8.2 Hz, 2H), 7.43 (m, 1H), 7.28 (dt, J=8.0, 1.0 Hz, 1H), 7.06 (ddd, J=8.2, 7.1, 1.2 Hz, 1H), 7.00 (ddd, J=8.0, 7.1, 1.1 Hz, 1H), 6.55 (d, J=15.9 Hz, 1H), 5.48 (dd, j=11.1, 3.3 Hz, 1H), 5.40 (dd, j=3.4, 1.4 Hz, 1H), 5.33 (d, j=3.9 Hz, 1H), 5.24 (d, j=10.3 Hz, 1H), 4.70 (hr. s, 1H), 4.28 (s, 2H), 3.26 (m, 2H), 3.17-3.10 (m, 2H), 2.73 (m, 1H), 2.67 (s, 2H), 2.47 (m, 1H), 2.42 (s, 3H), 1.31-1.15 (m, 15H), 1.12 (d, j=7.0 Hz, 6H).

Example 16: Preparation of (2R,3S,4S,5R,6S)-2-(Acetoxymethyl)-6-((2-(((2-(6-methoxypyridin-3-yl)-4-morpholinothieno[3,2-d]pyrimidin-6-yl)methyl)(methyl)amino)pyrimidine-5-carboxamido)oxy)tetrahydro-2H-pyran-3,4,5-triyl Triacetate (123)

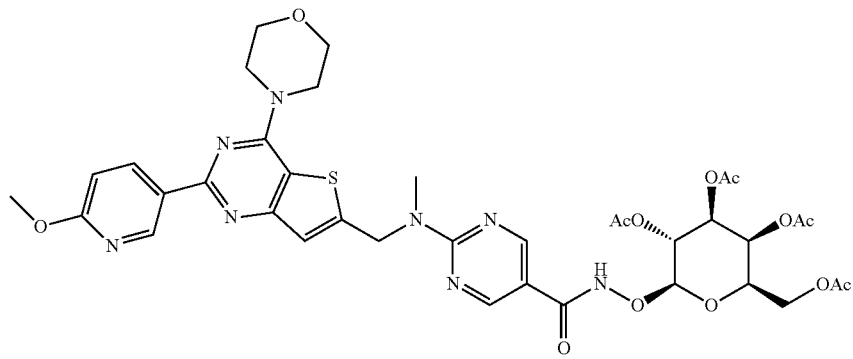

(123)

To a solution of methyl 2-(N-((2-(6-methoxypyridin-3-yl)-4-morpholinothieno[3,2-d]pyrimidin-6-yl)methyl)-N-methylamino)pyrimidine-5-carboxylate (prepared as described in WO2018085342A1) (1.8 g, 3.5 mmol) in dioxane (60 mL) and water (15 mL) was added LiOH (340 mg, 14.2 mmol) and the resulting mixture was stirred at 50° C. for 16 h. Reaction mixture was cooled to room temperature, diluted with water (10 mL) and acidified to pH 5 with aqueous 2M HCl. The reaction mixture was then concentrated in vacuo to remove dioxane. Precipitated product was filtered, washed with water (15 mL) and dried under high vacuum to provide 2-(N-((2-(6-methoxypyridin-3-yl)-4-morpholinothieno[3,2-d]pyrimidin-6-yl)methyl)-N-methylamino)pyrimidine-5-carboxylic acid as an off white solid (1.5 g, 85%). LC/MS: RT=2.52 min; m/z=494.4 [M+H]⁺.

To a suspension of 2-(N-((2-(6-methoxypyridin-3-yl)-4-morpholinothieno[3,2-d]pyrimidin-6-yl)methyl)-N-methylamino)pyrimidine-5-carboxylic acid (740 mg, 1.5 mmol) in DMF (4.2 mL) was added EDC.HCl (401 mg, 2.1 mmol) followed by HOBt (321 mg, 2.1 mmol) and the resulting mixture was stirred for 5 min at room temperature. Compound (24) (700 mg, 1.92 mmol) was added in one portion. The reaction mixture was cooled in an ice/water bath and Et₃N (0.3 mL, 2.1 mmol) was added. The reaction mixture was gradually warmed up to room temperature and stirred for 12 h. Saturated aqueous NH₄Cl (6 mL) was added and the resulting precipitate was filtered and washed with water (10 mL). The residue was dissolved in EtOAc (20 mL), washed with brine, dried over anhydrous Na₂SO₄, filtered and concentrated to give the crude product (1 g, 80% yield, 90% purity) as a white foamy solid. 350 mg of this crude material was purified on reversed phase HPLC to obtain 146 mg of the title compound (2R,3S,4S,5R,6S)-2-(acetoxymethyl)-6-((2-(((2-(6-methoxypyridin-3-yl)-4-morpholinothieno[3,2-d]pyrimidin-6-yl)methyl)(methyl)amino)pyrimidine-5-carboxamido)oxy)tetrahydro-2H-pyran-3,4,5-triyl triacetate (123). LC/MS: RT=1.92 min; m/z=839.4 [M+H]⁺.
¹H NMR (500 MHz, Methanol-d₄) δ 9.08 (d, J=2.6 Hz, 1H), 8.79 (s, 2H), 8.51 (dd, J=8.8, 2.6 Hz, 1H), 7.56 (s, 1H), 7.04 (d, J=8.7 Hz, 1H), 5.45 (d, J=3.3 Hz, 1H), 5.33 (s, 2H), 5.30 (dd, j=10.4, 8.1 Hz, 1H), 5.24 (dd, j=10.4, 3.4 Hz, 1H), 5.06 (d, j=8.1 Hz, 1H), 4.29-4.16 (m, 7H), 4.06 (s, 3H), 3.91 (m, 4H), 3.38 (s, 3H), 2.18 (s, 3H). 2.16 (s, 3H), 2.04 (s, 3H), 1.98 (s, 3H).

Example 17: Preparation of 2-(((2-(6-Methoxypyridin-3-yl)-4-morpholinothieno[3,2-d]pyrimidin-6-yl)methyl)(methyl)amino)-N-(((2S,3R,4S,5R,6R)-3,4,5-trihydroxy-6-(hydroxymethyl)tetrahydro-2H-pyran-2-yl)oxy)pyrimidine-5-carboxamide (124)

(124)

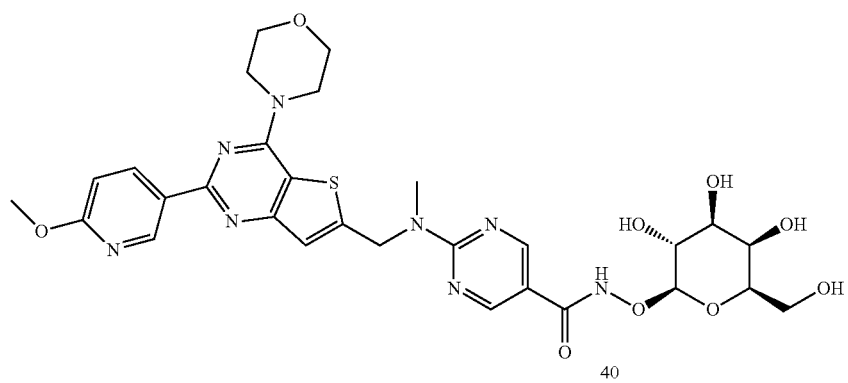

To a solution of compound (123) (650 mg, 0.77 mmol) in MeOH (7.7 mL) was added 25% NaOMe solution in MeOH (0.21 mL, 1 mmol) dropwise in an ice/water bath. The reaction mixture was then warmed up to room temperature and stirred for 1 h. The reaction mixture was quenched by the addition of aqueous lN HCl to adjust the pH to 7. Solvents were removed under reduced pressure and the residue was purified by reversed-phase HPLC to obtain the title compound 2-(((2-(6-methoxypyridin-3-yl)-4-morpholinothieno[3,2-d]pyrimidin-6-yl)methyl)(methyl)amino)-N-(((2S,3R,4S,5R,6R)-3,4,5-trihydroxy-6-(hydroxymethyl)tetrahydro-2H-pyran-2-yl)oxy)pyrimidine-5-carboxamide (124) (267 mg) as a white powder. LC/MS: RT=1.34 min; m/z=671.6 [M+H]⁺. ¹H NMR (500 MHz, Methanol-d₄) δ 9.08 (dd, j=2.7, 0.7 Hz, 1H), 8.85 (s, 2H), 8.51 (dd, j=8.9, 2.6 Hz, 1H), 7.58 (d, j=1.0 Hz, 1H), 7.05 (dd, j=8.9, 0.7 Hz, 1H), 5.36-5.34 (m, 2H), 4.63 (d, j=7.9 Hz, 1H), 4.27 (m, 4H), 4.07 (s, 3H), 3.94-3.82 (m, 6H), 3.78 (dd, j=11.4, 4.6 Hz, 1H), 3.71 (dd, j=9.7, 7.9 Hz, 1H), 3.65 (ddd, J=7.6, 4.6, 1.1 Hz, 1H), 3.58 (dd, J=9.6, 3.4 Hz, 1H), 3.38 (s, 3H).

Example 18: Preparation of (2S,3S,4R,5R,6S)-2-((2-(((2-(6-Methoxypyridin-3-yl)-4-morpholinothieno[3,2-d]pyrimidin-6-yl)methyl)(methyl)amino)pyrimidine-5-carboxamido)oxy)-6-methyltetrahydro-2H-pyran-3,4,5-triyl Triacetate (125)

(125)

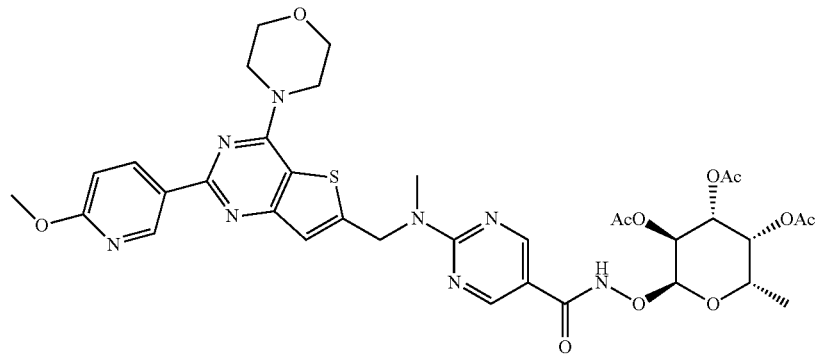

To a solution of 2-(N-((2-(6-methoxypyridin-3-yl)-4-morpholinothieno[3,2-d]pyrimidin-6-yl)methyl)-N-methylamino)pyrimidine-5-carboxylic acid (700 mg, 1.4 mmol) in DMF (4.6 mL) was added EDC.HCl (377 mg, 1.9 mmol) followed by HOBt (290 mg, 1.9 mmol) in one portion at room temperature. After 20 min, reaction mixture was cooled in an ice/water bath and compound (32) (491 mg, 1.6 mmol) and DIPEA (0.34 mL, 1.4 equiv.) was added at 0° C. The resulting mixture was brought to room temperature and stirred for 2 h. A cold saturated aqueous solution of $NH_4Cl$ (10 mL) was added and the precipitated product was filtered and washed with water (5 mL). The residue was dissolved in EtOAc (20 mL) and washed with brine, dried over anhydrous $Na_2SO_4$, filtered and concentrated to give the crude product (125) (1.1 g, quant., 90% purity) as a white foamy solid. 350 mg of this crude material was purified on reversed-phase HPLC to afford 153 mg of the title compound (2S,3S,4R,5R,6S)-2-((2-(((2-(6-methoxypyridin-3-yl)-4-morpholinothieno[3,2-d]pyrimidin-6-yl)methyl)(methyl)amino)pyrimidine-5-carboxamido)oxy)-6-methyltetrahydro-2H-pyran-3,4,5-triyl triacetate (125). LC/MS: RT=1.96 min; m/z=781.5 [M+H]$^+$. $^1$H NMR (500 MHz, Methanoic): δ 9.08 (dd, J=2.6, 0.8 Hz, 1H), 8.80 (s, 2H), 8.52 (dd, J=8.8, 2.6 Hz, 1H), 7.51 (d, J=0.9 Hz, 1H), 7.00 (d, J=8.8 Hz, 1H), 5.46-5.36 (m, 3H), 5.32 (s, 2H), 5.17 (dd, J=11.1, 4.0 Hz, 1H), 4.70 (d, J=6.7 Hz, 1H), 4.20 (m, 4H), 4.05 (s, 3H), 3.90 (m, 4H), 3.37 (s, 3H), 2.19 (s, 3H), 2.17 (s, 3H), 2.01 (s, 3H), 1.19 (d, J=6.5 Hz, 3H), Example 19: Preparation of 2-(((2-(6-Methoxypyridin-3-yl)-4-morphohnothieno[3,2-d]pyrimidin-6-yl)methyl)(methyl)amino)-N-(((2S,3S,4R,5S,6S)-3,4,5-trihydroxy-6-methyltetrahydro-2H-pyran-2-yl)oxy)pyrimidine-5-carboxamide (126)

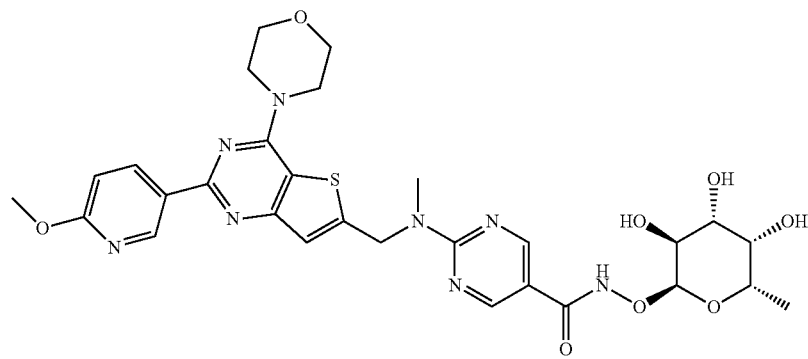

(126)

To a solution of compound (125) (750 mg, 0.96 mmol) in MeOH (9.6 mL) was added 25% NaOMe solution in MeOH (0.22 mL, 1.06 mmol) dropwise in an ice/water bath. The reaction mixture was then warmed up to room temperature and stirred for 1 h. The reaction mixture was quenched by the addition of aqueous IN HCl to adjust the pH to 7. Solvents were removed under reduced pressure and the residue was purified by reversed-phase HPLC to afford the title compound 2-(((2-(6-methoxypyridin-3-yl)-4-morpholinothieno[3,2-d]pyrimidin-6-yl)methyl)(methyl)amino)-N-(((2S,3S,4R,5S,6S)-3,4,5-trihydroxy-6-methyltetrahydro-2H-pyran-2-yl)oxy)pyrimidine-5-carboxamide (126) (359 mg) as a white powder. LC/MS: RT=1.40 min; m/z=655.4 [M+H]$^+$. $^1$H NMR (500 MHz, Methanoic): δ 9.08 (dd, J=2.7, 0.7 Hz, 1H), 8.81 (s, 2H), 8.51 (dd, J=8.8, 2.6 Hz, 1H), 7.57 (d, J=0.9 Hz, 1H), 7.05 (dd, J=8.8, 0.7 Hz, 1H), 5.34 (m, 2H), 5.15 (d, J=3.7 Hz, 1H), 4.42 (m, 1H), 4.27 (m, 4H), 4.07 (s, 3H), 3.95-3.84 (m, 6H), 3.76 (dd, J=3.0, 1.3 Hz, 1H), 3.38 (s, 3H), 1.26 (d, J=6.5 Hz, 3H).

Example 20: Preparation of (2-Hydroxy-5-isopropyl-4-(((2S,3R,4S,5R,6R)-3,4,5-trihydroxy-6-(hydroxymethyl)tetrahydro-2H-pyran-2-yl)oxy)phenyl)(5-((4-methylpiperazin-1-yl)methyl)isoindolin-2-yl)methanone (46) and (4-Hydroxy-5-isopropyl-2-(((2S,3R,4S,5R,6R)-3,4,5-trihydroxy-6-(hydroxymethyl)tetrahydro-2H-pyran-2-yl)oxy)phenyl)(5-((4-methylpiperazin-1-ylmethyl)isoindolin-2-ylmethanone (47)

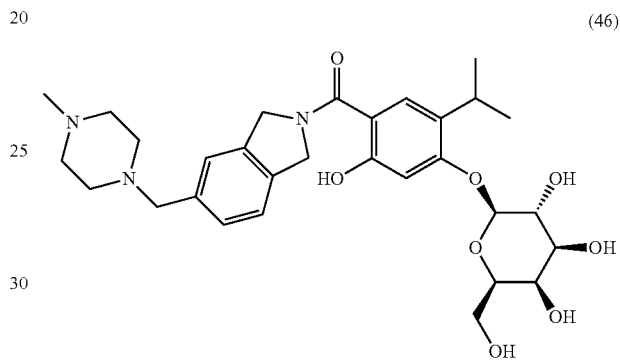

(46)

-continued

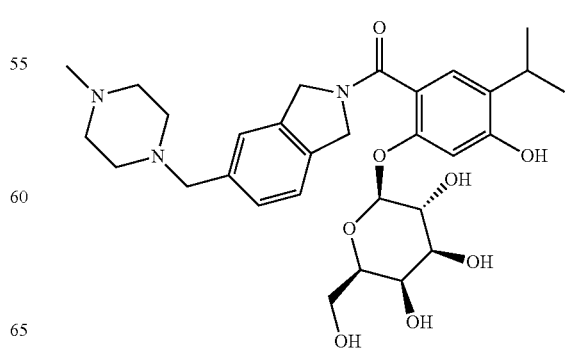

(47)

The β-D-galactosyl conjugates (46) and (47) were synthesized by adaptation of the synthetic protocol of Wadzinski et al (*Nature Chem. Biol.*, 10 (2018) 644-652) for rapid O-phenolic glycosylation in aqueous medium. Starting from the commercially available (2,4-dihydroxy-5-isopropylphenyl)(5-((4-methylpiperazin-1-yl)methyl)isoindolin-2-yl)methanone, AT13387 (36), treatment with α-D-galactopyranosyl fluoride in the presence of Ca(OH)$_2$ provided a regioisomeric mixture of β-D-galactosides that were separated by HPLC.

α-D-Galactopyranosyl fluoride was prepared as follows: to 3-D-galactose pentaacetate (10 g, 25.7 mmol, 1 equiv.) in a plastic bottle cooled under ice/water bath was added a cold solution of 70% HF.pyridine (17 mL, 1.5 M) slowly via syringe. The reaction vessel was screw capped and gradually warmed up to room temperature and stirred for 16 h. Reaction mixture was quenched by the addition of cold water (50 mL). DCM (50 mL) was added and the resulting mixture was stirred for 30 min. The organic layer was then separated and the aqueous layer was extracted with DCM (2×50 mL). The combined organic layers were washed with saturated aqueous NaHCO$_3$ solution (150 mL), brine (100 mL), dried over anhydrous sodium sulfate, filtered and concentrated in vacuo and dried under high vacuum to give a crude residue.

To the above residue was added absolute MeOH (130 mL) and the resulting mixture was stirred for 15 min. The reaction mixture was then cooled in an ice/water for 10 min, NaOMe (139 mg, 2.57 mmol) was added and after 10 min, ice/water bath was removed and the reaction mixture was gradually left to warm up to room temperature over 3 h. The reaction mixture was cooled again in an ice/water bath and silica gel (11 g) was added. The resulting suspension was concentrated to a thick paste. A solution of 7:3 EtOAc:MeOH (50 mL) was added, stirred well for 5 min and filtered. The residue was washed with 7:3 EtOAc MeOH (60 mL) and the combined filtrate was concentrated to dryness using a rotary evaporator. The residue was dried under high vacuum over night to give desired product α-D-galactopyranosyl fluoride (4.2 g, 91%) as foamy solid which was used in the next step without any further purification.

To a solution of AT13387 (36) (90 mg, 0.22 mmol) and α-D-galactopyranosyl fluoride (1.2 g, 6.6 mmol) in water (7 mL) and DMSO (7 mL) was added Ca(OH)$_2$ (488 mg, 6.6 mmol) and the resulting mixture was stirred at room temperature for 8 h. LC/MS indicated significant conversion to the desired compounds (46) and (47). The reaction mixture was quenched by the addition of aqueous 1M HCl to adjust to pH 8 and the resulting mixture was concentrated in vacuo to remove water. A DMSO solution of the residue was directly purified by reversed phase HPLC and two regioisomeric products were isolated. The regiochemical identity of the products was inferred by correlation the retention time on reversed phase LC/MS with the calculated Log P values (the isomer calculated to be less lipophilic being assigned to the earlier eluting peak on HPLC).

The earlier eluting peak yielded 34 mg of (2-hydroxy-5-isopropyl-4-(((2S,3R,4S,5R,6R)-3,4,5-trihydroxy-6-(hydroxymethyl)tetrahydro-2H-pyran-2-yl)oxy)phenyl)(5-((4-methylpiperazin-1-yl)methyl)isoindolin-2-ylmethanone (46) as a white solid (c Log P=1.8). LC/MS: R T=1.13 min; m/z=572.5 [M+H]$^+$. $^1$H NMR (500 MHz, Methanol-d$_4$): δ 7.41-7.35 (br s, 2H), 7.33 (s, 1H), 7.30 (s, 2H), 5.01-4.90 (m, 6H), 4.10-4.00 (m, 2H), 3.83-3.63 (m, 9H), 3.29 (m, 4H), 2.88 (s, 3H), 1.25 (d, J=6.9 Hz, 3H) 1.24 (d, J=6.9 Hz, 3H).

The later eluting peak yielded 22 mg of (4-hydroxy-5-isopropyl-2-(((2S,3R,4S,5R,6R)-3,4,5-trihydroxy-6-(hydroxymethyl)tetrahydro-2H-pyran-2-yl)oxy)phenyl)(5-((4-methylpiperazin-1-yl)methyl)isoindolin-2-ylmethanone (47) as a white solid (c Log P=2.0). LC/MS: RT=1.20 min; m/z=572.5 [M+H]$^+$. $^1$H NMR (500 MHz, Methanoic): δ 7.42-7.35 (m, 1H), 7.35-7.27 (m, 1H), 7.25-7.18 (m, 1H), 7.12 (d, J=1.7 Hz, 1H), 6.78 (s, 1H), 4.98-4.78 (m, 6H), 4.71 (m, 1H), 3.92-3.86 (m, 1H), 3.85-3.62 (m, 6H), 3.55 (m, 1H), 3.30-3.22 (m, 7H), 2.88 (d, J=8.8 Hz, 3H), 1.24 (d, J=6.8 Hz, 3H), 1.22 (d, J=6.8 Hz, 3H).

Example 21: Preparation of N-Ethyl-5-(2-hydroxy-5-isopropyl-4-(((2S,3R,4S,5R,6R)-3,4,5-trihydroxy-6-(hydroxymethyl)tetrahydro-2H-pyran-2-yl)oxy)phenyl)-4-(4-(morpholinomethyl)phenyl)isoxazole-3-carboxamide (48) and N-Ethyl-5-(4-hydroxy-5-isopropyl-2-(((2S,3R,4S,5R,6R)-3,4,5-trihydroxy-6-(hydroxymethyl)tetrahydro-2H-pyran-2-yl)oxy)phenyl)-4-(4-(morpholinomethyl)phenyl)isoxazole-3-carboxamide (49)

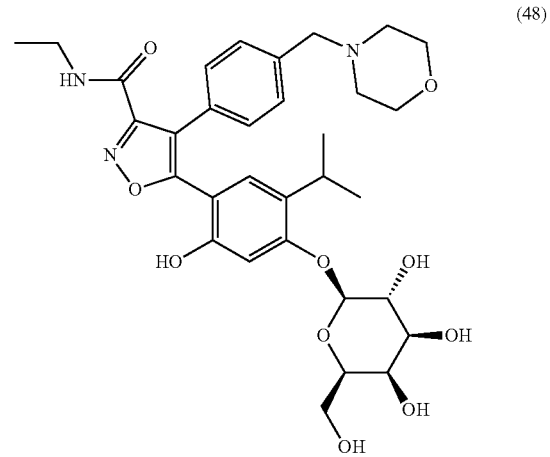

(48)

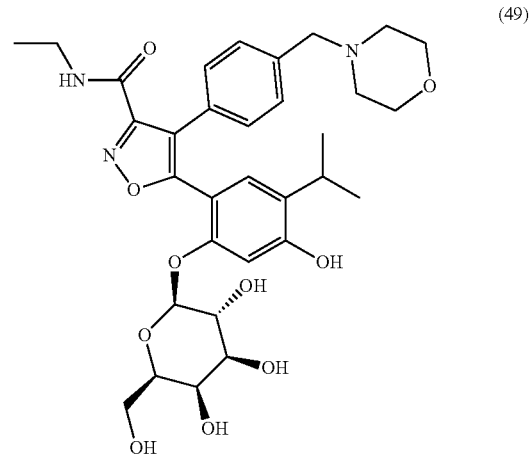

(49)

The β-D-galactosyl conjugates (48) and (49) were synthesized by adaptation of the synthetic protocol of Wadzinski et al (*Nature Chem. Biol.*, 10 (2018) 644-652) for rapid O-phenolic glycosylation in aqueous medium. Starting from the commercially available resorcinol compounds NVP-AUY922 (37), treatment with α-D-galactopyranosyl fluoride in the presence of Ca(OH)$_2$ provided a regioisomeric mixture of β-D-galactosides that were separated by HPLC. In a 4 mL vial was suspended 5-(2,4-dihydroxy-5-isopropylphenyl)-N-ethyl-4-(4-(morpholinomethyl)phenyl)isoxazole-3-carboxamide, NVP-AUY922 (37), (100 mg, 0.21 mmol), α-D-galactopyranosyl fluoride (352 mg, 1.9 mmol) and Ca(OH)$_2$ (47 mg, 0.64 mmol) in water (0.4 mL). The reaction vial was screw capped and the resulting mixture was stirred at room temperature for 3 h. LC/MS indicated significant conversion to the desired compounds (48) and (49). The reaction mixture was quenched by the addition of aqueous 1M HCl to adjust to pH 8 and the resulting mixture was directly purified by reversed phase HPLC to afford two regioisomeric products. The regiochemical identity of the products was inferred by correlation the retention time on reversed phase LC/MS with the calculated Log P values (the isomer calculated to be less lipophilic being assigned to the earlier eluting peak on HPLC).

The earlier eluting peak yielded 7 mg of N-ethyl-5-(2-hydroxy-5-isopropyl-4-(((2S,3R,4S,5R,6R)-3,4,5-trihydroxy-6-(hydroxymethyl)tetrahydro-2H-pyran-2-yl)oxy)phenyl)-4-(4-(morpholinomethyl)phenyl)isoxazole-3-carboxamide (48) as a white solid (c Log P=0.88). LC/MS: RT=1.29 min; m/z=628.4 [M+H]$^+$. $^1$H NMR (500 MHz, Methanoic): δ 7.44 (m, 4H), 6.98 (s, 1H), 6.73 (s, 1H), 4.83 (m, 1H), 4.31 (s, 1H), 3.94 (s, 1H), 3.87-3.76 (m, 4H), 3.71 (m, 1H), 3.59 (m, 1H), 3.39-3.15 (m, 11H), 1.23 (t, J=7.3 Hz, 3H), 1.06 (d, 7=6.9 Hz, 3H), 1.05 (d, J=6.9 Hz, 3H).

The later eluting peak yielded 22 mg of N-ethyl-5-(4-hydroxy-5-isopropyl-2-(((2S,3R,4S,5R,6R)-3,4,5-trihydroxy-6-(hydroxymethyl)tetrahydro-2H-pyran-2-yl)oxy)phenyl)-4-(4-(morpholinomethyl)phenyl)isoxazole-3-carboxamide (49) as a white solid (c Log P=1.02). LC/MS: RT=1.43 min; m/z=628.4 [M+H]$^+$. $^1$H NMR (500 MHz, Methanoic): δ 7.45 (s, 4H), 7.05 (s, 1H), 6.72 (s, 1H), 4.71 (d, J=7.7 Hz, 1H), 4.35 (q, J=7.3 Hz, 2H), 4.06 (hr. s, 1H), 3.86 (m, 1H), 3.77-3.70 (m, 3H), 3.60 (m, 1H), 3.48-3.20 (m, 10H), 3.16 (m, 1H), 1.23 (t, J=7.3 Hz, 3H), 1.10 (d, 7=6.9 Hz, 3H), 1.09 (d, J=6.9 Hz, 3H).

Example 22: Preparation of 5-(2-Hydroxy-5-isopropyl-4-(((2S,3R,4S,5R,6R)-3,4,5-trihydroxy-6-(hydroxymethyl)tetrahydro-2H-pyran-2-yl)oxy)phenyl)-4-(1-methyl-1H-indol-5-yl)-2,4-dihydro-3H-1,2,4-triazol-3-one (127) and 5-(4-Hydroxy-5-isopropyl-2-(((2S,3R,4S,5R,6R)-3,4,5-trihydroxy-6-(hydroxymethyl)tetrahydro-2H-pyran-2-yl)oxy)phenyl)-4-(1-methyl-1H-indol-5-yl)-2,4-dihydro-3H-1,2,4-triazol-3-one (128)

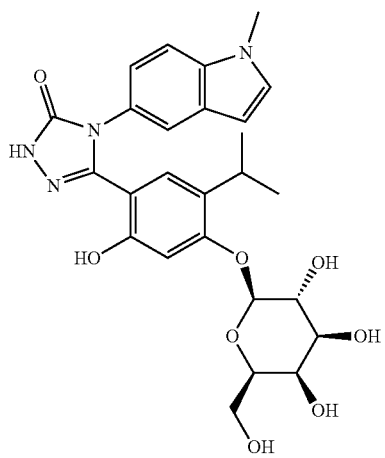

(127)

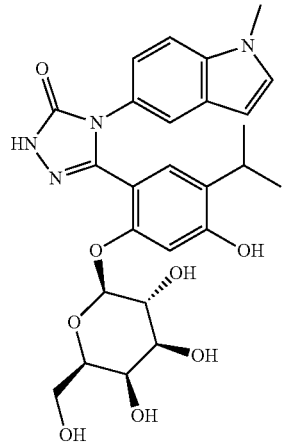

(128)

To a mixture of 5-(2,4-dihydroxy-5-isopropylphenyl)-4-(1-methyl-1H-indol-5-yl)-2,4-dihydro-3H-1,2,4-triazol-3-one, ganetespib (38), (200 mg, 0.55 mmol) and 2,3,4,6-tetra-O-acetyl-α-D-galactopyranosyl bromide (1.35 g, 3.3 mmol) in anhydrous DMF (10 mL) was added Cs$_2$CO$_3$ (3.2 g, 9.8 mmol) and the resulting mixture was stirred at room temperature for 15 h. Water (100 mL) was added and the resulting mixture was extracted with EtOAc (3×50 mL). The combined organic layers were washed with brine, dried over anhydrous sodium sulfate, filtered and concentrated in vacuo. The residue was dried under high vacuum overnight.

To the above residue was added MeOH (5 mL) and NaOMe (25% solution in MeOH, 25 uL, 0.11 mmol) and the resulting mixture was stirred for 1 h at room temperature. LC/MS indicated significant conversion to desired compounds (127) and (128). The reaction mixture was quenched by the addition of 4M HCl in dioxane solution to adjust to pH 8. The reaction mixture was then concentrated in vacuo and purified by reversed phase HPLC to afford two regioisomeric products. The regiochemical identity of the products was inferred by correlation the retention time on reversed phase LC/MS with the calculated Log P values (the isomer calculated to be less lipophilic being assigned to the earlier eluting peak on HPLC). The earlier eluting peak yielded 25 mg of 5-(2-hydroxy-5-isopropyl-4-(((2S,3R,4S,5R,6R)-3,4,5-trihydroxy-6-(hydroxymethyl)tetrahydro-2H-pyran-2-yl)oxy)phenyl)-4-(1-methyl-1H-indol-5-yl)-2,4-dihydro-3H-1,2,4-triazol-3-one (127) as a white solid (c Log P=1.96). LC/MS: RT=1.30 min; m/z=527.2 [M+H]$^+$. $^1$H NMR (500 MHz, Methanoic): δ 7.53-7.46 (m, 2H), 7.29 (d, J=3.2 Hz, 1H), 7.08 (dd, J=8.6, 2.1 Hz, 1H), 6.71 (s, 1H), 6.67 (s, 1H), 6.49 (dd, 7=3.1, 0.8 Hz, 1H), 4.80 (d, J=7.8 Hz, 1H), 3.90 (d, J=2D Hz, 1H), 3.86 (s, 3H), 3.82-3.71 (m, 3H), 3.67 (m, 1H), 3.55 (dd, J=9.7, 3.4 Hz, 1H), 3.14 (m, 1H), 0.73 (dd, J=6.9, 1.7 Hz, 6H). The later eluting peak yielded 35 mg of 5-(4-hydroxy-5-isopropyl-2-(((2S,3R,4S,5R,6R)-3,4,5-trihydroxy-6-(hydroxymethyl)tetrahydro-2H-pyran-2-yl)oxy)phenyl)-4-(1-methyl-1H-indol-5-yl)-2,4-dihydro-3H-1,2,4-triazol-3-one (128) as a white solid (c Log P=2.09). LC/MS: RT=1.54 min; m/z=527.2 [M+H]$^+$. $^1$H NMR (500 MHz, Methanoic): δ 7.55-7.49 (m, 2H), 7.30 (d, J=3.1 Hz, 1H), 7.09 (dd, J=8.6, 2.0 Hz, 1H), 6.59 (s, 1H), 6.51 (d, J=3.0 Hz, 1H), 6.29 (s, 1H), 5.27 (d, J=9.1 Hz, 1H), 4.40 (m, 1H), 3.98 (d, J=3.3 Hz, 1H), 3.87 (s, 3H), 3.85-3.75 (m, 3H), 3.72 (dd, J=9.6, 3.3 Hz, 1H), 2.91 (m, 1H), 0.67 (d, J=6.9 Hz, 3H), 0.65 (d, J=6.9 Hz, 3H).

Example 23: Compound Toxicity Towards Normal Proliferative, Senescent or Quiescent Fibroblasts Normal human fibroblasts (IMR90) and patient-derived β-galactosidase (GLB1) or α-fucosidase (FUCA1) deficient cells were used to determine change in cell viability after exposure to compound. Cells were cultured with DMEM and 10% heat inactivated FBS under a controlled atmosphere of 5% carbon dioxide and 5% oxygen, was induced by cell contact inhibition and confirmed by the absence of senescence associated β-galactosidase (SA-β-Gal) staining and the capacity to re-enter the cell cycle. Senescence was induced by treatment with doxorubicin and confirmed by SA-β-Gal positive staining and the lack of DNA replication. Cells were treated with compound for three days. Cell viability was determined by mitochondrial dehydrogenase activity (XTT assay. Cayman Chemical) at ten concentrations of the tested compound. To generate dose-response curves, data was fitted to a four-parameter Hill function and the $IC_{50}$ was determined at Y=0.5 viability. The senolytic index (S.I.) for each compound was determined by dividing the $IC_{50}$ against normal, proliferating cells by the $IC_{50}$ versus senescent cells. Senolytic index data is shown in Table 1 with compounds having S.I.<1 (−), S.I.>1 (+), S.I.>5 (++) and S.I.>10 (+++).

| Compound | Senolytic Index (S.I.) |
|---|---|
| (26) | ++ |
| (35) | + |
| (46) | − |
| (47) | − |
| (48) | + |
| (49) | + |
| (101) | +++ |
| (112) | + |
| (113) | +++ |
| (114) | + |
| (115) | +++ |
| (119) | +++ |
| (120) | + |
| (121) | +++ |
| (122) | + |
| (123) | + |
| (124) | − |
| (125) | ++ |
| (126) | − |
| (127) | + |
| (128) | − |

Example 24: Senolytic Effect of 5-Fluorouridine-5'-O-β-D-Galactopyranoside (FURGal) (101) on Mouse Embryonic Fibroblast Cells (MEFs)

Mouse embryonic fibroblast cells were incubated with 300 nM doxorubicin for 24 hrs to induce senescence. Cells were washed and after incubation in media for 7 days, senescence was confirmed by staining for SA-β-Gal (Itahana et al., Methods Mol. Biol. 371 (2007) 21-31) and lack of incorporation of 5-ethynyl-2'-deoxyuridine (EdU) (see Yu et al., J. Immunol. Methods 350 (2009) 29-35).

Proliferating or senescent MEFs were treated with increasing concentrations of either FURGal (101) or 5-fluorouridine (FUR) (102) for 4 days. Cells were washed and stained with 4',6-diamidino-2-phenylindole (DAPI) and propidium iodide (PI) and the fraction of viable cells was assessed from the ratio of PI-positive nuclei over PI-negative nuclei. The results illustrated in FIG. 1A demonstrate that active drug (102) dramatically reduces cell viability whereas prodrug (101) is completely non-toxic towards proliferating cells at concentrations as high as 4 mM. By contrast both compounds (101) and (102) are equitoxic towards senescent MEFs, as illustrated in FIG. 1B indicating that prodrug (101) is efficiently converted to cytotoxic FUR (102) by hydrolase enzymes within the senescent cell population.

Example 25: Comparative Toxicity of 5-Fluorouridine-5'-O-β-D-Galactopyranoside (FURGal) (101) and 5-Fluorouridine (FUR) (102) to C57BL/6 Mice Equimolar doses of (101)(160 mg/kg) and (102) (100 mg/kg) were administered by single dose intraperitoneal injection to 2 groups of mice (N=3 each). Six days after treatment blood cell counts were determined by standard methods (FIG. 2A), bone marrow cells from femur were counted (FIG. 2B) and spleen weights (FIG. 2C) determined to compare the toxicity of the two drugs. Prodrug (101) shows negligible toxicity towards platelets, neutrophils, lymphocytes and bone marrow cells whereas FUR (102) induces dramatic reductions in all cell populations. Prodrug (101) also shows minimal effects on spleen weight in comparison to FUR (102).

Figures 3A, 3B:
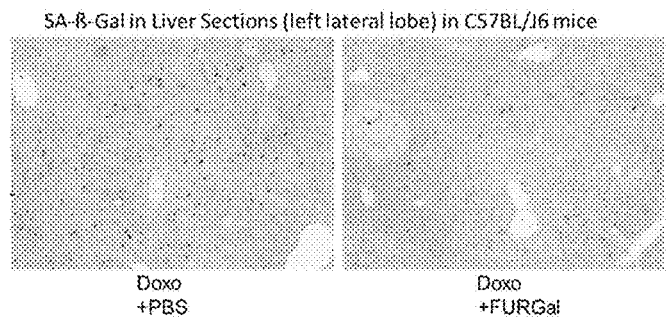
FIG. 3A illustrates a representative image of a liver section of C57BL/6 mice injected with doxorubicin (25 mg/kg).
FIG. 3B illustrates a representative image of a liver section of C57BL/6 mice injected with doxorubicin (25 mg/kg) and FURGal (140 mg/kg).
Figure 3C:
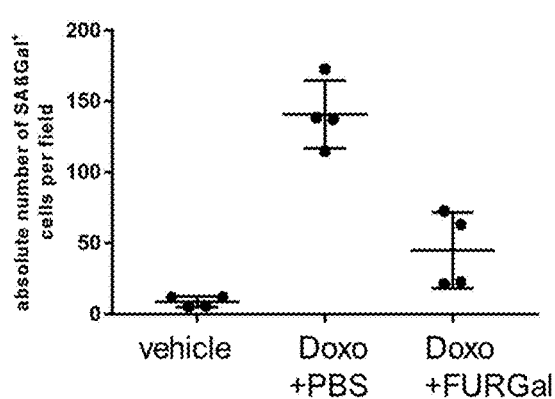
FIG. 3C illustrates quantification of liver sections of FIG. 3A and FIG. 3B along with a control.
Figure 3D:
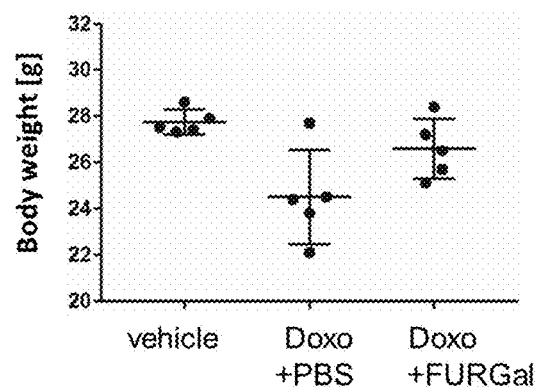
FIG. 3D illustrates the mean body weight of C57BL/6 mice on day of analysis.

Example 26: Effect of 5-Fluorouridine-5'-O-β-D-Galactopyranoside (FURGal) (101) on Senescent C57BL/6 Mouse Hepatocytes after In Vivo Administration Two groups of C57BL/6 mice (N=5/group) were injected intraperitoneally with doxorubicin (25 mg/kg) to induce hepatocellular senescence. 4 and 6 days later groups were injected with PBS or FURGal (140 mg/kg) (101). A third group of 5 animals served as controls. After an additional 4 days livers were removed and sectioned (30 μm) before staining for SA-β-Gal (6 fields/animal were assessed) (FIGS. 3A and 3B). As shown in FIG. 3C, quantitation revealed a numerical trend for a reduction in senescent hepatocytes following FURGal treatment. The mean body weight of the mice on the day of analysis is shown in FIG. 3D.

Figure 4A:
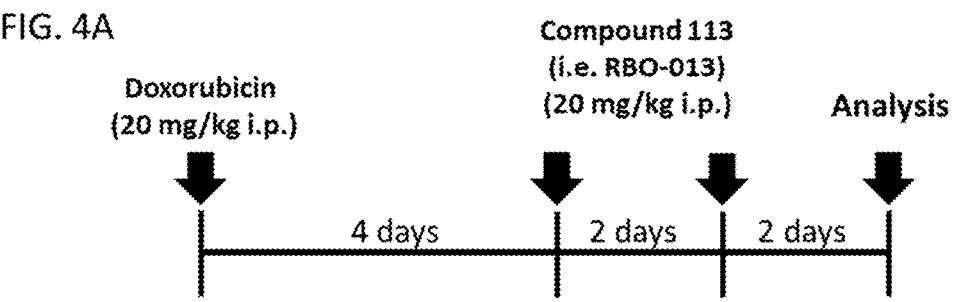
FIG. 4A illustrates the protocol for induction of senescence in hepatocytes in C57BL/6 mice and subsequent treatment with compound (113).
Figure 4B:
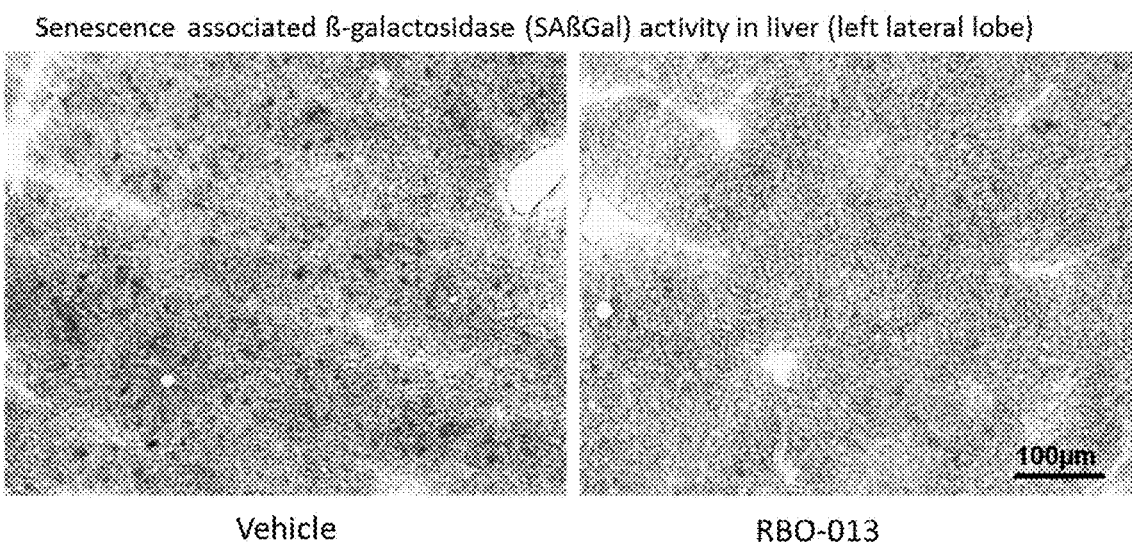
FIG. 4B compares a representative images of liver sections of C57BL/6 mice injected with doxorubicin (20 mg/kg) followed by vehicle or compound (113).
Figure 4C:
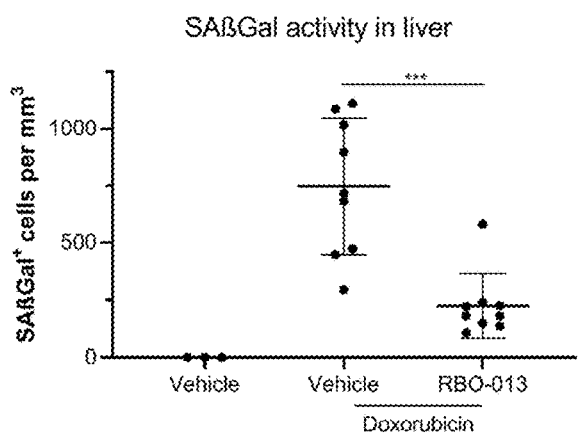
FIG. 4C illustrates quantification of SA-β-Gal in liver sections from FIG. 4B along with a control.
Figure 4D:
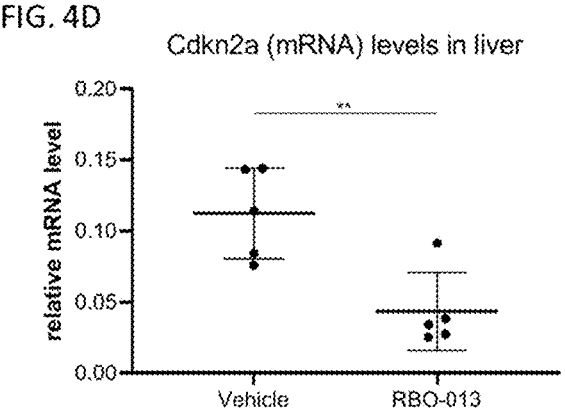
FIG. 4D illustrates quantification of Cdkn2a expression in liver of C57BL/6 mice injected with doxorubicin (20 mg/kg) followed by vehicle or compound (113).
Figure 4E:
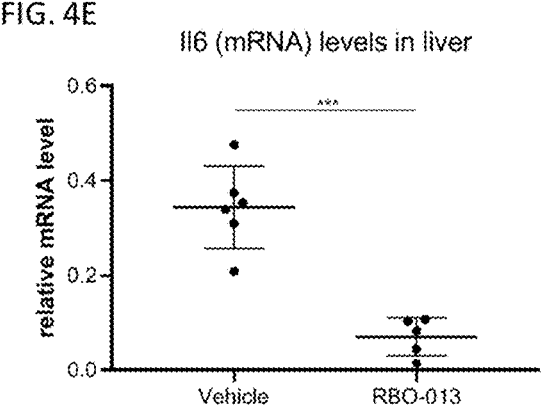
FIG. 4E illustrates quantification of IL-6 expression in liver of C57BL/6 mice injected with doxorubicin (20 mg/kg) followed by vehicle or compound (113).

Example 27: Effect of (2R,3S,4S,5R,6S)-2-(Acetoxymethyl)-6-(((E)-3-(4-(((2-(2-methyl-1H-indol-3yl)ethyl)amino)methyl)phenyl)acrylamido)oxy)tetrahydro-2H-pyran-3,4,5-triyl Triacetate (113) (Aka RBO-013) on Senescent C57BL/6 Mouse Hepatocytes after In Vivo Administration Two groups of C57BL/6 mice (N=9/group) were injected intraperitoneally with doxorubicin (20 mg/kg) to induce hepatocellular senescence. 4 and 6 days later groups were injected i.p. with PBS or compound (113) (aka RBO-013) (2×20 mg/kg). A third group of animals served as controls. After an additional 2 days livers were removed and sectioned (30 μm) before staining for SA-β-Gal as previously described (FIGS. 4A and 4B). As shown in FIG. 4C, quantitation revealed a reduction in senescent hepatocytes (as visualized by SA-β-Gal staining) following treatment with (113). This senolytic effect was also corroborated by using quantitative PCR to detect mRNA levels of Cdkn2a (p16$^{INK4a}$) and IL-6 (N.B. Cdkn2a expression was exclusively detected in animals that received doxorubicin). Expression levels were reported relative to Actb as the reference gene. FIGS. 4D and 4E show a significant reduction in Cdkn2a and IL-6 gene expression respectively.

Figure 5A:
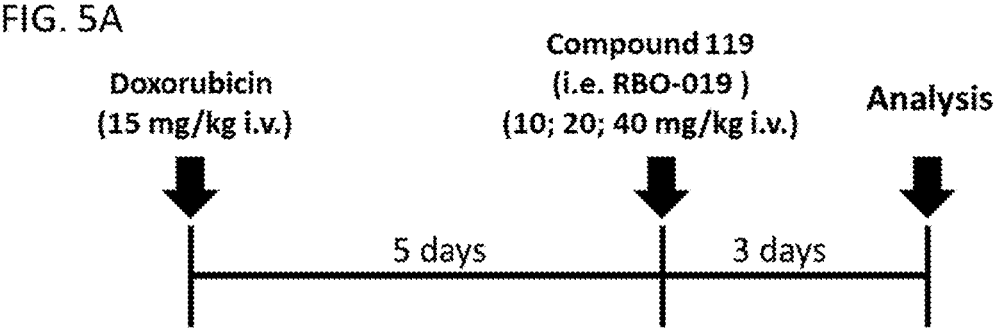
FIG. 5A illustrates the protocol for observation of a senolytic effect of compound (119) in lung tissue in C57BL/6 mice.
Figure 5B:
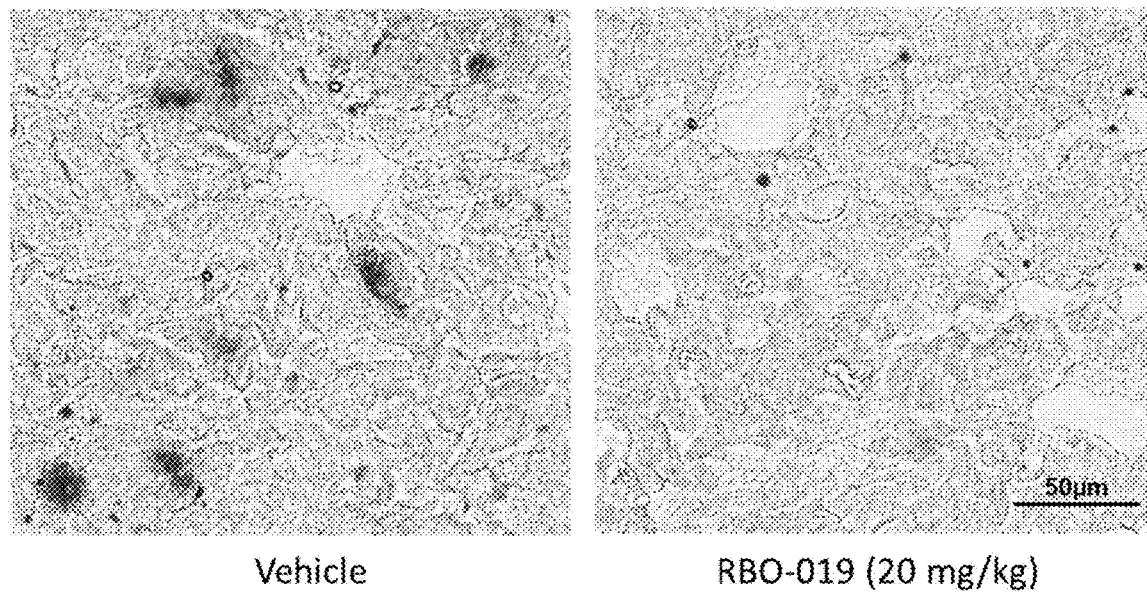
FIG. 5B compares a representative images of lung sections of C57BL/6 mice injected with doxorubicin (15 mg/kg) followed by vehicle or compound (119) at 20 mg/kg.

Example 28: Senolytic Effect of (2S,3R,4R,5S,6S)-2-Methyl-6-(((E)-3-(4-(((2-(2-methyl-1H-indol-3-yl)ethyl)amino)methyl)phenyl)acrylamido)oxy)tetrahydro-2H-pyran-3,4,5-triyl Triacetate (119) (Aka RBO-019) on Senescent Lung Cells in C57BL/6 Mice after In Vivo Administration Four groups of C57BL/6 mice (N=9/group) were injected intravenously with doxorubicin (15 mg/kg) to induce senescence in lung tissue. Five days later groups were injected with vehicle or compound (119) (aka RBO-019) (10, 20 or 40 mg/kg i.v.). After an additional 3 days lungs were removed and the left lobes sectioned before staining for SA-β-Gal as previously described (FIGS. 5A and 5B). As shown in FIG. 5C, quantitation revealed a dose-dependent reduction in SA-β-Gal staining following treatment with (119). This senolytic effect was also corroborated by using quantitative PCR to detect mRNA levels of Cdkn2a (p16$^{INK4a}$). Expression levels were reported relative to Actb as the reference gene. FIG. 5D shows a dose-dependent reduction in Cdkn2a gene expression in lung.

What is claimed is:

1. A compound having the structure:

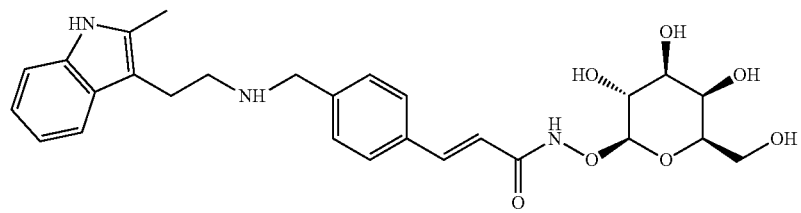 [SMILES: Cc1[nH]c2ccccc2c1CCNCc1ccc(/C=C/C(=O)NO[C@@H]2O[C@H](CO)[C@H](O)[C@H](O)[C@H]2O)cc1]

or pharmaceutically acceptable salts, hydrates or solvates thereof.

2. A pharmaceutical composition comprising the compound of claim 1 and a pharmaceutically acceptable excipient.

3. A compound having the structure:

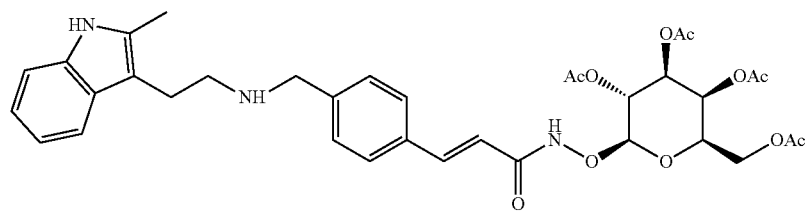 [SMILES: CC(=O)OC[C@H]1O[C@@H](ONC(=O)/C=C/c2ccc(CNCCc3c(C)[nH]c4ccccc34)cc2)[C@H](OC(C)=O)[C@@H](OC(C)=O)[C@H]1OC(C)=O]

or pharmaceutically acceptable salts, hydrates or solvates thereof.

4. A pharmaceutical composition comprising the compound of claim 3 and a pharmaceutically acceptable excipient.

5. A compound having the structure:

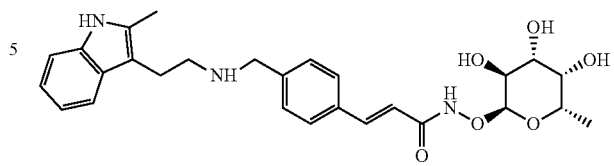

or pharmaceutically acceptable salts, hydrates or solvates thereof.

6. A pharmaceutical composition comprising the compound of claim 5 and a pharmaceutically acceptable excipient.

7. A compound having the structure:

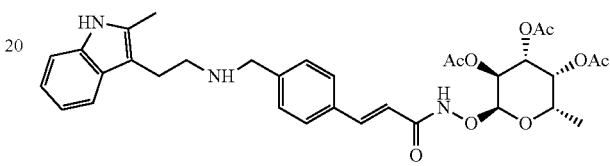

or pharmaceutically acceptable salts, hydrates or solvates thereof.

8. A pharmaceutical composition comprising the compound of claim 7 and a pharmaceutically acceptable excipient.

9. A method for treating a senescence-associated disease or disorder comprising administering to a subject in need thereof a therapeutically-effective amount of the compound of claim 1.

10. A method for treating a senescence-associated disease or disorder comprising administering to a subject in need thereof a therapeutically-effective amount of the pharmaceutical composition of claim 2.

11. A method for treating a senescence-associated disease or disorder comprising administering to a subject in need thereof a therapeutically-effective amount of the compound of claim 3.

12. A method for treating a senescence-associated disease or disorder comprising administering to a subject in need thereof a therapeutically-effective amount of the pharmaceutical composition of claim 4.

13. A method for treating a senescence-associated disease or disorder comprising administering to a subject in need thereof a therapeutically-effective amount of the compound of claim 5.

14. A method for treating a senescence-associated disease or disorder comprising administering to a subject in need thereof a therapeutically-effective amount of the pharmaceutical composition of claim 6.

15. A method for treating a senescence-associated disease or disorder comprising administering to a subject in need thereof a therapeutically-effective amount of the compound of claim 7.

16. A method for treating a senescence-associated disease or disorder comprising administering to a subject in need thereof a therapeutically-effective amount of a pharmaceutical composition of claim 8.

\* \* \* \* \*